US008039486B2

(12) United States Patent
Yeung et al.

(10) Patent No.: US 8,039,486 B2
(45) Date of Patent: Oct. 18, 2011

(54) INDOLE, AZAINDOLE AND RELATED HETEROCYCLIC N-SUBSTITUTED PIPERAZINE DERIVATIVES

(75) Inventors: Kap-Sun Yeung, Madison, CT (US); Michelle E. Farkas, Pasadena, CA (US); John F. Kadow, Wallingford, CT (US); Nicholas A. Meanwell, East Hampton, CT (US); Malcolm Taylor, Didcot (GB); David Johnston, Didcot (GB); Thomas Stephen Coulter, Wantage (GB); J. J. Kim Wright, Redwood City, CA (US)

(73) Assignee: Bristol-Myers Squibb Company, Princeton, NJ (US)

(*) Notice: Subject to any disclaimer, the term of this patent is extended or adjusted under 35 U.S.C. 154(b) by 923 days.

(21) Appl. No.: 12/028,189

(22) Filed: Feb. 8, 2008

(65) Prior Publication Data
US 2008/0132516 A1    Jun. 5, 2008

Related U.S. Application Data

(63) Continuation-in-part of application No. 11/029,673, filed on Jan. 5, 2005, now abandoned.

(60) Provisional application No. 60/541,970, filed on Feb. 5, 2004, provisional application No. 60/493,283, filed on Aug. 7, 2003, provisional application No. 60/484,224, filed on Jul. 1, 2003.

(51) Int. Cl.
A61K 31/04    (2006.01)
C07D 215/38    (2006.01)

(52) U.S. Cl. .................................... 514/312; 546/159

(58) Field of Classification Search ................... 546/159; 514/312
See application file for complete search history.

(56) References Cited

U.S. PATENT DOCUMENTS

| | | | | |
|---|---|---|---|---|
| 3,135,794 | A * | 6/1964 | Archer | 564/212 |
| 3,188,313 | A * | 6/1965 | Archer | 544/364 |
| 5,023,265 | A | 6/1991 | Scherlock et al. | |
| 5,124,327 | A | 6/1992 | Greenlee et al. | |
| 5,424,329 | A | 6/1995 | Boschelli et al. | |
| 6,008,231 | A | 12/1999 | Lebaut et al. | |
| 6,232,327 | B1 | 5/2001 | Nickel et al. | |
| 6,344,467 | B1 * | 2/2002 | Lebaut et al. | 514/339 |
| 6,469,006 | B1 | 10/2002 | Blair et al. | |
| 6,476,034 | B2 | 11/2002 | Wang et al. | |
| 6,573,262 | B2 | 6/2003 | Wallace et al. | |
| 6,632,819 | B1 | 10/2003 | Wang et al. | |
| 6,919,344 | B2 * | 7/2005 | Lebaut et al. | 514/256 |
| 7,807,671 | B2 * | 10/2010 | Wang et al. | 514/234.5 |
| 2003/0207910 | A1 | 11/2003 | Wang et al. | |
| 2004/0063744 | A1 | 4/2004 | Wang et al. | |
| 2005/0075364 | A1 | 4/2005 | Yeung et al. | |

FOREIGN PATENT DOCUMENTS

| | | |
|---|---|---|
| EP | 0530907 A1 | 3/1993 |
| WO | WO 91/09849 | 7/1991 |
| WO | WO 93/01181 | 1/1993 |
| WO | WO 95/04742 | 2/1995 |
| WO | WO 96/11929 | 4/1996 |
| WO | WO 96/18628 | 6/1996 |
| WO | WO 99/51224 | 10/1999 |
| WO | WO 02/085301 | 10/2002 |
| WO | WO 03/092695 | 11/2003 |
| WO | WO 04/000210 A2 | 12/2003 |
| WO | WO 2004/011425 A2 | 2/2004 |
| WO | WO 2005/090367 | 9/2005 |

OTHER PUBLICATIONS

Chemical Abstracts Service—Proceedings of the National Academy of Sciences of the USA, 1963, v50(4), pp. 679-686 Okubo, S. et al, "Separation of the transforming and viral deoxyribonucleic acids of a transducing bacteriophage of *Bacillus subtilis*".

M. Font, et al., "Indoles and Pyridazino[4,5-*b*]indoles as Non-nucleoside Analog Inhibitors of HIV-1 Reverse Transcriptase," Eur. J. Med. Chem., 30, pp. 963-971, 1995.

D.L. Romero, et al., Bis(heteroaryl)pipera;zine (BHAP) Reverse Transcriptase Inhibitors: Structure-Activity Relationships of Novel Substituted Indole Analogues and the Identification of 1-[(5-Methanesulfonamido-1*H*-indole-2-yl)-carbonyl]-4-[3-[(1-methylethyl)amino]-pyridinyl]piperazine Monomethanesulfonate (U-90152S), a Second-Generation Clinical Candidate, J. Med. Chem., 36, pp. 1505-1508, 1993.

S.D. Young, et al., "2-Heterocyclic Indole-3-Sulfones as Inhibitors of HIV-1 Reverse Transcriptase," Bioorganic & Medicinal Chemistry Letters, 5(5), pp. 491-496, 1995.

M.J. Genin, et al., "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.

R. Silvestri, et al., "Synthesis and biological evaluation of 5*H*-indole[3,2-b][1,5]benzothiazepine derivatives, designed as conformationally constrained analogues of the human immunodeficiency virus type 1 reverse transcriptase inhibitor L737,126," Antiviral Chemistry & Chemotherapy, 9, pp. 139-148,1998.

A. Fredenhagen, et al., "Semicochliodinol A and B: Inhibitors of HIV-1 Protease and EGF-R Protein Tyrosine Kinase Related to Asterriquinones Produced by the Fungus *Chrysosporium merdarium*," Journal of Antibiotics, 50(5), pp. 395-401, 1997.

M. Kato, et al., "New 5-HT$_3$ (Serotonin-3) Receptor Antagonists. IV. Synthesis and Structure-Activity Relationships of Azabicycloalkaneacetamide Derivatives," Chem. Pharm. Bull., 43(8), pp. 1351-1357, 1995.

V. Levacher, et al., "Broadening in the Scope of NADH Models by Using Chiral and Non-Chiral Pyrrolo[2,3-b]Pyridine Derivatives, "Tetrahedron, 47(3), pp. 429-440, 1991.

Romero, D.L., "Discovery, Synthesis, and Bioactivity of Bis(heteroaryl)piperazines. 1. A Novel Class of Non-Nucleoside HIV-1 Reverse Transcriptase Inhibitors," J. Med. Chem., 1994, vol. 37, No. 7, pp. 999-1014.

* cited by examiner

*Primary Examiner* — D M Seaman
(74) *Attorney, Agent, or Firm* — John F. Levis

(57) ABSTRACT

This invention provides compounds of Formula I, including pharmaceutically acceptable salts thereof, having drug and bio-affecting properties, their pharmaceutical compositions and method of use. These compounds possess unique antiviral activity, whether used alone or in combination with other antivirals, antiinfectives, immunomodulators or HIV entry inhibitors. More particularly, the present invention relates to the treatment of HIV and AIDS. The compounds of Formula I have the formula

(I)

wherein:
Z is

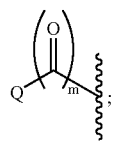

Q is selected from the group consisting of

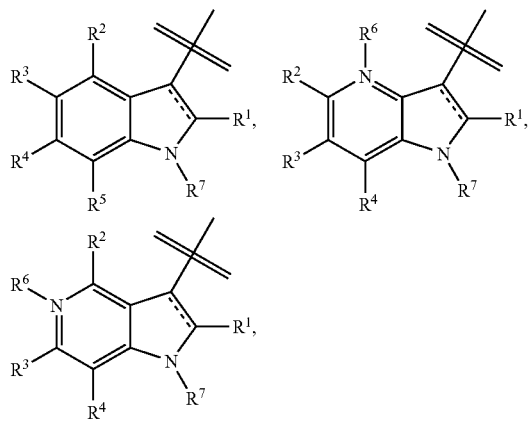

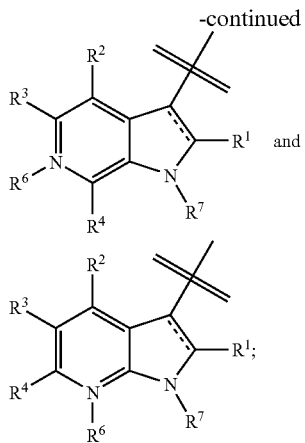

m is 2;

A is selected from the group consisting of cinnolinyl, napthyridinyl, quinoxalinyl, pyridinyl, pyrimidinyl, quinolinyl, isoquinolinyl, quinazolinyl, azabenzofuryl, and phthalazinyl each of which may be optionally substituted with one or two groups independently selected from methyl, methoxy, hydroxy, amino and halogen; and —W— is

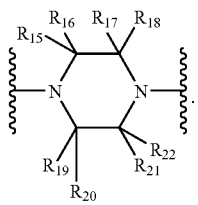

11 Claims, No Drawings

US 8,039,486 B2

INDOLE, AZAINDOLE AND RELATED HETEROCYCLIC N-SUBSTITUTED PIPERAZINE DERIVATIVES

REFERENCE TO RELATED APPLICATIONS

This application is a Continuation application of U.S. Continuation-in-Part application Ser. No. 11/029,673 filed Jan. 5, 2005 now abandoned, and claims benefit of that application and U.S. Non-Provisional application Ser. No. 10/871,931 filed Jun. 18, 2004 and U.S. Provisional Application Ser. Nos. 60/541,970 filed Feb. 5, 2004, 60/493,283 filed Aug. 7, 2003 and 60/484,224 filed Jul. 1, 2003.

FIELD OF THE INVENTION

This invention provides compounds having drug and bio-affecting properties, their pharmaceutical compositions and method of use. In particular, the invention is concerned with new N-heteroaryl and N-aryl piperazine derivatives that possess unique antiviral activity. More particularly, the present invention relates to compounds useful for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include ten nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine), Emtriva® (emtricitabine); three non-nucleoside reverse transcriptase inhibitors: nevirapine (or Viramune®), delavirdine (or Rescriptor®) and efavirenz (or Sustiva®), and eight peptidomimetic protease inhibitors or approved formulations: saquinavir, indinavir, ritonavir, nelfinavir, amprenavir, lopinavir, Kaletra® (lopinavir and Ritonavir), and Reyataz® (atazanavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl)piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection. has appeared (Buckheit, reference 99). A review covering both NRTI and NNRTIs has appeared (De clercq, reference 100). An overview of the current state of the HIV drugs has been published (De clercq, reference 101).

Several indole derivatives including indole-3-sulfones, piperazino indoles, pyrazino indoles, and 5H-indolo[3,2-b] [1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Dompe Spa, WO-09504742, Ref. 5(a); SmithKline Beecham PLC, WO-09611929, Ref. 5(b); Schering Corp., U.S. Pat. No. 5,023,265, Ref. 5(c)). However, these structures differ from those claimed herein in that they are aza-indole mono-amide rather than oxoacetamide derivatives, and there is no mention of the use of these compounds for treating viral infections, particularly HIV. PCT International Patent Application WO9951224 by Bernd Nickel et. al. (reference 107) describes N-indolylglyoxamides for the treatment of cancer. Although some of these compounds contain N-heteroaryl or N-aryl piperazines, the substitution patterns at the other positions are outside the scope of this invention.

The compounds of this invention inhibit HIV entry by attaching to the exterior viral envelop protein gp120 and interrupting the viral entry process, possibly by interfering with recognition of the cellular receptor CD4. Compounds in this class have been reported to have antiviral activity against a variety of laboratory and clinical strains of HIV-1 and are effective in treating HIV infection (see Hanna et al., *Abstract 141* presented at the 11th Conference on Retroviruses and Opportunistic Infections, San Francisco, Calif., Feb. 8-11, 2004; Lin et al., Poster 534 presented at the 11th Conference on Retroviruses and Opportunistic Infections, San Francisco, Calif., Feb. 8-11, 2004; Hanna et al., Poster 535 presented at the 11th Conference on Retroviruses and Opportunistic Infections, San Francisco, Calif., Feb. 8-11, 2004).

N-(3-aryl-3-oxo)acetyl piperidines have been disclosed. See Blair et al., U.S. Pat. No. 6,469,006; Wang et al., U.S. Pat. No. 6,476,034; Wang et al., U.S. Pat. No. 6,632,819; Wallace et al., U.S. Pat. No. 6,573,262 (continuation-in-part application of U.S. Ser. No. 09/888,686, filed Jun. 25, 2001); Wang et al., U.S. patent application Ser. No. 10/214,982 filed Aug. 7, 2002 (continuation-in-part application of U.S. Ser. No. 10/038,306 filed Jan. 2, 2002); Wang et al., patent application WO 03/092695, published Nov. 13, 2003; Kadow et. al. patent application WO 04/000210 published Dec. 31, 2003; Regueiro-Ren et. al. patent application WO 04/011425 published Feb. 5, 2004; Wang et al., US patent application US 20040063744, published Apr. 1, 2004. Nothing in these references teaches or suggests the novel compounds of this invention or their use to inhibit HIV infection.

REFERENCES CITED

Patent Documents
1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications
6. Larder, B. A.; Kemp, S. D. Multiple mutations in the HIV-1 reverse transcriptase confer high-level resistance to zidovudine (AZT). *Science*, 1989, 246, 1155-1158.
7. Gulick, R. M. Current antiretroviral therapy: An overview. *Quality of Life Research*, 1997, 6, 471-474.
8. Kuritzkes, D. R. HIV resistance to current therapies. *Antiviral Therapy*, 1997, 2 (Supplement 3), 61-67.
9. Morris-Jones, S.; Moyle, G.; Easterbrook, P. J. Antiretroviral therapies in HIV-1 infection. *Expert Opinion on Investigational Drugs*, 1997, 6(8), 1049-1061.
10. Schinazi, R. F.; Larder, B. A.; Mellors, J. W. Mutations in retroviral genes associated with drug resistance. *International Antiviral News*, 1997, 5, 129-142.
11. Vacca, J. P.; Condra, J. H. Clinically effective HIV-1 protease inhibitors. *Drug Discovery Today*, 1997, 2, 261-272.
12. Flexner, D. HIV-protease inhibitors. *Drug Therapy*, 1998, 338, 1281-1292.
13. Berkhout, B. HIV-1 evolution under pressure of protease inhibitors: Climbing the stairs of viral fitness. *J. Biomed. Sci.*, 1999, 6, 298-305.
14. Ren, S.; Lien, E. J. Development of HIV protease inhibitors: A survey. *Prog. Drug Res.*, 1998, 51, 1-31.
15. Pedersen, O. S.; Pedersen, E. B. Non-nucleoside reverse transcriptase inhibitors: the NNRTI boom. *Antiviral Chem. Chemother.* 1999, 10, 285-314.
16. (a) De Clercq, E. The role of non-nucleoside reverse transcriptase inhibitors (NNRTIs) in the therapy of HIV-1 infection. *Antiviral Research*, 1998, 38, 153-179. (b) De Clercq, E. Perspectives of non-nucleoside reverse transcriptase inhibitors (NNRTIs) in the therapy of HIV infection. IL. *Farmaco*, 1999, 54, 26-45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino [4,5-b]indoles as nonnucleoside analog inhibitors of HIV-1 reverse transcriptase. *Eur. J. Med. Chem.*, 1995, 30, 963-971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.*, 1993, 36, 1505-1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.*, 1995, 5, 491-496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.*, 1996, 39, 5267-5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139-148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium*. *Antibiotics*, 1997, 50, 395-401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.*, 1995, 43, 1351-1357.
24. Levacher, V.; Benoit, R.; Duflos, J; Dupas, G.; Bourguignon, J.; Queguiner, G. Broadening the scope of NADH models by using chiral and non chiral pyrrolo[2,3-b]pyridine derivatives. *Tetrahedron*, 1991, 47, 429-440.
25. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.*, 1987, 1206-1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.*, 1987, 100-106.

27. (a) Desai, M.; Watthey, J. W. H.; Zuckerman, M. A convenient preparation of 1-aroylpiperazines. *Org. Prep. Proced. Int.*, 1976, 8, 85-86. (b) Adamczyk, M.; Fino, J. R. Synthesis of procainamide metabolites. N-acetyl desethylprocainamide and desethylprocainamide. *Org. Prep. Proced. Int.* 1996, 28, 470-474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419-6422. (d) Wang, T.; Zhang, Z.; Meanwell, N. A. Benzoylation of Dianions: Preparation of mono-Benzoylated Symmetric Secondary Diamines. *J. Org. Chem.*, 1999, 64, 7661-7662.

28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.*, 1999, 1, 91-93.

29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.*, 1997, 45, 134-137.

30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.*, 1980, 45, 4045-4048.

31. Shiotani, S.; Tanigochi, K. Furopyridines. XXII [1]. Elaboration of the C-substitutents alpha to the heteronitrogen atom of furo[2,3-b]-, -[3.2-b]-, -[2,3-c]- and -[3,2-c] pyridine. *J. Het. Chem.*, 1997, 34, 901-907.

32. Minakata, S.; Komatsu, M.; Ohshiro, Y. Regioselective functionalization of 1H-pyrrolo[2,3-b]pyridine via its N-oxide. *Synthesis*, 1992, 661-663.

33. Klemm, L. H.; Hartling, R. Chemistry of thienopyridines. XXIV. Two transformations of thieno[2,3-b]pyridine 7-oxide (1). *J. Het. Chem.*, 1976, 13, 1197-1200.

34. Antonini, I.; Claudi, F.; Cristalli, G.; Franchetti, P.; Crifantini, M.; Martelli, S. Synthesis of 4-amino-1-β-D-ribofuranosyl-1H-pyrrolo[2,3-b]pyridine (1-Deazatubercidin) as a potential antitumor agent. *J. Med. Chem.*, 1982, 25, 1258-1261.

35. (a) Regnouf De Vains, J. B.; Papet, A. L.; Marsura, A. New symmetric and unsymmetric polyfunctionalized 2,2'-bipyridines. *J. Het. Chem.*, 1994, 31, 1069-1077. (b) Miura, Y.; Yoshida, M.; Hamana, M. Synthesis of 2,3-fused quinolines from 3-substituted quinoline 1-oxides. Part II, *Heterocycles*, 1993, 36, 1005-1016. (c) Profft, V. E.; Rolle, W. Uber 4-merkaptoverbindungendes 2-methylpyridins. *J. Prakt. Chem.*, 1960, 283 (11), 22-34.

36. Nesi, R.; Giomi, D.; Turchi, S.; Tedeschi, P., Ponticelli, F. A new one step synthetic approach to the isoxazolo[4,5-b] pyridine system. *Synth. Comm.*, 1992, 22, 2349-2355.

37. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378-1381. (b) Barker, G.; Ellis, G. P. Benzopyrone. Part I. 6-Amino- and 6-hydroxy-2-substituted chromones. *J. Chem. Soc.*, 1970, 2230-2233.

38. Ayyangar, N. R.; Lahoti, R J.; Daniel, T. An alternate synthesis of 3,4-diaminobenzophenone and mebendazole. *Org. Prep. Proced. Int.*, 1991, 23, 627-631.

39. Mahadevan, I.; Rasmussen, M. Ambident heterocyclic reactivity: The alkylation of pyrrolopyridines (azaindoles, diazaindenes). *Tetrahedron*, 1993, 49, 7337-7352.

40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654-660.

41. Bodanszky, M.; Bodanszky, A. "*The Practice of Peptide Synthesis*" 2$^{nd}$ Ed., Springer-Verlag: Berlin Heidelberg, Germany, 1994.

42. Albericio, F. et al. *J. Org. Chem.* 1998, 63, 9678.

43. Knorr, R. et al. *Tetrahedron Lett.* 1989, 30, 1927.

44. (a) Jaszay Z. M. et al. *Synth. Commun.*, 1998 28, 2761 and references cited therein; (b) Bernasconi, S. et al. *Synthesis*, 1980, 385.

45. (a) Jaszay Z. M. et al. *Synthesis*, 1989, 745 and references cited therein; (b) Nicolaou, K. C. et al. *Angew. Chem. Int. Ed.* 1999, 38, 1669.

46. Ooi, T. et al. *Synlett.* 1999, 729.

47. Ford, R. E. et al. *J. Med. Chem.* 1986, 29, 538.

48. (a) Yeung, K.-S. et al. Bristol-Myers Squibb Unpublished Results. (b) Wang, W. et al. *Tetrahedron Lett.* 1999, 40, 2501.

49. Brook, M. A. et al. *Synthesis*, 1983, 201.

50. Yamazaki, N. et al. *Tetrahedron Lett.* 1972, 5047.

51. Barry A. Bunin "The Combinatorial Index" 1998 Academic Press, San Diego/London pages 78-82.

52. Richard C. Larock Comprehensive Organic Transormations 2nd Ed. 1999, John Wiley and Sons New York.

53. M. D. Mullican et. al. *J. Med. Chem.* 1991, 34, 2186-2194.

54. Protective groups in organic synthesis 3rd ed./Theodora W. Greene and Peter G. M. Wuts. New York: Wiley, 1999.

55. Katritzky, Alan R. Lagowski, Jeanne M. The principles of heterocyclic Chemistry New York: Academic Press, 1968.

56. Paquette, Leo A. Principles of modern heterocyclic chemistry New York: Benjamin.

57. Katritzky, Alan R.; Rees, Charles W.; Comprehensive heterocyclic chemistry: the structure, reactions, synthesis, and uses of heterocyclic compounds 1st ed. Oxford (Oxfordshire); New York: Pergamon Press, 1984. 8 v.

58. Katritzky, Alan RHandbook of heterocyclic 1st edOxford (Oxfordshire); New York: Pergamon Press, 1985.

59. Davies, David I Aromatic Heterocyclic Oxford; New York: Oxford University Press, 1991.

60. Ellis, G. P. Synthesis of fused Chichester [Sussex]; New York: Wiley, c1987-c1992. Chemistry of heterocyclic compounds; v. 47.

61. Joule, J. A Mills, K., Smith, G. F. Heterocyclic Chemistry, 3rd ed London; New York Chapman & Hall, 1995.

62. Katritzky, Alan R., Rees, Charles W., Scriven, Eric F. V. Comprehensive heterocyclic chemistry II: a review of the literature 1982-1995.

63. The structure, reactions, synthesis, and uses of heterocyclic compounds 1st ed. Oxford; New York: Pergamon, 1996. 11 v. in 12: ill.; 28 cm.

64. Eicher, Theophil, Hauptmann, Siegfried. The chemistry of heterocycles: structure, reactions, syntheses, and applications Stuttgart; New York: G. Thieme, 1995.

65. Grimmett, M. R. Imidazole and benzimidazole Synthesis London; San Diego: Academic Press, 1997.

66. Advances in heterocyclic chemistry. Published in New York by Academic Press, starting in 1963-present.

67. Gilchrist, T. L. (Thomas Lonsdale) Heterocyclic chemistry 3rd ed. Harlow, Essex: Longman, 1997, 414 p: ill.; 24 cm.

68. Farina, Vittorio; Roth, Gregory P. Recent advances in the Stille reaction; *Adv. Met.-Org. Chem.* 1996, 5, 1-53.

69. Farina, Vittorio; Krishnamurthy, Venkat; Scott, William J. The Stille reaction; Org. React. (N.Y.) (1997), 50, 1-652.

70. Stille, J. K. *Angew. Chem. Int. Ed. Engl.* 1986, 25, 508-524.
71. Norio Miyaura and Akiro Suzuki *Chem. Rev.* 1995, 95, 2457.
72. Home, D. A. *Heterocycles* 1994, 39, 139.
73. Kamitori, Y. et. al. *Heterocycles,* 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52-53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828-5832.
85. Bowden, K. et. al. *J. Chem. Soc.* 1946, 953.
86. Nitz, T. J. et. al. *J. Org. Chem.* 1994, 59, 5828-5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (c) Jenneskens, L. W.; Mahy, J.; den Berg, E. M. M. de B.-v.; Van der Hoef, I.; Lugtenburg, *J. Recl. Trav. Chim. Pays-Bas* 1995, 114, 97.
89. Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470-474. (b) Wang, T.; Zhang, Z.; Meanwell, N. A. Regioselective mono-Benzoylation of Unsymmetrical piperazines. *J. Org. Chem.,* in press.
91. Masuzawa, K.; Kitagawa, M.; Uchida, H. *Bull Chem. Soc. Jpn.* 1967, 40, 244-245.
92. Furber, M.; Cooper, M. E.; Donald, D. K. *Tetrahedron Lett.* 1993, 34, 1351-1354.
93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives U.S. Pat. No. 6,469,006. Preparation of antiviral indoleoxoacetyl piperazine derivatives. PCT Int. Appl. (PCT/US00/14359), WO 0076521 A1, filed May 24, 2000, published Dec. 21, 2000.
94. Wang, Tao; Wallace, Owen B.; Zhang, Zhongxing; Meanwell, Nicholas A.; Bender, John A. Antiviral azaindole derivatives. U.S. Pat. No. 6,476,034 and Wang, Tao; Wallace, Owen B.; Zhang, Zhongxing; Meanwell, Nicholas A.; Bender, John A. Preparation of antiviral azaindole derivatives. PCT Int. Appl. (PCT/US01/02009), WO 0162255 A1, filed Jan. 19, 2001, published Aug. 30, 2001.
95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. U.S. patent application Ser. No. 10/027,612 filed Dec. 19, 2001, which is a continuation-in-part application of U.S. Ser. No. 09/888,686 filed Jun. 25, 2001 (corresponding to PCT Int. Appl. (PCT/US01/20300), WO 0204440 A1, filed Jun. 26, 2001, published Jan. 17, 2002.
96. J. L. Marco, S. T. Ingate, and P. M. Chinchon Tetrahedron 1999, 55, 7625-7644.
97. C. Thomas, F. Orecher, and P. Gmeiner Synthesis 1998, 1491.
98. M. P. Pavia, S. J. Lobbestael, C. P. Taylor, F. M. Hershenson, and D. W. Miskell.
99. Buckheit, Robert W., Jr. Expert Opinion on Investigational Drugs 2001, 10(8), 1423-1442.
100. Balzarini, J.; De Clercq, E. Antiretroviral Therapy 2001, 31-62.
101. E. De clercq Journal of Clinical Virology, 2001, 22, 73-89.
102. Merour, Jean-Yves; Joseph, Benoit. Curr. Org. Chem. (2001), 5(5), 471-506.
103. T. W. von Geldern et al. J. Med. Chem. 1996, 39, 968.
104. M. Abdaoui et al. Tetrahedron 2000, 56, 2427.
105. W. J. Spillane et al. J. Chem. Soc., Perkin Trans. 1, 1982, 3, 677.
106. Wang, Tao; Wallace, Owen B.; Zhang, Zhongxing; Meanwell, Nicholas A.; Kadow, John F. Yin, Zhiwei. Composition and Antiviral Activity of Substituted Azaindoleoxoacetic piperazine Derivatives. U.S. patent application Ser. No. 10/214,982 filed Aug. 7, 2002, which is a continuation-in-part application of U.S. Ser. No. 10/038,306 filed Jan. 2, 2002 (corresponding to PCT Int. Appl. (PCT/US02/00455), WO 02/062423 A1, filed Jan. 2, 2002, published Aug. 15, 2002.
107. Preparation of indolylglyoxylamides as antitumor agents, Nickel, Bernd; Szelenyi, Istvan; Schmidt, Jurgen; Emig, Peter; Reichert, Dietmar; Gunther, Eckhard; Brune, Kay, PCT Int. Appl. WO 9951224, published Oct. 14, 1999.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts thereof, have the formula and meaning as described below.

The present invention comprises compounds of Formula I, including pharmaceutically acceptable salts thereof, which are effective antiviral agents, particularly as inhibitors of HIV.

An embodiment are compounds of Formula I, including pharmaceutically acceptable salts thereof,

wherein:
Z is

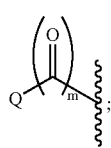

Q is selected from the group consisting of

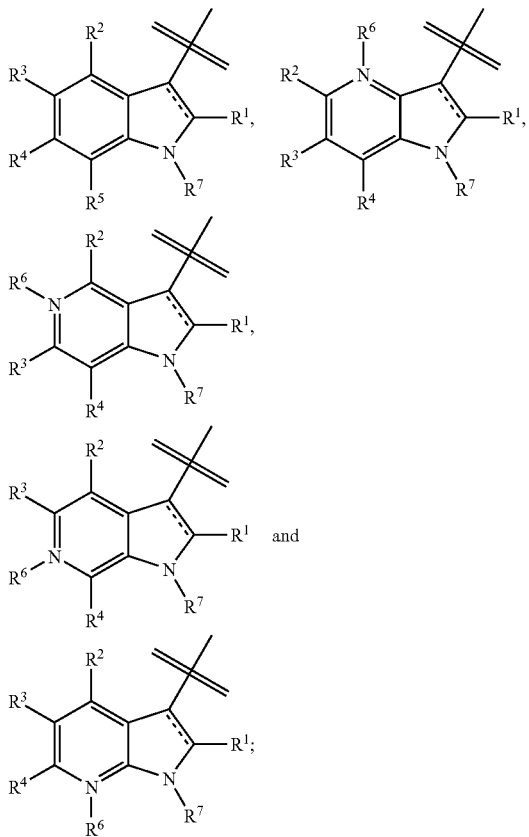

R[1] is hydrogen;
R[2], R[3], R[4], and R[5], are independently selected from the group consisting of hydrogen, halogen, cyano, COOR[8], XR[9] and B;
m is 2;
R[6] is O or does not exist;
R[7] is hydrogen;
R[10] is selected from the group consisting of $(C_{1-6})$alkyl, —CH$_2$CN, —CH$_2$COOH, —CH$_2$C(O)NR[11]R[12], phenyl and pyridinyl;
R[11] and R[12] are each independently H or $(C_{1-3})$alkyl;
— represents a carbon-carbon bond;
A is selected from the group consisting of cinnolinyl, napthyridinyl, quinoxalinyl, pyridinyl, pyrimidinyl, quinolinyl, isoquinolinyl, quinazolinyl, azabenzofuryl, and phthalazinyl each of which may be optionally substituted with one or two groups independently selected from methyl, methoxy, hydroxy, amino and halogen;
—W— is

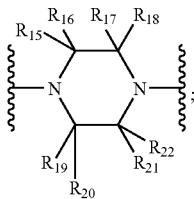

R[15], R[16], R[17], R[18], R[19], R[20], R[21], R[22] are each independently H or one of them is methyl;
B is selected from the group consisting of C(O)NR[11]R[12] C(=NH)NHNHC(O)—R[10], C(=NH)cyclopropyl, C(=NOH)NH$_2$, and heteroaryl; wherein said heteroaryl is independently optionally substituted with a substituent selected from F;
heteroaryl is selected from the group consisting of pyridinyl, pyrazinyl, pyrimidinyl, thiazolyl, pyrrolyl, imidazolyl, benzoimidazolyl, oxadiazolyl, pyrazolyl, tetrazolyl and triazolyl;
F is selected from the group consisting of $(C_{1-6})$alkyl, $(C_{1-6})$ alkoxy, cyano, COOR[8]—CONR[11]R[12]; —CH$_2$CN, —CH$_2$COOH, —CH$_2$C(O)NR[11]R[12], phenyl and pyridinyl;
R[8] and R[9] are independently selected from the group consisting of hydrogen and $(C_{1-6})$alkyl;
X is O;
provided that when A is pyridinyl or pyrimidinyl and Q is

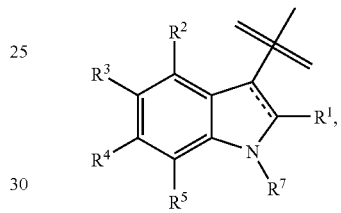

then R[5] is B.

Another embodiment are compounds of Formula I, including pharmaceutically acceptable salts thereof, wherein:
R[15], R[16], R[17], R[18], R[20], R[21], R[22] are H;
R[6] does not exist;
A is selected from members of the group consisting of

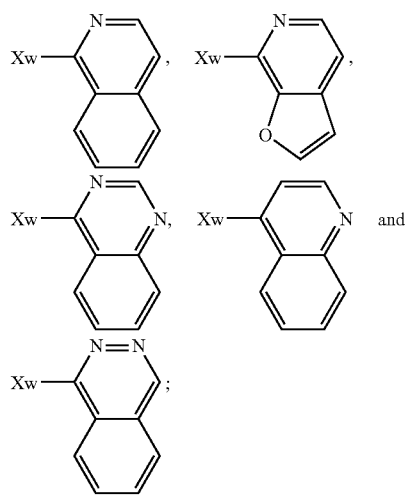

where Xw is the point of attachment and each member is independently optionally substituted with one group selected from the group consisting of methyl, methoxy, hydroxy, amino and halogen;

Q is selected from the group consisting of

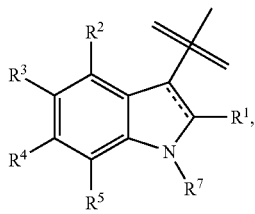

, and

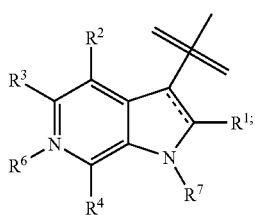;

provided when Q is

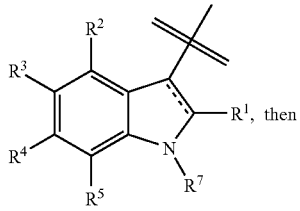, then $R^2$ is hydrogen, methoxy or halogen; $R^3$ and $R^4$ are hydrogen; and $R^5$ is selected from the group consisting of hydrogen, halogen, cyano, $COOR^8$, $XR^9$ and B;

or provided when Q is

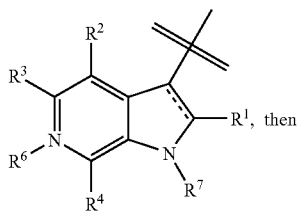, then $R^2$ is hydrogen, methoxy or halogen; $R^3$ is hydrogen; and $R^4$ is selected from the group consisting of hydrogen, halogen, cyano, $COOR^8$, $XR^9$ and B;

or provided when Q is

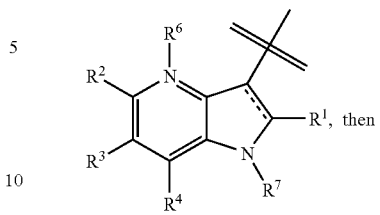, then $R^2$ and $R^3$ are each hydrogen; and $R^4$ is selected from the group consisting of hydrogen, halogen, cyano, $COOR^8$, $XR^9$ and B.

Another embodiment are compounds of Formula I, including pharmaceutically acceptable salts thereof,
wherein:
B is selected from the group consisting of $C(O)NR^{11}R^{12}$ and heteroaryl; wherein said heteroaryl is independently optionally substituted with a substituent selected from F;
heteroaryl is selected from the group consisting of pyridinyl, pyrazinyl, pyrimidinyl, thiazolyl, pyrrolyl, imidazolyl, benzoimidazolyl, oxadiazolyl, tetrazolyl and triazolyl.

Another embodiment are compounds of Formula I, including pharmaceutically acceptable salts thereof,
wherein:
B is heteroaryl wherein said heteroaryl is independently optionally substituted with a substituent selected from F.

Another embodiment are compounds of Formula I, including pharmaceutically acceptable salts thereof,
wherein:
A is selected from the group consisting of

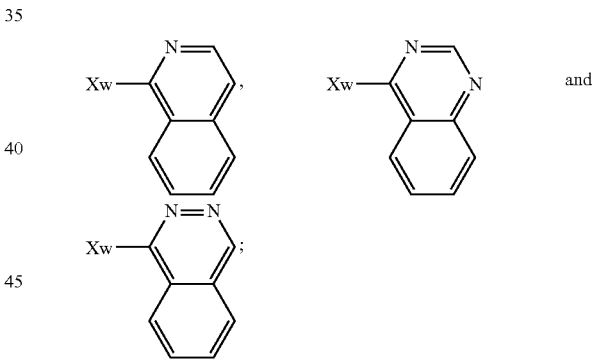

where Xw is the point of attachment.

Another embodiment are compounds of Formula I, including pharmaceutically acceptable salts thereof,
wherein:
B is heteroaryl; wherein said heteroaryl is independently optionally substituted with a substituent selected from F; and
heteroaryl is selected from the group consisting of triazolyl, pyridinyl, pyrazinyl and pyrimidinyl.

Another embodiment are compounds of Formula I, including pharmaceutically acceptable salts thereof,
wherein:
B is heteroaryl; wherein said heteroaryl is independently optionally substituted with a substituent selected from F; and
heteroaryl is selected from the group consisting of triazolyl.

Another embodiment are compounds of Formula I, including pharmaceutically acceptable salts thereof, wherein:

F is methyl.

Another embodiment is a pharmaceutical composition which comprises an antiviral effective amount of a compound of Formula I, including pharmaceutically acceptable salts thereof, as claimed in claim 1, and one or more pharmaceutically acceptable carriers, excipients or diluents; optionally which additionally comprises an antiviral effective amount of an AIDS treatment agent selected from the group consisting of:

(a) an AIDS antiviral agent;
(b) an anti-infective agent;
(c) an immunomodulator; and
(d) HIV entry inhibitors.

Another embodiment is a method for treating a mammal infected with the HIV virus comprising administering to said mammal an antiviral effective amount of a compound of Formula I, including pharmaceutically acceptable salts thereof, and one or more pharmaceutically acceptable carriers, excipients or diluents; optionally in combination with an antiviral effective amount of an AIDS treatment agent selected from the group consisting of an AIDS antiviral agent; an anti-infective agent; an immunomodulator; and an HIV entry inhibitor.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

DEFINITIONS

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art.

Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS$(=O)$_2NR^x$— group with Z and $R^x$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2NR^XR^Y$, with $R^X$ and $R^Y$ as defined herein.

A "N-Sulfonamido" group refers to a R"S(=O)$_2NR_X$— group with $R_x$ as defined herein.

A "O-carbamyl" group refers to a —OC(=O)$NR^xR^y$ as defined herein.

A "N-carbamyl" group refers to a $R^xOC$(=O)$NR^y$ group, with $R^x$ and $R^y$ as defined herein.

A "O-thiocarbamyl" group refers to a —OC(=S)$NR^xR^y$ group with $R^x$ and $R^y$ as defined herein.

A "N-thiocarbamyl" group refers to a $R^xOC$(=S)$NR^y$— group with $R^x$ and $R^y$ as defined herein.

An "amino" group refers to an —$NH_2$ group.

A "C-amido" group refers to a —C(=O)$NR^xR^y$ group with $R^x$ and $R^y$ as defined herein.

A "C-thioamido" group refers to a —C(=S)$NR^xR^y$ group, with $R^x$ and $R^y$ as defined herein.

A "N-amido" group refers to a $R^xC$(=O)$NR^y$— group, with $R^x$ and $R^y$ as defined herein.

An "ureido" group refers to a —$NR^xC$(=O)$NR^yR^{y2}$ group with $R^x$ and $R^y$ as defined herein and $R^{y2}$ defined the same as $R^x$ and $R^y$.

An "thioureido" group refers to a —$NR^xC$(=S)$NR^yR^{y2}$ group with $R^x$ and $R^y$ as defined herein and $R^{y2}$ defined the same as $R^x$ and $R^y$.

A "guanidino" group refers to a —$R^xNC$(=N)$NR^yR^{y2}$ group, with $R^x$, $R^y$ and $R^{y2}$ as defined herein.

A "guanyl" group refers to a $R^xR^yNC$(=N)— group, with $R^x$ and $R^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with $R^x$ as defined herein.

A "hydrazino" group refers to a —$NR^xR^yR^{y2}$ group with $R^x$, $R^y$ and $R^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compounds of this invention will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 2 lists some agents useful in treating AIDS and HIV infection which are suitable for this invention.

TABLE 2

| Drug Name | Manufacturer | Indication |
|---|---|---|
| Antivirals | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, |
| AL-721 | Ethigen (Los Angeles, CA) | PGL HTV positive, AIDS |
| Alpha Interferon HTV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |

TABLE 2-continued

| Drug Name | Manufacturer | Indication |
|---|---|---|
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |

TABLE 2-continued

| Drug Name | Manufacturer | Indication |
|---|---|---|
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| Immunomodulators | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE | Ciba-Geigy Corp. | Kaposi's sarcoma AIDS, |

TABLE 2-continued

| Drug Name | Manufacturer | Indication |
|---|---|---|
| Muramyl-Tripeptide Granulocyte Colony Stimulating Factor | Amgen | in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| Anti-infectives | | |
| Clindamycin with Primaguine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Seguus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194, and Meanwell, Nicholas A.; Kadow, John F. Inhibitors of the entry of HIV into host cells. Current Opinion in Drug Discovery & Development (2003), 6(4), 451-461.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase or the compound may be combined with one or two nucleoside inhibitor of HIV reverse transcriptase. An optional fourth component in the combination from the list of available drugs may be added. A preferred inhibitor of HIV protease is Reyataz® (atazanavir sulfate). Reyataz® is generally administered at a dosage of 400 mg once a day but may also be administered in combination with Ritonavir®. Another preferred protease inhibitor is Kaletra®. Preferred non-nucleoside inhibitors of HIV reverse transcriptase include efavirenz. The compounds in this invention could be administered in combination with Emtriva® (emtricitabine) and Viread® (Tenofovir dipivoxil) for example. These compounds are typically administered at doses of 200 mg or 300 mg once daily respectively. These combinations may have unexpected effects on limiting the spread and degree of infection of HIV.

In such combinations the compound of the present invention and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the invention and the examples. Some of the abbreviations used are as follows:

h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydrofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate Chemistry The present invention comprises compounds of Formula I, their pharmaceutical formulations, and their use in patients suffering from or susceptible to HIV infection. The compounds of Formula I include pharmaceutically acceptable salts thereof.

The synthesis procedures and anti-HIV-1 activities of substituted indole or azaindole oxoacetic N-heteroaryl piperazine containing analogs are described below. Scheme A depicts a typical method of completing the synthesis of the compounds of claim 1. Coupling of the appropriate oxo acetic acid with the desired N-aryl piperazine or its acid salt can be carried out using a variety of conditions as described for step D.

Scheme A

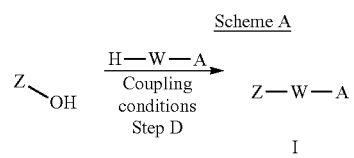

Step D. The acid intermediate Z—OH from Scheme A (which can also be depicted as intermediates QC(O)C(O)OH) or 4a-e, from step C of Schemes 1a-1e respectively are coupled with either a substituted piperazine, H—W-A as shown in Schemes A and 1a-1e or a protected piperazine, for example t-butyl 1-piperazinecarboxylate (Boc-piperazine, H—W-tBoc), as shown in Scheme (where W corresponds to the W in Formula I and H is hydrogen). They can be coupled with the acid using standard amide bond or peptide bond forming coupling reagents. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU (L. A. Carpino et. al. J. Chem. Soc. Chem. Comm. 1994, 201-203; A. Virgilio et. al. J. Am. Chem. Soc. 1994, 116, 11580-11581). A general procedure for using this reagent is Acid (1 eq) and H—W-Boc or H—W—$SO_2$-A or HCl salt (2 eq) in DMF are stirred at rt for between 1 h and 2 days. HATU (2 eq) was added in one portion and then DMAP (3 eq). The reaction was stirred at rt for 2 to 15 h (reaction progress monitored by standard methods ie TLC, LC/MS). The mixture is filtered through filter paper to collect the solid. The filtrate is concentrated and water is added. The mixture is filtered again and the solid is washed with water. The solid is combined and washed with water. Many reagents for amide bond couplings are known by an organic chemist skilled in the art and nearly all of these are applicable for realizing coupled amide products.

As mentioned above, DEPBT (3-(diethoxyphosphoryloxy)-1,2,3-benzotriazin-4(3H)-one) and N,N-diisopropylethylamine, commonly known as Hunig's base, represents another efficient method to form the amide bond (step D) and provide compounds of Claim I. DEPBT is either purchased from Adrich or prepared according to the procedure of Ref. 28, Li, H.; Jiang, X.; Ye, Y.-H.; Fan, C.; Romoff, T.; Goodman, M. *Organic Lett.*, 1999, 1, 91-93. Typically an inert solvent such as DMF or THF is used but other aprotic solvents could be used.

The amide bond construction reaction could be carried out using the preferred conditions described above, the EDC conditions described below, other coupling conditions described in this application, or alternatively by applying the conditions or coupling reagents for amide bond construction described later in this application for construction of substituents $R_2$-$R_5$. Some specific nonlimiting examples are given in this application.

Alternatively, the acid could be converted to a methyl ester using excess diazomethane in THF/ether. The methyl ester in dry THF could be reacted with the lithium amide of intermediate H—W. The lithium amide of H—W, Li—W is formed by reacting intermediate 1 with lithium bistrimethylsilylamide in THF for 30 minutes in an ice water cooling bath. Sodium or potassium amides could be formed similarly and utilized if additional reactivity is desired. Other esters such as ethyl, phenyl, or pentafluorophenyl could be utilized and would be formed using standard methodology.

The amide bond construction reaction could be carried out using the preferred conditions described above, the EDC conditions described below, other coupling conditions described in this application, or alternatively by applying the conditions or coupling reagents for amide bond construction described later in this application for construction of substituents $R_2$-$R_5$. Some specific nonlimiting examples are given in this application. In addition, the acid can be converted to the acid chloride using oxalyl chloride in a solvent such as benzene or thionyl chloride either neat or containing a catalystic amount of DMF. Temperatures between 0° C. and reflux may be utilized depending on the substrate. Compounds of Formula I can be obtained from the resultant compounds of formula Z—Cl by reaction with the appropriate H—W-A in the presence of a tertiary amine (3-10 eq.) such as triethylamine or diisopropylethylamine in an anhydrous aprotic solvent such as dichloromethane, dichloroethane, diethyl ether, dioxane, THF, acetonitrile, DMF or the like at temperatures ranging from 0° C. to reflux. Most preferred are dichloromethane, dichloroethane, or THF. The reaction can be monitored by LC/MS.

It should be noted that in many cases reactions are depicted for only one position of an intermediate, such as the $R^5$ position, for example. It is to be understood that such reactions could be used at other positions, such as $R^2$-$R^4$, of the various intermediates. Reaction conditions and methods given in the specific examples are broadly applicable to compounds with other substitution and other tranformations in this application. Schemes A and 1a-1e describe general reaction schemes for taking appropriately substituted Q (indoles and azaindoles) and converting them to compounds of Formula I. While these schemes are very general, other permutations such as carrying a precursor or precursors to substituents $R^2$ through $R^5$ through the reaction scheme and then converting it to a compound of Formula I in the last step are also contemplated methods of this invention. Nonlimiting examples of such strategies follow in subsequent schemes. Procedures for coupling piperazine amides to oxoacetyl derivatives are described in the Blair, Wang, Wallace, or Wang references 93-95 and 106 respectively. The entire disclosures in U.S. Pat. No. 6,469,006 granted Oct. 22, 2002; U.S. Pat. No. 6,476,034 granted Nov. 5, 2002; U.S. patent application Ser. No. 10/027,612 filed Dec. 19, 2001, which is a continuation-in-part of U.S. Ser. No. 09/888,686 filed Jun. 25, 2001 (corresponding to PCT WO 02/04440, published Jan. 17, 2002); and U.S. patent application Ser. No. 10/214,982 filed Aug. 7, 2002, which is a continuation-in-part of U.S. Ser. No. 10/038,306 filed Jan. 2, 2002 (corresponding to PCT WO 02/62423 published Aug. 15, 2002) are incorporated by reference herein. The procedures used to couple indole or azaindole oxoacetic acids to piperazine amides in these references can be used analogously to form the compounds of this invention except the N-heteroaryl piperazines are used in place of the piperazine benzamides. It should be stated that the procedures incorporated from these applications encompass the preparation of starting materials and transformations which are useful for enabling the preparation of compounds of this invention.

Procedures for making Z (as defined in Formula I of the description of the invention) are described in the Blair, Wang, Wallace, or Wang references 93-95 and 106 respectively. The entire disclosures in U.S. Pat. No. 6,469,006 granted Oct. 22, 2002; U.S. Pat. No. 6,476,034 granted Nov. 5, 2002; U.S. patent application Ser. No. 10/027,612 filed Dec. 19, 2001, which is a continuation-in-part of U.S. Ser. No. 09/888,686 filed Jun. 25, 2001 (corresponding to PCT WO 02/04440, published Jan. 17, 2002); and U.S. patent application Ser. No. 10/214,982 filed Aug. 7, 2002, which is a continuation-in-part of U.S. Ser. No. 10/038,306 filed Jan. 2, 2002 (corresponding to PCT WO 02/62423 published Aug. 15, 2002) are incorporated by reference herein.

Additional general procedures to construct substituted azaindole Q and Z of Formula I and intermediates useful for their synthesis are described in the following Schemes.

Scheme 1a

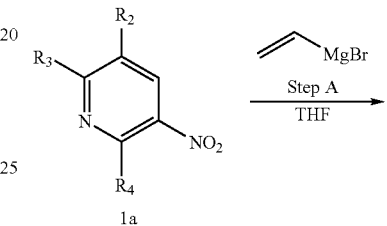

1a

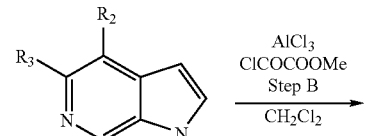

2a

3a

4a

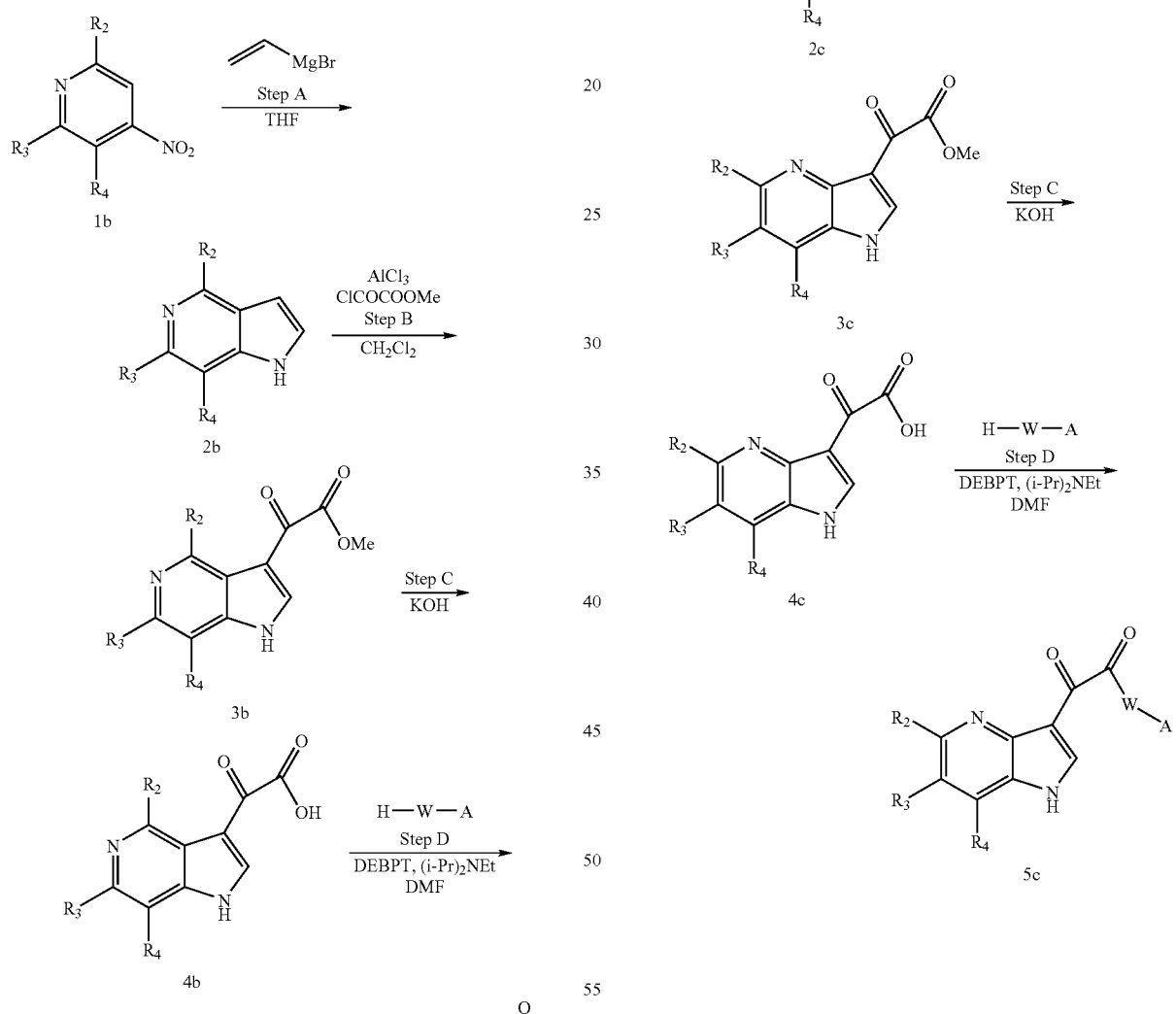

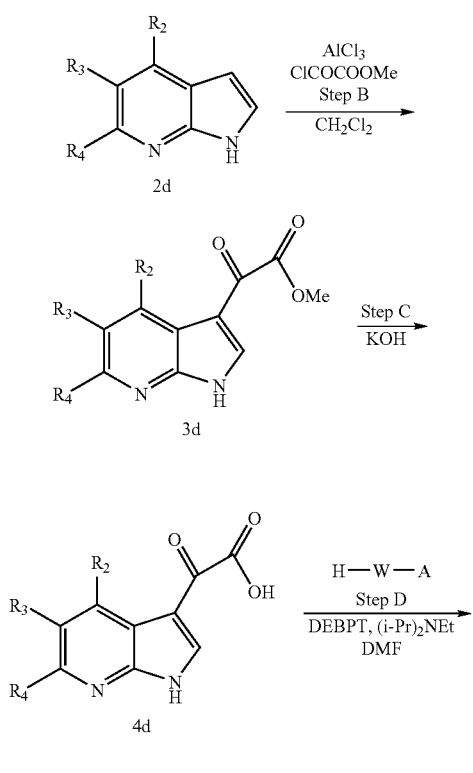

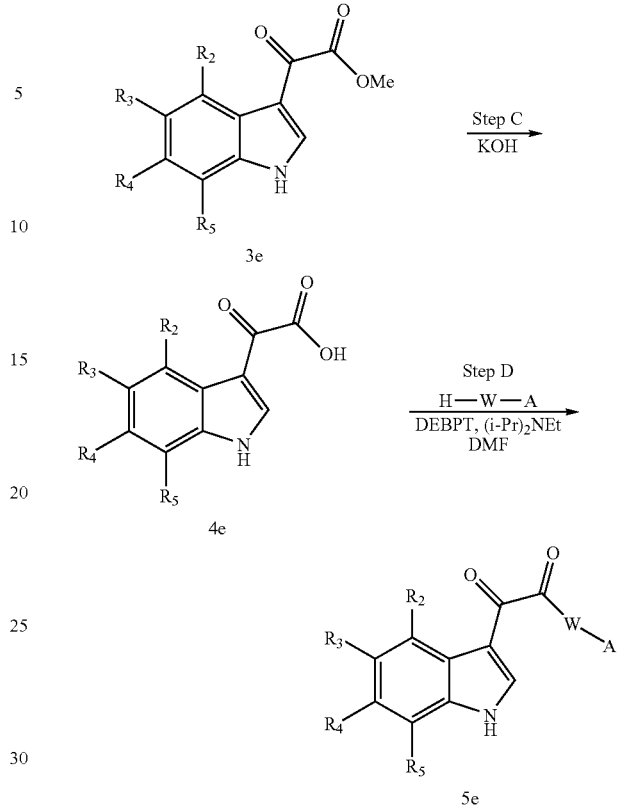

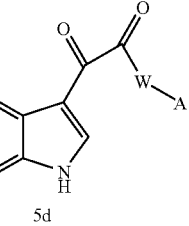

Scheme 1e

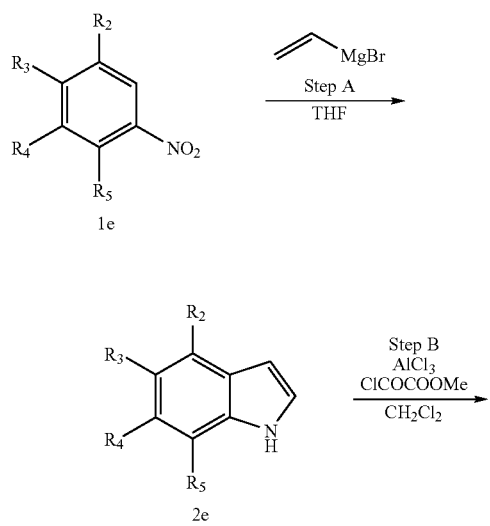

Step A. In Schemes 1a-1e depict the synthesis of a aza indole or indole intermediates, 2a-2e via the well known Bartoli reaction in which vinyl magnesium bromide reacts with an aryl or heteroaryl nitro group, such as in 1a-1e, to form a five-membered nitrogen containing ring as shown. Some references for details on how to carry out the transformation include: Bartoli et al. a) *Tetrahedron Lett.* 1989, 30, 2129. b) *J. Chem. Soc. Perkin Trans.* 1 1991, 2757. c) *J. Chem. Soc. Perkin Trans. II* 1991, 657. d) Synthesis (1999), 1594. e) Zhang, Zhongxing; Yang, Zhong; Meanwell, Nicholas A.; Kadow, John F.; Wang, Tao. "A General Method for the Preparation of 4- and 6-Azaindoles". *Journal of Organic Chemistry* 2002, 67 (7), 2345-2347 WO 02/62423 Aug. 15, 2002 "Preparation and antiviral activity for HIV-1 of substituted azaindoleoxoacetylpiperazines" Wang, Tao; Zhang, Zhongxing; Meanwell, Nicholas A.; Kadow, John F.; Yin, Zhiwei.

In the preferred procedure, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide. In some cases modified procedures might occasionally provide enhanced yield. An inverse addition procedure can some-times be employed. (The nitro pyridine solution is added to the vinyl Grignard solution). Occasionally solvents such as dimethoxy ethane or dioxane may prove useful. A procedure in which the nitro compound in THF is added to a 1M solution of vinyl magnesium bromide in THF at −40° C. may prove beneficial. Following completion of the reaction by TLC the reaction is quenched with sat ammonium chloride aqueous solution and purified by standard methods. A reference for this alternative procedure is contained in M. C. Pirrung, M. Wedel, and Y. Zhao et. al. Syn Lett 2002, 143-145.

Substituted azaindoles may be prepared by methods described in the literature or may be available from commercial sources. Thus there are many methods for synthesizing intermediates 2a-2d and the specific examples are too numerous to even list. Methodology for the preparation of many compounds of interest is described in references of Blair, Wang, Wallace, and Wang references 93-95 and 106 respectively. A review on the synthesis of 7-azaindoles has been published (Merour et. al. reference 102). Alternative syntheses of aza indoles and general methods for synthesizing intermediates 2 include, but are not limited to, those described in the following references (a-k below): a) Prokopov, A. A.; Yakhontov, L. N. *Khim.-Farm. Zh.* 1994, 28(7), 30-51; b) Lablache-Combier, A. Heteroaromatics. Photoinduced Electron Transfer 1988, Pt. C, 134-312; c) Saify, Zafar Said. *Pak. J. Pharmacol.* 1986, 2(2), 43-6; d) Bisagni, E. *Jerusalem Symp. Quantum Chem. Biochem.* 1972, 4, 439-45; e) Yakhontov, L. N. *Usp. Khim.* 1968, 37(7), 1258-87; f) Willette, R. E. *Advan. Heterocycl. Chem.* 1968, 9, 27-105; g) Mahadevan, I.; Rasmussen, M. *Tetrahedron* 1993, 49(33), 7337-52; h) Mahadevan, I.; Rasmussen, M. *J. Heterocycl. Chem.* 1992, 29(2), 359-67; i) Spivey, A. C.; Fekner, T.; Spey, S. E.; Adams, H. *J. Org. Chem.* 1999, 64(26), 9430-9443; j) Spivey, A. C.; Fekner, T.; Adams, H. *Tetrahedron Lett.* 1998, 39(48), 8919-8922; k) Advances in Heterocyclic Chemistry (Academic press) 1991, Vol. 52, pg 235-236 and references therein. Other references later in this application. Starting indole intermediates of formula 2e (Scheme 10) are known or are readily prepared according to literature procedures, such as those described in Gribble, G. (Refs. 24 and 99), Bartoli et al (Ref. 36), reference 37, or the book by Richard A. Sundberg in reference 40. Other methods for the preparation of indole intermediates include: the Leimgruber-Batcho Indole synthesis (reference 93); the Fisher Indole synthesis (references 94 and 95); the 2,3-rearrangement protocol developed by Gassman (reference 96); the annelation of pyrroles (reference 97); tin mediated cyclizations (reference 98); and the Larock palladium mediated cyclization of 2-alkynyl anilines. Many other methods of indole synthesis are known and a chemist with typical skill in the art can readily locate conditions for preparation of indoles which can be utilized to prepare compounds of Formula I.

Scheme 1f

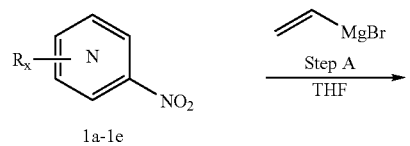

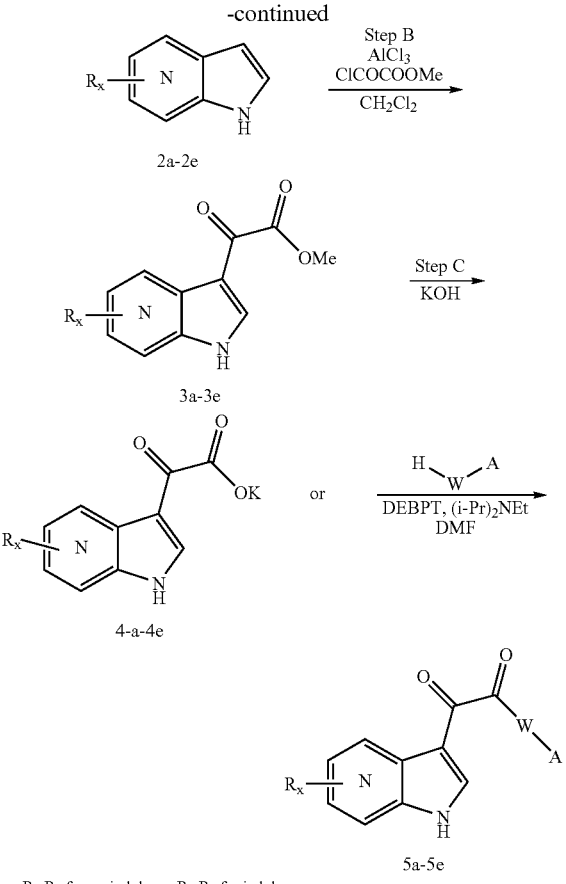

$R_x = R_2-R_4$ for azaindoles or $R_2-R_5$ for indoles

= Q (most generic definition unless specified except for caveats)

$R_6$ is nothing
$R_2$ is not depicted (in the interest of convenience) but is considered hydrogen. Other R2 groups would work similarly in these transformations within reactivity limits of a chemist skilled in the art.
$R_7$ is Hydrogen Scheme 1f depicts a shorthand method for representing the intermediates used for reactions in Schemes 1a-1c, and Schemes 2-7 and generic Q. It is understood, for the purposes of Scheme 1f and further Schemes, that 1b is used to synthesize 2b-5b, 1c provides 2c-5c and 1d provides 2d-5d etc. The substituents $R_x$ represent for azaindoles $R_2-R_4$ and for indoles $R_2-R_5$. In formulas in following schemes, one of the substituents may be depicted but it is understood that each formula can represent the appropriate generic azaindoles or indole in order to keep the application succinct.

Step B. Intermediates 3a-e can be prepared by reaction of indoles or azaindoles (intermediates 2), with an excess of ClCOCOOMe in the presence of AlCl$_3$ (aluminum chloride) (Sycheva et al, Ref. 26, Sycheva, T. V.; Rubtsov, N. M.; Sheinker, Yu. N.; Yakhontov, L. N. Some further descriptions of the exact procedures to carry out this reaction are contained in a) Zhang, Zhongxing; Yang, Zhong; Wong, Henry; Zhu, Juliang; Meanwell, Nicholas A.; Kadow, John F.; Wang, Tao. "An Effective Procedure for the Acylation of Azaindoles at C-3." *J. Org. Chem.* 2002, 67(17), 6226-6227; b) Tao Wang et. al. U.S. Pat. No. 6,476,034 B2 "Antiviral Azaindole derivatives" published Nov. 5, 2002; c) W. Blair et al. PCT patent application WO 00/76521 A1 published Dec. 21, 2000; d) O. Wallace et. al. PCT application WO 02/04440A1 published Jan. 17, 2002. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106). Typically an inert solvent such as $CH_2Cl_2$ is used but others such as THF, $Et_2O$, DCE, dioxane, benzene, or toluene may find applicability either alone or in mixtures. Other oxalate esters such as ethyl or benzyl mono esters of oxalic acid could also suffice for either method shown above. More lipophilic esters ease isolation during aqueous extractions. Phenolic or substituted phenolic (such as pentafluorophenol) esters enable direct coupling of the HW-protecting group, such as a Boc-piperazine, in Step D without activation. Lewis acid catalysts, such as tin tetrachloride, titanium IV chloride, and aluminum chloride are employed in Step B with aluminum chloride being most preferred. Alternatively, the azaindole is treated with a Grignard reagent such as MeMgI (methyl magnesium iodide), methyl magnesium bromide or ethyl magnesium bromide and a zinc halide, such as $ZnCl_2$ (zinc chloride) or zinc bromide, followed by the addition of an oxalyl chloride mono ester, such as ClCOCOOMe (methyl chlorooxoacetate) or another ester as above, to afford the aza-indole glyoxyl ester (Shadrina et al, Ref. 25). Oxalic acid esters such as methyl oxalate, ethyl oxalate or as above are used. Aprotic solvents such as $CH_2Cl_2$, $Et_2O$, benzene, toluene, DCE, or the like may be used alone or in combination for this sequence. In addition to the oxalyl chloride mono esters, oxalyl chloride itself may be reacted with the azaindole and then further reacted with an appropriate amine, such as a piperazine derivative.

Step C. Hydrolysis of the methyl ester, (intermediates 3a-3e, Schemes 1a-1e) affords a potassium salt of intermediates 4, which is coupled with N-substituted piperazine derivatives, H—W-A as shown in Step D of the Schemes 1a-1e. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as $CH_2Cl_2$ or THF in the presence of Triton B. Temperatures of $-78°$ C. to the boiling point of the solvent may be employed but $-10°$ C. is preferred. Other conditions for ester hydrolysis are listed in reference 41 and both this reference and many of the conditions for ester hydrolysis are well known to chemists of average skill in the art.

Alternative Procedures for Step B and C:
Imidazolium Chloroaluminate:

We found that ionic liquid 1-alkyl-3-alkylimidazolium chloroaluminate is generally useful in promoting the Friedel-Crafts type acylation of indoles and azaindoles. The ionic liquid is generated by mixing 1-alkyl-3-alkylimidazolium chloride with aluminium chloride at room temperature with vigorous stirring. 1:2 or 1:3 molar ratio of 1-alkyl-3-alkylimidazolium chloride to aluminium chloride is preferred. One particular useful imidazolium chloroaluminate for the acylation of azaindole with methyl or ethyl chlorooxoacetate is the 1-ethyl-3-methylimidazolium chloroaluminate. The reaction is typically performed at ambient temperature and the azaindoleglyoxyl ester can be isolated. More conveniently, we found that the glyoxyl ester can be hydrolyzed in situ at ambient temperature on prolonged reaction time (typically overnight) to give the corresponding glyoxyl acid (intermediates 4a-4-e) for amide formation (Scheme 2).

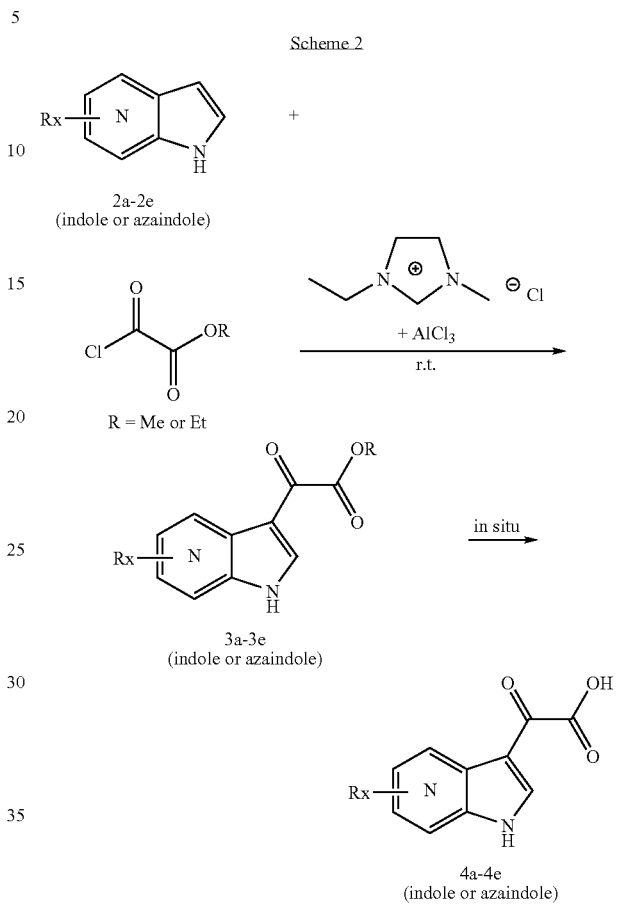

A representative experimental procedure is as follows: 1-ethyl-3-methylimidazolium chloride (2 equiv.; purchased from TCI; weighted under a stream of nitrogen) was stirred in an oven-dried round bottom flask at r.t. under a nitrogen atmosphere, and added aluminium chloride (6 equiv.; anhydrous powder packaged under argon in ampules purchased from Aldrich preferred; weighted under a stream of nitrogen). The mixture was vigorously stirred to form a liquid, which was then added azaindole (1 equiv.) and stirred until a homogenous mixture resulted. The reaction mixture was added dropwise ethyl or methyl chlorooxoacetate (2 equiv.) and then stirred at r.t. for 16 h. After which time, the mixture was cooled in an ice-water bath and the reaction quenched by carefully adding excess water. The precipitates were filtered, washed with water and dried under high vacuum to give the azaindoleglyoxylic acid. For some examples, 3 equivalents of 1-ethyl-3-methylimidazolium chloride and chlorooxoacetate may be required. A more comprehensive reference with additional examples is contained in: Yeung, Kap-Sun; Farkas, Michelle E.; Qiu, Zhilei; Yang, Zhong. Friedel-Crafts acylation of indoles in acidic imidazolium chloroaluminate ionic liquid at room temperature. Tetrahedron Letters (2002), 43(33), 5793-5795.

Related references: (1) Welton, T. *Chem. Rev.* 1999, 99, 2071; (2) Surette, J. K. D.; Green, L.; Singer, R. D. *Chem. Commun.* 1996, 2753; (3) Saleh, R. Y. WO 00/15594.

Step D. Was described above.

It should be noted that in many cases reactions are depicted for only one position of an intermediate, such as the $R^5$ position, for example. It is to be understood that such reactions could be used at other positions, such as $R^2$-$R^4$, of the various intermediates. Reaction conditions and methods given in the specific examples are broadly applicable to compounds with other substitution and other tranformations in this application. Schemes 1 and 2 describe general reaction schemes for taking appropriately substituted Q (indoles and azaindoles) and converting them to compounds of Formula I. While these schemes are very general, other permutations such as carrying a precursor or precursors to substituents $R^2$ through $R^5$ through the reaction scheme and then converting it to a compound of Formula I in the last step are also contemplated methods of this invention. Nonlimiting examples of such strategies follow in subsequent schemes.

The amide bond construction reactions depicted in step D of schemes 1a-1e could be carried out using the specialized conditions described herein or alternatively by applying the conditions or coupling reagents for amide bond construction described in Wallace, reference 95. Some specific nonlimiting examples are given in this application.

Additional procedures for synthesizing, modifying and attaching groups are contained in references 93-95 and 106 or are described below.

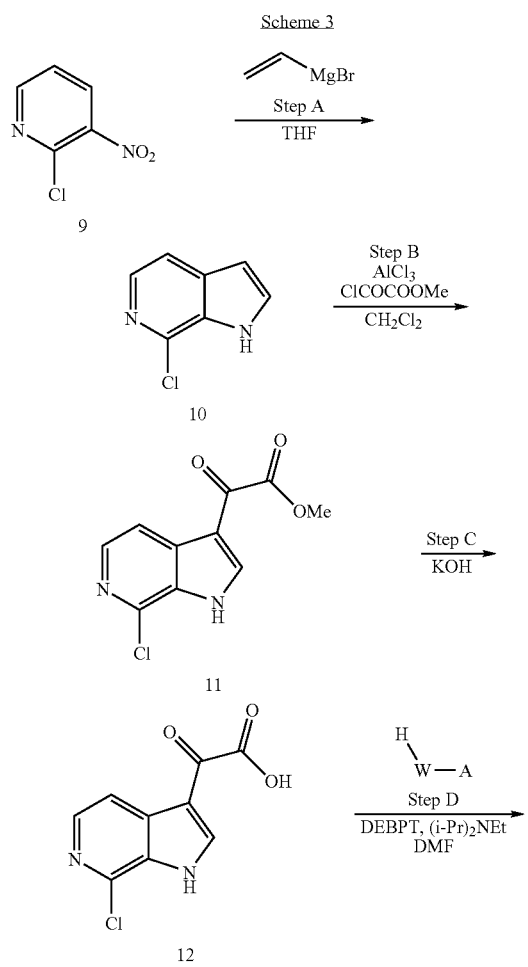

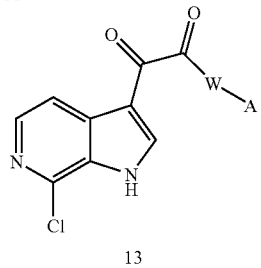

Scheme 3 provides more specific examples of the transformation previously described in Schemes A and Schemes 1a-f. Intermediates 9-13 are prepared by the methodologies as described for intermediates 1c-5c in Scheme 1c. Scheme 4 is another embodiment of the transformations described in Schemes 1a-1e and 3. Conversion of the phenol to the chloride (Step S, Scheme 4) may be accomplished according to the procedures described in Reimann, E.; Wichmann, P.; Hoefner, G.; Sci. Pharm. 1996, 64(3), 637-646; and Katritzky, A. R.; Rachwal, S.; Smith, T. P.; Steel, P. J.; J. Heterocycl. Chem. 1995, 32(3), 979-984. Step T of Scheme 4 can be carried out as described for Step A of Scheme 1. The bromo intermediate can then be converted into alkoxy, chloro, or fluoro intermediates as shown in Step U of Scheme 4. When step U is the conversion of the bromide into alkoxy derivatives, the conversion may be carried out by reacting the bromide with an excess of, for example, sodium methoxide or potassium methoxide in methanol with cuprous salts, such as copper I bromide, copper I iodide, and copper I cyanide. The reaction may be carried out at temperatures of between ambient and 175° C. but most likely will be around 115° C. or 100° C. The reaction may be run in a pressure vessel or sealed tube to prevent escape of volatiles such as methanol. Alternatively, the reaction can be run in a solvent such as toluene or xylene and the methanol allowed to partially escape the reaction vessel by heating and then achieving reflux by adding a condenser. The preferred conditions on a typically laboratory scale utilize 3 eq of sodium methoxide in methanol, CuBr as the reaction catalyst (0.2 to 3 equivalents with the preferred being 1 eq or less), and a reaction temperature of 115° C. The reaction is carried out in a sealed tube or sealed reaction vessel. The copper catalyzed displacement reaction of aryl halides by methoxide is described in detail in H. L. Aalten et al. 1989, Tetrahedron 45(17) pp 5565 to 5578 and these conditions described herein were also utilized in this application with azaindoles. The conversion of the bromide into alkoxy derivatives may also be carried out according to procedures described in. Palucki, M.; Wolfe, J. P.; Buchwald, S. L.; J. Am. Chem. Soc. 1997, 119(14), 3395-3396; Yamato, T.; Komine, M.; Nagano, Y.; Org. Prep. Proc. Int. 1997, 29(3), 300-303; Rychnovsky, S. D.; Hwang, K.; J. Org. Chem. 1994, 59(18), 5414-5418. Conversion of the bromide to the fluoro derivative (Step U, Scheme 4) may be accomplished according to Antipin, I. S.; Vigalok, A. I.; Konovalov, A. I.; Zh. Org. Khim. 1991, 27(7), 1577-1577; and Uchibori, Y.; Umeno, M.; Seto, H.; Qian, Z.; Yoshioka, H.; Synlett. 1992, 4, 345-346. Conversion of the bromide to the chloro derivative (Step U, Scheme 5) may be accomplished according to procedures described in Gilbert, E. J.; Van Vranken, D. L.; J. Am. Chem. Soc. 1996, 118(23), 5500-5501; Mongin, F.; Mongin, O.; Trecourt, F.; Godard, A.; Queguiner, G.; Tetrahedron Lett. 1996, 37(37), 6695-6698; and O'Connor, K. J.; Burrows, C. J.; J. Org. Chem. 1991, 56(3), 1344-1346. Steps V, W, and X of Scheme 4 are carried out according to the procedures previously described for Steps B, C, and D of Scheme 1a-1e, respectively. The steps of Scheme 4 may be carried out in a different order as shown in Schemes 5 and 6A.
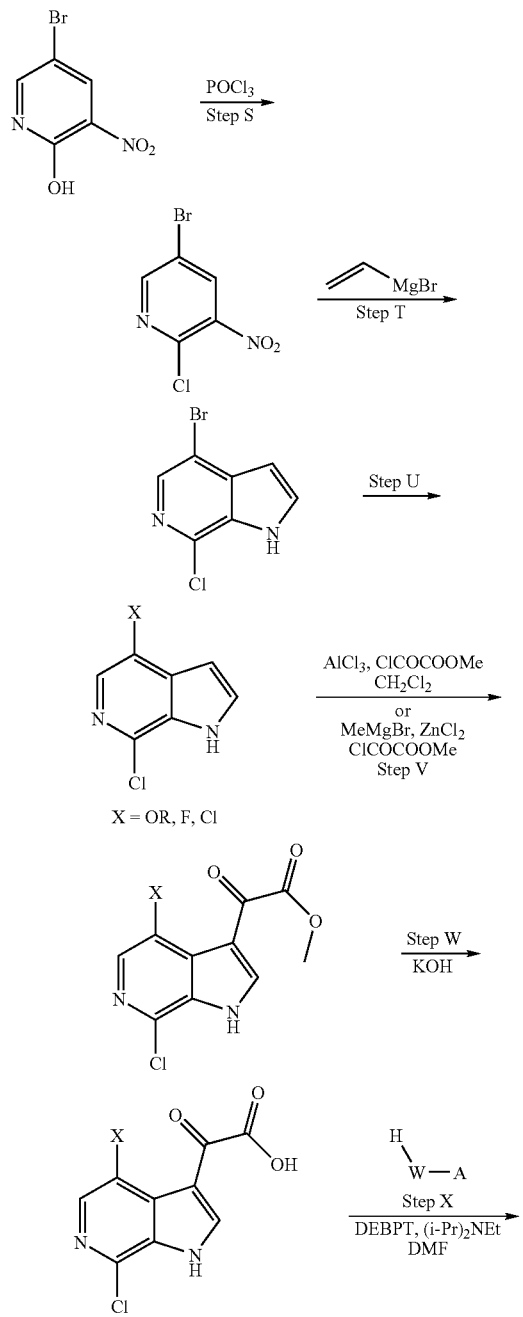
Scheme 4
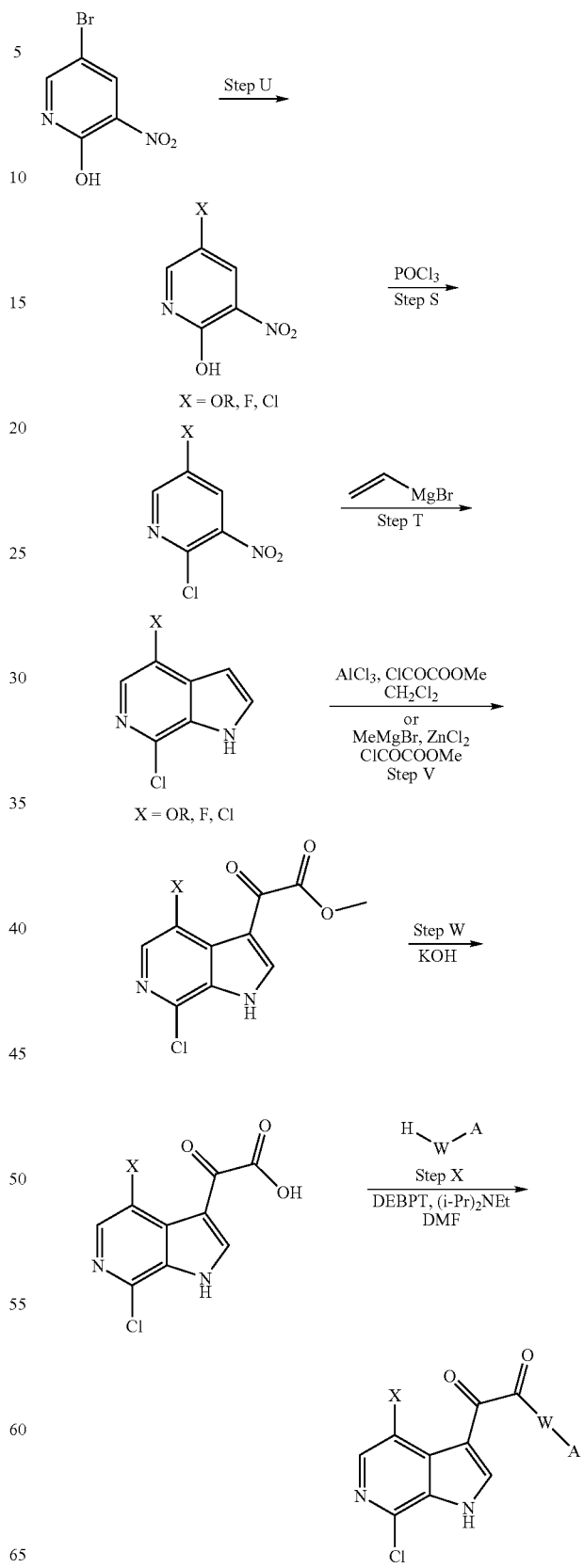
Scheme 5

Scheme 6A

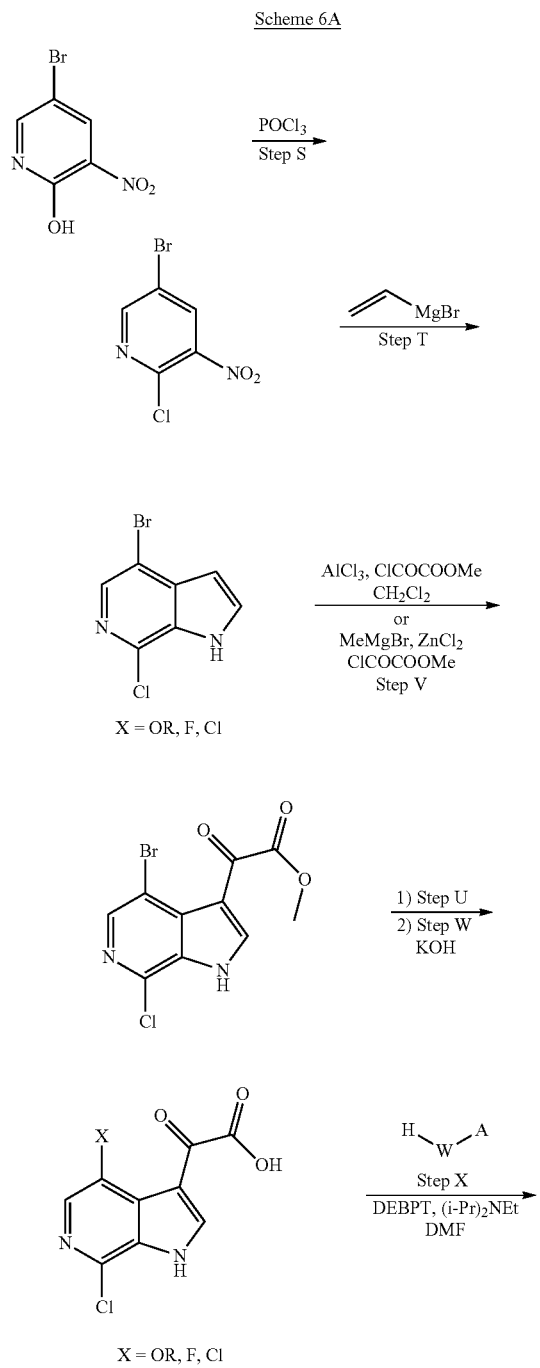

Scheme 6B

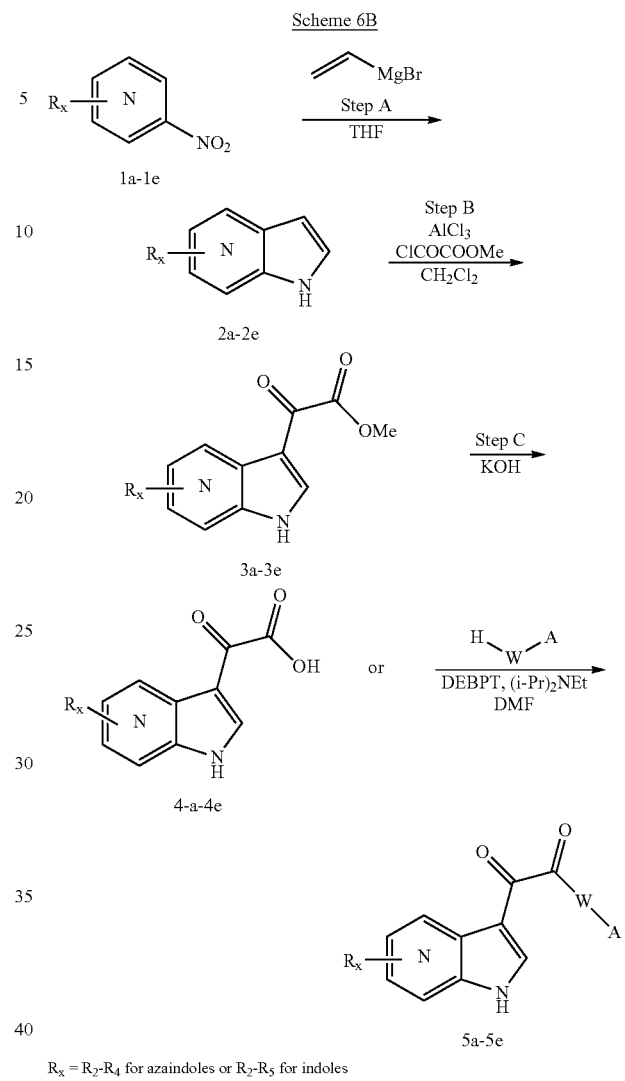

$R_x = R_2-R_4$ for azaindoles or $R_2-R_5$ for indoles

Scheme 6B depicts a shorthand method for depicting the reactions in Scheme 1a-1e. It is understood, for the purposes of Scheme 6B and further Schemes, that 1b is used to synthesize 2b-5b, 1c provides 2c-5c and 1d provides 2d-5d etc. The substituents $R_x$ represent for azaindoles $R_2-R_4$ and for indoles $R_2-R_5$. In formulas in following schemes, one of the substituents may be depicted but it is understood that each formula can represent the appropriate generic azaindoles or indole in order to keep the application succinct.

An alternative method for carrying out the sequence outlined in steps B-D (shown in Scheme 6C) involves treating an azaindole, such as 16, obtained by procedures described in the literature or from commercial sources, with MeMgI and $ZnCl_2$, followed by the addition of ClCOCOCl (oxalyl chloride) in either THF or $Et_2O$ to afford a mixture of a glyoxyl chloride azaindole, 17a, and an acyl chloride azaindole, 17b. The resulting mixture of glyoxyl chloride azaindole and acyl chloride azaindole is then coupled with mono-benzoylated piperazine derivatives under basic conditions to afford the products of step D as a mixture of compounds, 18a and 18b, where either one or two carbonyl groups link the azaindole and group W. Separation via chromatographic methods which are well known in the art provides the pure 18a and 18b. This sequence is summarized in Scheme 6C, below.

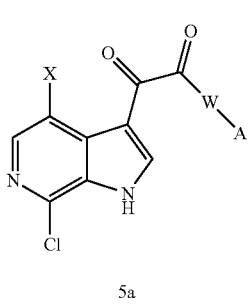

5a

Scheme 6C

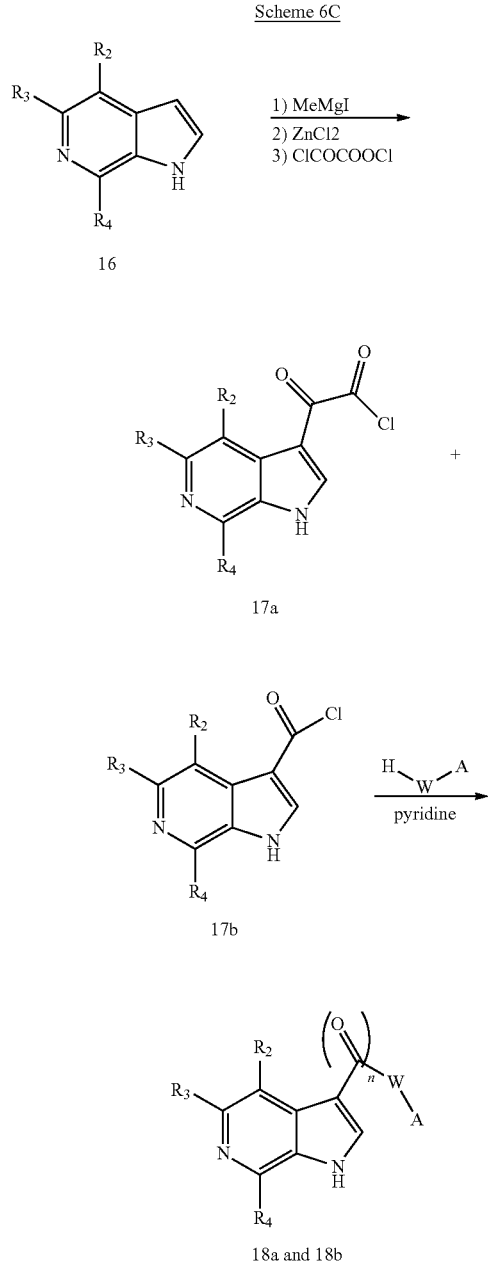

n = 1 or 2

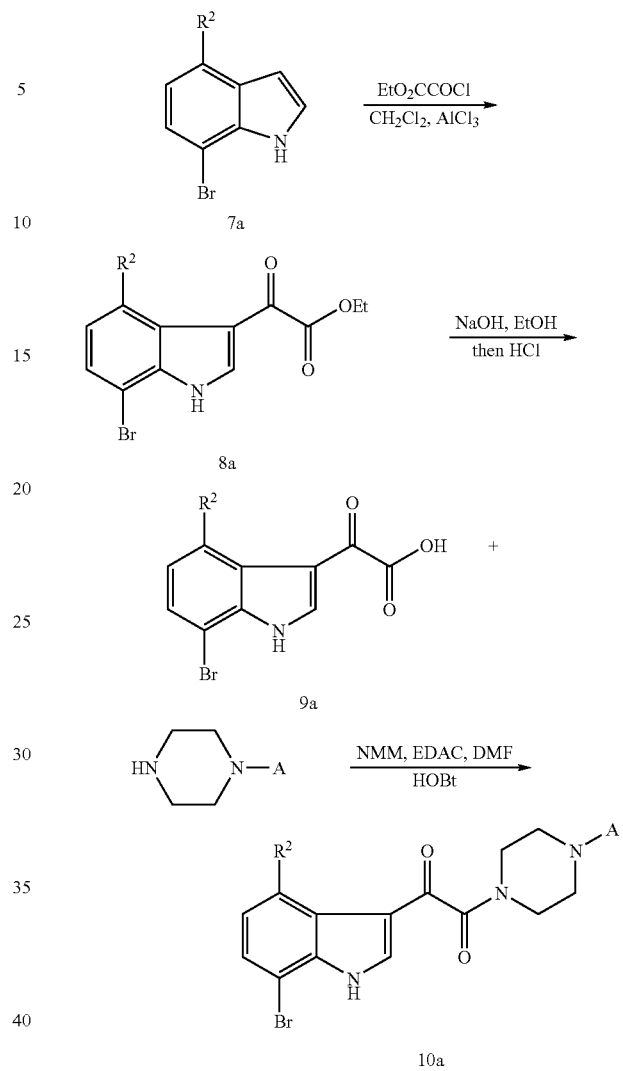

Scheme 6D shows the preparation of an indole intermediate 7a, acylation of 7a with ethyl oxalyl chloride to provide intermediate 8a, followed by ester hydrolysis to provide intermediate 9a, and amide formation to provide intermediate 10a.

Alternatively, the acylation of an indole intermediate, such as 7a', could be carried out directly with oxalyl chloride followed by base mediated piperazine coupling to provide an intermediate of Formula 10a' as shown in Scheme 6E.

Scheme 6D

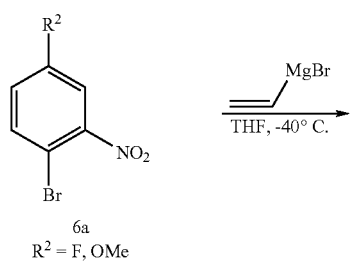

6a
$R^2$ = F, OMe

Scheme 6E

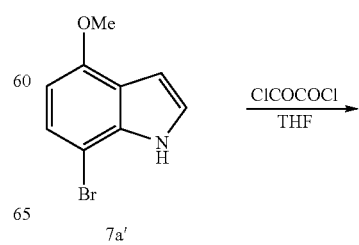

7a'

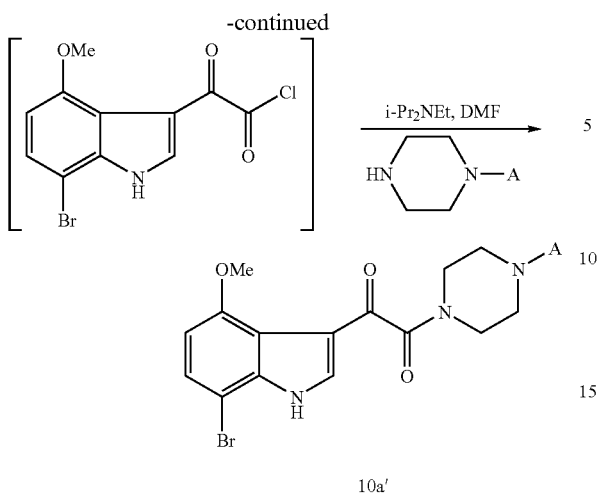

10a'

Other methods for introduction of an aldehyde group to form intermediates of formula 11 include transition metal catalyzed carbonylation reactions of suitable bromo, trifluoromethane sulfonates(yl), or stannanes(yl) indoles. Alternative the aldehydes can be introduced by reacting indolyl anions or indolyl Grignard reagents with formaldehyde and then oxidizing with $MnO_2$ or TPAP/NMO or other suitable oxidants to provide intermediate 11.

Some specific examples of general methods for preparing functionalized azaindoles or indoles or for interconverting functionality on aza indoles or indoles which will be useful for preparing the compounds of this invention are shown in the following sections for illustrative purposes. It should be understood that this invention covers substituted 4, 5, 6, and 7 azaindoles and also indoles that the methodology shown below may be applicable to all of the above series while other shown below will be specific to one or more. A typical practitioner of the art can make this distinction when not specifically delineated. Many methods are intended to be applicable to all the series, particularly functional group installations or interconversions. For example, a general strategy for providing further functionality of this invention is to position or install a halide such as bromo, chloro, or iodo, aldehyde, cyano, or a carboxy group on the azaindole and then to convert that functionality to the desired compounds. In particular, conversion to substituted heteroaryl, aryl, and amide groups on the ring are of particular interest.

General routes for functionalizing azaindole rings are shown in Schemes 7, 8 and 9. As depicted in Scheme 7, the azaindole, 17, can be oxidized to the corresponding N-oxide derivative, 18, by using mCPBA (meta-Chloroperbenzoic Acid) in acetone or DMF (eq. 1, Harada et al, Ref. 29 and Antonini et al, Ref. 34). The N-oxide, 18, can be converted to a variety of substituted azaindole derivatives by using well documented reagents such as phosphorus oxychloride ($POCl_3$) (eq. 2, Schneller et al, Ref. 30), tetramethylammonium fluoride ($Me_4NF$) (eq. 3), Grignard reagents RMgX (R=alkyl or aryl, X=Cl, Br or I) (eq. 4, Shiotani et al, Ref. 31), trimethylsilyl cyanide (TMSCN) (eq. 5, Minakata et al, Ref. 32) or $Ac_2O$ (eq. 6, Klemm et al, Ref. 33). Under such conditions, a chlorine (in 19), fluorine (in 20), nitrile (in 22), alkyl (in 21), aromatic (in 21) or hydroxyl group (in 24) can be introduced to the pyridine ring. Nitration of azaindole N-oxides results in introduction of a nitro group to azaindole ring, as shown in Scheme 8 (eq. 7, Antonini et al, Ref. 34). The nitro group can subsequently be displaced by a variety of nucleophilic agents, such as OR, $NR^1R^2$ or SR, in a well established chemical fashion (eq. 8, Regnouf De Vains et al, Ref. 35(a), Miura et al, Ref. 35(b), Profft et al, Ref. 35(c)). The resulting N-oxides, 26, are readily reduced to the corresponding azaindole, 27, using phosphorus trichloride ($PCl_3$) (eq. 9, Antonini et al, Ref. 34 and Nesi et al, Ref. 36). Similarly, nitro-substituted N-oxide, 25, can be reduced to the azaindole, 28, using phosphorus trichloride (eq. 10). The nitro group of compound 28 can be reduced to either a hydroxylamine (NHOH), as in 29, (eq. 11, Walser et al, Ref. 37(a) and Barker et al, Ref. 37(b)) or an amino ($NH_2$) group, as in 30, (eq. 12, Nesi et al, Ref. 36 and Ayyangar et al, Ref. 38) by carefully selecting different reducing conditions.

Scheme 7

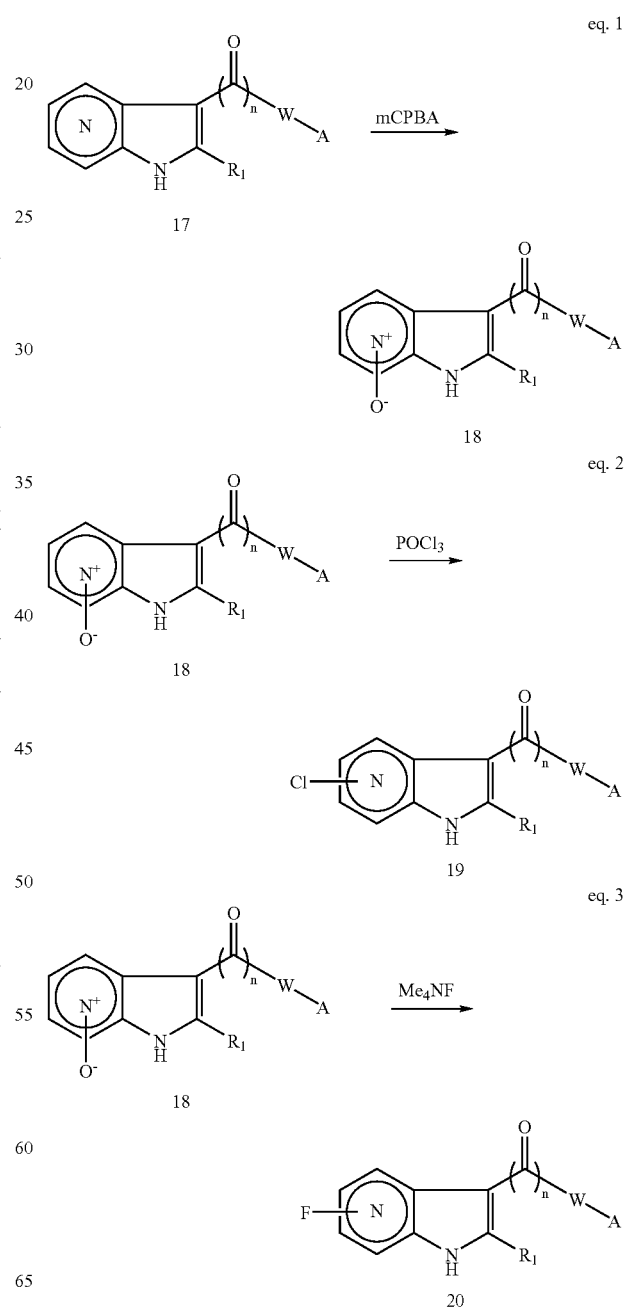

-continued
eq. 4
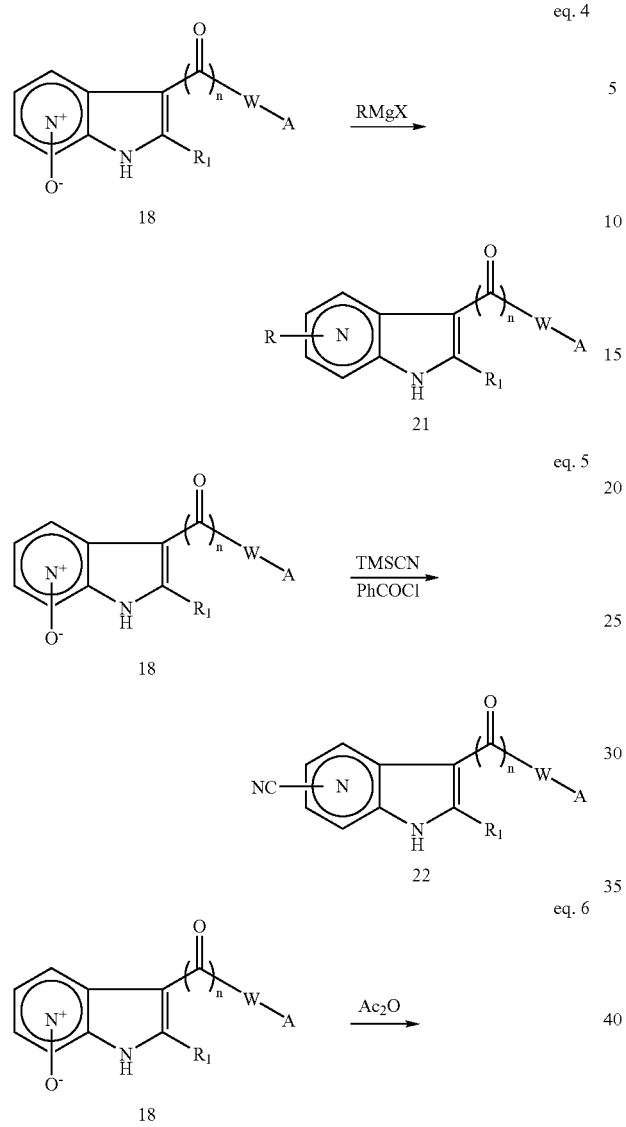
Scheme 8
eq. 7
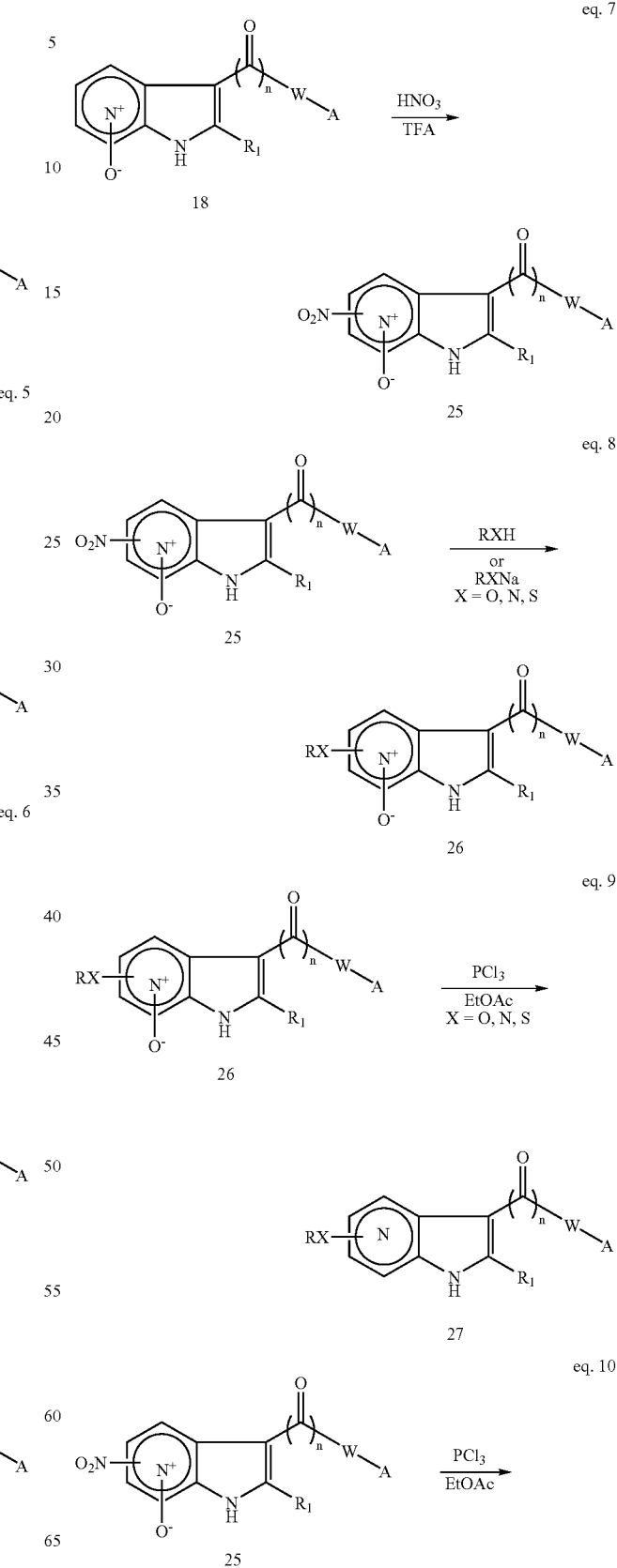

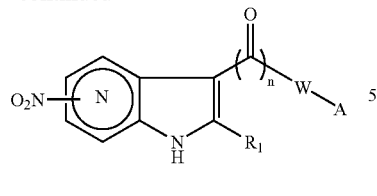

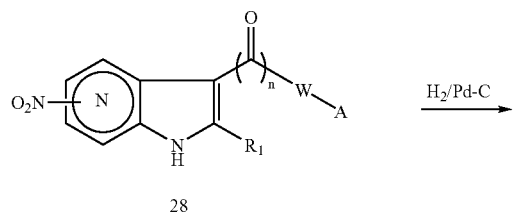

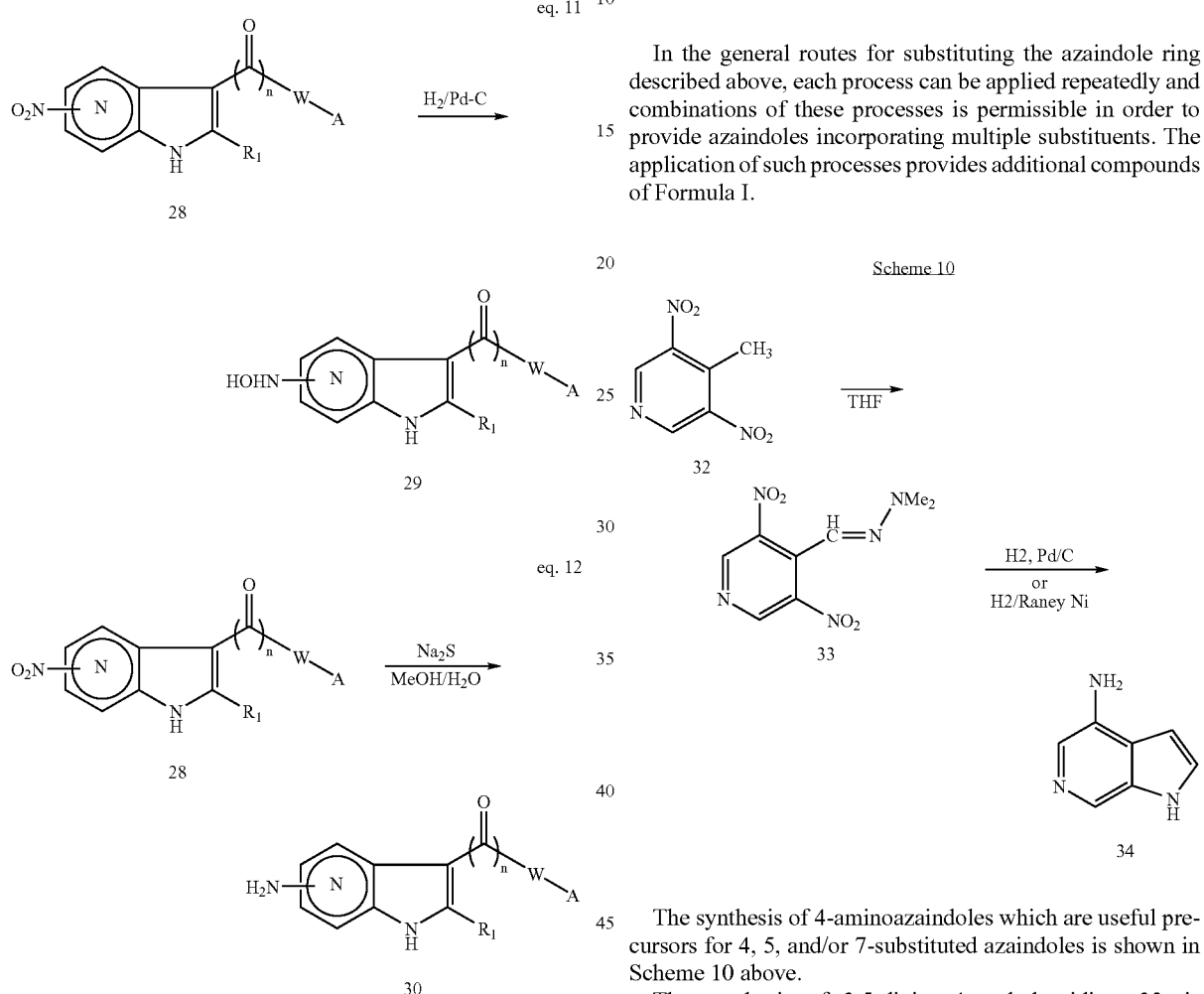

The alkylation of the nitrogen atom at position 1 of the azaindole derivatives can be achieved using NaH as the base, DMF as the solvent and an alkyl halide or sulfonate as alkylating agent, according to a procedure described in the literature (Mahadevan et al, Ref. 39) (Scheme 9).

Scheme 9

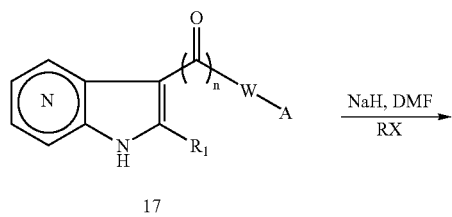

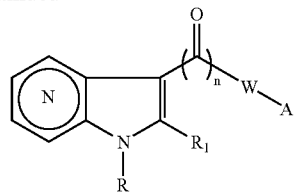

In the general routes for substituting the azaindole ring described above, each process can be applied repeatedly and combinations of these processes is permissible in order to provide azaindoles incorporating multiple substituents. The application of such processes provides additional compounds of Formula I.

Scheme 10

The synthesis of 4-aminoazaindoles which are useful precursors for 4, 5, and/or 7-substituted azaindoles is shown in Scheme 10 above.

The synthesis of 3,5-dinitro-4-methylpyridine, 32, is described in the following two references by Achremowicz et. al.: Achremowicz, Lucjan. *Pr. Nauk. Inst. Chem. Org. Fiz. Politech. Wroclaw.* 1982, 23, 3-128; Achremowicz, Lucjan. *Synthesis* 1975, 10, 653-4. In the first step of Scheme 10, the reaction with dimethylformamide dimethyl acetal in an inert solvent or neat under conditions for forming Batcho-Leimgruber precursors provides the cyclization precursor, 33, as shown. Although the step is anticipated to work as shown, the pyridine may be oxidized to the N-oxide prior to the reaction using a peracid such as MCPBA or a more potent oxidant like meta-trifluoromethyl or meta nitro peroxy benzoic acids. In the second step of Scheme 10, reduction of the nitro group using for example hydrogenation over Pd/C catalyst in a solvent such as MeOH, EtOH, or EtOAc provides the cyclized product, 34. Alternatively the reduction may be carried out using tin dichloride and HCl, hydrogenation over Raney nickel or other catalysts, or by using other methods for nitro reduction such as described elsewhere in this application. A general method for preparing indoles and azaindoles of the invention utilize the Leim-Gruber Batcho-reation sequence as shown in the scheme below:

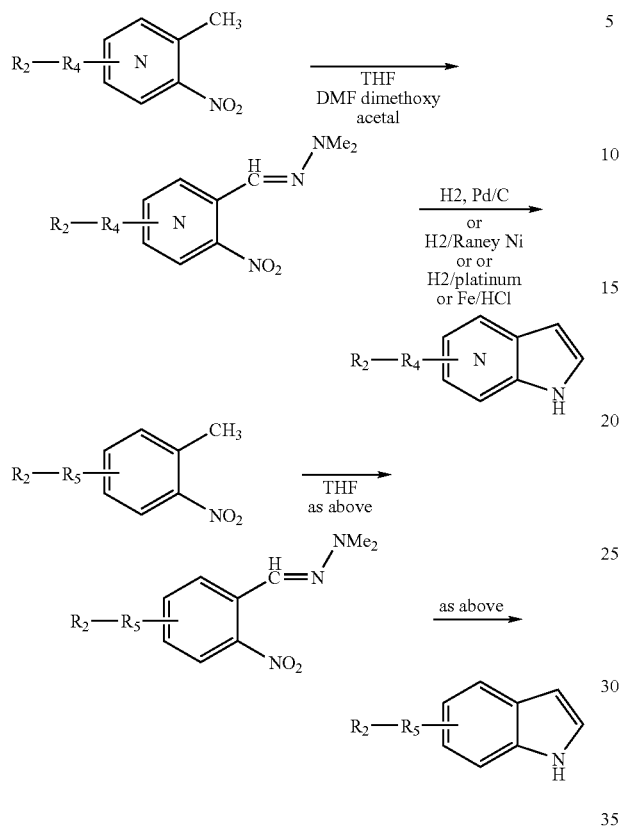

The amino indole, 34, can now be converted to compounds of Formula I via, for example, diazotization of the amino group, and then conversion of the diazonium salt to the fluoride, chloride or alkoxy group. See the discussion of such conversions in the descriptions for Schemes 17 and 18. The conversion of the amino moiety into desired functionality could then be followed by installation of the oxoacetopiperazine moiety by the standard methodology described above. 5 or 7-substitution of the azaindole can arise from N-oxide formation at position 6 and subsequent conversion to the chloro via conditions such as POCl$_3$ in chloroform, acetic anhydride followed by POCl$_3$ in DMF, or alternatively TsCl in DMF. Literature references for these and other conditions are provided in some of the later Schemes in this application. The synthesis of 4-bromo-7-hydroxy or protected hydroxy-4-azaindole is described below as this is a useful precursor for 4 and/or 7 substituted 6-aza indoles.

The synthesis of 5-bromo-2-hydroxy-4-methyl-3-nitro pyridine, 35, may be carried out as described in the following reference: Betageri, R.; Beaulieu, P. L.; Llinas-Brunet, M; Ferland, J. M.; Cardozo, M.; Moss, N.; Patel, U.; Proudfoot, J. R. PCT Int. Appl. WO 9931066, 1999. Intermediate 36 is prepared from 35 according to the method as described for Step 1 of Scheme 11. PG is an optional hydroxy protecting group such as triallylsilyl, methyl, benzyl or the like. Intermediate 37 is then prepared from 36 by the selective reduction of the nitro group in the presence of bromide and subsequent cyclization as described in the second step of Scheme 10. Fe(OH)$_2$ in DMF with catalytic tetrabutylammonium bromide can also be utilized for the reduction of the nitro group. The bromide may then be converted to alkoxy using the conditions employed in step U of scheme 4. The compounds are then converted to compounds of Formula I as above. The protecting group on the C-7 position may be removed with TMSI, hydrogenation or in the case of allyl standard palladium deprotection conditions in order to generate the free C-7 hydroxy compound which can also be depicted as its pyridone tautomer. As described earlier POBr$_3$ or POCl$_3$ can be used to convert the hydroxy intermediate to the C-7 bromo or chloro intermediate respectively.

Scheme 11

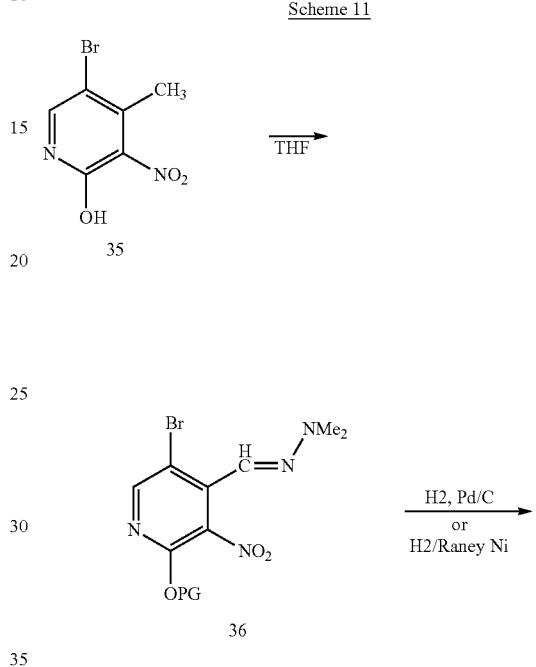

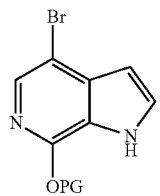

37

Step E. Scheme 14 depicts the nitration of an azaindole, 41, (R$_2$=H). Numerous conditions for nitration of the azaindole may be effective and have been described in the literature. N$_2$O$_5$ in nitromethane followed by aqueous sodium bisulfite according to the method of Bakke, J. M.; Ranes, E.; *Synthesis* 1997, 3, 281-283 could be utilized. Nitric acid in acetic may also be employed as described in Kimura, H.; Yotsuya, S.; Yuki, S.; Sugi, H.; Shigehara, I.; Haga, T.; *Chem. Pharm. Bull.* 1995, 43(10), 1696-1700. Sulfuric acid followed by nitric acid may be employed as in Ruefenacht, K.; Kristinsson, H.; Mattern, G.; *Helv Chim Acta* 1976, 59, 1593. Coombes, R. G.; Russell, L. W.; *J. Chem. Soc., Perkin Trans.* 1 1974, 1751 describes the use of a Titanium based reagent system for nitration. Other conditions for the nitration of the azaindole can be found in the following references: Lever, O. W. J.; Werblood, H. M.; Russell, R. K.; *Synth. Comm.* 1993, 23(9), 1315-1320; Wozniak, M.; Van Der Plas, H. C.; *J. Heterocycl Chem.* 1978, 15, 731.

Scheme 14

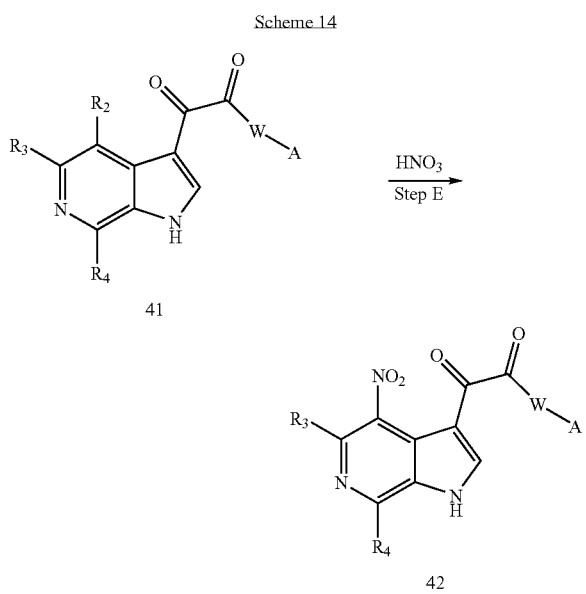

LG = Cl, Br, I, OTf, OPO(Oalkyl)$_2$

Step F. As shown above in Scheme 15, Step F, substituted azaindoles containing a chloride, bromide, iodide, triflate, or phosphonate undergo coupling reactions with a boronate (Suzuki type reactions) or a stannane (Stille type coupling) to provide substituted indoles or azaindoles. This type of coupling as mentioned previously can also be used to functionalize vinyl halides, triflates or phosphonates to add groups D or A or precursors. Stannanes and boronates are prepared via standard literature procedures or as described in the experimental section of this application. The substituted indoles, azaindoles, or alkenes may undergo metal mediated coupling to provide compounds of Formula I wherein $R_4$ is aryl, heteroaryl, or heteroalicyclic for example. The indoles or azaindole intermediates, (halogens, triflates, phosphonates) may undergo Stille-type coupling with heteroarylstannanes as shown in Scheme 15 or with the corresponding vinyl reagents as described in earlier Schemes. Conditions for this reaction are well known in the art and the following are three example references a) Farina, V.; Roth, G. P. Recent advances in the Stille reaction; *Adv. Met.-Org. Chem.* 1996, 5, 1-53. b) Farina, V.; Krishnamurthy, V.; Scott, W. J. The Stille reaction; *Org. React.* (N.Y.) 1997, 50, 1-652. and c) Stille, J. K. *Angew. Chem. Int. Ed. Engl.* 1986, 25, 508-524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art in addition to the specific examples provided in Scheme 15 and in the specific embodiments. It can be well recognized that an indole stannane could also couple to a heterocyclic or aryl halide or triflate to construct compounds of Formula I. Suzuki coupling (Norio Miyaura and Akiro Suzuki *Chem. Rev.* 1995, 95, 2457.) between a triflate, bromo, or chloro azaindole intermediate and a suitable boronate could also be employed and some specific examples are contained in this application. Palladium catalyzed couplings of stannanes and boronates between halo azaindole or indole intermediates or vinyl halides or vinyl triflates or similar vinyl substrate are also feasible and have been utilized extensively for this invention. Preferred procedures for coupling of a chloro or bromo azaindole or vinyl halide and a stannane employ dioxane, stoichiometric or an excess of the tin reagent (up to 5 equivalents), 0.1 to 1 eq of tetrakis triphenyl phosphine Palladium (0) in dioxane heated for 5 to 15 h at 110 to 120°. Other solvents such as DMF, THF, toluene, or benzene could be employed. Another useful procedure for coupling a halo indole or azaindole with a suitable tributyl heteroaryl or other stannane employs usually a slight excess (1.1 eqs) but up to several equivalents of the stannane, 0.1 eqs CuI, 0.1 equivalents of tetrakis triphenyl phosphine palladium (O) all of which is usually dissolved in dry DMF (approximately 5 mmol of halide per 25 mL of DMF but this concentration can be reduced for sluggish reactions or increased if solubility is an issue). The reaction is usually heated at an elevated temperature of about 90° C. and the reaction is usually run in a sealed reaction vessel or sealed tube. When the reaction is completed it is usually allowed to cool, filtered through methanesulfonic acid SCX cartridges with MeOH to remove triphenyl phosphine oxide, and then purified by standard crystallization or chromatographic methods. Examples of the utility of these conditions are shown in Scheme Z below.

SCHEME Z

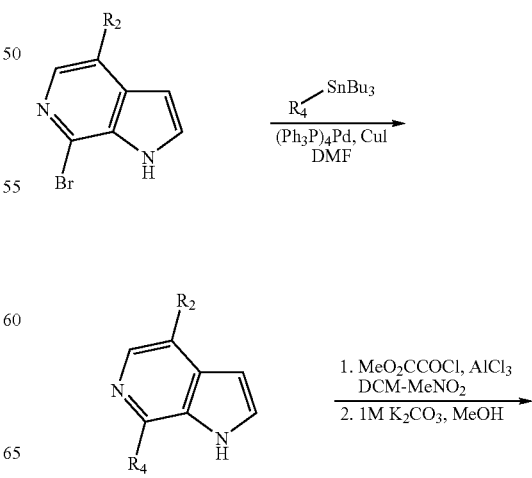

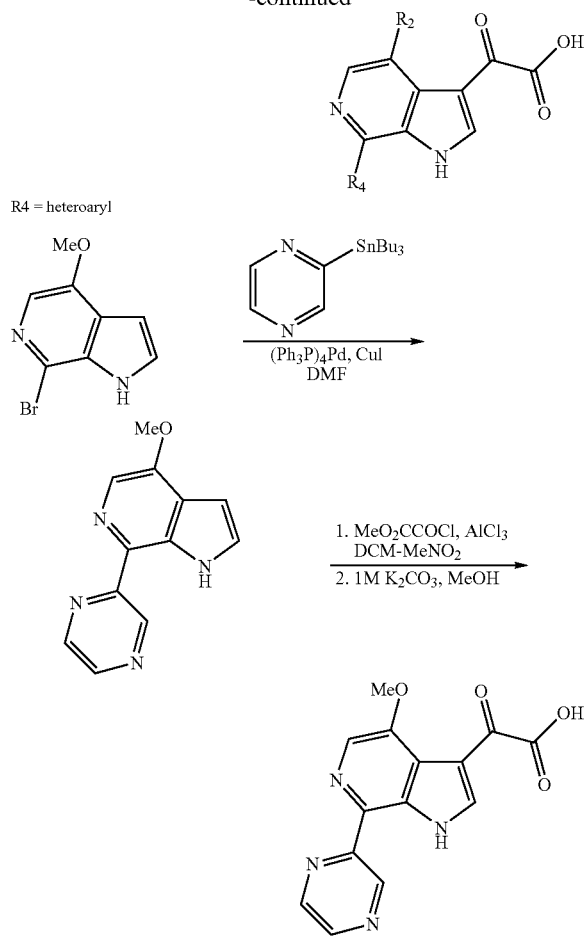

Alternatively, the Stille type coupling between a stannane (~1.1 eqs) and a vinyl, heteroaryl, or aryl halide may proceed better using (0.05 to 0.1 eq) bvPd2(dba)3 as catalyst and tri-2-furylphosphine (~0.25 eq) as the added ligand. The reaction is usually heated in THF or dioxane at a temperature between 70 and 90° C. Preferred procedures for Suzuki coupling of a chloro azaindole and a boronate employ 1:1 DMF water as solvent, 2 equivalents of potassium carbonate as base stoichiometric or an excess of the boron reagent (up to 5 equivalents), 0.1 to 1 eq of Palladium (0) tetrakis triphenyl phosphine heated for 5 to 15 h at 110 to 120°. Less water is occasionally employed. Another useful condition for coupling a heteroaryl or aryl boronic acid to a stoichiometric amount of vinyl halide or triflate utilizes DME as solvent (~0.33 mmol halide per 3 mL DME), ~4 eq of 2M sodium carbonate, and 0.05 eq Pd2dba3 heated in a sealed tube or sealed vessel at 90° C. for ~16 h. Reaction times vary with substrate. Another useful method for coupling involves use of coupling an aryl, heteroaryl or vinyl zinc bromide or chloride coupled with a vinyl, aryl or heteroaryl halide using tetrakis triphenyl phosphine palladium (O) heated in THF. Detailed example procedures for preparing the zinc reagents from halides via lithium bromide exchange and then transmetalation and reaction conditions are contained in the experimental section. If standard conditions fail new specialized catalysts and conditions can be employed. Discussions on details, conditions, and alternatives for carrying out the metal mediated couplings described above can also be found in the book "Organometallics in Organic Synthesis; A Manual; 2002, 2$^{nd}$ Ed. M. Schlosser editor, John Wiley and Sons, West Sussex, England, ISBN 0 471 98416 7.

Some references (and the references therein) describing catalysts which are useful for coupling with aryl and heteroaryl chlorides are:

Littke, A. F.; Dai, C.; Fu, G. C. J. Am. Chem. Soc. 2000, 122(17), 4020-4028;
Varma, R. S.; Naicker, K. P. Tetrahedron Lett. 1999, 40(3), 439-442; Wallow, T. I.;
Novak, B. M. J. Org. Chem. 1994, 59(17), 5034-7; Buchwald, S.; Old, D. W.;
Wolfe, J. P.; Palucki, M.; Kamikawa, K.; Chieffi, A.; Sadighi, J. P.; Singer, R. A.;
Ahman, J PCT Int. Appl. WO 0002887 2000; Wolfe, J. P.; Buchwald, S. L. Angew.
Chem., Int. Ed. 1999, 38(23), 3415; Wolfe, J. P.; Singer, R. A.; Yang, B. H.;
Buchwald, S. L. J. Am. Chem. Soc. 1999, 121(41), 9550-9561; Wolfe, J. P.;
Buchwald, S. L. Angew. Chem., Int. Ed. 1999, 38(16), 2413-2416; Bracher, F.;
Hildebrand, D.; Liebigs Ann. Chem. 1992, 12, 1315-1319; and Bracher, F.;
Hildebrand, D.; Liebigs Ann. Chem. 1993, 8, 837-839.

Alternatively, the boronate or stannane may be formed on the azaindole via methods known in the art and the coupling performed in the reverse manner with aryl or heteroaryl based halogens or triflates.

Known boronate or stannane agents could be either purchased from commercial resources or prepared following disclosed documents. Additional examples for the preparation of tin reagents or boronate reagents are contained in the experimental section, and references 93-95 and 106.

Novel stannane agents could be prepared from one of the following routes which should not be viewed as limiting.

Scheme Tin-01

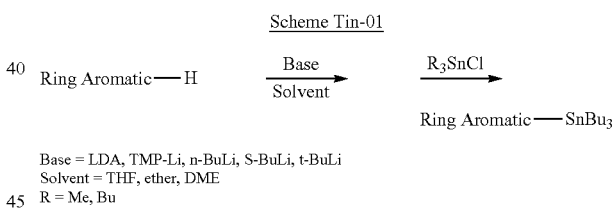

Base = LDA, TMP-Li, n-BuLi, S-BuLi, t-BuLi
Solvent = THF, ether, DME
R = Me, Bu

Scheme Tin-02

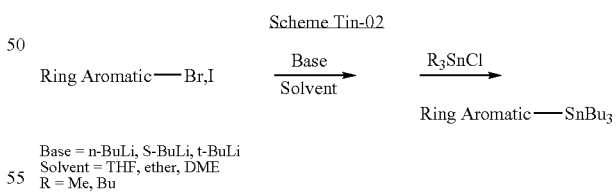

Base = n-BuLi, S-BuLi, t-BuLi
Solvent = THF, ether, DME
R = Me, Bu

Scheme Tin-03

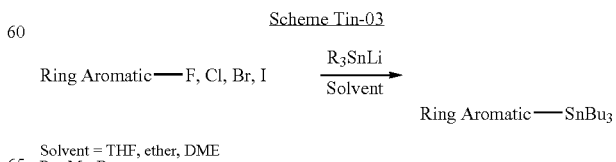

Solvent = THF, ether, DME
R = Me, Bu

Scheme Tin-04

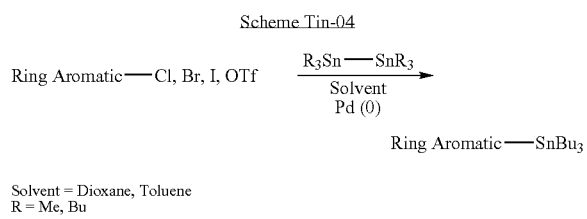

Solvent = Dioxane, Toluene
R = Me, Bu

Scheme Tin-05

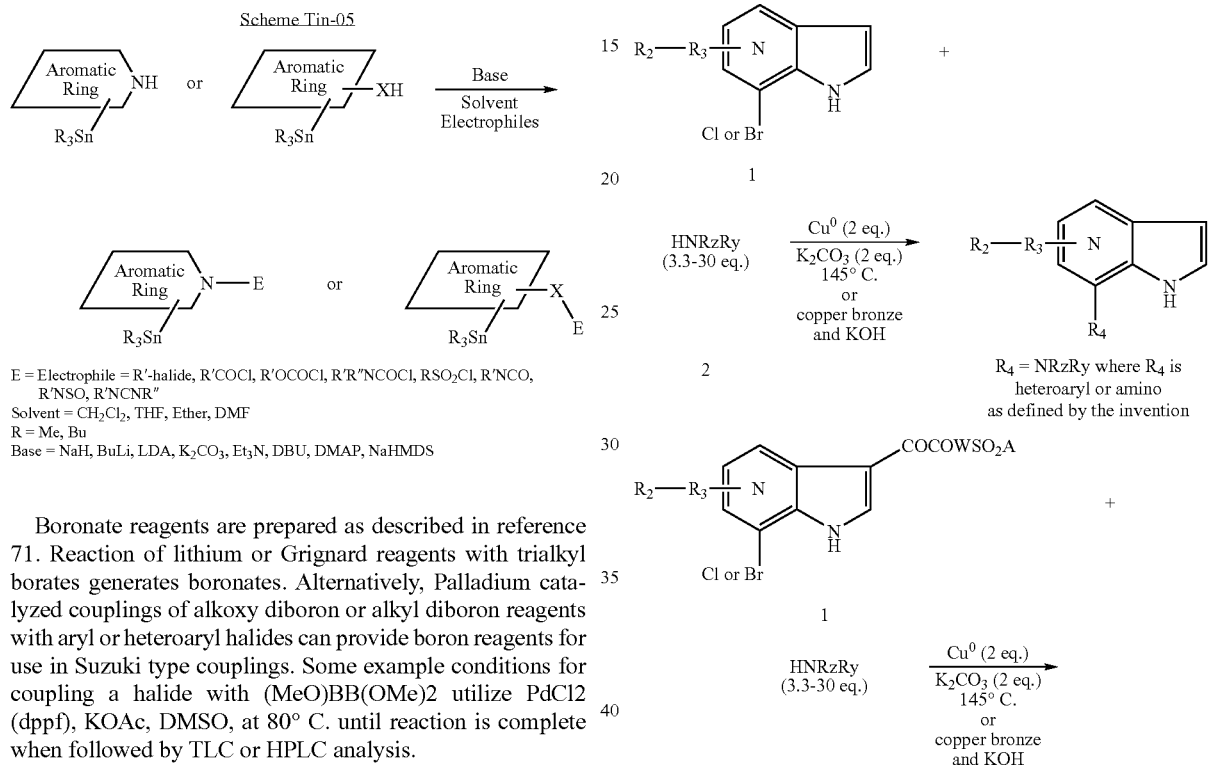

E = Electrophile = R'-halide, R'COCl, R'OCOCl, R'R"NCOCl, RSO₂Cl, R'NCO, R'NSO, R'NCNR"
Solvent = CH₂Cl₂, THF, Ether, DMF
R = Me, Bu
Base = NaH, BuLi, LDA, K₂CO₃, Et₃N, DBU, DMAP, NaHMDS Boronate reagents are prepared as described in reference 71. Reaction of lithium or Grignard reagents with trialkyl borates generates boronates. Alternatively, Palladium catalyzed couplings of alkoxy diboron or alkyl diboron reagents with aryl or heteroaryl halides can provide boron reagents for use in Suzuki type couplings. Some example conditions for coupling a halide with (MeO)BB(OMe)2 utilize PdCl2 (dppf), KOAc, DMSO, at 80° C. until reaction is complete when followed by TLC or HPLC analysis.

Related examples are provided in the following experimental section.

Methods for direct addition of aryl or heteroaryl organometallic reagents to alpha chloro nitrogen containing heterocycles or the N-oxides of nitrogen containing heterocycles are known and applicable to the azaindoles. Some examples are Shiotani et. Al. *J. Heterocyclic Chem.* 1997, 34(3), 901-907; Fourmigue et. al. *J. Org. Chem.* 1991, 56(16), 4858-4864.

SCHEME 12

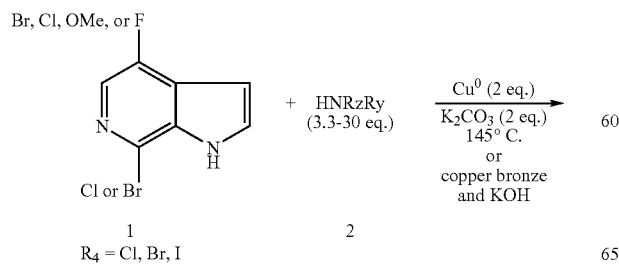

SCHEME 13

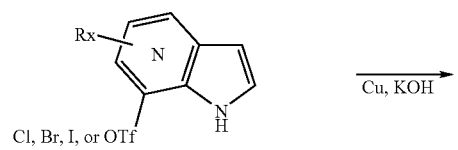

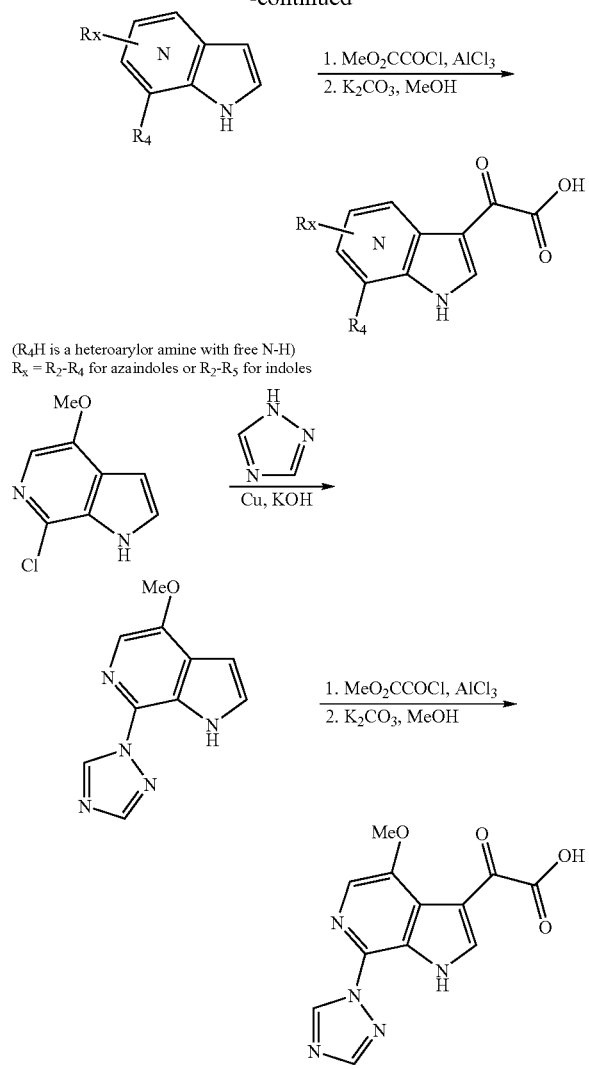

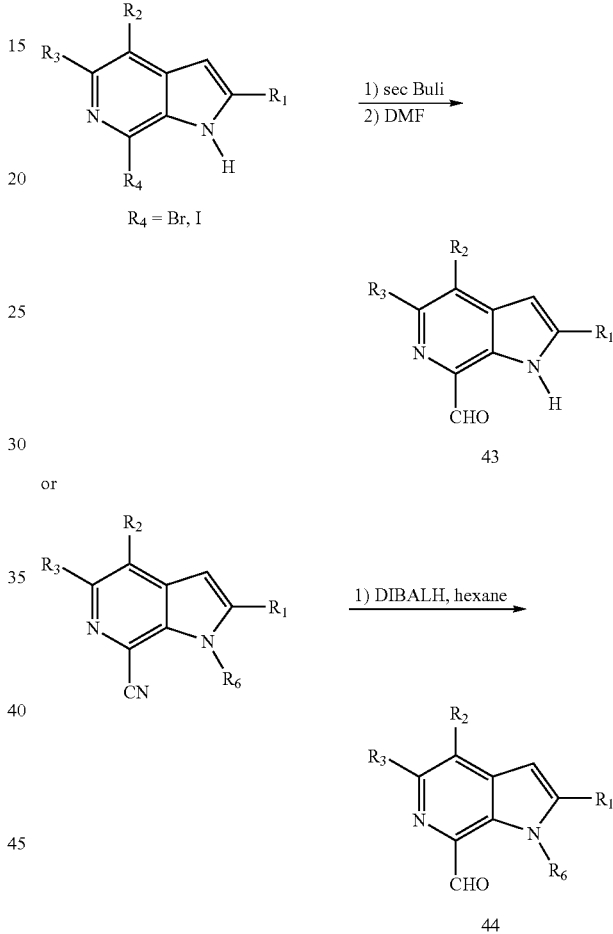

Scheme 16

As shown in Schemes 12 and 13, a mixture of halo-indole or halo-azaindole intermediate, 1-2 equivalents of copper powder, with 1 equivalent preferred for the 4-F,6-azaindole series and 2 equivalents for the 4-methoxy,6-azaindole series; 1-2 equivalents of potassium carbonate, with 1 equivalent preferred for the 4-F,6-azaindole series and 2 equivalents for the 4-methoxy,6-azaindole series; and a 2-30 equivalents of the corresponding heterocyclic reagent, with 10 equivalents preferred; was heated at 135-160° C. for 4 to 9 hours, with 5 hours at 160° C. preferred for the 4-F,6-azaindole series and 7 hours at 135° C. preferred for the 4-methoxy,6-azaindole series. The reaction mixture was cooled to room temperature and filtered through filter paper. The filtrate was diluted with methanol and purified either by preparative HPLC or silica gel. In many cases no chromatography is necessary, the product can be obtained by crystallization with methanol.

Alternatively, the installation of amines or N linked heteroaryls may be carried out by heating 1 to 40 equivalents of the appropriate amine and an equivalent of the appropriate aza indole chloride, bromide or iodide with copper bronze (from 0.1 to 10 equivalents (preferably about 2 equivalents) and from 1 to 10 equivalents of finely pulverized potassium hydroxide (preferably about 2 equivalents). Temperatures of 120° to 200° may be employed with 140-160° generally preferred. For volatile starting materials a sealed reactor may be employed. The reaction is most commonly used when the halogen being displaced is at the 7-position of a 6-aza or 4-azaindole but the method can work in the 5-azaseries or when the halogen is at a different position (4-7 position possible). As shown above the reaction could be employed on azaindoles unsubstituted at position 3 or intermediates which contain the dicarbonyl or the intact dicarbonyl N-heteroaryl piperazine.

A possible preparation of a key aldehyde intermediate, 43, using a procedure adapted from the method of Gilmore et. Al. *Synlett* 1992, 79-80, is shown in Scheme 16 above. The aldehyde substituent is shown only at the $R_4$ position for the sake of clarity, and should not be considered as a limitation of the methodology. The bromide or iodide intermediate is converted into an aldehyde intermediate, 43, by metal-halogen exchange and subsequent reaction with dimethylformamide in an appropriate aprotic solvent. Typical bases which could be used include, but are not limited to, alkyl lithium bases such as n-butyl lithium, sec butyl lithium or tert butyl lithium or a metal such as lithium metal. A preferred aprotic solvent is THF. Typically the transmetallation is initiated at −78° C. The reaction may be allowed to warm to allow the transmetalation to go to completion depending on the reactivity of the bromide intermediate. The reaction is then recooled to −78° C. and allowed to react with dimethylformamide (allowing the reaction to warm may be required to enable complete reaction) to provide an aldehyde which is elaborated to compounds of Formula I. Other methods for introduction of an aldehyde group to form intermediates of formula 43 include transition metal catalyzed carbonylation reactions of suitable bromo, trifluoromethane sulfonyl, or stannyl azaindoles. Alternatively the aldehydes could be introduced by reacting indolyl anions or indolyl Grignard reagents with formaldehyde and then oxidizing with $MnO_2$ or TPAP/NMO or other suitable oxidants to provide intermediate 43.

The methodology described in T. Fukuda et. al. *Tetrahedron* 1999, 55, 9151 and M. Jwao et. Al. *Heterocycles* 1992, 34(5), 1031 provide methods for preparing indoles with substituents at the 7-position. The Fukuda references provide methods for functionalizing the C-7 position of indoles by either protecting the indole nitrogen with 2,2-diethyl propanoyl group and then deprotonating the 7-position with sec/ Buli in TMEDA to give an anion. This anion may be quenched with DMF, formaldehyde, or carbon dioxide to give the aldehyde, benzyl alcohol, or carboxylic acid respectively and the protecting group removed with aqueous t butoxide. Similar tranformations could be achieved by converting indoles to indoline, lithiation at C-7 and then reoxidation to the indole such as described in the Iwao reference above. The oxidation level of any of these products may be adjusted by methods well known in the art as the interconversion of alcohol, aldehyde, and acid groups has been well studied. It is also well understood that a cyano group can be readily converted to an aldehyde. A reducing agent such as DIBALH in hexane such as used in Weyerstahl, P.; Schlicht, V.; *Liebigs Ann/Recl.* 1997, 1, 175-177 or alternatively catecholalane in THF such as used in Cha, J. S.; Chang, S. W.; Kwon, O. O.; Kim, J. M.; *Synlett.* 1996, 2, 165-166 will readily achieve this conversion to provide intermediates such as 44 (Scheme 16). Methods for synthesizing the nitriles are shown later in this application. It is also well understood that a protected alcohol, aldehyde, or acid group could be present in the starting azaindole and carried through the synthetic steps to a compound of Formula I in a protected form until they can be converted into the desired substituent at $R_1$ through $R_4$. For example, a benzyl alcohol can be protected as a benzyl ether or silyl ether or other alcohol protecting group; an aldehyde may be carried as an acetal, and an acid may be protected as an ester or ortho ester until deprotection is desired and carried out by literature methods.

Scheme 17

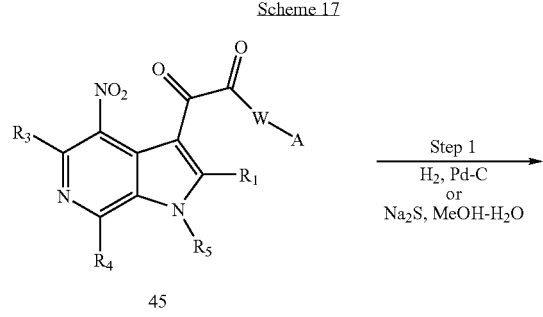

45

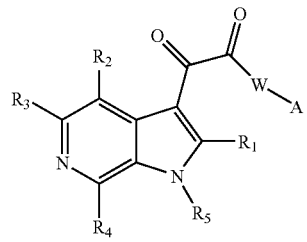

46

47

Step G. Step 1 of Scheme 17 shows the reduction of a nitro group on 45 to the amino group of 46. Although shown on position 4 of the azaindole, the chemistry is applicable to other nitro isomers. The procedure described in Ciurla, H.; Puszko, A.; *Khim Geterotsikl Soedin* 1996, 10, 1366-1371 uses hydrazine Raney-Nickel for the reduction of the nitro group to the amine. Robinson, R. P.; DonahueO, K. M.; Son, P. S.; Wagy, S. D.; *J. Heterocycl. Chem.* 1996, 33(2), 287-293 describes the use of hydrogenation and Raney Nickel for the reduction of the nitro group to the amine. Similar conditions are described by Nicolai, E.; Claude, S.; Teulon, J. M.; *J. Heterocycl. Chem.* 1994, 31(1), 73-75 for the same transformation. The following two references describe some trimethylsilyl sulfur or chloride based reagents which may be used for the reduction of a nitro group to an amine. Hwu, J. R.; Wong, F. F.; Shiao, M. J.; *J. Org. Chem.* 1992, 57(19), 5254-5255; Shiao, M. J.; Lai, L. L.; Ku, W. S.; Lin, P. Y.; Hwu, J. R.; *J. Org. Chem.* 1993, 58(17), 4742-4744.

Step 2 of Scheme 17 describes general methods for conversion of amino groups on azaindoles or indoles into other functionality. Scheme 18 also depicts transformations of an amino azaindole into various intermediates and compounds of Formula I.

The amino group at any position of the azaindole, such as 46 (Scheme 17), could be converted to a hydroxy group using sodium nitrite, sulfuric acid, and water via the method of Klemm, L. H.; Zell, R.; *J. Heterocycl. Chem.* 1968, 5, 773. Bradsher, C. K.; Brown, F. C.; Porter, H. K.; *J. Am. Chem. Soc.* 1954, 76, 2357 describes how the hydroxy group may be alkylated under standard or Mitsonobu conditions to form ethers. The amino group may be converted directly into a methoxy group by diazotization (sodium nitrite and acid) and trapping with methanol.

The amino group of an azaindole, such as 46, could be converted to fluoro via the method of Sanchez using $HPF_6$, $NaNO_2$, and water by the method described in Sanchez, J. P.; Gogliotti, R. D.; *J. Heterocycl. Chem.* 1993, 30(4), 855-859. Other methods useful for the conversion of the amino group to fluoro are described in Rocca, P.; Marsais, F.; Godard, A.; Queguiner, G.; *Tetrahedron Lett.* 1993, 34(18), 2937-2940 and Sanchez, J. P.; Rogowski, J. W.; *J. Heterocycl. Chem.* 1987, 24, 215.

The amino group of the azaindole, 46, could also be converted to a chloride via diazotization and chloride displacement as described in Ciurla, H.; Puszko, A.; *Khim Geterotsikl Soedin* 1996, 10, 1366-1371 or the methods in Raveglia, L. F.; Giardina, G. A.; Grugni, M.; Rigolio, R.; Farina, C.; *J. Heterocycl. Chem.* 1997, 34(2), 557-559 or the methods in Matsumoto, J. I.; Miyamoto, T.; Minamida, A.; Mishimura, Y.; Egawa, H.; Mishimura, H.; *J. Med. Chem.* 1984, 27(3), 292; or as in Lee, T. C.; Salemnick, G.; *J. Org. Chem.* 1975, 24, 3608.

The amino group of the azaindole, 46, could also be converted to a bromide via diazotization and displacement by bromide as described in Raveglia, L. F.; Giardina, G. A.; Grugni, M.; Rigolio, R.; Farina, C.; *J. Heterocycl. Chem.* 1997, 34(2), 557-559; Talik, T.; Talik, Z.; Ban-Oganowska, H.; *Synthesis* 1974, 293; and Abramovitch, R. A.; Saha, M.; *Can. J. Chem.* 1966, 44, 1765.

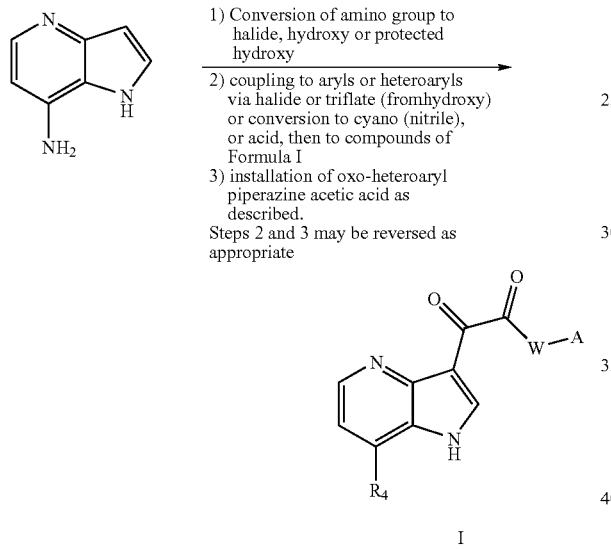

The preparation of 4-amino 4-azaindole and 7-methyl-4-azaindole is described by Mahadevan, I.; Rasmussen, M. *J. Heterocycl. Chem.* 1992, 29(2), 359-67. The amino group of the 4-amino 4-azaindole can be converted to halogens, hydroxy, protected hydroxy, triflate, as described above in Schemes 17-18 for the 4-amino compounds or by other methods known in the art. Protection of the indole nitrogen of the 7-methyl-4-azaindole via acetylation or other strategy followed by oxidation of the 7-methyl group with potassium permanganate or chromic acid provides the 7-acid/4-N-oxide. Reduction of the N-oxide, as described below, provides an intermediate from which to install various substituents at position $R_4$. Alternatively the parent 4-azaindole which was prepared as described in Mahadevan, I.; Rasmussen, M. *J. Heterocycl. Chem.* 1992, 29(2), 359-67 could be derivatized at nitrogen to provide the 1-(2,2-diethylbutanoyl)azaindole which could then be lithiated using TMEDA/sec BuLi as described in T. Fukuda et. Al. *Tetrahedron* 1999, 55, 9151-9162; followed by conversion of the lithio species to the 7-carboxylic acid or 7-halogen as described. Hydrolysis of the N-amide using aqueous tert-butoxide in THF regenerates the free NH indole which could then be converted to compounds of Formula I. The chemistry used to functionalize position 7 can also be applied to the 5 and 6 indole series.

Scheme 19 shows the preparation of a 7-chloro-4-azaindole, 50, which could be converted to compounds of Formula I by the chemistry previously described, especially the palladium catalyzed tin and boron based coupling methodology described above. The chloro nitro indole, 49, is commercially available or can be prepared from 48 according to the method of Delarge, J.; Lapiere, C. L. *Pharm. Acta Helv.* 1975, 50(6), 188-91.

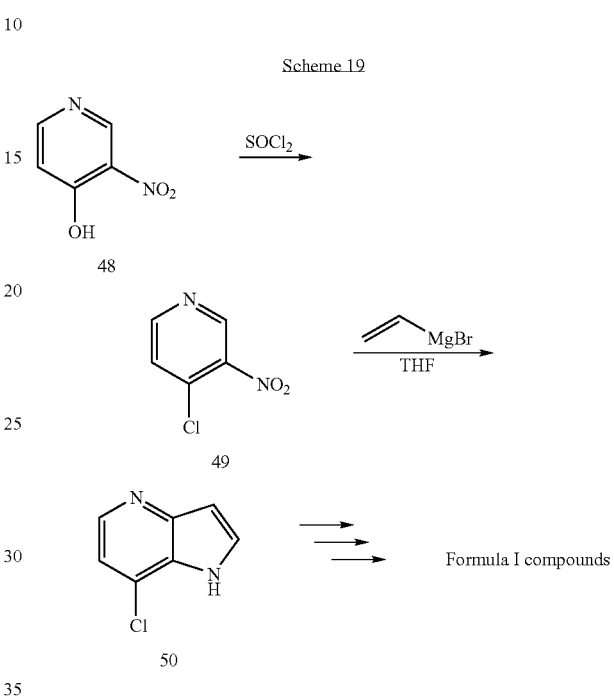

Scheme 20, below, shows another synthetic route to substituted 4-aza indoles. The 3-aminopyrrole, 51, was reacted to provide the pyrrolopyridinone, 52, which was then reduced to give the hydroxy azaindole, 53. The pyrrolo[2,3-b]pyridines described were prepared according to the method of Britten, A. Z.; Griffiths, G. W. G. *Chem. Ind.* (London) 1973, 6, 278. The hydroxy azaindole, 53, could then be converted to the triflate then further reacted to provide compounds of Formula I.

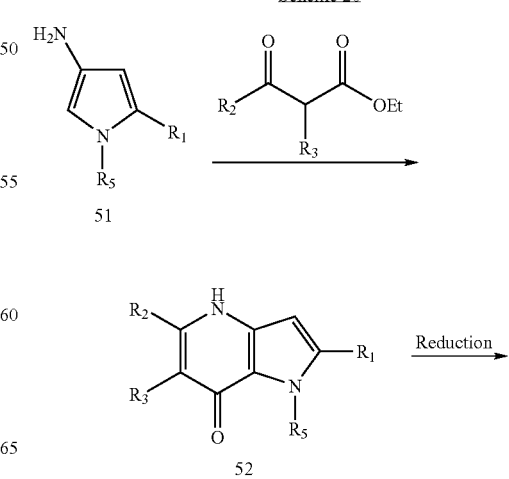

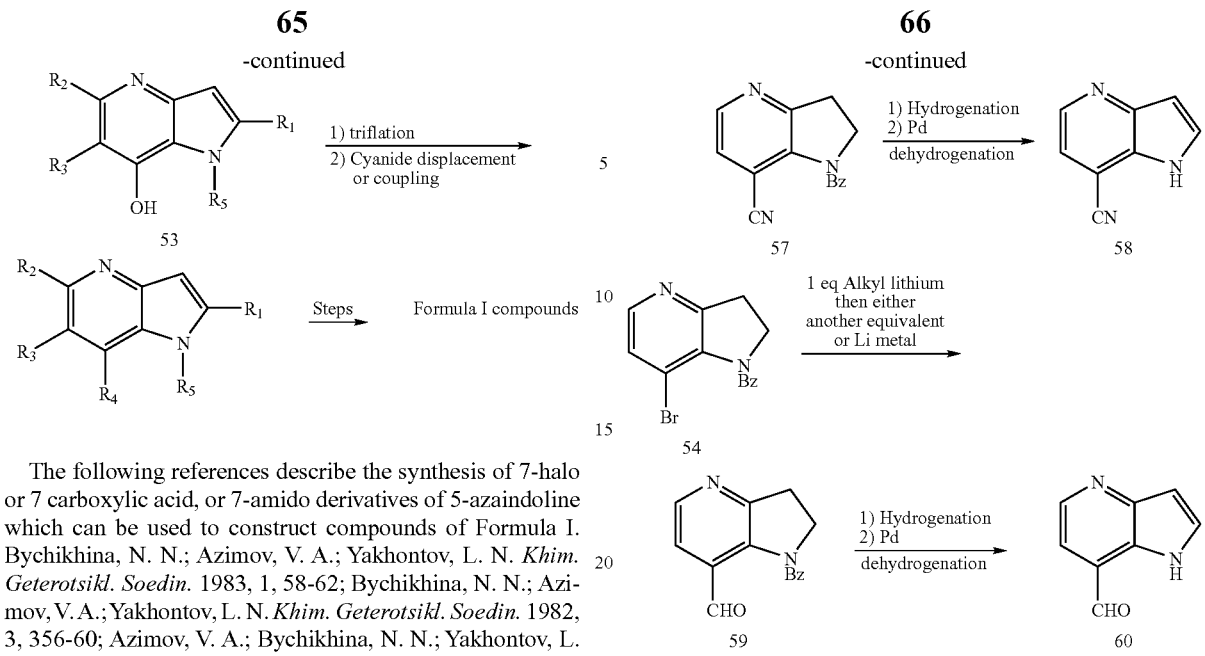

The following references describe the synthesis of 7-halo or 7 carboxylic acid, or 7-amido derivatives of 5-azaindoline which can be used to construct compounds of Formula I. Bychikhina, N. N.; Azimov, V. A.; Yakhontov, L. N. *Khim. Geterotsikl. Soedin.* 1983, 1, 58-62; Bychikhina, N. N.; Azimov, V. A.; Yakhontov, L. N. *Khim. Geterotsikl. Soedin.* 1982, 3, 356-60; Azimov, V. A.; Bychikhina, N. N.; Yakhontov, L. N. *Khim. Geterotsikl. Soedin.* 1981, 12, 1648-53; Spivey, A. C.; Fekner, T.; Spey, S. E.; Adams, H. *J. Org. Chem.* 1999, 64(26), 9430-9443; Spivey, A. C.; Fekner, T.; Adams, H. *Tetrahedron Lett.* 1998, 39(48), 8919-8922. The methods described in Spivey et al. (preceding two references) for the preparation of 1-methyl-7-bromo-4-azaindoline can be used to prepare the 1-benzyl-7-bromo-4-azaindoline, 54, shown below in Scheme 21. This could be utilized in Stille or Suzuki couplings to provide 55, which is deprotected and dehydrogenated to provide 56. Other useful azaindole intermediates, such as the cyano derivatives, 57 and 58, and the aldehyde derivatives, 59 and 60, can then be further elaborated to compounds of Formula I.

Alternatively the 7-functionalized 5-azaindole derivatives could be obtained by functionalization using the methodologies of T. Fukuda et. al. *Tetrahedron* 1999, 55, 9151 and M. Jwao et. Al. *Heterocycles* 1992, 34(5), 1031 described above for the 4 or 6 azaindoles. The 4 or 6 positions of the 5 aza indoles can be functionalized by using the azaindole N-oxide.

The conversion of indoles to indolines is well known in the art and can be carried out as shown or by the methods described in Somei, M.; Saida, Y.; Funamoto, T.; Ohta, T. *Chem. Pharm. Bull.* 1987, 35(8), 3146-54; M. Jwao et. Al. *Heterocycles* 1992, 34(5), 1031; and Akagi, M.; Ozaki, K. *Heterocycles* 1987, 26(J), 61-4.

Scheme 21

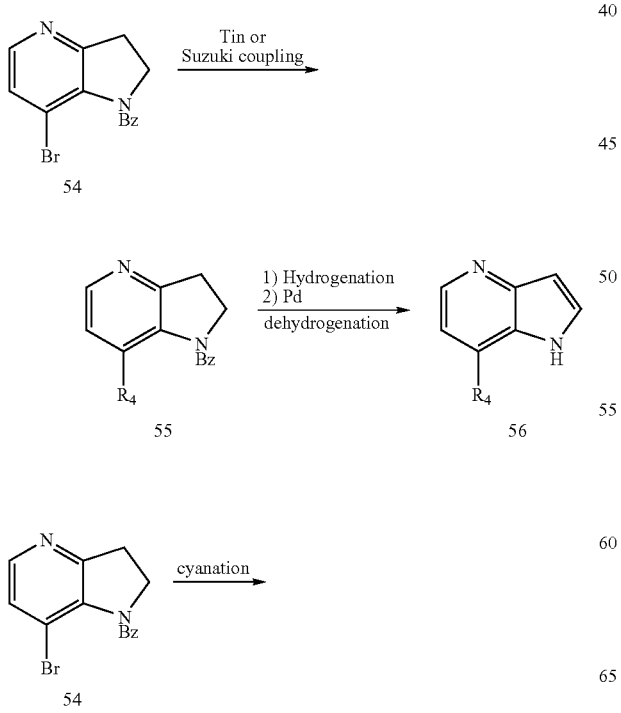

Scheme 22

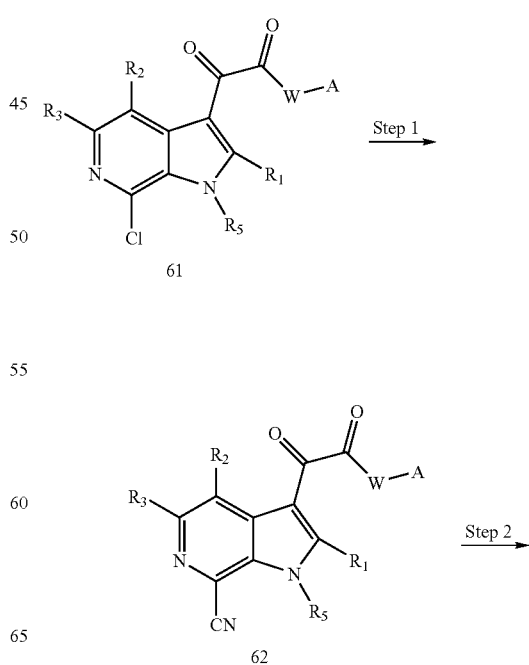

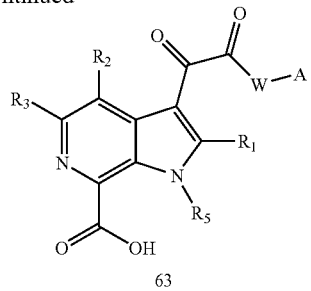

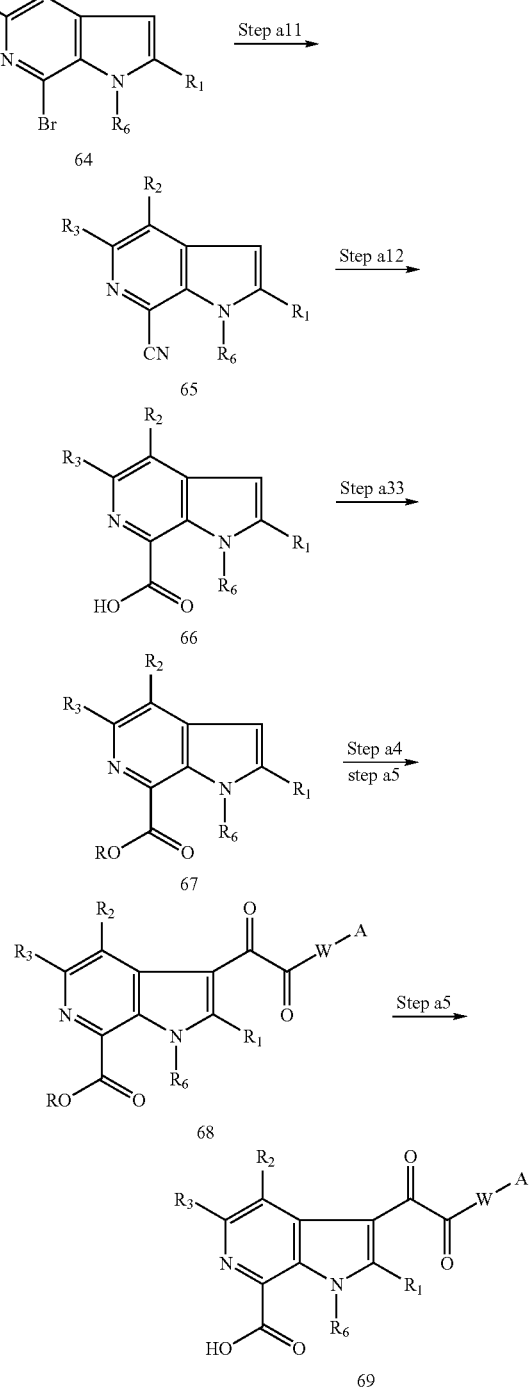

Scheme 23

The preparation of azaindole oxoacetyl or oxo piperidines with carboxylic acids could be carried out from nitrile, aldehyde, or anion precursors via hydrolysis, oxidation, or trapping with $CO_2$ respectively. As shown in the Scheme 22, Step 1, or the scheme below step a12 one method for forming the nitrile intermediate, 62, is by cyanide displacement of a halide in the aza-indole ring. The cyanide reagent used can be sodium cyanide, or more preferably copper or zinc cyanide. The reactions could be carried out in numerous solvents which are well known in the art. For example DMF is used in the case of copper cyanide. Additional procedures useful for carrying out step 1 of Scheme 24 are Yamaguchi, S.; Yoshida, M.; Miyajima, I.; Araki, T.; Hirai, Y.; *J. Heterocycl. Chem.* 1995, 32(5), 1517-1519 which describes methods for copper cyanide; Yutilov, Y. M.; Svertilova, I. A.; *Khim Geterotsikl Soedin* 1994, 8, 1071-1075 which utilizes potassium cyanide; and Prager, R. H.; Tsopelas, C.; Heisler, T.; *Aust. J. Chem.* 1991, 44 (2), 277-285 which utilizes copper cyanide in the presence of $MeOS(O)_2F$. The chloride or more preferably a bromide on the azaindole could be displaced by sodium cyanide in dioxane via the method described in *Synlett.* 1998, 3, 243-244. Alternatively, Nickel dibromide, Zinc, and triphenyl phosphine in can be used to activate aromatic and heteroaryl chlorides to displacement via potassium cyanide in THF or other suitable solvent by the methods described in Eur. Pat. Appl., 831083, 1998.

The conversion of the cyano intermediate, 62, to the carboxylic acid intermediate, 63, is depicted in step 2, Scheme 22 or in step a12, Scheme 23. Many methods for the conversion of nitrites to acids are well known in the art and may be employed. Suitable conditions for step 2 of Scheme 22 or the conversion of intermediate 65 to intermediate 66 below employ potassium hydroxide, water, and an aqueous alcohol such as ethanol. Typically the reaction must be heated at refluxing temperatures for one to 100 h. Other procedures for hydrolysis include those described in:

Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; Macor, J. E.; Post, R.; Ryan, K.; *J. Heterocycl. Chem.* 1992, 29(6), 1465-1467.

The acid intermediate, 66 (Scheme 23), could then be esterified using conditions well known in the art. For example, reaction of the acid with diazomethane in an inert solvent such as ether, dioxane, or THF would give the methyl ester. Intermediate 67 may then be converted to intermediate 68 according to the procedure described in Scheme 2. Intermediate 68 could then be hydrolyzed to provide intermediate 69.

As shown in Scheme 24, step a13 another preparation of the indoleoxoacetylpiperazine 7-carboxylic acids, 69, is carried out by oxidation of the corresponding 7-carboxaldehyde, 70. Numerous oxidants are suitable for the conversion of aldehyde to acid and many of these are described in standard organic chemistry texts such as: Larock, Richard C., Comprehensive organic transformations: a guide to functional group preparations $2^{nd}$ ed. New York: Wiley-VCH, 1999. One preferred method is the use of silver nitrate or silver oxide in a solvent such as aqueous or anhydrous methanol at a temperature of ~25° C. or as high as reflux. The reaction is typically carried out for one to 48 h and is typically monitored by TLC or LC/MS until complete conversion of product to starting material has occurred. Alternatively, KmnO$_4$ or CrO$_3$/H$_2$SO$_4$ could be utilized.

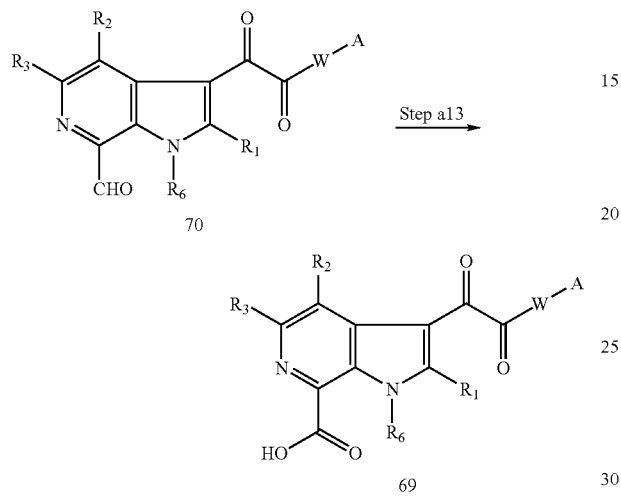

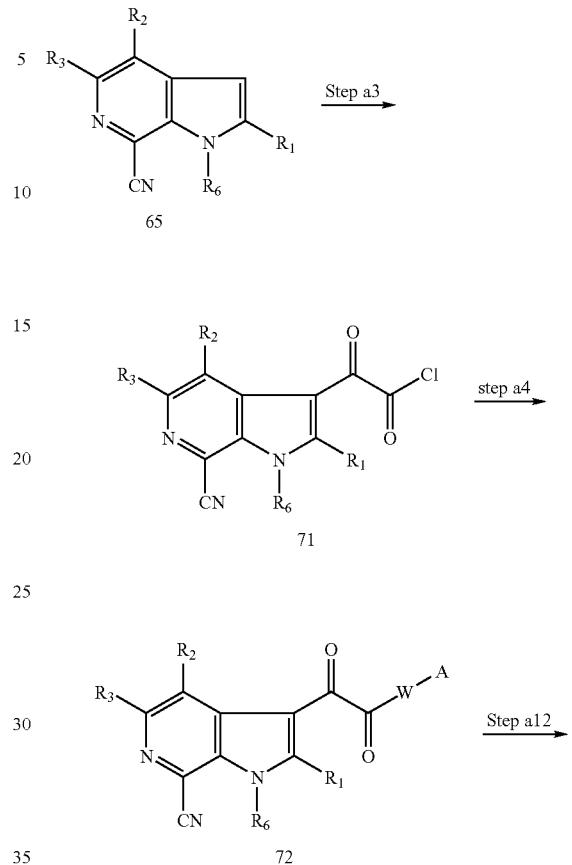

Scheme 25 gives a specific example of the oxidation of an aldehyde intermediate, 70a, which could be used to provide the carboxylic acid intermediate, 69a.

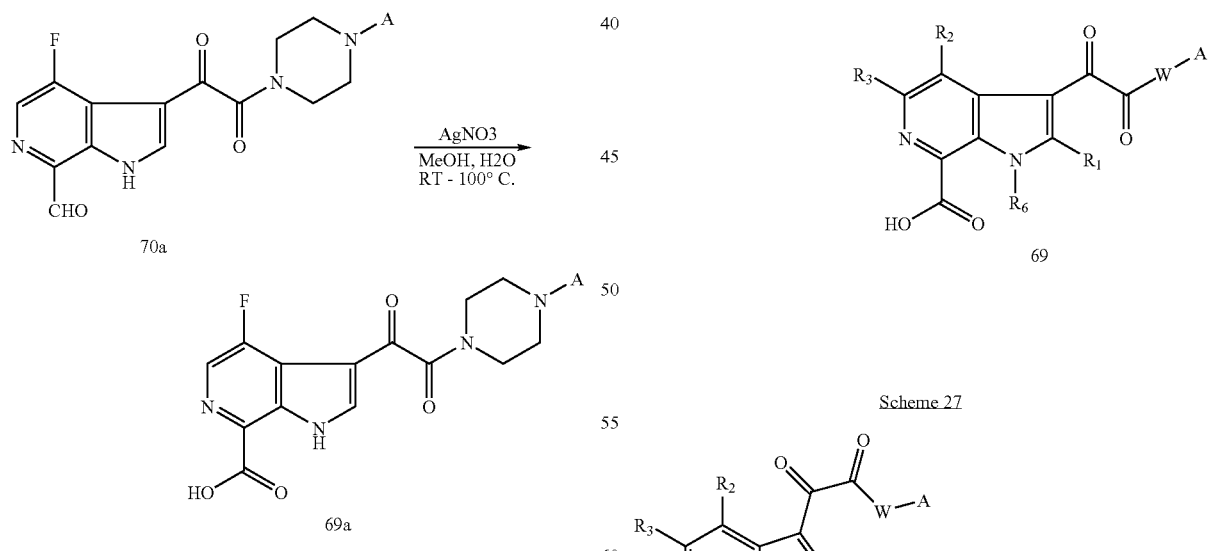

Alternatively, intermediate 69 could be prepared by the nitrile method of synthesis carried out in an alternative order as shown in Scheme 26. The nitrile hydrolyis step can be delayed and the nitrile carried through the synthesis to provide a nitrile which could be hydrolyzed to provide the free acid, 69, as above.

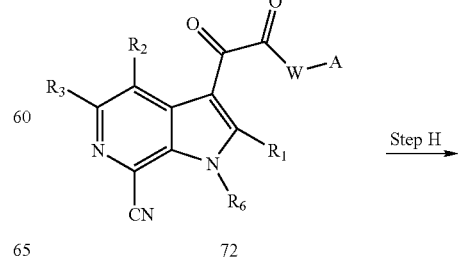

Step J.

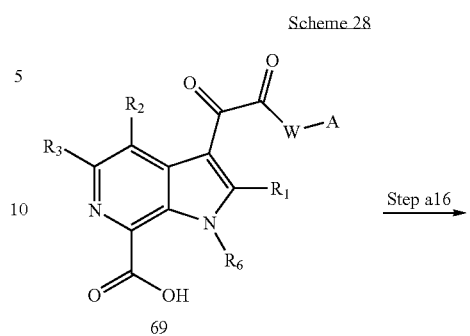

Scheme 28

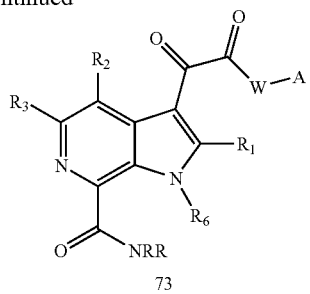

Step H. The direct conversion of nitrites, such as 72, to amides, such as 73, shown in Scheme 27, Step H, could be carried out using the conditions as described in Shiotani, S.; Taniguchi, K.; *J. Heterocycl. Chem.* 1996, 33(4), 1051-1056 (describes the use of aqueous sulfuric acid); Memoli, K. A.; *Tetrahedron Lett.* 1996, 37(21), 3617-3618; Adolfsson, H.; Waernmark, K.; Moberg, C.; *J. Org. Chem.* 1994, 59(8), 2004-2009; and El Hadri, A.; Leclerc, G.; *J. Heterocycl. Chem.* 1993, 30(3), 631-635.

Step I. For NH2

Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; Macor, J. E.; Post, R.; Ryan, K.; *J. Heterocycl. Chem.* 1992, 29(6), 1465-1467.

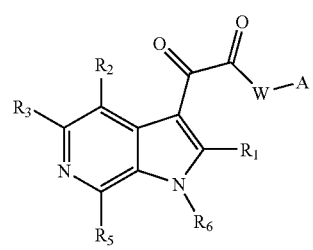

The following scheme (28A) shows an example for the preparation of 4-fluoro-7substituted azaindoles from a known starting materials. References for the Bartoli indole synthesis were mentioned earlier. The conditions for transformation to the nitrites, acids, aldehydes, heterocycles and amides have also been described in this application.

Scheme 28A

Either:

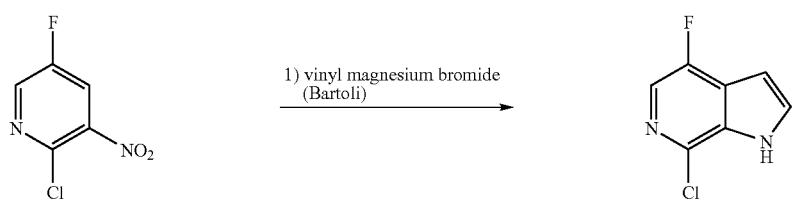

Prepared as in U.S. Pat. No. 5,811,432

Or:

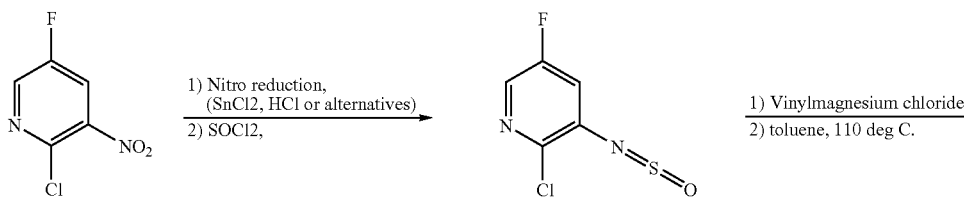

Prepared as in U.S. Pat No. 5,811,432    Tetrahedron Letters 1986, 27,837.

73 74
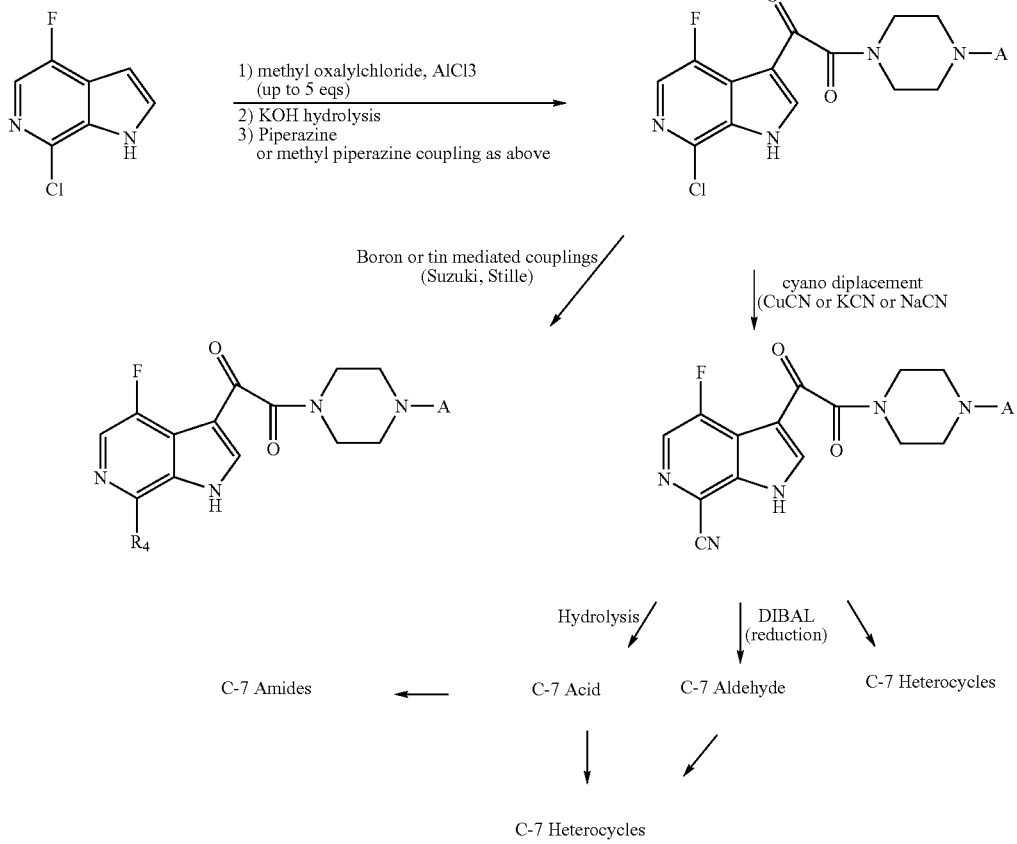
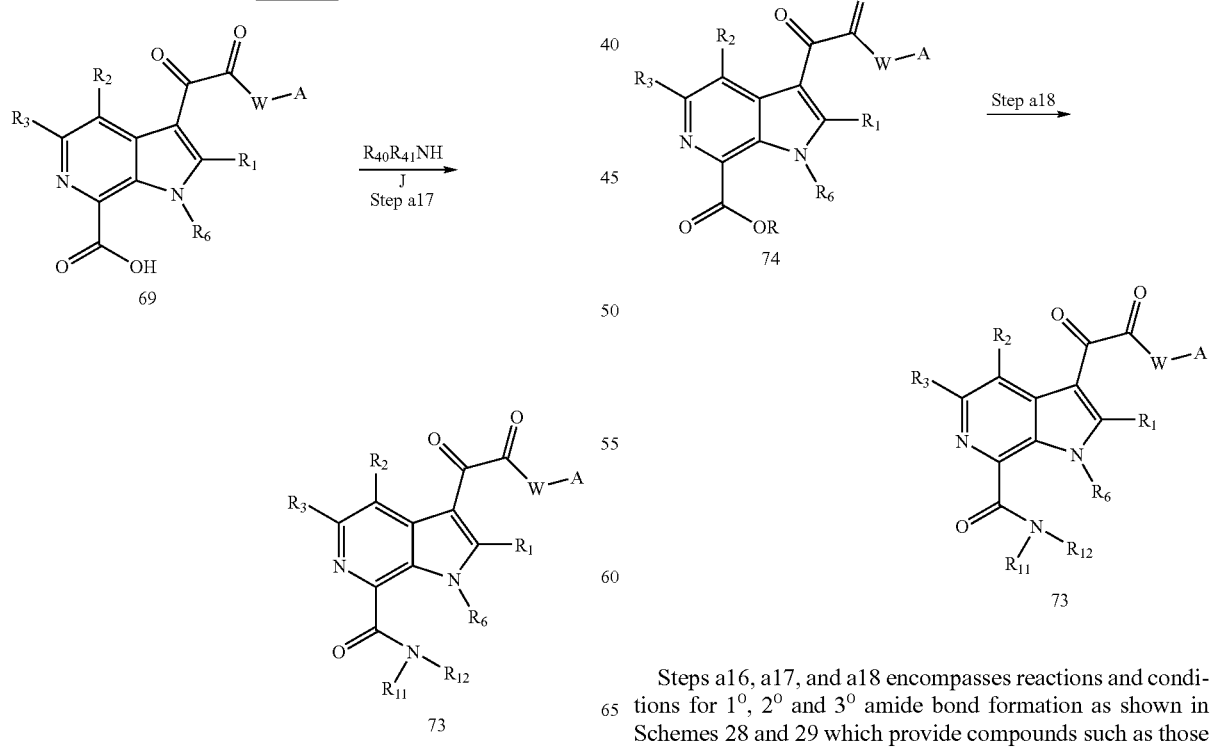
Steps a16, a17, and a18 encompasses reactions and conditions for 1°, 2° and 3° amide bond formation as shown in Schemes 28 and 29 which provide compounds such as those of Formula 73.

The reaction conditions for the formation of amide bonds encompass any reagents that generate a reactive intermediate for activation of the carboxylic acid to amide formation, for example (but not limited to), acyl halide, from carbodiimide, acyl iminium salt, symmetrical anhydrides, mixed anhydrides (including phosphonic/phosphinic mixed anhydrides), active esters (including silyl ester, methyl ester and thioester), acyl carbonate, acyl azide, acyl sulfonate and acyloxy N-phosphonium salt. The reaction of the indole carboxylic acids with amines to form amides may be mediated by standard amide bond forming conditions described in the art. Some examples for amide bond formation are listed in references 41-53 but this list is not limiting. Some carboxylic acid to amine coupling reagents which are applicable are EDC, Diisopropylcarbodiimide or other carbodiimides, PyBop (benzotriazolyloxytris(dimethylamino) phosphonium hexafluorophosphate), 2-(1H-benzotriazole-1-yl)-1,1,3,3-tetramethyl uronium hexafluorophosphate (HBTU). A particularly useful method for azaindole 7-carboxylic acid to amide reactions, likely to be based on an analogous series, is the use of carbonyl imidazole as the coupling reagent as described in reference 53. The temperature of this reaction could be lower than in the cited reference, from 80° C. (or possibly lower) to 150° C. or higher. A more specific possible application in which W is piperazinyl is depicted in Scheme 30.

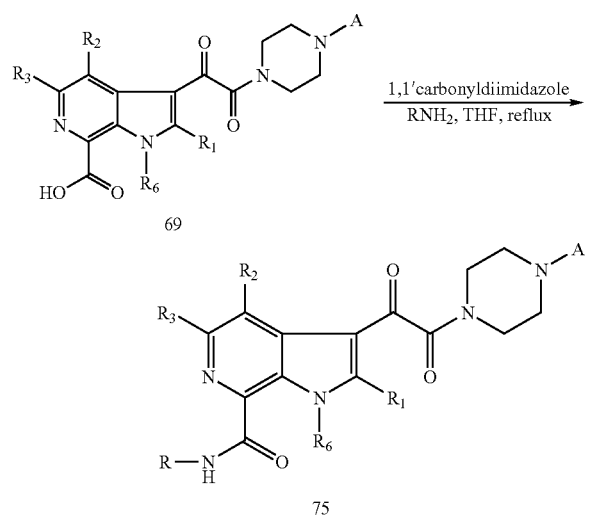

The following four general methods provide a more detailed description for the preparation of indolecarboamides and these methods were employed for the synthesis of compounds similar to Formula I, except that A formed a carboxamide. These methods should work as written to provide compounds of Formula I.

Method 1:

To a mixture of an acid intermediate, such as 75, (1 equiv), an appropriate amine (4 equiv.) and DMAP 0.1 tp 1 eq would be dissolved $CH_2Cl_2$ (1 mL) and then EDC added (1 eq). The resulting mixture should be shaken at rt for ~12 h, and then evaporated in vacuo. The residue could be dissolved in a solvent such as MeOH, and subjected to preparative reverse phase HPLC purification.

Method 2:

To a mixture of an appropriate amine (4 equiv.) and HOBT (16 mg, 0.12 mmol) in THF (0.5 mL) should be added an acid intermediate, such as 74, and NMM ~1 eq followed by EDC. The reaction mixture could be shaken at rt for 12 h. The volatiles should be evaporated in vacuo; and the residue dissolved in MeOH and subjected to preparative reverse phase HPLC purification.

Method 3:

To a mixture of an acid intermediate, such as 74, amine (4 equiv.) and DEPBT (prepared according to Li, H.; Jiang, X. Ye, Y.; Fan, C.; Todd, R.; Goodman, M. *Organic Letters* 1999, 1, 91); in DMF would be added TEA. The resulting mixture should be shaken at rt for 12 h; and then diluted with MeOH and purified by preparative reverse phase HPLC.

Method 4:

A mixture of an acid intermediate, such as 74, and of 1,1-carbonyldiimidazole in anhydrous THF could be heated to reflux under nitrogen. After 2.5 h, amine was added and heating continued. After an additional period of 3~20 h at reflux, the reaction mixture could be cooled and concentrated in vacuo. The residue could be purified by chromatography on silica gel to provide a compound of Formula I.

In addition, the carboxylic acid could be converted to an acid chloride using reagents such as thionyl chloride (neat or in an inert solvent) or oxalyl chloride in a solvent such as benzene, toluene, THF, or $CH_2Cl_2$. The amides could alternatively, be formed by reaction of the acid chloride with an excess of ammonia, primary, or secondary amine in an inert solvent such as benzene, toluene, THF, or $CH_2Cl_2$ or with stoichiometric amounts of amines in the presence of a tertiary amine such as triethylamine or a base such as pyridine or 2,6-lutidine. Alternatively, the acid chloride could be reacted with an amine under basic conditions (usually sodium or potassium hydroxide) in solvent mixtures containing water and possibly a miscible co solvent such as dioxane or THF. Additionally, the carboxylic acid could be converted to an ester preferably a methyl or ethyl ester and then reacted with an amine. The ester could be formed by reaction with diazomethane or alternatively trimethylsilyl diazomethane using standard conditions which are well known in the art. References and procedures for using these or other ester forming reactions can be found in reference 52 or 54.

Additional references for the formation of amides from acids are: Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans* 1 1997, 14, 2083-2088; Langry, K. C.; *Org. Prep. Proc. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014; Bhattacharjee, A.; Mukhopadhyay, R.; Bhattacharjya, A.; *Indian J. Chem., Sect B* 1994, 33(7), 679-682.

It is well known in the art that heterocycles may be prepared from an aldehyde, carboxylic acid, carboxylic acid ester, carboxylic acid amide, carboxylic acid halide, or cyano moiety or attached to another carbon substituted by a bromide or other leaving group such as a triflate, mesylate, chloride, iodide, or phosphonate. The methods for preparing such intermediates from intermediates typified by the carboxylic acid intermediate, 69, bromo intermediate, 76, or aldehyde intermediate, 70 described above are known by a typical chemist practitioner. The methods or types of heterocycles which may be constructed are described in the chemical literature. Some representative references for finding such heterocycles and their construction are included in reference 55 through 67 but should in no way be construed as limiting. However, examination of these references shows that many versatile methods are available for synthesizing diversely substituted heterocycles and it is apparent to one skilled in the art that these can be applied to prepare compounds of Formula I. Chemists well versed in the art can now easily, quickly, and routinely find numerous reactions for preparing heterocycles, amides, oximes or other substituents from the above mentioned starting materials by searching for reactions or preparations using a conventional electronic database such as Scifinder (American Chemical Society), Crossfire (Beilstein), Theilheimer, or Reaccs (MDS). The reaction conditions identified by such a search can then be employed using the substrates described in this application to produce all of the compounds envisioned and covered by this invention. In the case of amides, commercially available amines can be used in the synthesis. Alternatively, the above mentioned search programs can be used to locate literature preparations of known amines or procedures to synthesize new amines. These procedures are then carried out by one with typical skill in the art to provide the compounds of Formula I for use as antiviral agents.

As shown below in Scheme 32, step a13, suitable substituted azaindoles, such as the bromoazaindole intermediate, 76, may undergo metal mediated couplings with aryl groups, heterocycles, or vinyl stannanes to provide compounds of Formula I wherein $R_5$ is aryl, heteroaryl, or heteroalicyclic for example. The bromoazaindole intermediates, 76 (or azaindole triflates or iodides) may undergo Stille-type coupling with heteroarylstannanes as shown in Scheme 32, step a13. Conditions for this reaction are well known in the art and references 68-70 as well as reference 52 provide numerous conditions in addition to the specific examples provided in Scheme 33 and in the specific embodiments. It can be well recognized that an indole stannane could also couple to a heterocyclic or aryl halide or triflate to construct compounds of Formula I. Suzuki coupling (reference 71) between the bromo intermediate, 76, and a suitable boronate could also be employed and some specific examples are contained in this application.

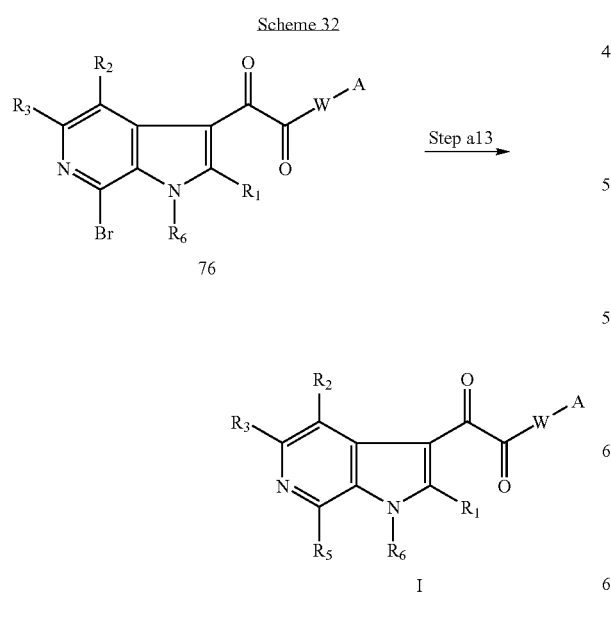

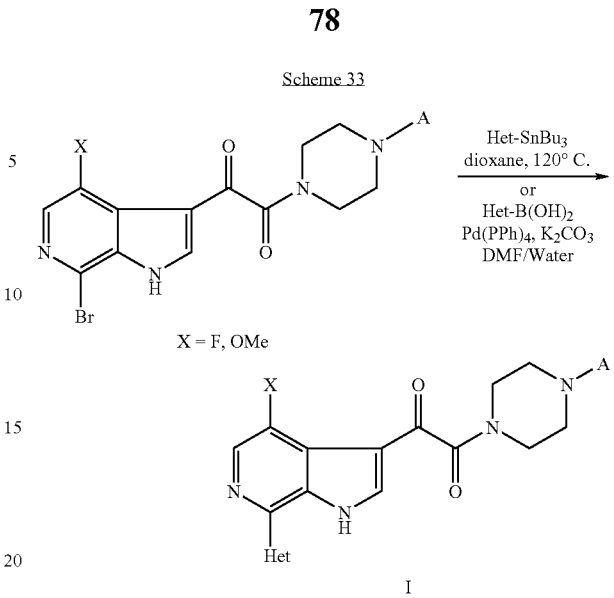

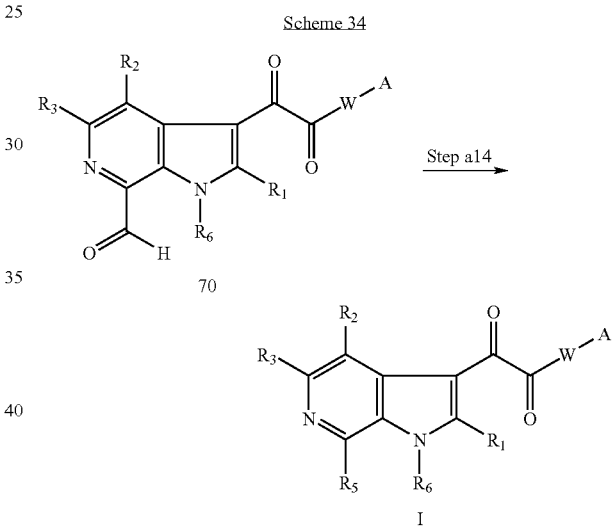

As shown in Scheme 34, step a14, aldehyde intermediates, 70, could be used to generate numerous compounds of Formula I. The aldehyde group could be a precursor for any of the substituents $R_1$ through $R_5$ but the transformation for $R_5$ is depicted above for simplicity. The aldehyde intermediate 70, could be reacted to become incorporated into a ring as described in the claims or be converted into an acyclic group. The aldehyde, 70, could be reacted with a Tosmic based reagent to generate oxazoles (references 42 and 43 for example). The aldehyde, 70, could be reacted with a Tosmic reagent and than an amine to give imidazoles as in reference 72 or the aldehyde intermediate, 70, could be reacted with hydroxylamine to give an oxime which is a compound of Formula I as described below. Oxidation of the oxime with NBS, t-butyl hypochlorite, or the other known reagents should provide the N-oxide which react with alkynes or 3 alkoxy vinyl esters to give isoxazoles of varying substitution. Reaction of the aldehyde intermediate 70, with the known reagent, 77 (reference 70) shown below under basic conditions would provide 4-aminotrityl oxazoles.

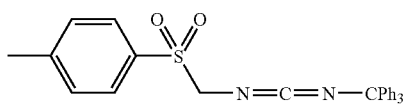

Removal of the trityl group should provide 4-amino oxazoles which could be substituted by acylation, reductive alkylation or alkylation reactions or heterocycle forming reactions. The trityl could be replaced with an alternate protecting group such as a monomethoxy trityl, CBZ, benzyl, or appropriate silyl group if desired. Reference 73 demonstrates the preparation of oxazoles containing a triflouoromethyl moiety and the conditions described therein demonstrates the synthesis of oxazoles with fluorinated methyl groups appended to them.

The aldehyde could also be reacted with a metal or Grignard (alkyl, aryl, or heteroaryl) to generate secondary alcohols. These would be efficacious or could be oxidized to the ketone with TPAP or $MnO_2$ or PCC for example to provide ketones of Formula I which could be utilized for treatment or reacted with metal reagents to give tertiary alcohols or alternatively converted to oximes by reaction with hydroxylamine hydrochlorides in ethanolic solvents. Alternatively the aldehyde could be converted to benzyl amines via reductive amination. An example of oxazole formation via a Tosmic reagent is shown below in Scheme 35. The same reaction would work with aldehydes at other positions and also in the 5 and 6 aza indole series.

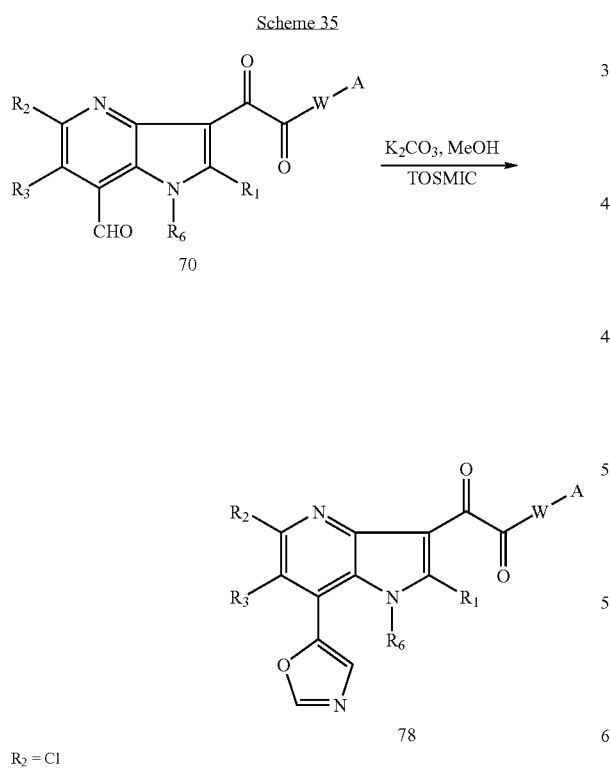

Scheme 36 shows in step a15, a cyano intermediate, such as 62, which could be directly converted to compounds of Formula I via heterocycle formation or reaction with organometallic reagents.

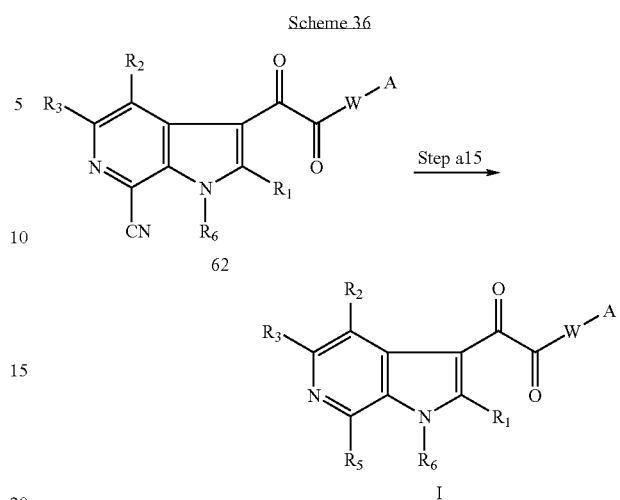

Scheme 37 shows a method for acylation of a cyanoindole intermediate of formula 65' with oxalyl chloride which would give acid chloride, 79', which could then be coupled with the appropriate amine in the presence of base to provide 80'.

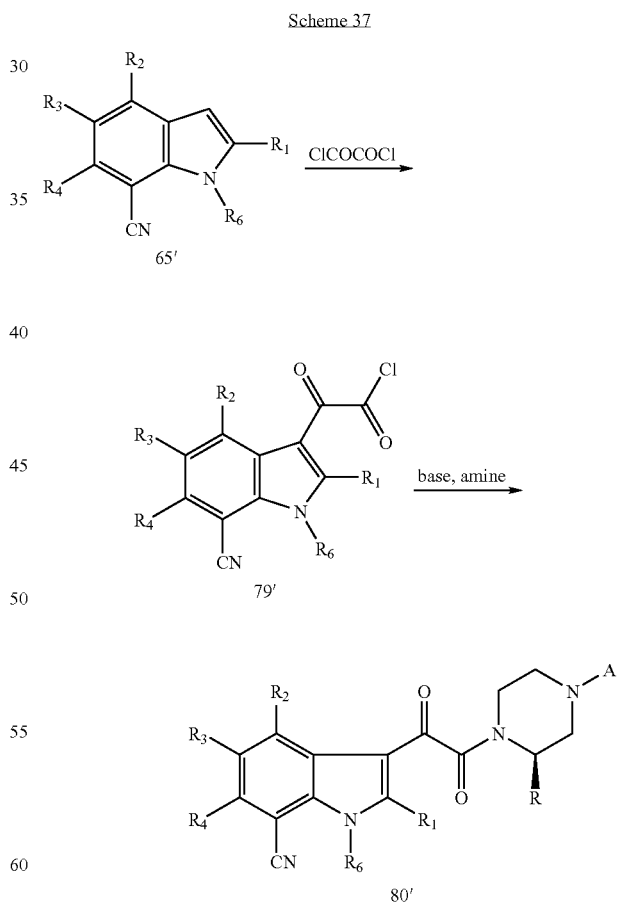

The nitrile intermediate, 80, could be converted to the tetrazole of formula 81, which could then be alkylated with trimethylsilyldiazomethane to give the compound of formula 82 (Scheme 38).

Scheme 38

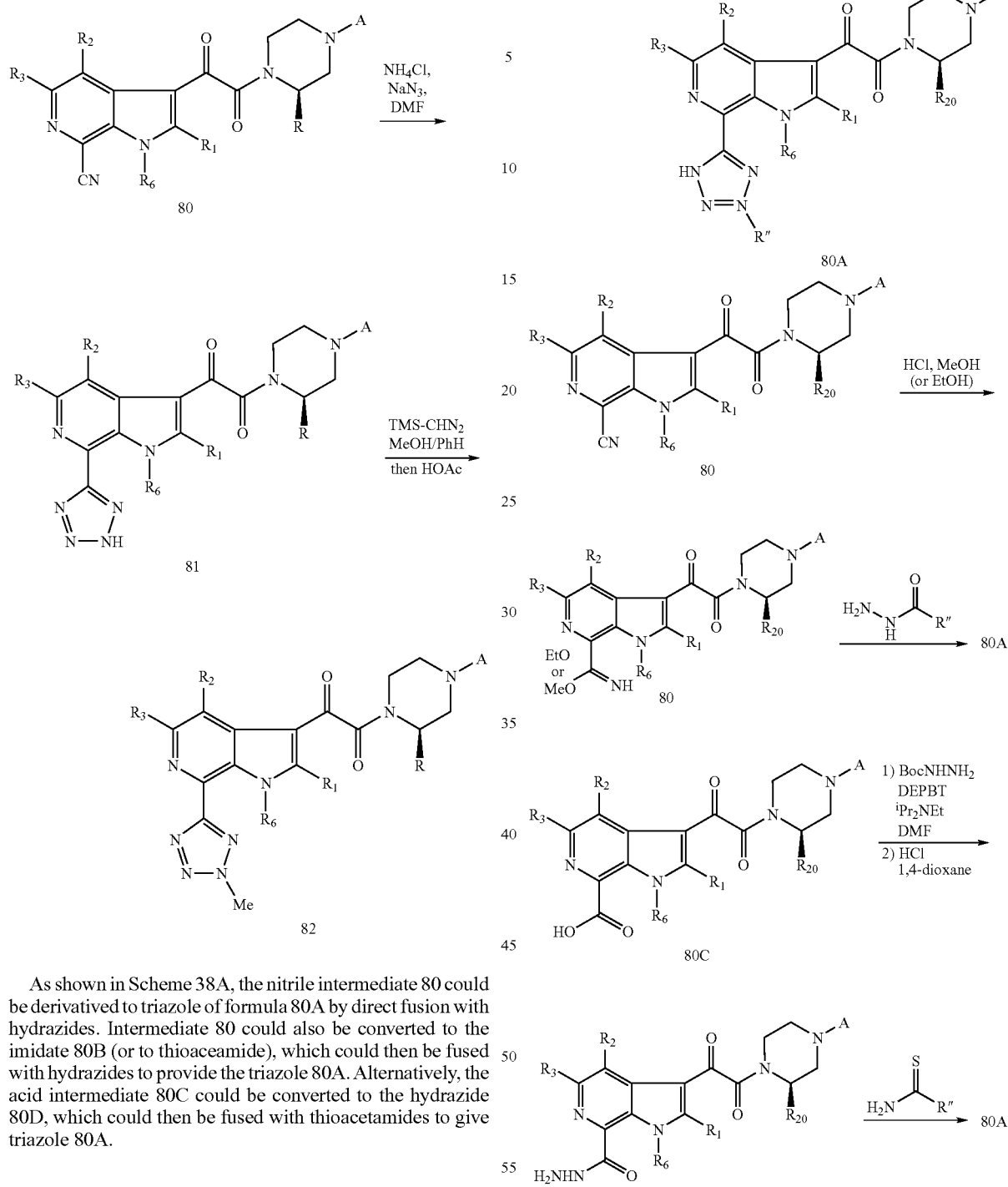

As shown in Scheme 38A, the nitrile intermediate 80 could be derivatived to triazole of formula 80A by direct fusion with hydrazides. Intermediate 80 could also be converted to the imidate 80B (or to thioaceamide), which could then be fused with hydrazides to provide the triazole 80A. Alternatively, the acid intermediate 80C could be converted to the hydrazide 80D, which could then be fused with thioacetamides to give triazole 80A.

Scheme 38A

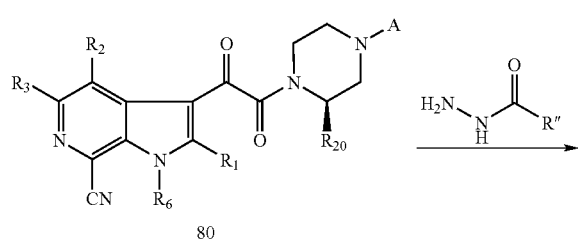

Tetrazole alkylation with alkyl halides would be carried out prior to azaindole acylation as shown in Scheme 39. Intermediate 65 could be converted to tetrazole, 83, which could be alkylated to provide 84. Intermediate 84 could then be acylated and hydrolyzed to provide 85 which could be subjected to amide formation conditions to provide 86. The group appended to the tetrazole may be quite diverse and still exhibit impressive potency.

Scheme 39

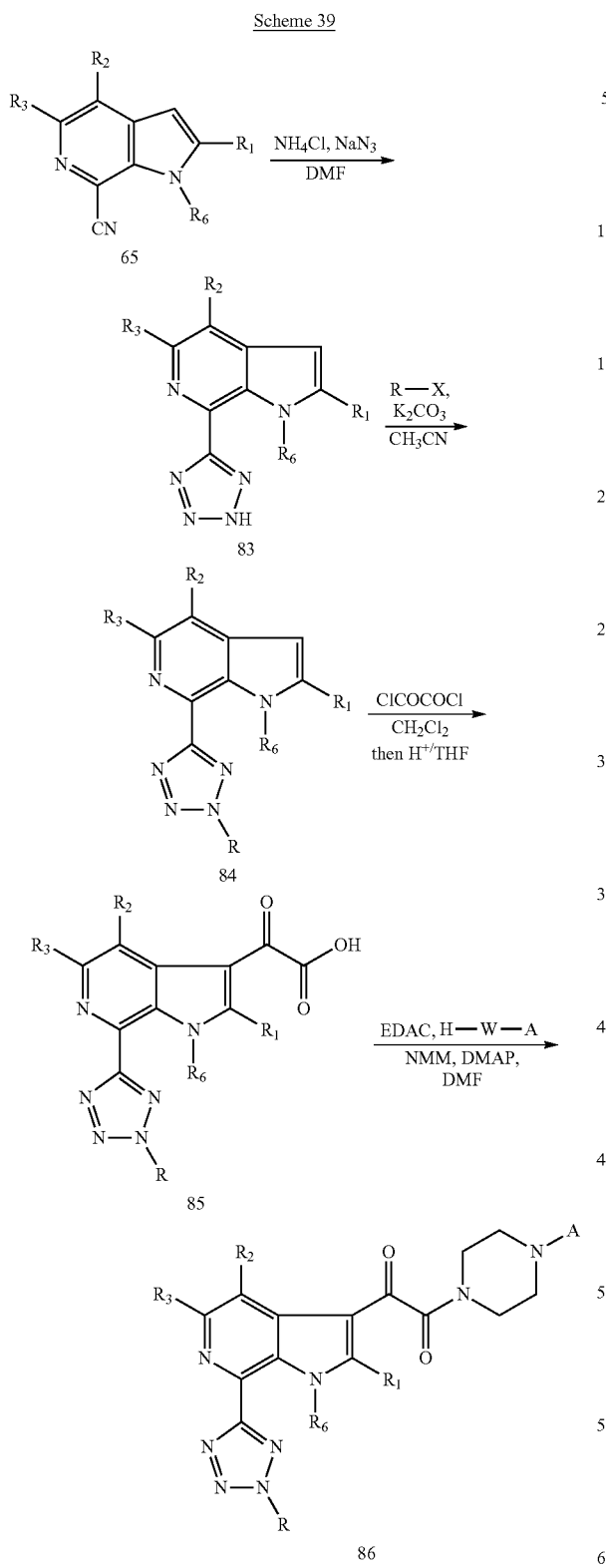

Scheme 40

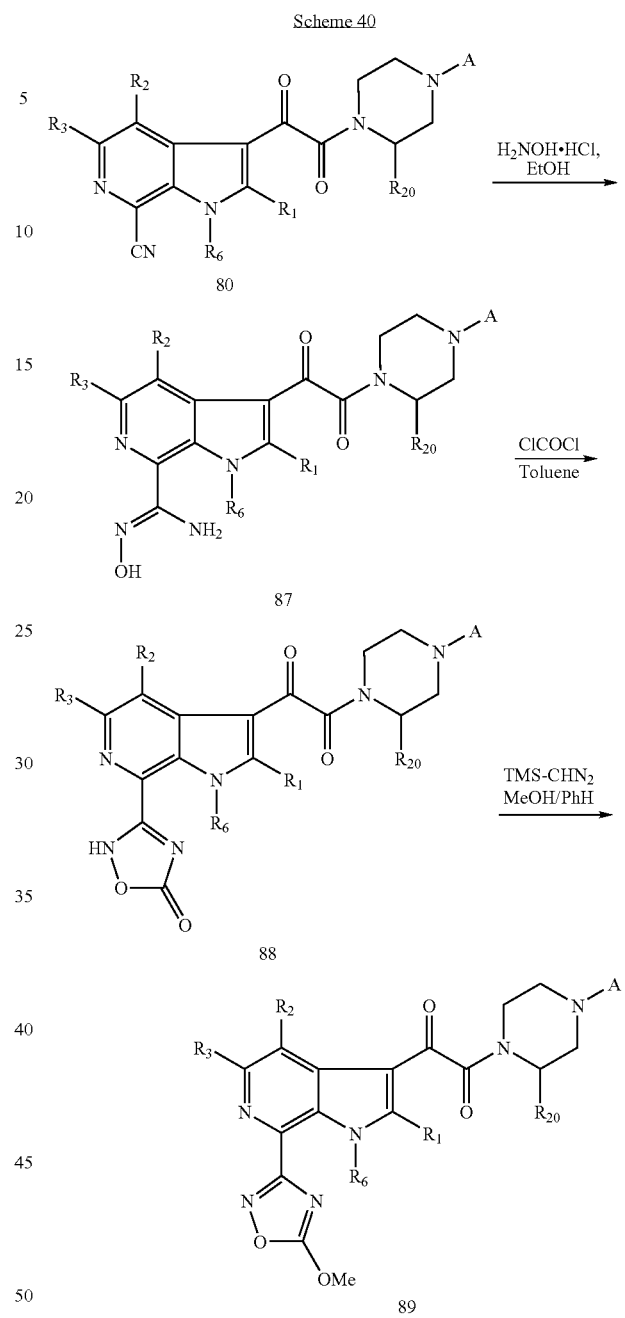

Scheme 40 shows that an oxadiazolone such as, 88, may be prepared by the addition of hydroxylamine to the nitrile, 80, followed by ring closure of intermediate 87 with phosgene. Alkylation of oxadiazolone, 88, with trimethylsilyldiazomethane would give the compound of formula 89.

A 7-cyanoindole, such as 80, could be efficiently converted to the imidate ester under conventional Pinner conditions using 1,4-dioxane as the solvent. The imidate ester can be reacted with nitrogen, oxygen and sulfur nucleophiles to provide C7-substituted indoles, for example: imidazolines, benzimidazoles, azabenzimidazoles, oxazolines, oxadiazoles, thiazolines, triazoles, pyrimidines and amidines etc. For example the imidate may be reacted with acetyl hydrazide with heating in a nonparticipating solvent such as dioxane, THF, or benzene for example. (aqueous base or aqueous base in an alcoholic solvent may need to be added to effect final dehydrative cyclization in some cases) to form a methyl triazine. Other hydrazines can be used. Triazines can also be installed via coupling of stannyl triazines with 4,5,6, or 7-bromo or chloro azaindoles. The examples give an example of the formation of many of these heterocycles.

REFERENCES (1) Das, B. P.; Boykin, D. W. *J. Med. Chem.* 1977, 20, 531.
(2) Czamy, A.; Wilson, W. D.; Boykin, D. W. *J. Heterocyclic Chem.* 1996, 33, 1393.
(3) Francesconi, I.; Wilson, W. D.; Tanious, F. A.; Hall, J. E.; Bender, B. C.; Tidwell, R. R.; McCurdy, D.; Boykin, D. W. *J. Med. Chem.* 1999, 42, 2260.

Scheme 41 shows addition of either hydroxylamine or hydroxylamine acetic acid to aldehyde intermediate 90 could provide oximes of Formula 91.

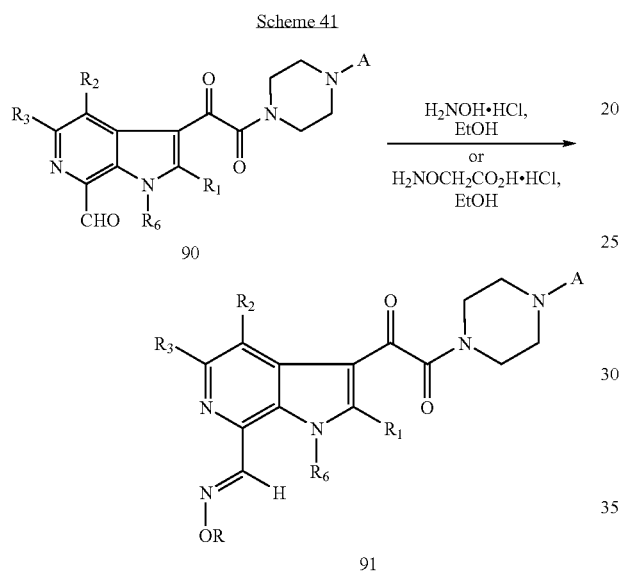

An acid may be a precursor for substituents $R_1$ through $R_5$ when it occupies the corresponding position such as $R_5$ as shown in Scheme 42.

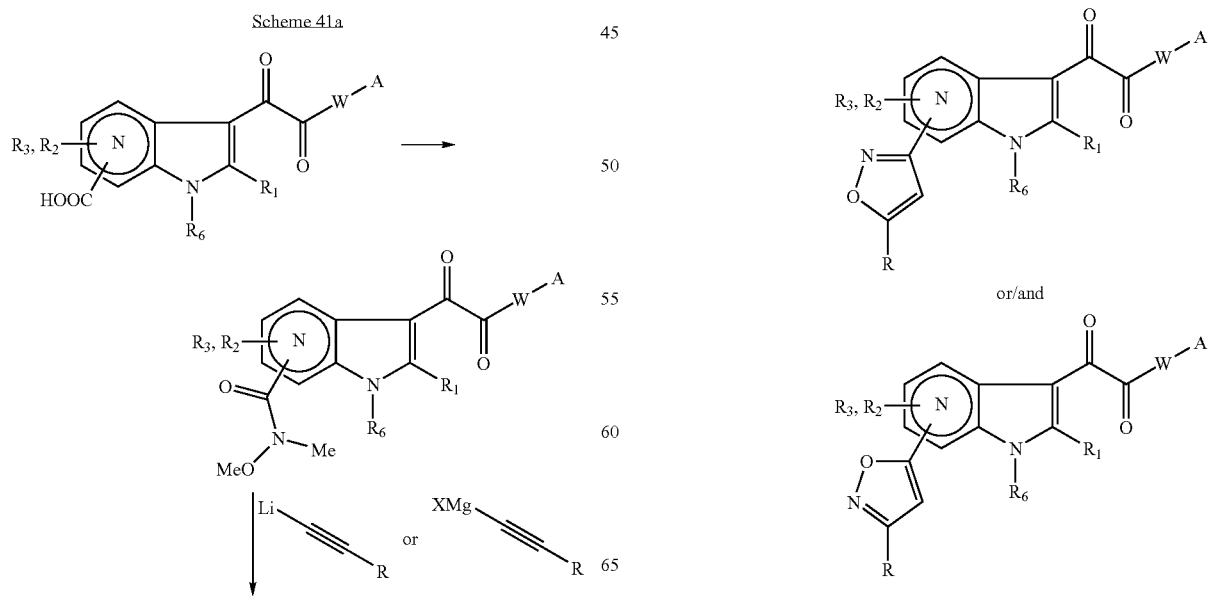

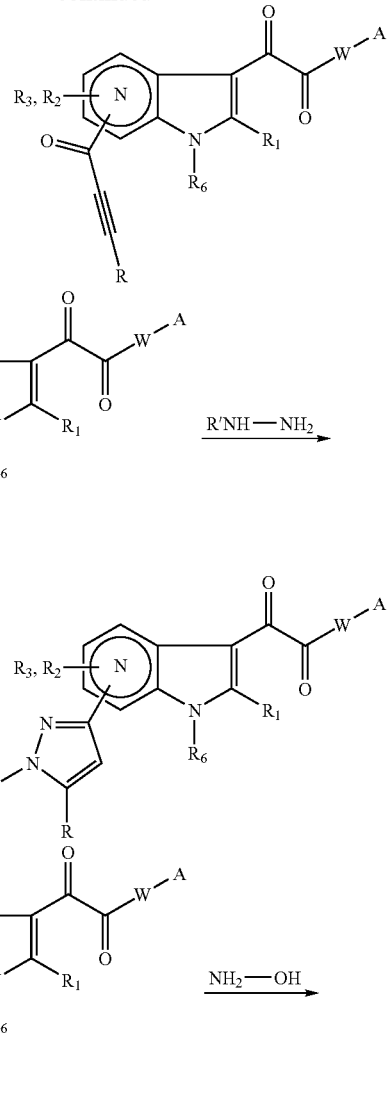

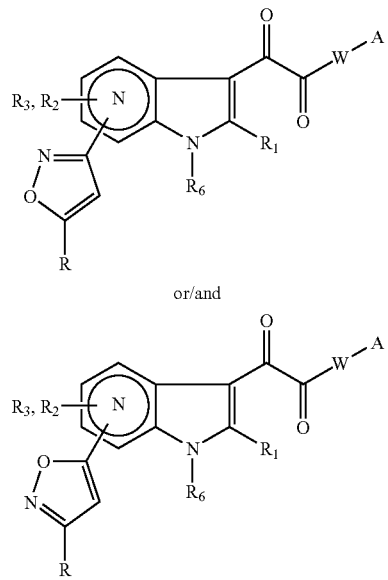

Scheme 42

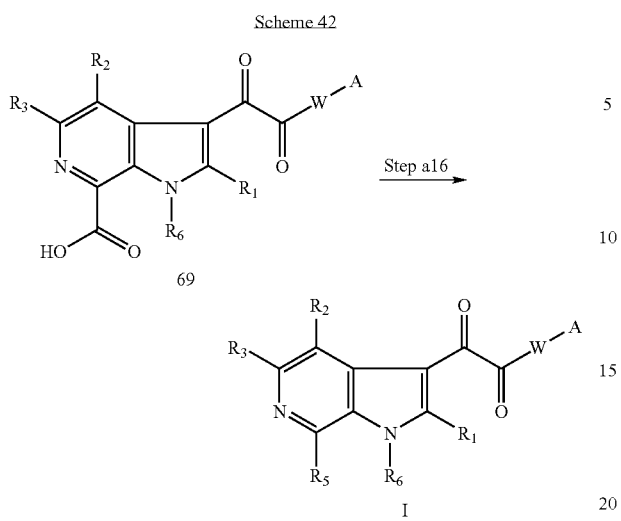

An acid intermediate, such as 69, could be used as a versatile precursor to generate numerous substituted compounds. The acid could be converted to hydrazonyl bromide and then a pyrazole via reference 74. One method for general heterocycle synthesis would be to convert the acid to an alpha bromo ketone (ref 75) by conversion to the acid chloride using standard methods, reaction with diazomethane, and finally reaction with HBr. The alpha bromo ketone could be used to prepare many different compounds of Formula I as it can be converted to many heterocycles or other compounds of Formula I. Alpha amino ketones can be prepared by displacement of the bromide with amines. Alternatively, the alpha bromo ketone could be used to prepare heterocycles not available directly from the aldeheyde or acid. For example, using the conditions of Hulton in reference 76 to react with the alpha bromo ketone would provide oxazoles. Reaction of the alpha bromoketone with urea via the methods of reference 77 would provide 2-amino oxazoles. The alpha bromoketone could also be used to generate furans using beta keto esters(ref 78-80) or other methods, pyrroles (from beta dicarbonyls as in ref 81 or by Hantsch methods (ref 82) thiazoles, isoxazoles and imidazoles (ref 83) example using literature procedures. Coupling of the aforementioned acid chloride with N-methyl-O-methyl hydroxylamine would provide a "Weinreb Amide" which could be used to react with alkyl lithiums or Grignard reagents to generate ketones. Reaction of the Weinreb anion with a dianion of a hydroxylamine would generate isoxazoles (ref 84). Reaction with an acetylenic lithium or other carbanion would generate alkynyl indole ketones, a transformation depicted in Scheme 41a. Reaction of this alkynyl intermediate with diazomethane or other diazo compounds would give pyrazoles (ref 85, Scheme 41a). Reaction with azide or hydroxylamine would give heterocycles after elimination of water. Nitrile oxides would react with the alkynyl ketone to give isoxazoles (ref 86). Reaction of the initial acid to provide an acid chloride using for example oxalyl chloride or thionyl chloride or triphenyl phosphine/carbon tetrachloride provides a useful intermediate as noted above. Reaction of the acid chloride with an alpha ester substituted isocyanide and base would give 2-substituted oxazoles (ref 87). These could be converted to amines, alcohols, or halides using standard reductions or Hoffman/Curtius type rearrangements.

Scheme 43 describes alternate chemistry for installing the oxoacetyl piperazine moiety onto the 3 position of the azaindoles. Step A''' in Scheme 43 depicts reaction with formaldehyde and dimethylamine using the conditions in Frydman, B.; Despuy, M. E.; Rapoport, H.; *J. Am. Chem. Soc.* 1965, 87, 3530 will provide the dimethylamino compound shown.

Step B''' shows displacement with potassium cyanide would provide the cyano derivative according to the method described in Miyashita, K.; Kondoh, K.; Tsuchiya, K.; Miyabe, H.; Imanishi, T.; *Chem. Pharm. Bull* 1997, 45(5), 932-935 or in Kawase, M.; Sinhababu, A. K.; Borchardt, R. T.; *Chem. Pharm. Bull.* 1990, 38(11), 2939-2946. The same transformation could also be carried out using TMSCN and a tetrabutylammonium flouride source as in Iwao, M.; Motoi, O.; *Tetrahedron Lett.* 1995, 36(33), 5929-5932. Sodium cyanide could also be utilized.

Scheme 43

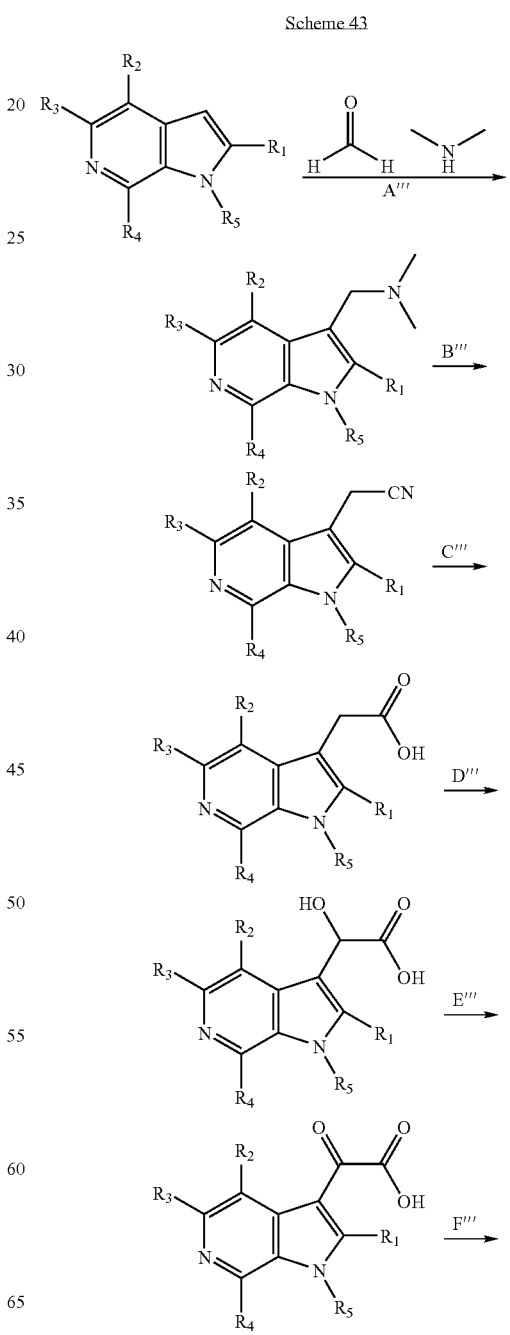

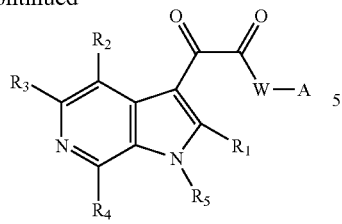

Step C''' of Scheme 43 depicts hydrolysis of the nitrile with sodium hydroxide and methanol would provide the acid via the methods described in Iwao, M.; Motoi, O.; *Tetrahedron Lett.* 1995, 36(33), 5929-5932 for example. Other basic hydrolysis conditions using either NaOH or KOH as described in Thesing, J.; et al.; *Chem. Ber.* 1955, 88, 1295 and Geissman, T. A.; Armen, A.; *J. Am. Chem. Soc.* 1952, 74, 3916. The use of a nitrilase enzyme to achieve the same transformation is described by Klempier N, de Raadt A, Griengl H, Heinisch G, *J. Heterocycl. Chem.,* 1992 29, 93, and may be applicable.

Step D''' of Scheme 43 depicts an alpha hydroxylation which may be accomplished by methods as described in Hanessian, S.; Wang, W.; Gai, Y.; *Tetrahedron Lett.* 1996, 37(42), 7477-7480; Robinson, R. A.; Clark, J. S.; Holmes, A. B.; *J. Am. Chem. Soc.* 1993, 115(22), 10400-10401 (KN(TMS)$_2$ and then camphorsulfonyloxaziridine or another oxaziridine; and Davis, F. A.; Reddy, R. T.; Reddy, R. E.; *J. Org. Chem.* 1992, 57(24), 6387-6389.

Step E''' of Scheme 43 shows methods for the oxidation of the alpha hydroxy ester to the ketone which may be accomplished according to the methods described in Mohand, S. A.; Levina, A.; Muzart, J.; *Synth. Comm.* 1995, 25 (14), 2051-2059. A preferred method for step E''' is that of Ma, Z.; Bobbitt, J. M.; *J. Org. Chem.* 1991, 56(21), 6110-6114 which utilizes 4-(NH-Ac)-TEMPO in a solvent such as $CH_2Cl_2$ in the presence of para toluenesulfonic acid. The method described in Corson, B. B.; Dodge, R. A.; Harris, S. A.; Hazen, R. K.; *Org. Synth.* 1941, I, 241 for the oxidation of the alpha hydroxy ester to the ketone uses $KMnO_4$ as oxidant. Other methods for the oxidation of the alpha hydroxy ester to the ketone include those described in Hunaeus; Zincke; *Ber. Dtsch Chem. Ges.* 1877, 10, 1489; Acree; *Am. Chem.* 1913, 50, 391; and Claisen; *Ber. Dtsch. Chem. Ges.* 1877, 10, 846.

Step F''' of Scheme 43 depicts the coupling reactions which may be carried out as described previously in the application and by a preferred method which is described in Li, H.; Jiang, X.; Ye, Y.-H.; Fan, C.; Romoff, T.; Goodman, M. *Organic Lett.*, 1999, 1, 91-93 and employs 3-(Diethoxyphosphoryloxy)-1,2,3-benzotriazin-4(3H)-one (DEPBT); a new coupling reagent with remarkable resistance to racemization.

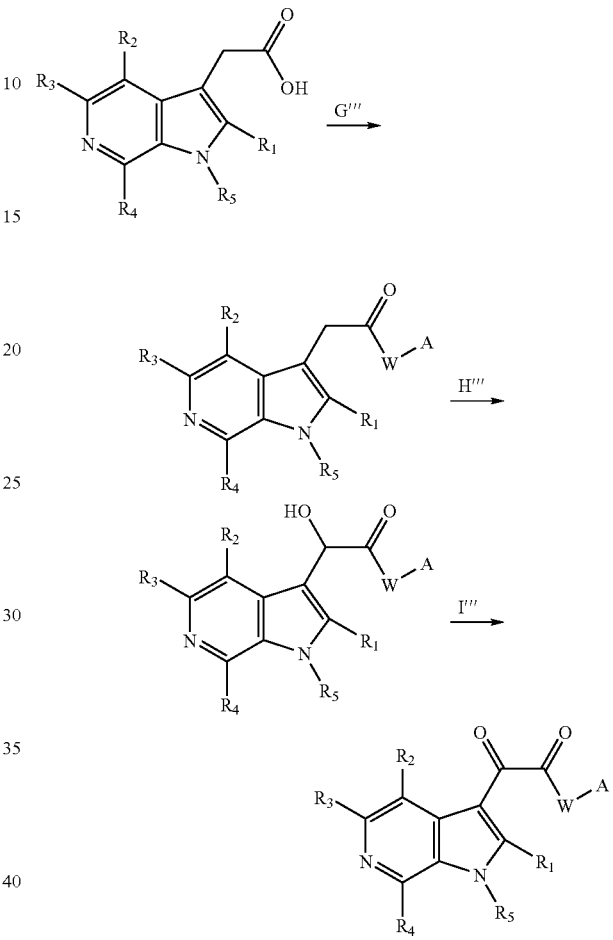

Scheme 44

Scheme 44 depicts the preparation of Formula I compounds by coupling HWC(O)A to the acid as described in Step F''' of Scheme 43, followed by hydroxylation as in Step D''' of Scheme 43 and oxidation as described in Step E''' of Scheme 43.

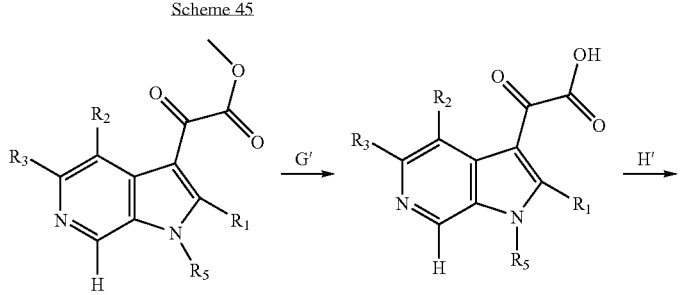

Scheme 45

-continued

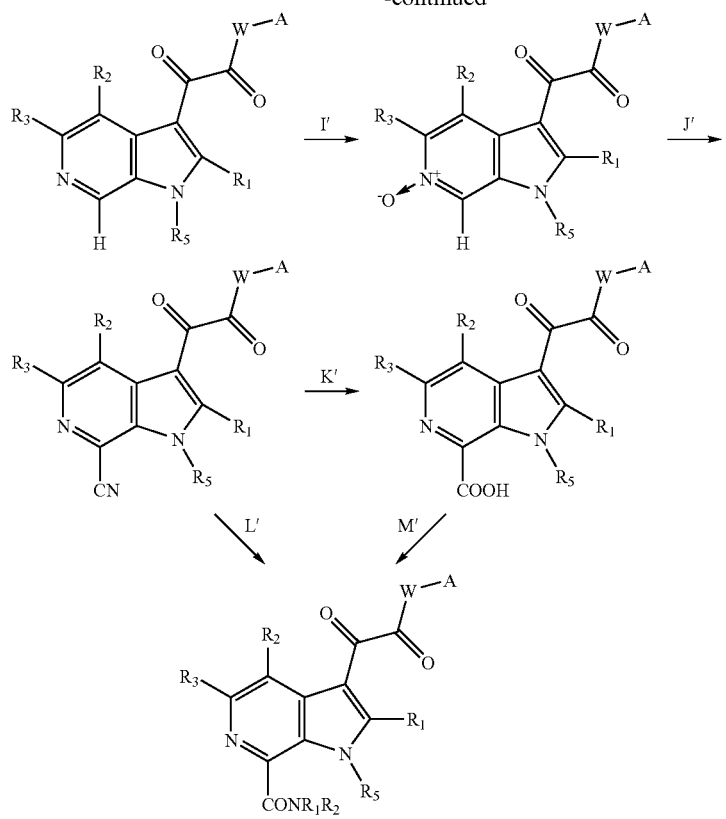

Scheme 45 depicts a method for the preparation which could be used to obtain amido compounds of Formula I. Step G' represents ester hydrolysis followed by amide formation (Step H' as described in Step F'" of Scheme 43). Step I' of Scheme 45 depicts the preparation of the N-oxide which could be accomplished according to the procedures in Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606; Suzuki, H.; Yokoyama, Y.; Miyagi, C.; Murakami, Y.; Chem. Pharm. Bull. 1991, 39(8), 2170-2172; and Ohmato, T.; Koike, K.; Sakamoto, Y.; Chem. Pharm. Bull. 1981, 29, 390. Cyanation of the N-oxide is shown in Step J' of Scheme 45 which may be accomplished according to Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606 and Suzuki, H.; Yokoyama, Y.; Miyagi, C.; Murakami, Y.; Chem. Pharm. Bull. 1991, 39(8), 2170-2172. Hydrolysis of the nitrile to the acid is depicted in Step K' of Scheme 45 according to procedures such as Shiotani, S.; Tanigucchi, K.; *J. Heterocycl. Chem.* 1996, 33(4), 1051-1056; Memoli, K. A.; *Tetrahedron Lett.* 1996, 37(21), 3617-3618; Adolfsson, H.; Waernmark, K.; Moberg, C.; *J. Org. Chem.* 1994, 59(8), 2004-2009; and El Hadri, A.; Leclerc, G.; *J. Heterocycl. Chem.* 1993, 30(3), 631-635. Step L' of Scheme 45 depicts a method which could be utilized for the preparation of amido compounds of Formula I from the cyano derivative which may be accomplished according to procedures described in Shiotani, S.; Taniguchi, K.; J. *Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; and Macor, J. E.; Post, R.; Ryan, K.; *J. Heterocycl. Chem.* 1992, 29(6), 1465-1467. Step M' of Scheme 45 shows a method which could be used for the preparation of amido compounds of Formula I from the acid derivative which may be accomplished according to procedures described in Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans* 1 1997, 14, 2083-2088; Langry, K. C.; *Org. Prep. Proced. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014 and Bhattacharjee, A.; Mukhopadhyay, R.; Bhattacharjya, A.; *Indian J. Chem.*, Sect B 1994, 33(7), 679-682.

Scheme 46

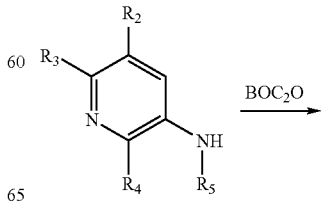

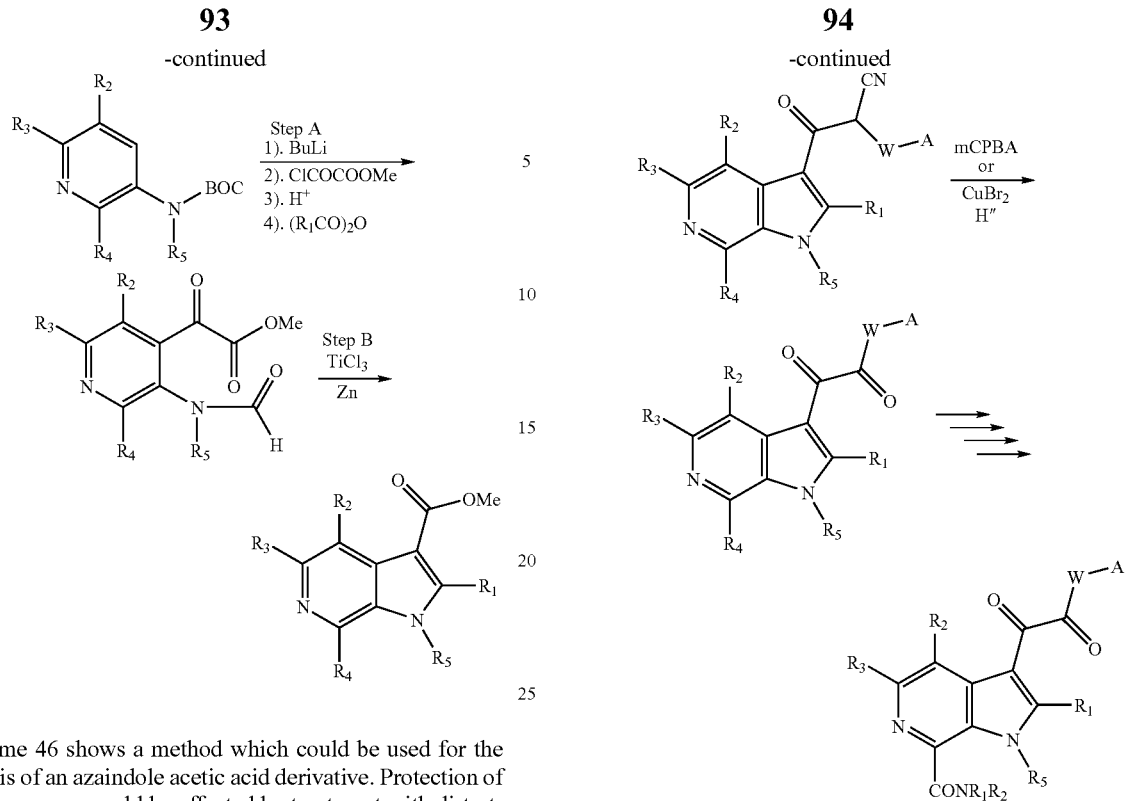

Scheme 46 shows a method which could be used for the synthesis of an azaindole acetic acid derivative. Protection of the amine group could be effected by treatment with di-tert-butyldicarbonate to introduce the t-Butoxycarbonyl (BOC) group. Introduction of the oxalate moiety may then be accomplished as shown in Step A of Scheme 46 according to the procedures described in Hewawasam, P.; Meanwell, N. A.; Tetrahedron Lett. 1994, 35(40), 7303-7306 (using t-Buli, or s-buli, THF); or Stanetty, P.; Koller, H.; Mihovilovic, M.; J. Org. Chem. 1992, 57(25), 6833-6837 (using t-Buli). The intermediate thus formed could then be cyclized to form the azaindole as shown in Step B of Scheme 46 according to the procedures described in Fuerstner, A.; Ernst, A.; Krause, H.; Ptock, A.; Tetrahedron 1996, 52(21), 7329-7344 (using. TiCl3, Zn, DME); or Fuerstner, A.; Hupperts, A.; J. Am. Chem. Soc. 1995, 117(16), 4468-4475 (using Zn, excess Tms-Cl, TiCl3 (cat.), MeCN).

Scheme 49 provides another route to azaindole intermediates which could then be further elaborated to provide compounds of Formula I, such as the amido derivatives shown. Steps G" and H" of Scheme 49 could be carried out according to the procedures described in Takahashi, K.; Shibasaki, K.; Ogura, K.; Iida, H.; Chem. Lett. 1983, 859; and Itoh, N.; Chem. Pharm. Bull. 1962, 10, 55. Elaboration of the intermediate to the amido compound of Formula I could be accomplished as previously described for Steps I'-M' of Scheme 45.

Scheme 49

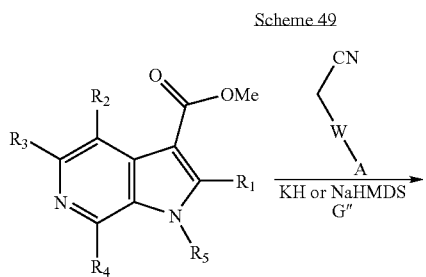

Scheme 50 shows the preparation of azaindole oxalic acid derivatives. The starting materials in Scheme 50 could be prepared according to Tetrahedron Lett. 1995, 36, 2389-2392. Steps A, B, C, and D' of Scheme 50 may be carried out according to procedures described in Jones, R. A.; Pastor, J.; Siro, J.; Voro, T. N.; Tetrahedron 1997, 53(2), 479-486; and Singh, S. K.; Dekhane, M.; Le Hyaric, M.; Potier, P.; Dodd, R. H.; Heterocycles 1997, 44(1), 379-391. Step E' of Scheme 50 could be carried out according to the procedures described in Suzuki, H.; Iwata, C.; Sakurai, K.; Tokumoto, K.; Takahashi, H.; Hanada, M.; Yokoyama, Y.; Murakami, Y.; Tetrahedron 1997, 53(5), 1593-1606; Suzuki, H.; Yokoyama, Y.; Miyagi, C.; Murakami, Y.; Chem. Pharm. Bull. 1991, 39(8), 2170-2172; Hagen, T. J.; Narayanan, K.; Names, J.; Cook, J. M.; J. Org. Chem. 1989, 54, 2170; Murakami, Y.; Yokoyama, Y.; Watanabe, T.; Aoki, C.; et al.; Heterocycles 1987, 26, 875; and Hagen, T. J.; Cook, J. M.; Tetrahedron Lett. 1988, 29(20), 2421. Step F' of Scheme 50 shows the conversion of the phenol to a fluoro, chloro or bromo derivative. Conversion of the phenol to the fluoro derivative could be carried out according to procedures described in Christe, K. O.; Pavlath, A. E.; J. Org. Chem. 1965, 30, 3170; Murakami, Y.; Aoyama, Y.; Nakanishi, S.; Chem. Lett. 1976, 857; Christe, K. O.; Pavlath, A. E.; J. Org. Chem. 1965, 30, 4104; and Christe, K. O.; Pavlath, A. E.; J. Org. Chem. 1966, 31, 559. Conversion of the phenol to the chloro derivative could be carried out according to procedures described in Wright, S. W.; Org. Prep. Proc. Int. 1997, 29(1), 128-131; Hartmann, H.; Schulze, M.; Guenther, R.; Dyes Pigm 1991, 16(2), 119-136; Bay, E.; Bak, D. A.; Timony, P. E.; Leone-Bay, A.; J. Org. Chem. 1990, 55, 3415; Hoffmann, H.; et al.; Chem. Ber. 1962, 95, 523; and Vanallan, J. A.; Reynolds, G. A.; J. Org. Chem. 1963, 28, 1022. Conversion of the phenol to the bromo derivative could be carried out according to procedures described in Katritzky, A. R.; Li, J.; Stevens, C. V.; Ager, D. J.; Org. Prep. Proc. Int. 1994, 26(4), 439-444; Judice, J. K.; Keipert, S. J.; Cram, D. J.; J. Chem. Soc., Chem. Commun. 1993, 17, 1323-1325; Schaeffer, J. P.; Higgins, J.; J. Org. Chem. 1967, 32, 1607; Wiley, G. A.; Hershkowitz, R. L.; Rein, R. M.; Chung, B. C.; J. Am. Chem. Soc. 1964, 86, 964; and Tayaka, H.; Akutagawa, S.; Noyori, R.; Org. Syn. 1988, 67, 20.

Scheme 50

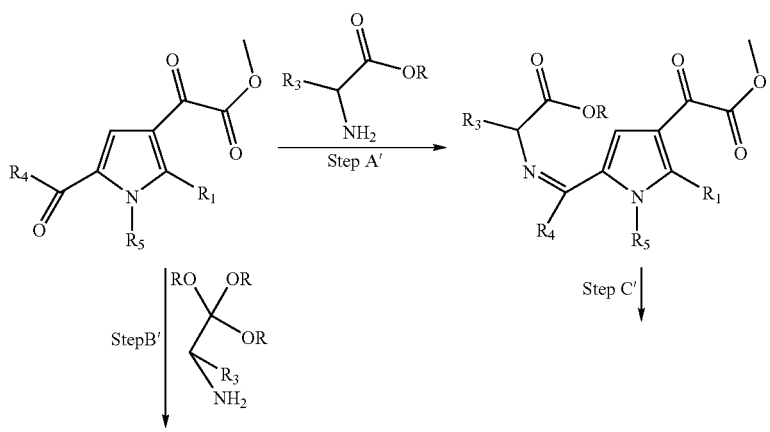

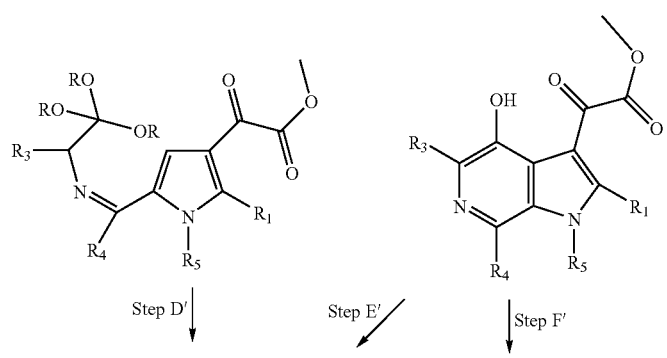

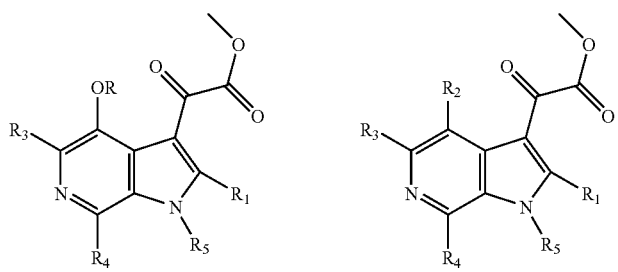

Scheme 51 describes methods for the preparation of aza-indole acetic acid derivatives by the same methods employed for the preparation of azaindole oxalic acid derivatives as shown and described in Scheme 50 above. The starting material employed in Scheme 51 could be prepared according to *J. Org. Chem.* 1999, 64, 7788-7801. Steps A", B", C", D", and E" of Scheme 51 could be carried out in the same fashion as previously described for Steps A', B', C', D', and E' of Scheme 50.

Scheme 51

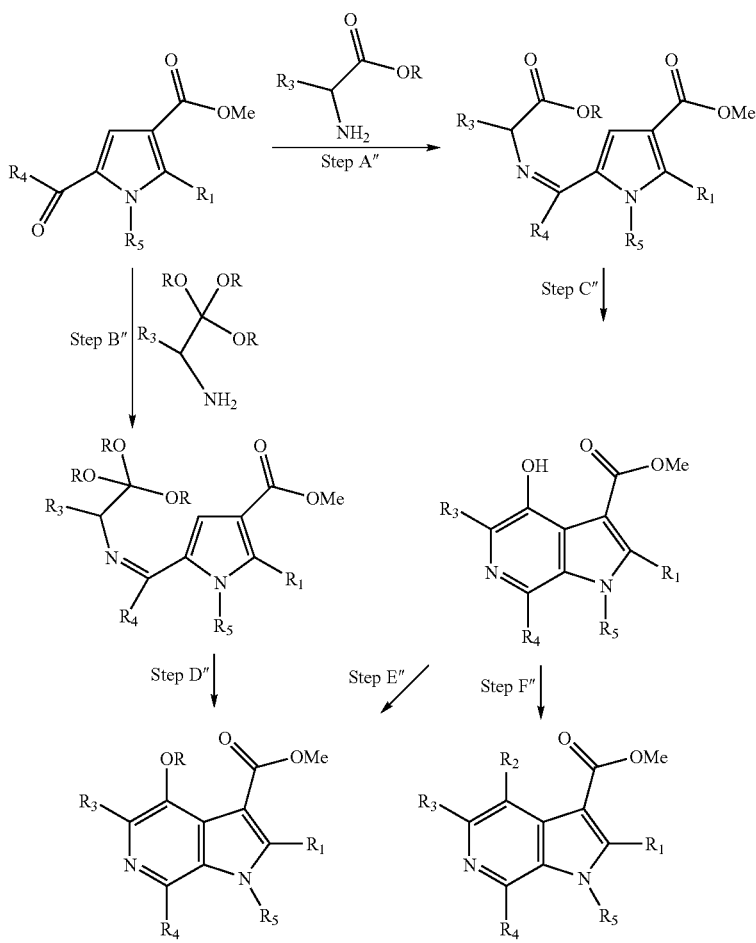

As shown in Scheme 52, the pieces HW-A can be prepared by a number of different methods. One useful way is by reacting a mono protected piperazine with a heteroaryl chloride, bromide, iodide, or triflate. This reaction is typically carried out at elevated temperature (50 to 250 degrees celsius) in a solvent such as ethylene glycol, DME, dioxane, NMP, or DMF. A tertiary amine base such as triethyl amide or diisopropyl ethyl amine is typically employed and usually 2 to 4 equivalents are employed. At least 2 equivalents are used if a salt of HWA is utilized. The piperazine is typically monoprotected with a BOC group since this material is commercially available. Removal of the Boc group is typically done using HCl (typically 1 to 6N) in dioxane to provide the HCl salt. TFA may also be used to generate the TFA salt. Alternatively, the conditions for coupling heterocycles using copper catalysis discussed earlier in Scheme 12 may be used to couple W to A via displacement of X in X-A. Alternatively Palladium catalysis in the presence of a bidentate catalyst via the procedures of Buckwald or the use of a ferrocenyl catalyst via the methods of Hartwig could be used to couple the piperazine to the heteroaryl (A).

The preparations of the naphthyridine (X-A) starting materials have been previously disclosed in the following references:
(1) Rapoport, H.; Batcho, A. D. J. Org. Chem. 1963, 28, 1753.
(2) Baldwin, J. J.; Mensler, K.; Ponticello, G. S. J. Org. Chem. 1978, 43, 4878.
(3) Baldwin, J. J.; Mensler, K.; Ponticello, G. S. U.S. Pat. No. 4,176,183.

Scheme 52

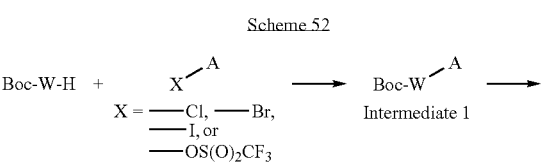

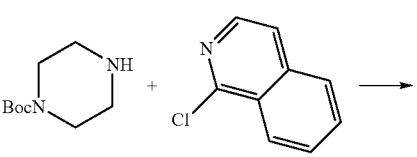

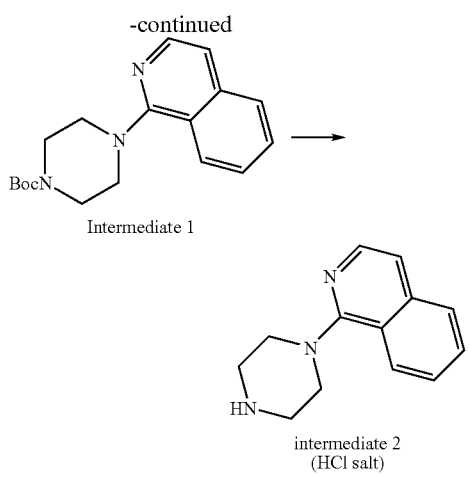

Intermediate 1 intermediate 2
(HCl salt)

Scheme 53

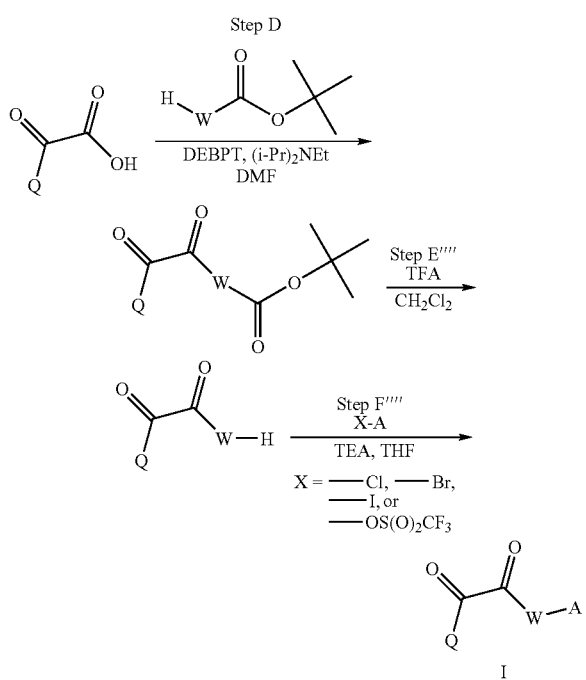

Scheme 53 describes how a protected piperazine can be coupled to Q-COOH via standard methodology in described in step D of Schemes A and 1a-1e. Conditions for removal of the amine protecting group which could be tBoc or other groups is protecting group specific. As shown in Scheme 53 where tBoc is the preferred protecting group used to exemplify the strategy, standard conditions for removal such as TFA in dichloromethane or alternatively aqueous HCl can provide the free amine. The free amine is coupled to A using the conditions described in Scheme 52 for step F''''.

Chemistry

All $^1$H NMR spectra were recorded on a 500 MHz Bucker DRX-500f instrument, unless otherwise stated (e.g. 300 MHz Bucker DPX-300). "app" was used as a abbreviation for "apparent" in the $^1$H NMR data. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (i.e. Compound Identification)

Note: column A is used unless otherwise indicated in the preparation of intermediates or examples.

| | |
|---|---|
| Column A: | YMC ODS-A S7 3.0 × 50 mm column |
| Column B: | PHX-LUNA C18 4.6 × 30 mm column |
| Column C: | XTERRA ms C18 4.6 × 30 mm column |
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Gradient: | 100% Solvent A/0% Solvent B to 0% Solvent A/ 100% Solvent B $R_t$ in min. |
| Gradient time: | 2 minutes |
| Hold time: | 1 minute |
| Flow rate: | 5 mL/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Compounds purified by preparative HPLC were diluted in MeOH and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

Preparative HPLC Method (i.e. Compound Purification)

Purification Method Initial gradient (40% B, 60% A) ramp to final gradient (100% B, 0% A) over 20 minutes, hold for 3 minutes (100% B, 0% A)

| | |
|---|---|
| Solvent A: | 10% MeOH/90% $H_2O$/0.1% Trifluoroacetic Acid |
| Solvent B: | 10% $H_2O$/90% MeOH/0.1% Trifluoroacetic Acid |
| Column: | YMC C18 S5 20 × 100 mm column |
| Detector Wavelength: | 220 nm |

General and Example Procedures Excerpted from Analogous Oxoacetyl Piperazineamide Applications The procedures described references 93-95 and 106 are applicable example procedures for synthesizing the compounds of formula I in this application and the intermediates used for their synthesis. The following guidelines are illustrative but not limiting.

The general Bartoli (vinyl Magnesium bromide) methods for preparing functionalized indoles or azaindoles described in the applications can be utilized for preparing new indoles or azaindoles from the appropriate nitro aromatics or heteroaromatics for this application. For example, in PCT/US02/00455, the general procedure for preparing intermediate 2a (7-chloro-6-azaindole) from 2-chloro-3-nitro pyridine can be considered a general procedure illustrating conditions which can be used to prepare azaindoles for this application. Similarly, the general procedure from the same application to prepare intermediate 3a, Methyl (7-chloro-6azaindol-3-yl) oxoacetate, provides experimental details for carrying our Step B of (Schemes 1-7 in this application). Similarly, the general procedure from the same application to prepare intermediate 4a (Potassium(7-chloro-6azaindol-3-yl) oxoacetate, provides an example of the general method for hydrolying oxoacteic esters (Step C of Schemes 1-1c, 3-7). General procedures for carrying out the same steps in the indole series are provided in references 93 and 95. An example Bartoli reaction preparation of a functionalized indole is given in the preparation of intermediate 1 of PCT/US01/20300 where the preparation of 4-fluoro-7-bromo-azaindole is described from 2-fluoro-5-bromonitrobenzene. The following Scheme provides an example of the preparation of 4,7-dibromo-6-azaindole via an extension of this methodology.

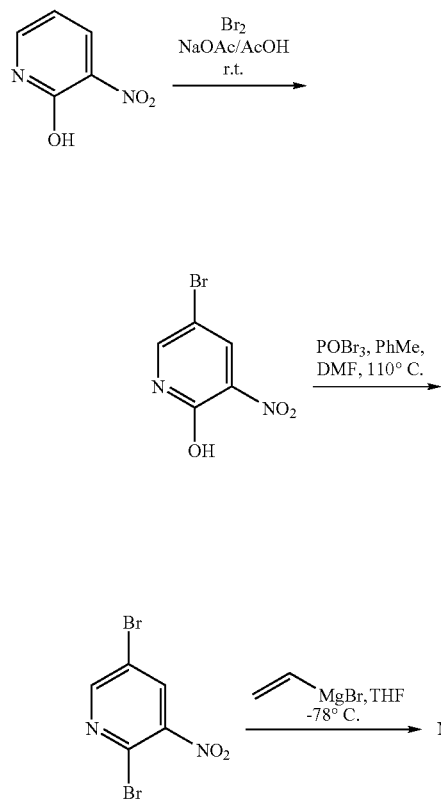

Subsequent procedures for the preparation of intermediates 2 and 3 describe procedures for adding the alkyl oxoacetate and then for ester hydrolysis to provide the carboxylate salt and then the carboxylic acid after acidification. Thus the chemistry described in the incorporated previous applications for preparing azaindole and indole intermediates is applicable since the desired compounds are the same.

Procedures for carrying out the coupling of the indole or azaindole oxoacetic acids to piperazine amides are described in the references 93-95 and 106. These can also be used as procedures for preparing the N-heteroaryl piperazines of this invention by taking the experimental procedures and substituting a N-heteroaryl piperazine or mono protected piperazine in place of the piperazine amide. This is possible because both groups have a free amine with relatively similar activity and since the other portions of both the piperazine benzamide and the N-heteroaryl piperazine are relatively unreactive to many conditions, they can be installed similarly. For example, the preparation of intermediate 4 of PCT/US01/20300 and the preparation of intermediate 5a of PCT/US02/00455 describe couplings of a piperazine benzamide or methyl piperazine benzamide to an indole or azaindole oxoacetic acid or carboxylate salt respectively. (The acid or salt can be used interchangeably). These same procedures can be used directly for the preparation of the compounds of this invention by substituting the desired N-heteroaryl piperazines for the piperazine amides utilized in earlier applications.

Preparation of Intermediate 5a from PCT/US02/00455

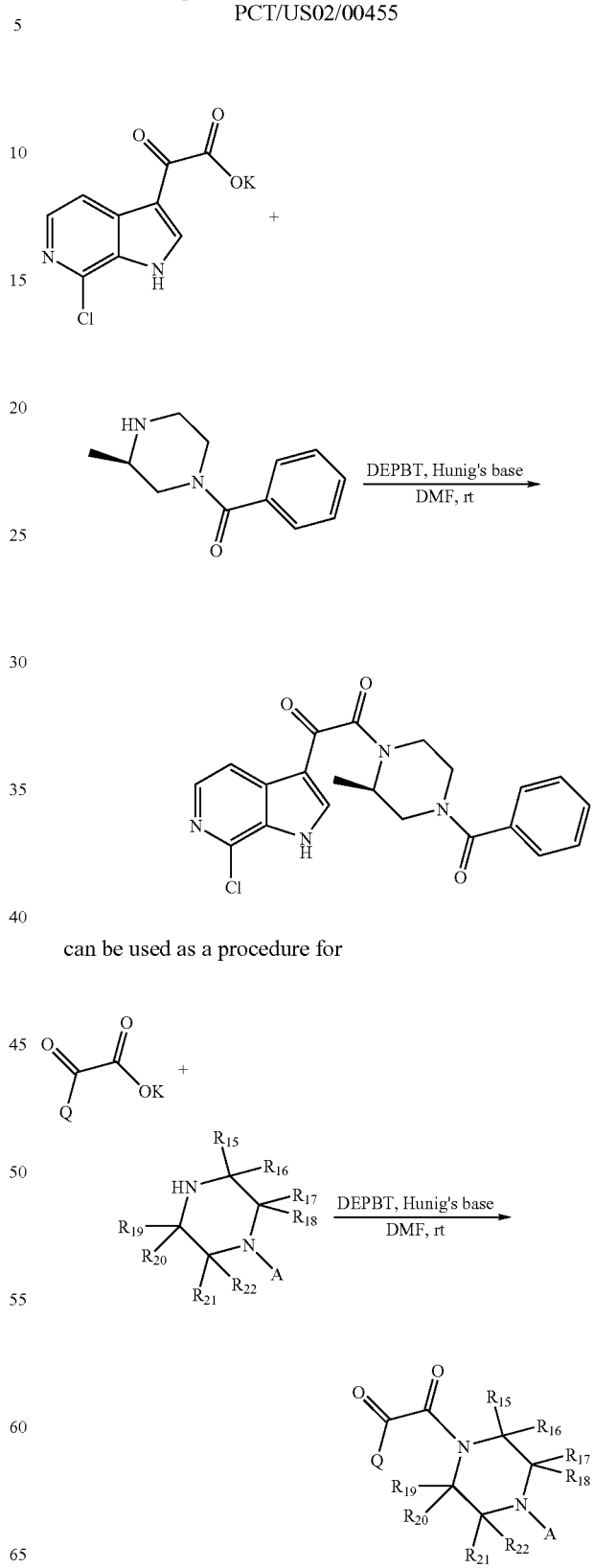

can be used as a procedure for

Preparation of Intermediate 4 from PCT/US01/20300

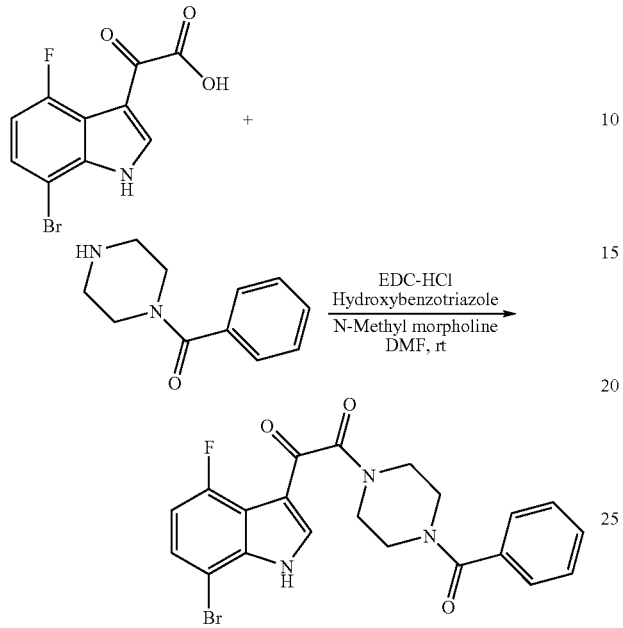

can be used as a procedure for

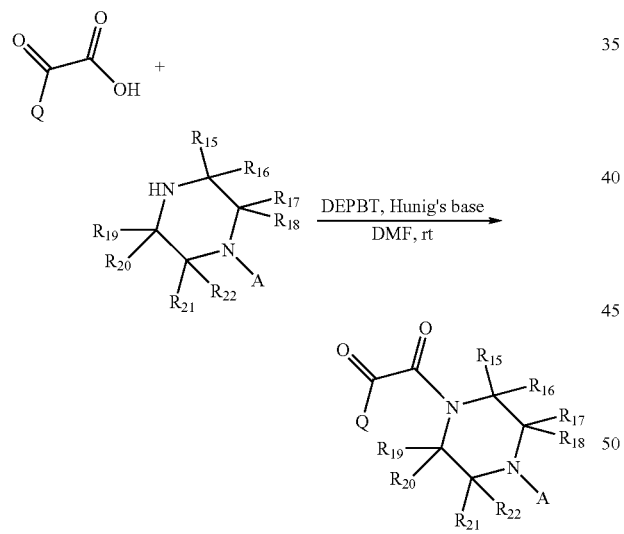

Once attached via a similar amide bond, both the piperazine benzamides and the N-heteroaryl piperazines moieties are relatively inert and thus reaction conditions used for functionalizing indoles or azaindoles in the presence of piperazine benzamides are useful for carrying out the same tranformations in the presence of the N-heteroaryl piperazines. Thus the methods and transformations described in references 93-95 and 106 including the experimental procedures which describe methods to functionalize the indole or azaindole moiety in the piperazine amide series are generally applicable for construction and functionalization of the N-heteroaryl piperazines of this invention. These same applications describe general methods and specific preparations for obtaining stannane and boronic acid reagents used for synthesizing the compounds of Formula I.

Preparation of Example 1 FROM PCT/US02/00455

Typical Boron/Palladium Coupling Procedure

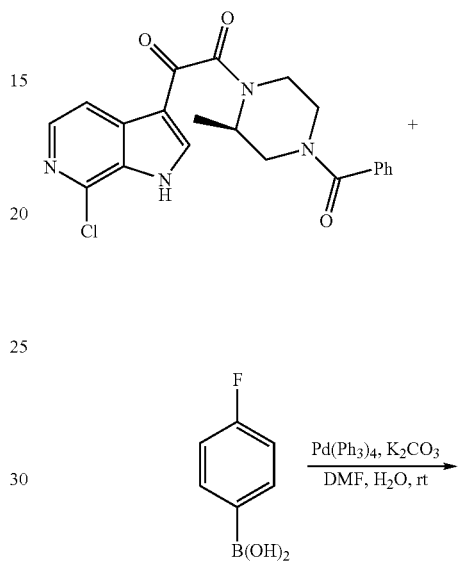

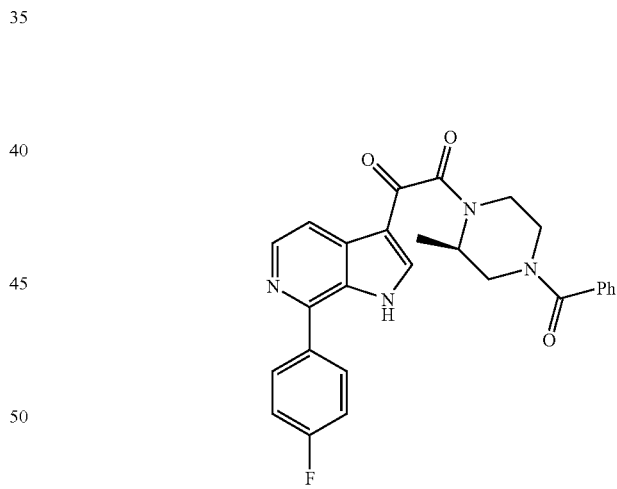

can be used as a procedure for

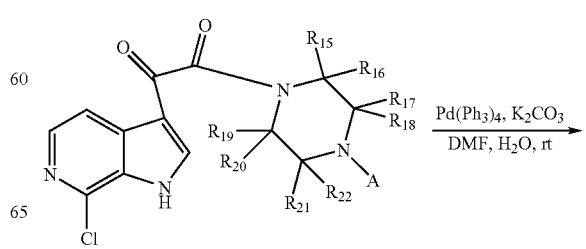

-continued
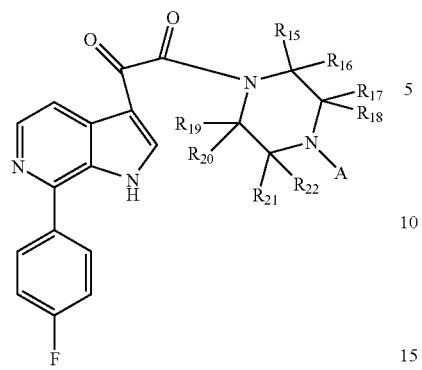
or even as a procedure for
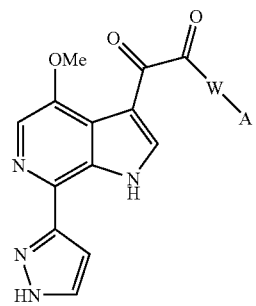
can be used as a procedure for
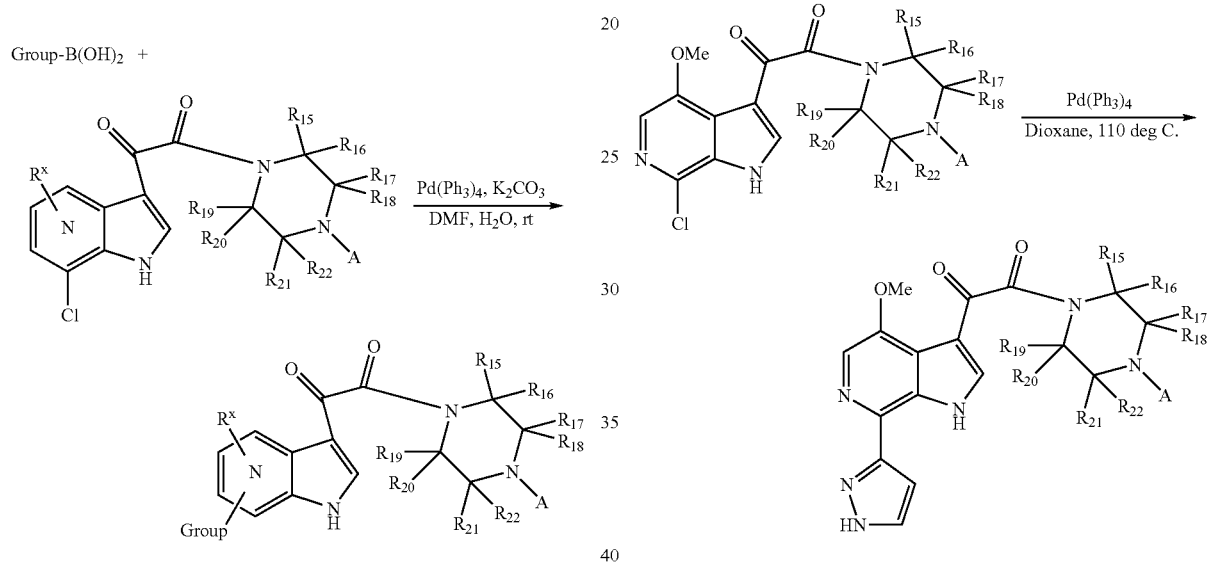
or even as a procedure for
Preparation of Example 39 from PCT/US02/00455
An example of the typical stannane/palladium coupling procedure
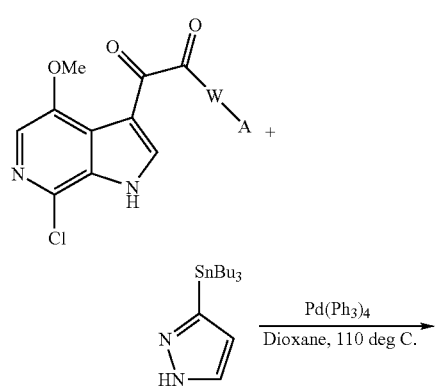
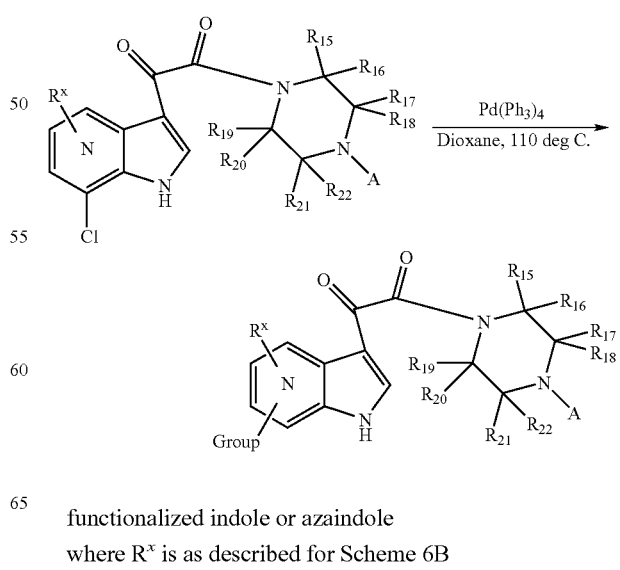
functionalized indole or azaindole
where $R^x$ is as described for Scheme 6B

Preparation of Example 20 from PCT/US01/20300

An example to show how functionalization procedures of oxoacetyl piperazine benzamides can be used to carry out similar tranformations in the corresponding piperidine alkenes

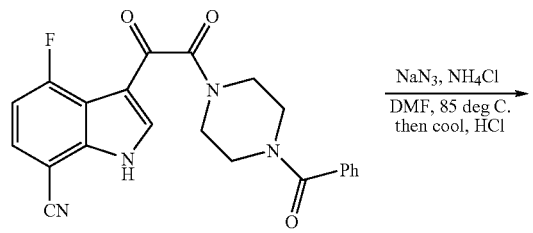

can be used as a procedure for

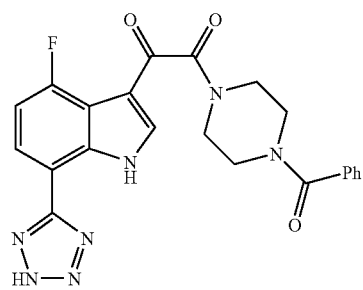

or even as a procedure for

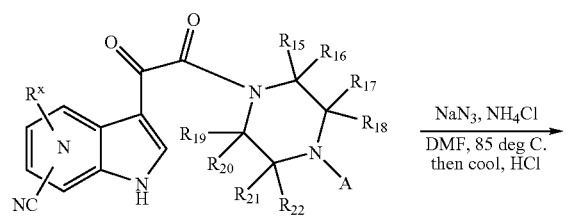

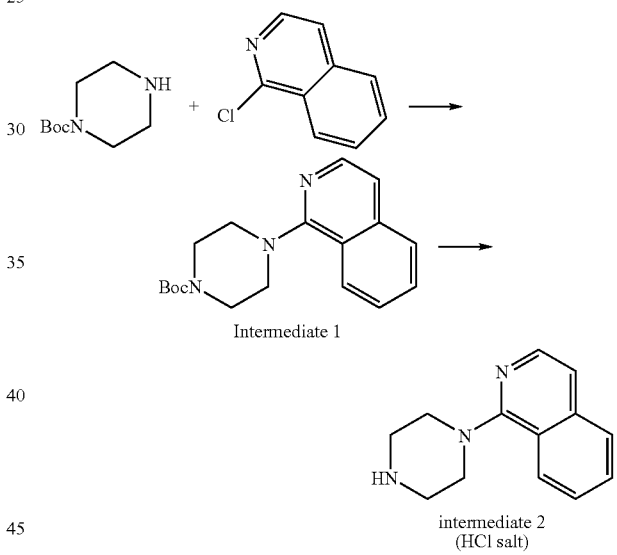

functionalized indole or azaindole
where $R^x$ is as described for Scheme 6B

Preparation of Intermediates and Examples

All starting materials, unless otherwise indicated can be purchased from commercial sources. Methods are given for the preparation of intermediates.
Note: Unless Otherwise indicated, HPLC conditions utilized column G.

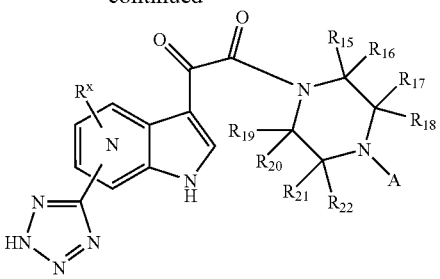

To a mixture of 1-chloroisoquinoline (527 mg, 3.22 mmol) and tert-butyl 1-piperazinecarboxylate (500 mg, 2.68 mmol) in ethylene glycol (8 ml) at r.t. was added triethylamine (2.0 ml, 14.3 mmol). The reaction mixture was then stirred at 100° C. for 6 to 20 h. After cooling to r.t., the mixture was diluted with water (30 ml), basified using saturated aqueous NaHCO$_3$, and extracted with CH$_2$Cl$_2$ (50 ml). The organic extract was evaporated in vacuo and the residue purified by flash column chromatography (0% to 10% EtOAc/hexane) to give Intermediate 1 as a white solid.
$^1$H NMR: (300 MHz, CD$_3$OD) δ 8.19 (d, 1H, J=8.4), 8.06 (d, 1H, J=5.7), 7.84 (d, 1H, J=8.1), 7.69 (b t, 1H), 7.60 (b t, 1H), 7.38 (d, 1H, J=5.7), 3.71-3.69 (b s, 4H), 3.33-3.30 (b s, 4H), 1.50 (s, 9H); LC/MS: (ES+) m/z (M+H)$^+$=314; HPLC R$_t$=1.063.
A mixture of Intermediate 1 (40 mg, 0.128 mmol) in a solution of HCl in 1,4-dioxane (0.5 ml, 4 N) was stirred at r.t. for 3 h. The excess reagent and volatile were then evaporated, and the residue further dried under high vacuum to give the hydrochloride salt of Intermediate 2 as a white solid. $^1$H NMR: (300 MHz, CD₃OD) δ 8.39 (d, 1H, J=8.7), 8.15-8.05 (overlapping m, 2H), 7.98-7.89 (overlapping m, 2H), 7.77 (d, 1H, J=6.6), 4.11-4.08 (m, 4H), 3.67-3.64 (m, 4H); LC/MS: (ES+) m/z (M+H)⁺=214; HPLC $R_t$=0.207.

Intermediate 2aa

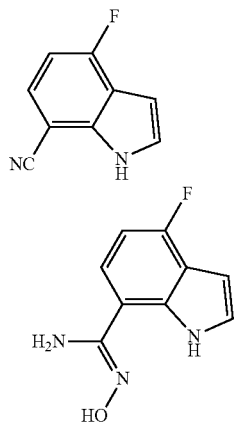

To a mixture of 4-fluoro-7-cyanoindole (1.0 g, 6.24 mmol) in EtOH (50 ml) was added hydroxylamine hydrochloride (651 mg, 9.37 mmol) and triethylamine (1.7 ml). The reaction mixture was refluxed for 16 hours. After removal of the volatile under high vacuum, the residue was added water (10 ml) and filtered to afford the crude hydroxyamidine intermediate. To this intermediate was added triethylorthoformate (10 ml) and the mixture heated at 110° C. for 16 hours. After removal of most of the excess reagent, the residue was purified by flash chromatography with (CH₂Cl₂) to give intermediate 2aa as pale yellow solid (419 mg, 33%). ¹H NMR (CDCl₃) δ 9.90 (s, 1H), 8.80 (s, 1H), 8.01 (app dd, J=8.3, 4.8, 1H), 7.34 (app t, J=2.8, 1H), 6.93 (app dd, J=9.8, 8.3, 1H), 6.74 (app dd, J=3.2, 2.3, 1H); LC/MS (ES+) m/z (M+H)⁺=204, HPLC $R_t$=1.910, Column YMC ODS-A C18 S7 (3.0×50 mm), Gradient Time=2 min, Flow rate 5 ml/min.

Intermediate 4aa

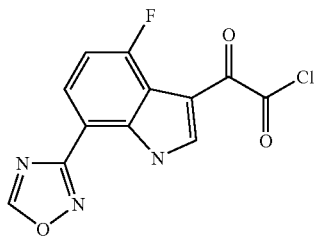

To a solution of intermediate 2aa (200 mg, 0.984) in CH₂Cl₂ (10 ml) was added oxalyl chloride (1 ml), and the reaction mixture stirred under gentle reflux for 16 hours. Removal of solvent in vacuo and the excess reagent under high vacuum afforded intermediate 4aa as a yellow solid, which was used without further purification.

The following HPLC conditions for the LCMS were used for compounds 2ac, 3aa, 2ad, 3ab, 4ab, and 4ac: Column: Xterra C18 S7 3×50 mm; Gradient Time=3 min; Flow rate=4 ml/min.

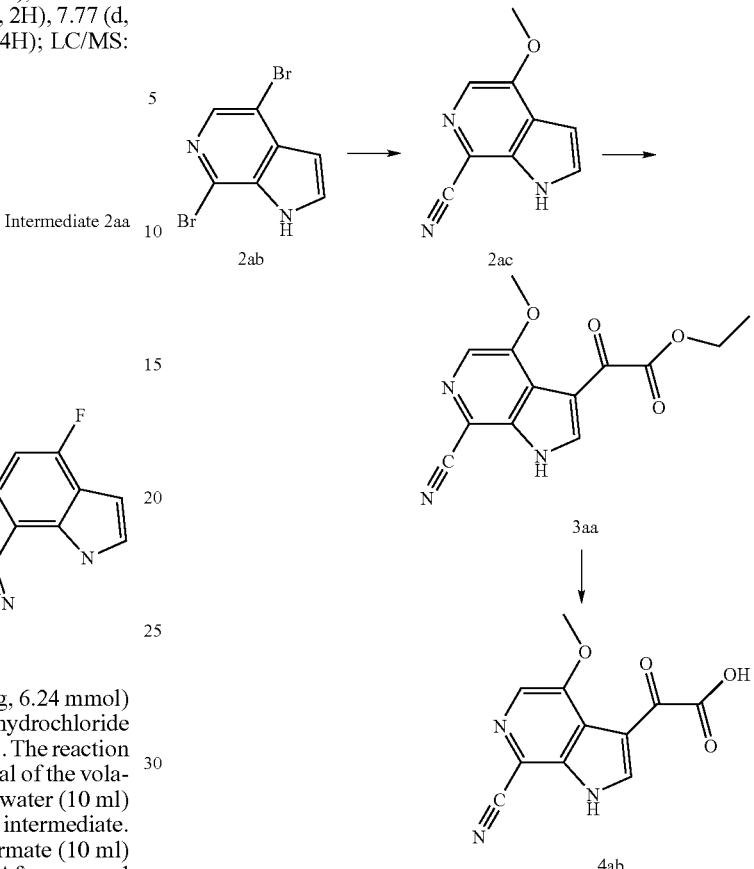

Preparation of Compound 2ac:

To a mixture of 2ab (2.0 g, 7.3 mmol) and CuCN (1.0 g, 11 mmol) was added DMF (20 ml). The reaction mixture was heated at 150° C. for 1 hour. After cooling to room temperature, the reaction mixture was added NaOMe (20 ml, 25 wt. % solution in MeOH), and was heated at 110° C. for 10 minutes. After cooling to room temperature, the reaction mixture was poured into an aqueous solution of ammonium acetate (sat. 500 ml). The resulting mixture was filtered through a short Celite® pad. The filtrate was extracted with EtOAc (4×500 ml). The combined extracts were dried over MgSO₄ and evaporated in vacuo to give a brownish residue, which was triturated with MeOH (5 ml×3) to provide 2ac as a yellow solid (317 mg, 25%). The structure was supported by NOE experiments. ¹H NMR: (DMSO-d₆) 12.47 (s, 1H), 8.03 (s, 1H), 7.65 (t, J=2.8, 1H), 6.70 (dd, J=2.8, 1.8, 1H), 4.08 (s, 3H); LC/MS: (ES+) m/z (M+H)⁺=174; HPLC $R_t$=1.320.

Preparation of Compound 3aa

To 1-ethyl-3-methylimidazolium chloride (85 mg, 0.58 mmol) in a capped vial was quickly added aluminum chloride (231 mg, 1.73 mmol). The mixture was vigorously stirred at room temperature until the formation of the ionic liquid. After cooling to room temperature, the ionic liquid was added compound 2ac (50 mg, 0.29 mmol) and ethyl chlorooxoacetate (0.2 ml, 1.79 mmol). The reaction mixture was stirred at room temperature for three hours, cooled to 0° C. and quenched by carefully adding ice-water (15 ml). The precipitates were filtered, washed with water (3×5 ml) and dried in vacuo to give 3aa as a grayish yellow solid (50 mg, 63%). $^1$H NMR: (DMSO-d$_6$) 13.73 (s, 1H), 8.54 (s, 1H), 8.26 (s, 1H), 4.35 (q, J=7.0, 2H), 4.06 (s, 3H), 1.29 (t, J=7.0, 3H); LC/MS: (ES+) m/z (M+H)$^+$=274; HPLC R$_t$=1.527.

Preparation of Compound 4ab

To a mixture of 3aa (200 mg, 0.73 mmol) in MeOH (1 ml) was added NaOH (2.5 ml, 1N aqueous). The reaction mixture was stirred at room temperature for 30 minutes, and then acidified with hydrochloric acid (~3 ml, 1N) to pH about 2. The solid was filtered, washed with water (4×5 ml), and dried in vacuo to give 4ab as a brownish solid (160 mg, 89%). Compound 4ab was used without further purification. LC/MS: (ES+) m/z (M+H)$^+$=246; HPLC R$_t$=0.777.

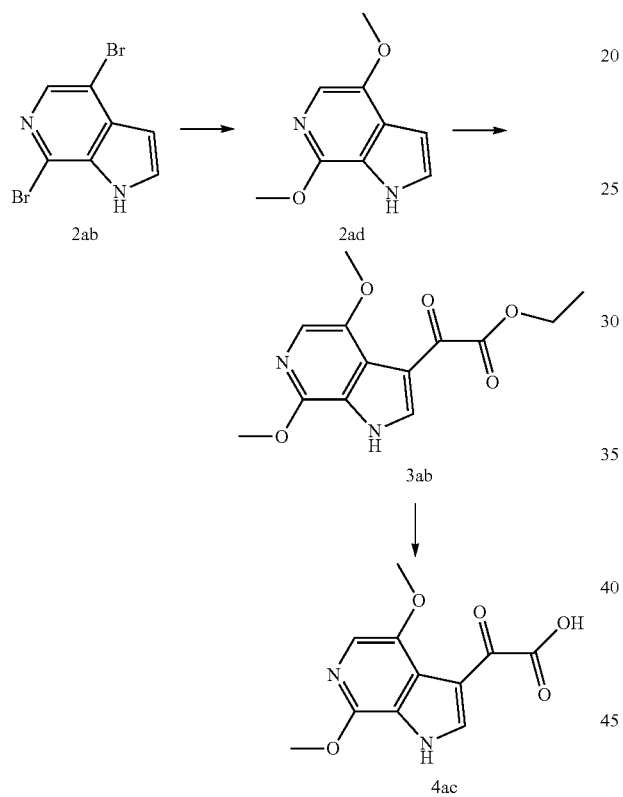

Preparation of Compound 2ad:

A mixture of 2ab, 4,7-dibromo-6-azaindole (2.0 g, 7.0 mmol), CuBr (2.0 g, 14 mmol) and NaOMe (20 ml, 25 wt. % solution in MeOH) was heated in a sealed tube at 100° C. for 12 h. Aftering cooling to r.t., the mixture was diluted with MeOH (20 ml) and then filtered. The filtrate was purified by preparative reverse phase HPLC using the method: Start % B=0, Final % B=50, Gradient time=10 min, Flow Rate=45 mL/min, Column: Xterra MS C18 5 um 30×50 mm, Fraction Collection: 2.20-4.30 min. LC/MS: (ES+) m/z (M+H)$^+$=179, HPLC R$_t$=0.857.

Compound 3ab was prepared in a similar manner to compound 3aa.

Intermediate 4ac was prepared in a similar manner to Intermediate 4ab.

LC/MS: (ES+) m/z (M+H)$^+$=251, HPLC R$_t$=0.503.

Intermediate 4ad

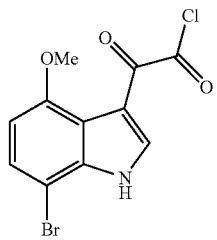

Intermediate 4ad

To 4-methoxy-7-bromoindole (500 mg, 2.21 mmol) was added a solution of oxalyl chloride in CH$_2$Cl$_2$ (10 ml, 20 mmol, 2 M), and the mixture was stirred at r.t. for 16 h. The solvent and the excess reagent were then evaporated and the crude product used for the next step without further purification.

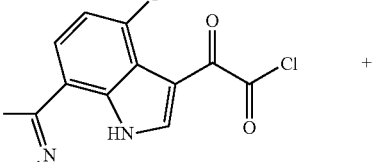

4aa

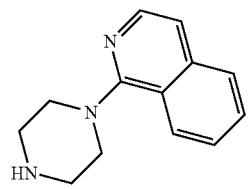

intermediate 2
(HCl salt)

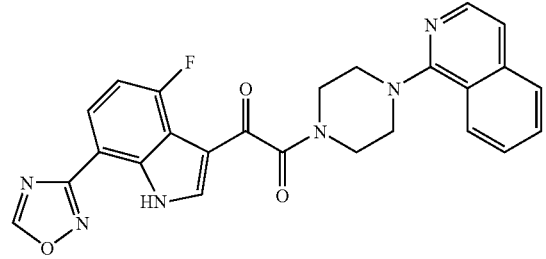

Example 1

A mixture of acid chloride intermediate 4aa (37 mg, 0.126 mmol) and Intermediate 2 (0.128 mmol) in CH$_2$Cl$_2$ (1 ml) at r.t. was added N,N-diisopropylethylamine (0.18 ml, 1.03 mmol), and the reaction mixture stirred for 17 h. The mixture was evaporated to dryness and the volatile further removed under high vacuum. The solid residue was then treated with water (3 ml), filtered, and further washed with water (3×2 ml) and minimum amount of MeOH (2×1 ml) to obtain Example 1 as a white solid. $^1$H NMR: (500 MHz, CDCl$_3$) δ 10.59 (s, 1H), 8.85 (s, 1H), 8.22 (d, 1H, J=3.0), 8.18-8.10 (overlapping m, 3H), 7.79 (b d, 1H), 7.68 (b m, 1H), 7.60 (b m, 1H), 7.32

(d, 1H, J=5.5), 7.14 (dd, 1H, J=8.5, 10.0), 4.06 (b m, 2H) 3.86 (b m, 2H), 3.64-3.42 (b m, 4H); LC/MS: (ES+) m/z (M+H)+= 471; HPLC R$_t$=1.210.

Intermediate 4, Intermediate 5 and Example 2 were prepared in a manner analogous to the methods used for Example 1.

Intermediate 4

Intermediate 5 (HCl salt)

Example 2

Intermediate 4
LC/MS: (ES+) m/z (M+H)+=304; HPLC R$_t$=1.053.
Intermediate 5
LC/MS: (ES+) m/z (M+H)+=204; HPLC R$_t$=0.083.

Example 2

$^1$H NMR: (500 MHz, CD$_3$OD) δ 9.40 (s, 1H), 8.25 (s, 1H), 8.16 (dd, 1H, J=4.5, 8.0), 7.88 (s, 1H), 7.87 (d, 1H, J=5.5), 7.18 (dd, 1H, J=8.0, 10.3), 7.10 (d, 1H, J=5.5), 6.86 (s, 1H), 3.97 (m, 2H), 3.94 (m, 2H) 3.85 (m, 2H), 3.70 (m, 2H); LC/MS: (ES+) m/z (M+H)+=461; HPLC R$_t$=1.073.

Intermediate 6, Intermediate 7 and Example 3 were prepared in the same manner as described for Example 1.

Intermediate 6

Intermediate 7 (HCl salt)

Example 3

Intermediate 6

LC/MS: (ES+) m/z (M+H)+=315; HPLC R$_t$=0.968.

Intermediate 7

Hydrochloride salt $^1$H NMR: (CD$_3$OD) δ 8.84 (s, 1H), 8.29 (d, J=10, 1H), 8.11 (app t, J=10, 1H), 7.90 (d, J=10, 1H), 7.83 (app t, J=10, 1H), 4.53 (b s, 4H), 3.53 (b s, 4H).

LC/MS: (ES+) m/z (M+H)+=215; HPLC R$_t$=0.080.

EXAMPLE 3

$^1$H NMR: (500 MHz, DMSO-d$_6$) δ 12.30 (s, 1H), 9.87 (s, 1H), 8.68 (s, 1H), 8.21 (b d, 1H), 8.10-8.06 (overlapping m, 2H), 7.84 (b d, 2H), 7.57 (m, 1H), 7.28 (app t, 1H), 3.88 (s, 4H), 3.74 (b s, 2H), 3.64 (b s, 2H); LC/MS: (ES+) m/z (M+H)+=472; HPLC R$_t$=1.000.

LCMS Conditions:
Solvent A: 10% MeOH—90% H2O—0.1% TFA
Solvent B: 90% MeOH—10% H2O—0.1% TFA
Column: XTERRA C18 S7 3.0×50 mm
Start % B=0
Final % B=100
Gradient Time=2 min
Flow Rate=5 ml/min
Wavelength=220

EXAMPLE 4

LC/MS: (ES+) m/z (M+H)$^+$=493, 495; HPLC R$_t$=1.128.

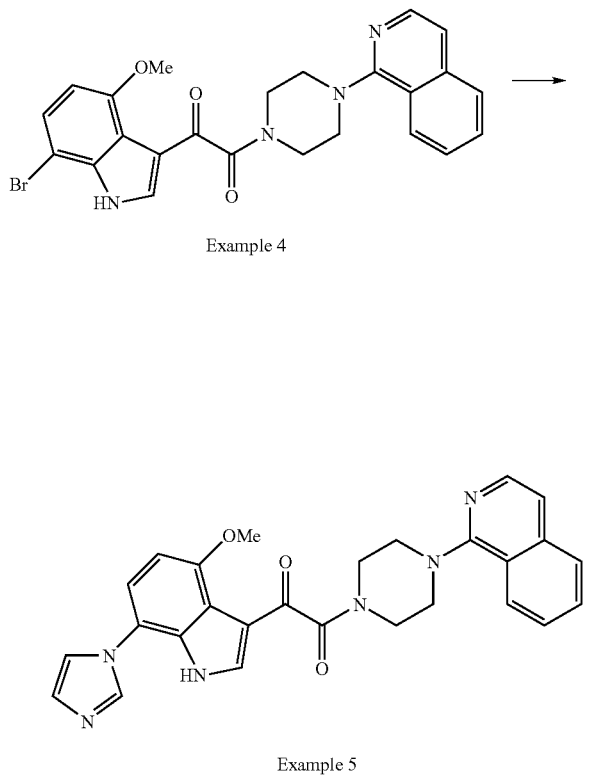

Example 4

Example 5

A mixture of Example 4 (50 mg, 0.101 mmol), imidazole (69 mg, 1.01 mmol) cesium carbonate (66 mg, 0.203 mmol) and copper bromide (30 mg, 0.212 mmol) was heated at 145° C. for 4 h. The reaction mixture was then cooled to r.t., diluted with MeOH (2 ml) and filtered. The residue was further washed with 3×2 ml MeOH. The filtrate was evaporated in vacuo to give the crude product, which was purified by preparative TLC (10% MeOH/CH$_2$Cl$_2$) to give Example 5; LC/MS: (ES+) m/z (M+H)$^+$=481; HPLC R$_t$=0.867.

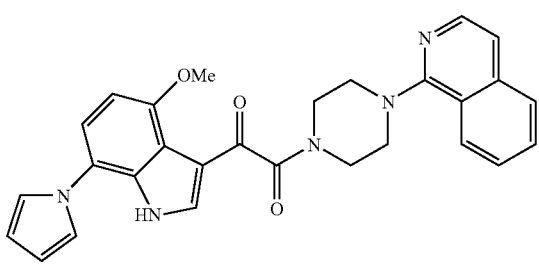

EXAMPLE 6

Example 6 was prepared in the same manner as Example 5.

LC/MS: (ES+) m/z (M+H)$^+$=480, 495; HPLC R$_t$=1.233.

The following HPLC conditions for the LCMS were used for Example 7, Example 8 and Example 9: Column: G; Gradient Time=3 min; Flow rate=4 ml/min.

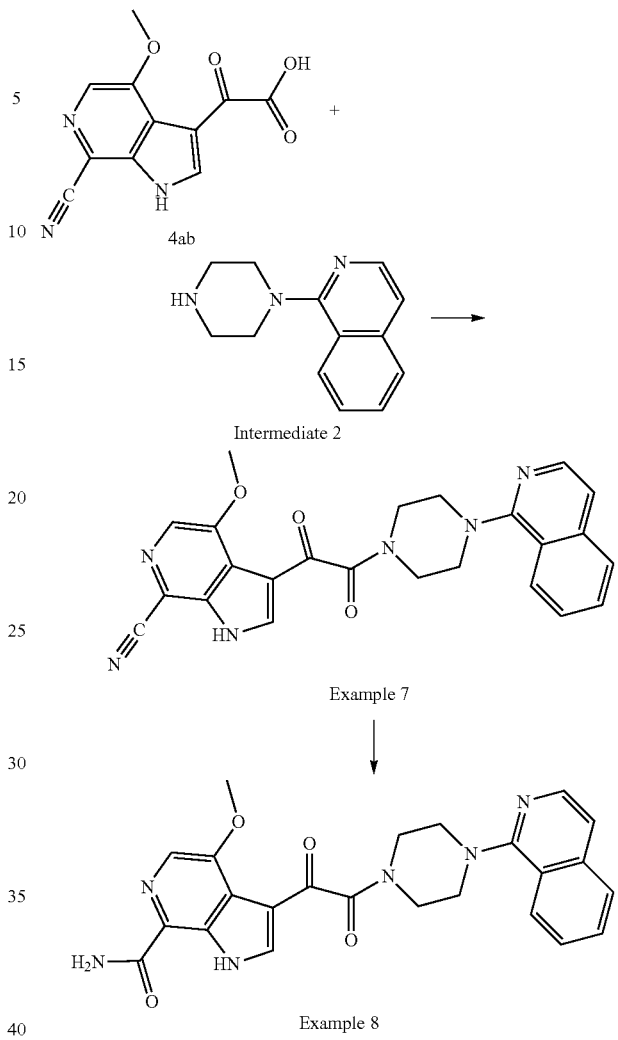

4ab

Intermediate 2

Example 7

Example 8

Preparation of Example 7

To a mixture of 4ab (crude, about 1.94 mmol), DEPBT (1.161 g, 3.88 mmol), intermediate 2 (952 mg, 2.91 mmol) in DMF (5 ml) was added N,N-diisopropylethylamine (3.0 ml, 17 mmol). The reaction mixture was stirred at room temperature for 16 hours. The reaction mixture was then diluted with MeOH (6 ml) and filtered. The filtrate was purified by preparative reverse phase HPLC using the method: Start % B=20, Final % B=60, Gradient time=15 min, Flow Rate=40 ml/min, Column: XTERRA C18 5 µm 30×50 mm, Fraction Collection: 6.169-6.762 min. $^1$H NMR: (DMSO-d$_6$) 13.71 (s, 1H), 8.50 (d, J=3.0, 1H), 8.27 (s, 1H), 8.23 (d, J=8.5, 1H), 8.06 (d, J=6.0, 1H), 7.97 (d, J=8.0, 1H), 7.82 (app t, J=7.5, 1H), 7.69 (d, J=7.5, 1H), 7.51 (d, J=6.0, 1H), 4.16 (s, 3H), 3.93 (b s, 2), 3.66 (b s, 2H), 3.63 (b s, 2H), 3.48 (b s, 2H); LC/MS: (ES+) m/z (M+H)$^+$=441, HPLC R$_t$=1.200.

Preparation of Example 8

Anhydrous hydrogen chloride gas was bubbled through a suspension of Example 7 (160 mg, 2.18 mmol) in MeOH (5 ml) at 0° C. for 15 minutes. After evaporation of most of the volatile, the residue was purified by preparative reverse phase HPLC using the method: Start % B=20, Final % B=60, Gradient time=15 min, Flow Rate=40 ml/min, Column: XTERRA C18 5 μm 30×50 mm, Fraction Collection: 6.169-6.762 min. ¹H NMR: (DMSO-d₆) 12.49 (s, 1H), 8.25 (m, 1H), 8.17 (s, 1H), 8.11 (d, J=9.5, 1H), 8.04 (m, 1H), 7.99 (d, J=8.5, 1H), 7.70 (app t, J=7.5, 1H), 7.53 (d, J=6.5, 1H), 7.0 (b s, 2H), 4.08 (s, 3H), 3.93 (b s, 2), 3.66 (b s, 4H), 3.50 (b s, 2H); LC/MS: (ES+) m/z (M+H)⁺=459, HPLC R$_f$=1.237.

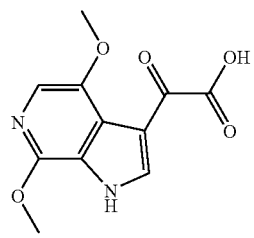

4ac

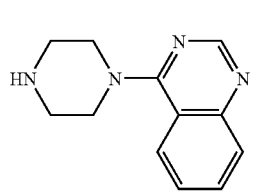

Intermediate 7

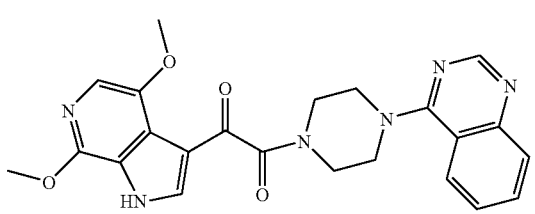

Example 9

Preparation of Example 9

To a mixture of Intermediate 4ac (crude, about 0.56 mmol), DEPBT (336 mg, 1.12 mmol) and intermediate 7 (220 mg, 0.67 mmol) in DMF (3 ml) was added N,N-diisopropylethylamine (1.0 ml, 5.7 mmol). The reaction mixture was stirred at room temperature for 16 hours. The reaction mixture was then diluted with MeOH (4 ml), and filtered. The filtrate was purified by preparative reverse phase HPLC using the method: Start % B=0, Final % B=55, Gradient time=15 min, Flow Rate=40 ml/min, Column: XTERRA C18 5 μm 30×100 mm, Fraction Collection: 8.71-9.16 min. ¹H NMR: (DMSO-d₆) 13.07 (s, 1H), 8.91 (s, 1H), 8.23 (m, 2H), 8.05 (app t, J=7.5, 1H), 7.85 (d, J=8.0, 1H), 7.73 (app t, J=7.7, 1H), 7.48 (s, 1H), 4.36 (b s, 2H), 4.20 (b s, 2H), 4.00 (s, 3H), 3.85 (s, 3H), 3.63 (b s, 4H); LC/MS: (ES+) m/z (M+H)⁺=447, HPLC R$_f$=0.987.

EXAMPLE 43

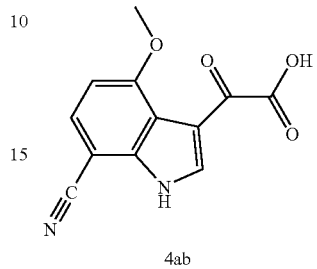

4ab

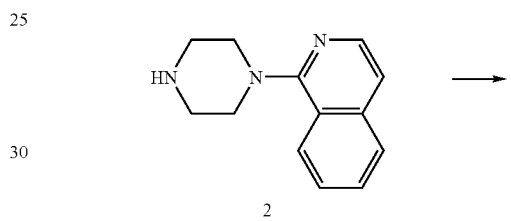

2

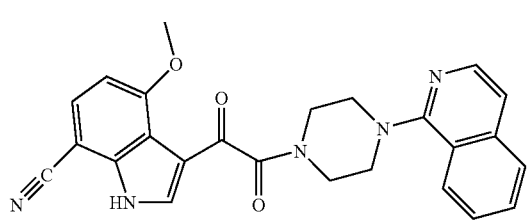

Example 43

A mixture of intermediate 4ab (0.671 g, 2.7 mmol), intermediate 2 (0.869 g, 4.1 mmol), EDC (0.928 g, 4.8 mmol), dimethylaminopyridine (0.618 g, 5.1 mmol) and N-methylmorpholine (2.4 ml, 21.6 mmol) in DMF (20 ml) was stirred at room temperature for 17 hr. The reaction mixture was then quenched with 1N HCl and extracted with ethyl acetate (6 times). The combined organic extracts were evaporated in vacuo and purified by flash columatography (0%→5% MeOH/CH₂Cl₂) to provide Example 43 as a dark solid; ¹H NMR (CDCl₃) δ 9.64 (b s, 1H), 8.15 (d, J=5.5, 1H), 8.11 (d, J=8.0, 1H), 8.05 (d, J=3.0, 1H), 7.79 (d, J=8.0, 1H), 7.65 (app t, J=9.0, 1H), 7.57 (d, J=8.5, 2H), 7.32 (d, J=6.0, 1H), 6.74 (d, J=8.5, 1H), 4.05 (s, 3H, overlapping with m), 4.05-4.00 (m, 2H), 3.79 (b s, 2H), 3.56 (b s, 2H), 3.48 (b s, 2H); LC/MS (ES+) m/z (M+H)⁺=440, HPLC R$_f$=0.993.

119

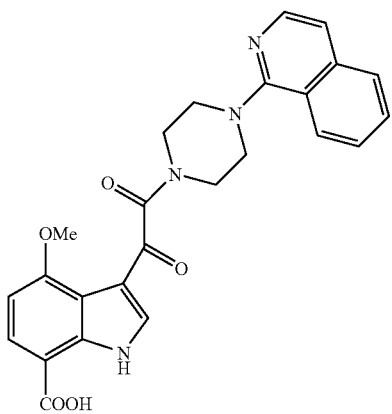

EXAMPLE 10

Example 10 was prepared by refluxing Example 43 (30 mg, 0.068 mmol) in 5N NaOH (0.8 ml, 40 mmol) for 17 hr. The reaction mixture was acidified by adding 1N HCl, and extracted with ethyl acetate (3 times). The crude product was purified by preparative reverse phase HPLC to give a brown film; Separation method: Start % B=0, Final % B=100, Gradient time=6 min, Flow Rate=30 ml/min, Column: YMC C18 S5 20×50 mm; $^1$H NMR: (CD$_3$OD) δ 8.40 (d, J=8.5, 1H), 8.19 (s, 1H), 8.06-7.98 (m, 2H), 7.86-7.811 (m, 3H), 7.61 (d, J=8.0, 1H), 6.86 (d, J=8.5, 1H), 4.12 (b s, 2H), 4.03 (s, 3H), 3.95 (b s, 2H), 3.86 (d, J=4, 4H); LC/MS: (ES+) m/z (M+H)$^+$= 458, HPLC R$_t$=0.787.

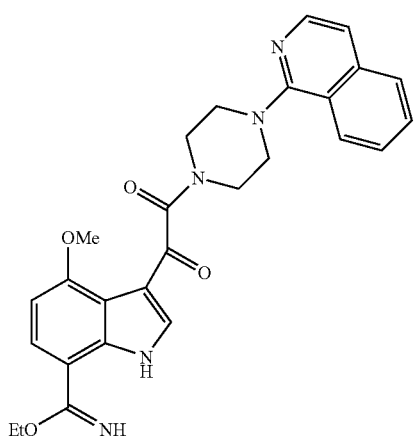

Intermediate 8

A solution of Example 43 (49 mg, 0.11 mmol) in anhydrous EtOH (0.5 ml, 200 proof) in a re-usable sealed tube was bubbled with anhydrous HCl gas at room temperature for approximately 15 min. After which time, the tube was closed and the mixture stirred at room temperature for 72 hours. The volatiles were then evaporated, and intermediate 8 was used without further purification; LC/MS: (ES+) m/z (M+H)$^+$= 486, HPLC R$_t$=0.837.

120

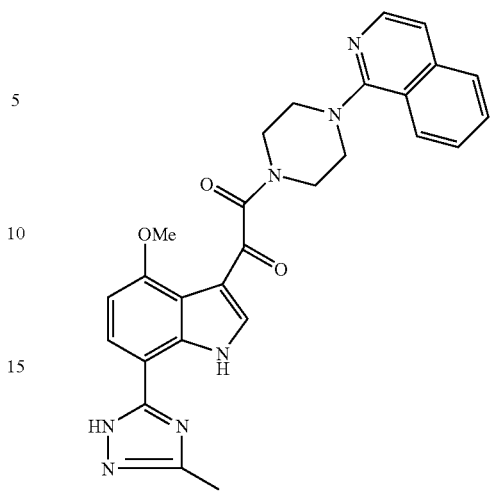

EXAMPLE 11

To a mixture of intermediate 8 (53 mg, 0.11 mmol) in anhydrous EtOH (1.5 ml, 200 proof) was added acetic hydrazide (45 mg, 0.61 mmol) and N,N-diisopropylethylamine (0.1 ml, 0.57 mmol). The reaction mixture was heated to 150° C. and refluxed for 3 hours. After cooling to room temperature, sodium methoxide (24 mg, 0.44 mmol) was added and the mixture was refluxed for 2 additional hours. The reaction was quenched with 1N HCl and diluted with H$_2$O. The crude product was purified by preparative reverse phase HPLC using the separation method: Start % B=25, Final % B=65, Gradient time=20 min, Flow Rate=30 ml/min, Column: YMC C18 S5 20×50 mm; $^1$H NMR (CD$_3$OD) δ 8.41 (d, J=8.5, 1H), 8.23 (s, 1H), 8.23-8.01 (m, 2H), 7.90 (d, J=8.0, 1H), 7.84-7.82 (m, 2H), 7.64 (d, J=6.5, 1H), 6.94 (d, J=8.5, 1H), 4.14-4.12 (m, 2H), 4.03 (s, 3H), 4.01-3.99 (m, 2H), 3.89 (s, 4H), 2.62 (s, 3H); LC/MS (ES+) m/z (M+H)$^+$=496, HPLC R$_t$=0.927.

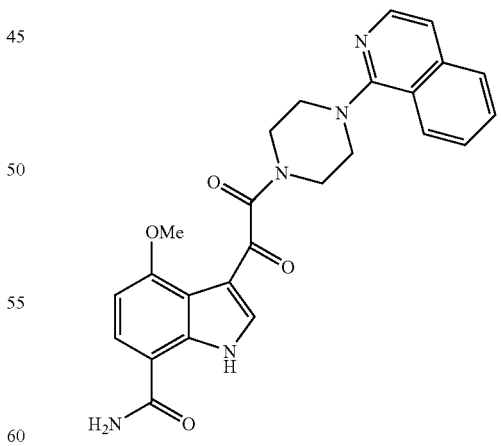

EXAMPLE 12

Example 12 was obtained as a side product from the reaction to make Example 11 and was isolated via preparative reverse phase HPLC using the same method as above; $^1$H NMR (CD₃OD) δ 8.41 (d, J=8.5, 1H), 8.18 (s, 1H), 8.07-7.99 (m, 2H), 7.86-7.79 (m, 3H), 7.64 (d, J=6.5, 1H), 6.86 (d, J=8.5, 1H), 4.12 (b s, 2H), 4.03 (s, 3H), 3.99 (b s, 2H), 3.87 (s, 4H); LC/MS (ES+) m/z (M+H)⁺=458, HPLC $R_t$=0.807.

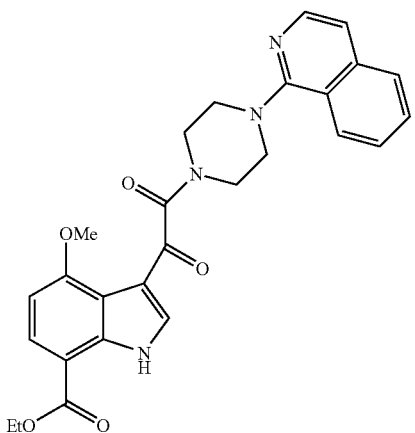

EXAMPLE 13

Example 13 was also obtained as a side-product from the reaction to make Example 11. The compound was isolated via preparative reverse phase HPLC using the same method as above; ¹H NMR (CD₃OD) δ 8.38 (d, J=8.0, 1H), 8.18 (s, 1H), 8.03-7.94 (m, 3H), 7.90 (d, J=6.5, 1H), 7.82 (app t, J=7.8, 1H), 7.60 (d, J=6.0, 1H), 6.91 (d, J=9.0, 1H), 4.47 (q, J=7.0, 2H), 4.11-4.10 (m, 2H), 4.05 (s, 3H), 3.90-3.85 (m, 4H), 3.78-3.74 (m, 2H), 1.44 (t, J=7.0, 3H); LC/MS: (ES+) m/z (M+H)⁺=487, HPLC $R_t$=1.170.

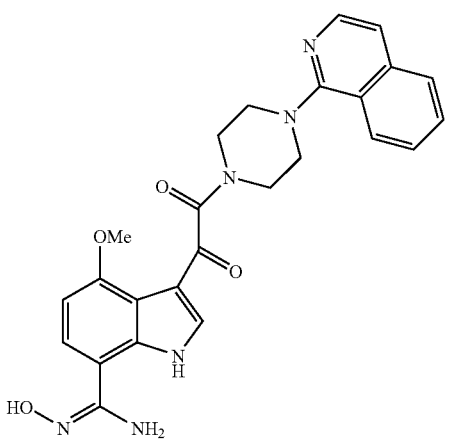

EXAMPLE 14

A mixture of hydroxylamine hydrochloride (20 mg, 0.29 mmol) and triethylamine (50 μl, 0.36 mmol) in anhydrous EtOH (1.5 ml, 200 proof) was added to Example 43 (80 mg, 0.18 mmol), and the resulting mixture stirred at room temperature. After 48 hours, the mixture was added additional hydroxylamine hydrochloride (47 mg, 0.68 mmol) and triethylamine (80 μl, 0.58 mmol), and stirred for 5 days. The precipitates were filtered and washed with excess EtOH to give Example 14 as a white solid. Further purification was performed by reverse phase preparative HPLC using the method: Start % B=0, Final % B=100, Gradient time=7 min, Flow Rate=30 ml/min, Column: YMC C18 S5 20×50 mm; ¹H NMR: (CD₃OD) δ 8.38 (d, J=9.0, 1H), 8.21 (s, 1H), 8.03 (d, J=7.0, 1H), 7.96-7.91 (m, 2H), 7.81 (app t, J=7.8, 1H), 7.60 (d, J=6.5, 1H), 7.53 (d, J=8.5, 1H), 6.97 (d, J=8.5, 1H), 4.11-4.10 (m, 2H), 4.05 (s, 3H), 3.87 (s, 4H), 3.79 (s, 2H); LC/MS: (ES+) m/z (M+H)⁺=473, HPLC $R_t$=0.663.

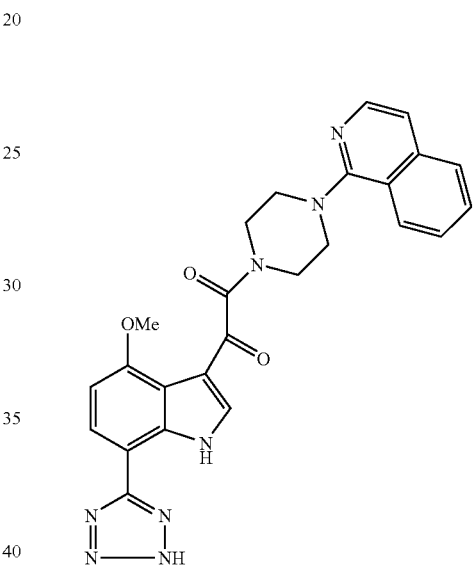

EXAMPLE 15

To a mixture of Example 43 (80 mg, 0.18 mmol) in DMF (2 ml) was added sodium azide (35 mg, 0.54 mmol) and ammonium chloride (29 mg, 0.54 mmol). The resulting mixture was heated to 90° C. and allowed to stir for 20 hr. After cooling to 0° C. in an ice-water bath, the reaction was quenched by adding several drops of 1N HCl and then diluted with water, upon which a precipitate was formed. The solids were filtered and washed with an excess of water to give Example 15 as a white solid; ¹H NMR: (CD₃OD) δ 8.25-8.22 (m, 2H), 8.07 (d, J=5.5, 1H), 7.91 (dd, J=8.0, 8.0, 2H), 7.72 (app t, J=7.5, 1H), 7.63 (app t, J=8.0, 1H), 7.42 (d, J=6.0, 1H), 7.00 (d, J=8.0, 1H), 4.06 (s, 3H, overlapping with m), 4.06-4.03 (m, 2H), 3.79 (b s, 2H), 3.55 (b s, 2H), 3.43 (b s, 2H); LC/MS: (ES+) m/z (M+H)⁺=483, HPLC $R_t$=0.947.

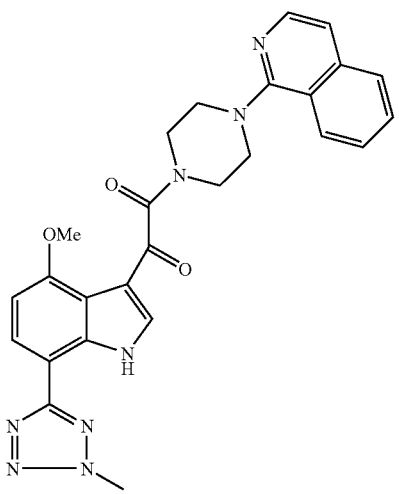

EXAMPLE 16

To a mixture of Example 15 (35 mg, 0.073 mmol) in MeOH (0.5 mL)/PhH (0.8 mL) at room temperature was added trimethylsilyldiazomethane (80 μl, 0.16 mmol, 2M in hexanes). After stirring for 2.5 hours, the reaction mixture was cooled to 0° C. in an ice-water bath and quenched using excess acetic acid. The volatiles were evaporated in vacuo, and the residue purified by reverse phase preparative HPLC using the method: Start % B=20, Final % B=60, Gradient time=20 min, Flow Rate=30 ml/min, Column: YMC C18 S5 20×50 mm, Fraction Collection: 8.37-8.97 min; $^1$H NMR: (CD$_3$OD) δ 8.40 (d, J=8.5, 1H), 8.25 (s, 1H), 8.10 (d, J=8.5, 1H), 8.05 (d, J=8.0, 1H), 7.99 (app t, J=7.3, 1H), 7.88 (d, J=6.5, 1H), 7.83 (app t, J=7.8, 1H), 7.61 (d, J=6.5, 1H), 6.98 (d, J=8.5, 1H), 4.48 (s, 3H), 4.13 (b s, 2H), 4.06 (s, 3H), 3.93 (b s, 2H), 3.89 (b s, 2H), 3.83 (b s, 2H). The position of N-methyl group was supported by HMBC NMR studies; LC/MS: (ES+) m/z (M+H)$^+$=497, HPLC R$_t$=1.083.

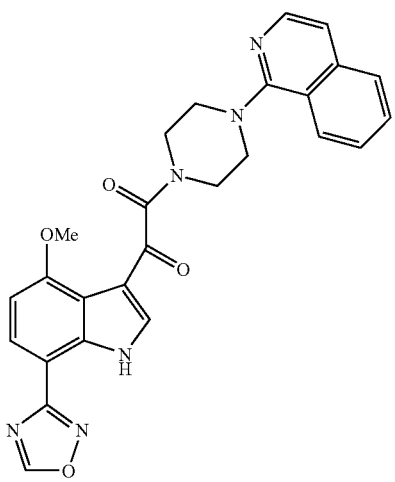

EXAMPLE 17

A flask charged with Example 14 (45 mg, 0.095 mmol) was added triethyl orthoformate (1 ml, 6.0 mmol) and the mixture heated at 110° C. for 24 hours. The volatiles were evaporated and the residue subjected to purification by reverse phase preparative HPLC using the method: Start % B=20, Final % B=60, Gradient time=20 min, Flow Rate=30 mL/min, Column: YMC C18 S5 20×50 mm, Fraction Collection: 7.73-8.10 min; $^1$H NMR: (CD$_3$OD) δ 9.34 (s, 1H), 8.39 (d, J=8.5, 1H), 8.24 (s, 1H), 8.13 (d, J=8.5, 1H), 8.04 (d, J=8.0, 1H), 7.98 (app t, J=7.8, 1H), 7.89 (d, J=6.5, 1H), 7.83 (app t, J=7.8, 1H), 7.61 (d, J=6.5, 1H), 7.00 (d, J=8.5, 1H), 4.14-4.12 (m, 2H), 4.06 (s, 3H), 3.92-3.87 (m, 4H), 3.82-3.80 (m, 2H); LC/MS: (ES+) m/z (M+H)$^+$=483, HPLC R$_t$=1.057.

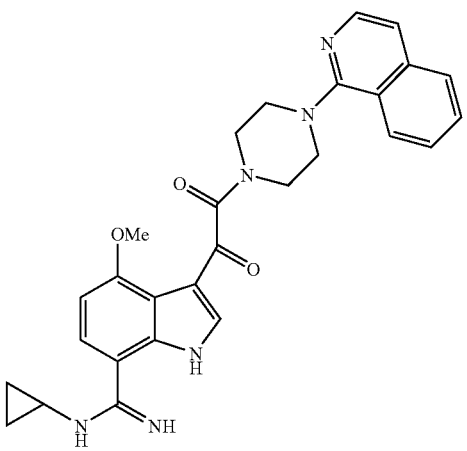

EXAMPLE 18

To a solution of intermediate 8 (30 mg, 0.062 mmol) in anhydrous EtOH (1.0 ml, 200 proof) was added cyclopropylamine (50 μL, 0.67 mmol). The reaction mixture was stirred at room temperature for 8 hours, then diluted with MeOH and subjected to purification via reverse phase preparative HPLC using the method: Start % B=0, Final % B=100, Gradient time=8 min, Flow Rate=30 mL/min, Column: YMC C18 S5 20×50 mm, Fraction Collection: 3.13-3.59 min. $^1$H NMR: (CD$_3$OD) δ 8.41 (d, J=8.5, 1H), 8.22 (s, 1H), 8.06-7.98 (m, 2H), 7.89-7.82 (m, 2H), 7.63 (d, J=6.0, 1H), 7.55 (d, J=8.0, 1H), 6.96 (d, J=8.5, 1H), 4.12 (b s, 2H), 4.04 (s, 3H), 3.95 (b s, 2H), 3.77 (b s, 4H), 2.86 (b s, 1H), 1.08 (b s, 2H), 0.93 (b s, 2H); LC/MS: (ES+) m/z (M+H)$^+$=497, HPLC R$_t$=0.720.

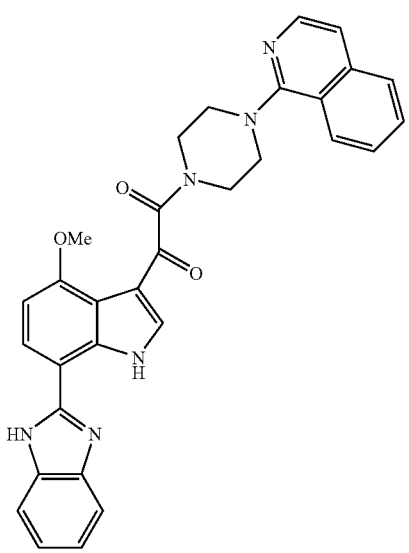

EXAMPLE 19

To a solution of intermediate 8 (30 mg, 0.062 mmol), in anhydrous EtOH (1.0 ml, 200 proof) was added 1,2-phenylenediamine (30 mg, 0.27 mmol). The mixture was stirred at room temperature for 8 hours, then diluted with MeOH and subjected to purification by reverse phase preparative HPLC using the method: Start % B=0, Final % B=100, Gradient time=8 min, Flow Rate=30 ml/min, Column: YMC C18 S5 20×50 mm, Fraction Collection: 4.24-4.82 min; $^1$H NMR: (CD$_3$OD) δ 8.40 (d, J=8.5, 1H), 8.31 (s, 1H), 8.04-7.78 (m, 7H), 7.61 (d, J=6.5, 1H), 7.52 (b s, 2H), 7.08 (d, J=8.0, 1H), 4.14-4.09 (m, 2H), 4.09 (s, 3H, overlapping with m), 3.92-3.84 (m, 6H); LC/MS: (ES+) m/z (M+H)$^+$=531, HPLC R$_t$=0.957.

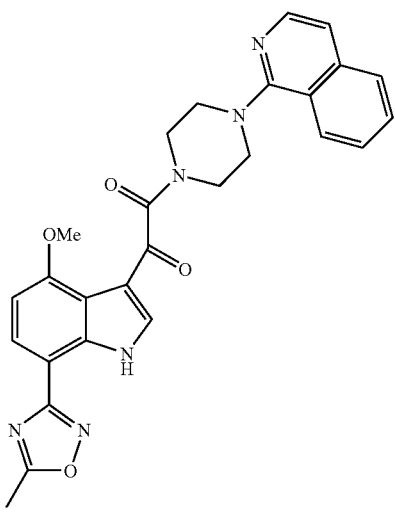

EXAMPLE 20

To a solution of Example 14 (45 mg, 0.095 mmol) in pyridine (1.0 ml) was added acetyl chloride (50 μL, 0.70 mmol). The reaction mixture was heated to 115° C. for two hours and then cooled to room temperature. After dilution with MeOH, the crude mixture was purified by preparative reverse phase HPLC using the method: Start % B=0, Final % B=100, Gradient time=16 min, Flow Rate=30 mL/min, Column: YMC C18 S5 20×50 mm; $^1$H NMR: (CD$_3$OD) δ 8.38 (d, J=8.0, 1H), 8.22 (s, 1H), 8.04-7.89 (m, 4H), 7.79 (s, 1H), 7.59 (d, J=6.0, 1H), 6.97 (d, J=8.0, 1H), 4.17-4.00 (m, 2H), 4.04 (s, 3H, overlapping with m), 3.87 (b s, 3H), 3.78 (b s, 3H), 2.70 (s, 3H); LC/MS: (ES+) m/z (M+H)$^+$=497, HPLC R$_t$=1.123.

EXAMPLE 21

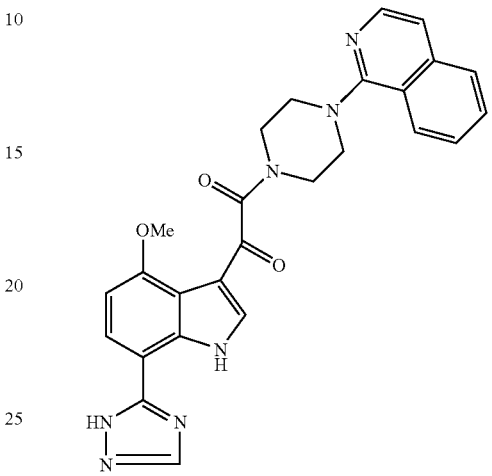

To intermediate 8 (40 mg, 0.082 mmol) in EtOH (2.0 mL) was added formyl hydrazide (25 mg, 0.41 mmol) and N,N-diisopropylethylamine (50 μL, 0.28 mmol). The mixture was refluxed at 130° C. for five hours. After cooling to room temperature, the mixture was diluted with MeOH, and purified by preparative reverse phase HPLC using the separation method: Start % B=0, Final % B=100, Gradient time=9 min, Flow Rate=30 mL/min, Column: YMC C18 S5 20×50 mm, Fraction Collection: 4.53-5.08 min. $^1$H NMR: (CD$_3$OD) δ 8.53 (s, 1H), 8.42 (d, J=8.4, 1H), 8.25 (s, 1H), 8.07-8.01 (m, 2H), 7.98 (d, J=8.4, 1H), 7.87-7.81 (m, 2H), 7.64 (d, J=6.6, 1H), 6.95 (d, J=8.4, 1H), 4.15-4.12 (m, 2H), 4.03 (s, 3H), 4.00-3.97 (m, 2H), 3.88 (s, 4H); LC/MS: (ES+) m/z (M+H)$^+$=482, HPLC R$_t$=0.920.

EXAMPLE 22

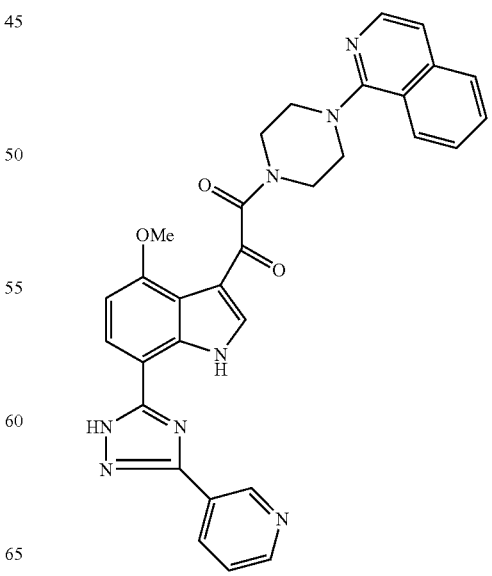

Example 22 was prepared in a similar manner as Example 21. Purification of the desired product was performed by preparative reverse phase HPLC using the separation method: Start % B=0, Final % B=100, Gradient time=12 min, Flow Rate=30 mL/min, Column: YMC C18 S5 20×50 mm, Fraction Collection: 5.93-6.49 min. The fraction collected was evaporated and further purified by using the method: Start % B=15, Final % B=80, Gradient time=20 min, Flow Rate=30 mL/min, Column: Xterra Prep MS C18 5 um 19×50 mm, Fraction Collection: 6.91-7.34 min. $^1$H NMR: (CD$_3$OD) δ 8.41 (d, J=8.4, 1H), 8.32 (s, 1H), 8.06-7.80 (m, 9H), 7.63 (d, J=6.6, 1H), 7.01 (d, J=8.4, 1H), 4.15-4.13 (m, 2H), 4.07 (s, 3H), 3.98-3.85 (m, 6H); LC/MS: (ES+) m/z (M+H)$^+$=559, HPLC R$_t$=1.023.

EXAMPLE 23

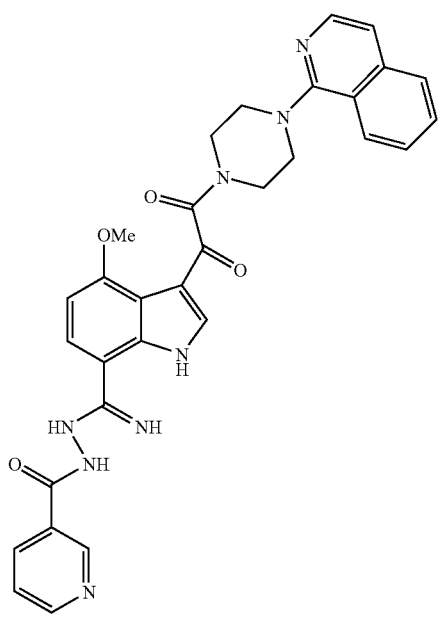

Example 23 was isolated as an intermediate/side product in the reaction to make Example 22. Purification was performed by preparative reverse phase HPLC using the separation method: Start % B=0, Final % B=100, Gradient time=12 min, Flow Rate=30 mL/min, Column: YMC C18 S5 20×50 mm, Fraction Collection: 3.82-4.22 min. $^1$H NMR: (CD$_3$OD) δ 9.20 (d, J=2.1, 1H), 8.85 (dd, J=8.0, 2.5, 1H), 8.50 (d t, J=14.0, 3.0, 1H), 8.43 (d, J=8.4, 1H), 8.31 (s, 1H), 8.08-7.97 (m, 2H), 7.89-7.81 (m, 2H), 7.76 (d, J=8.4, 1H), 7.71-7.66 (m, 1H), 7.65 (d, J=6.9, 1H), 7.06 (d, J=8.4, 1H), 4.15-4.13 (m, 2H), 4.09 (s, 3H), 4.00-3.90 (m, 6H); LC/MS: (ES+) m/z (M+H)$^+$=577, HPLC R$_t$=0.707.

EXAMPLE 24

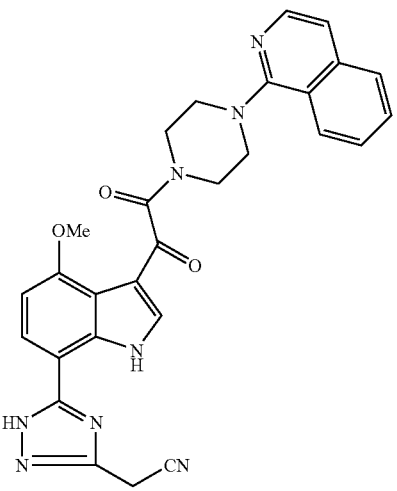

Example 24 was prepared in a similar manner as Example 21. Purification of the desired product was performed by preparative reverse phase HPLC using the separation method: Start % B=0, Final % B=100, Gradient time=12 min, Flow Rate=30 mL/min, Column: YMC C18 S5 20×50 mm, Fraction Collection: 5.57-6.14 min. $^1$H NMR: (CD$_3$OD) δ 8.40 (d, J=8.4, 1H), 8.25 (s, 1H), 8.05-7.96 (m, 2H), 7.87 (d, J=6.9, 2H), 7.82-7.79 (m, 1H), 7.62 (d, J=6.6, 1H), 6.94 (d, J=8.7, 1H), 4.16 (s, 2H), 4.15-4.11 (m, 2H), 4.03 (s, 3H), 3.96-3.93 (m, 2H), 3.87-3.85 (m, 4H); LC/MS: (ES+) m/z (M+H)$^+$=521, HPLC R$_t$=0.983.

EXAMPLE 25

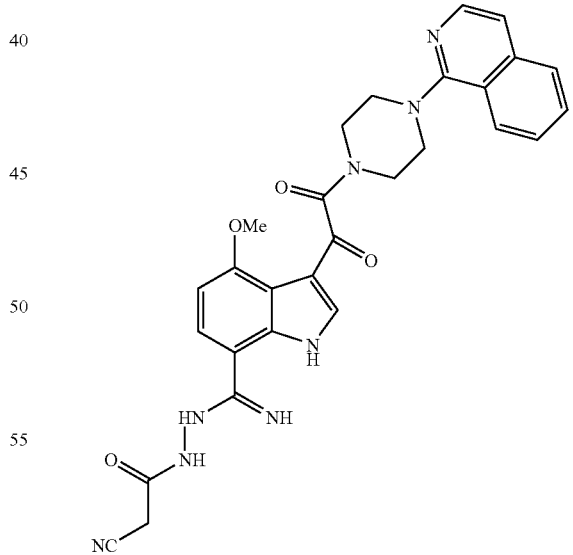

Example 25 was isolated as an intermediate in the reaction to make Example 24. Purification was performed by preparative reverse phase HPLC using the separation method: Start % B=0, Final % B=100, Gradient time=12 min, Flow Rate=30 mL/min, Column: YMC C18 S5 20×50 mm, Fraction Collection: 4.67-5.28 min. $^1$H NMR: (CD$_3$OD) δ 8.40 (d, J=8.7, 1H), 8.18 (s, 1H), 8.05-7.93 (m, 2H), 7.88-7.79 (m, 3H), 7.60

(d, J=10.2, 1H), 6.87 (d, J=8.4, 1H), 4.13-4.10 (m, 2H), 4.03 (s, 3H), 3.94-3.90 (m, 2H), 3.85-3.82 (m, 6H); LC/MS: (ES+) m/z (M+H)$^+$=539, HPLC R$_t$=0.797.

EXAMPLE 26

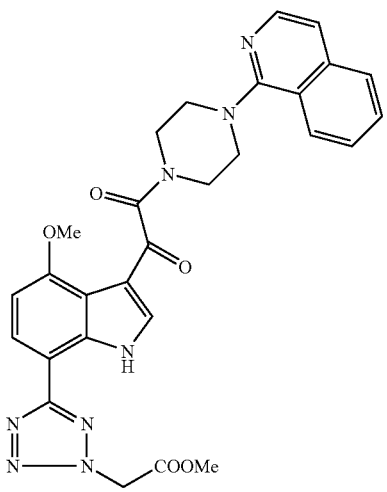

Example 15 (96 mg, 0.20 mmol) was dissolved in acetonitrile (1.5 mL), and to the mixture was added methyl bromoacetate (40 µL, 0.42 mmol), followed by potassium carbonate (38 mg, 0.27 mmol). The mixture was stirred at room temperature for three hours and the precipitate was then filtered to obtain the product, which was pure by $^1$H NMR and LC/MS analysis. The filtrate was extracted with EtOAc (4 times) and the combined extracts evaporated to obtain additional crude product. The crude product was purified using preparative reverse phase HPLC with the separation method: Start % B=0, Final % B=100, Gradient time=20 min, Flow Rate=20 mL/min, Column: YMC C18 S5 20×50 mm, Fraction Collection: 10.85-11.31 min. $^1$H NMR: (CD$_3$OD) δ 8.40 (d, J=8.5, 1H), 8.28 (s, 1H), 8.17 (d, J=8.5, 1H), 8.05 (d, J=8.0, 1H), 7.95 (d, J=6.5, 2H), 7.83 (t, J=7.5, 1H), 7.62 (t, J=6.5, 1H), 7.04 (d, J=8.0, 1H), 5.80 (s, 2H), 4.15 (b s, 2H), 4.08 (s, 3H), 3.89-3.87 (m, 6H), 3.87 (s, 3H), 3.78 (b s, 2H); LC/MS: (ES+) m/z (M+H)$^+$=555, HPLC R$_t$=1.087. Alkylation at the tetrazole N2 was supported by HMBC NMR analysis.

EXAMPLE 27

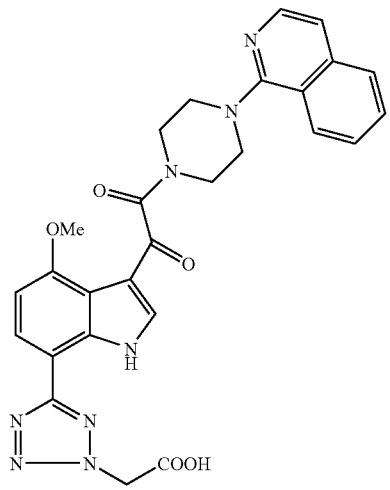

To a mixture of Example 26 (110 mg, 0.20 mmol) in MeOH (1.5 mL) at ambient temperature was added 1N NaOH (0.5 mL, 0.50 mmol) and stirred for three hours. The reaction was then quenched with 1N HCl (~10 drops) to induce precipitation of the product. The precipitates were filtered, washed with excess H$_2$O, and dried under high vacuum to give Example 27 as an off-white solid. $^1$H NMR: (CD$_3$OD) δ 8.27 (d, J=8.5, 1H), 8.24 (s, 1H), 8.13 (d, J=8.5, 1H), 8.03 (d, J=6.0, 1H), 7.90 (d, J=8.5, 1H), 7.78 (t, J=7.5, 1H), 7.68 (t, J=7.8, 1H), 7.46 (d, J=6.0, 1H), 6.99 (d, J=8.5, 1H), 4.37 (b s, 2H), 4.12-4.04 (m, 2H), 4.05 (s, 3H), 3.82-3.80 (m, 2H), 3.64 (m, 2H), 3.53-3.51 (m, 2H); LC/MS: (ES+) m/z (M+H)$^+$= 541, HPLC R$_t$=1.003.

EXAMPLE 28

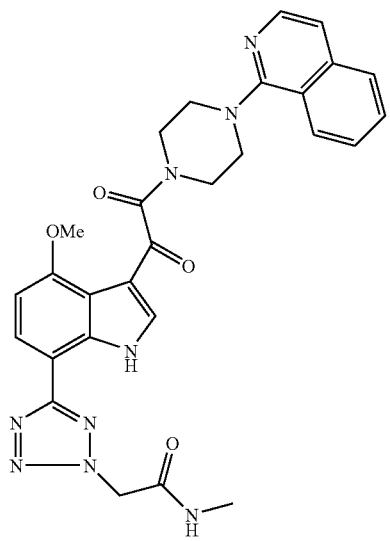

To a mixture of Example 27 (20 mg, 0.037 mmol) in DMF (1.5 mL) was added methylamine hydrochloride (12 mg, 0.39 mmol), HOBT (28 mg, 0.21 mmol), EDC (40 mg, 0.21 mmol) and NMM (50 μL, 0.45 mmol). The reaction mixture was stirred at ambient temperature for twenty-four hours, diluted with MeOH and then purified by preparative reverse phase HPLC using the separation method: Start % B=0, Final % B=100, Gradient time=18 min, Flow Rate=30 mL/min, Column: Xterra Prep MS C18 5 um 19×50 mm, Fraction Collection: 7.43-7.88 min. $^1$H NMR: (CD$_3$OD) δ 8.39 (d, J=8.5, 1H), 8.26 (s, 1H), 8.13 (d, J=8.5, 1H), 8.04 (d, J=7.0, 1H), 7.98 (t, J=7.5, 1H), 7.88 (d, J=6.5, 1H), 7.83 (t, J=8.3, 1H), 7.61 (d, J=6.0, 1H), 7.00 (d, J=8.5, 1H), 5.53 (s, 2H), 4.14-4.12 (m, 2H), 4.05 (s, 3H), 3.93-3.87 (m, 4H), 3.82-3.80 (m, 2H), 2.83 (s, 3H); LC/MS: (ES+) m/z (M+H)$^+$=554, HPLC R$_t$=0.953.

EXAMPLE 29

3H), 3.92-3.87 (m, 4H), 3.81-3.79 (m, 2H); LC/MS: (ES+) m/z (M+H)$^+$=540, HPLC R$_t$=0.910.

EXAMPLE 30

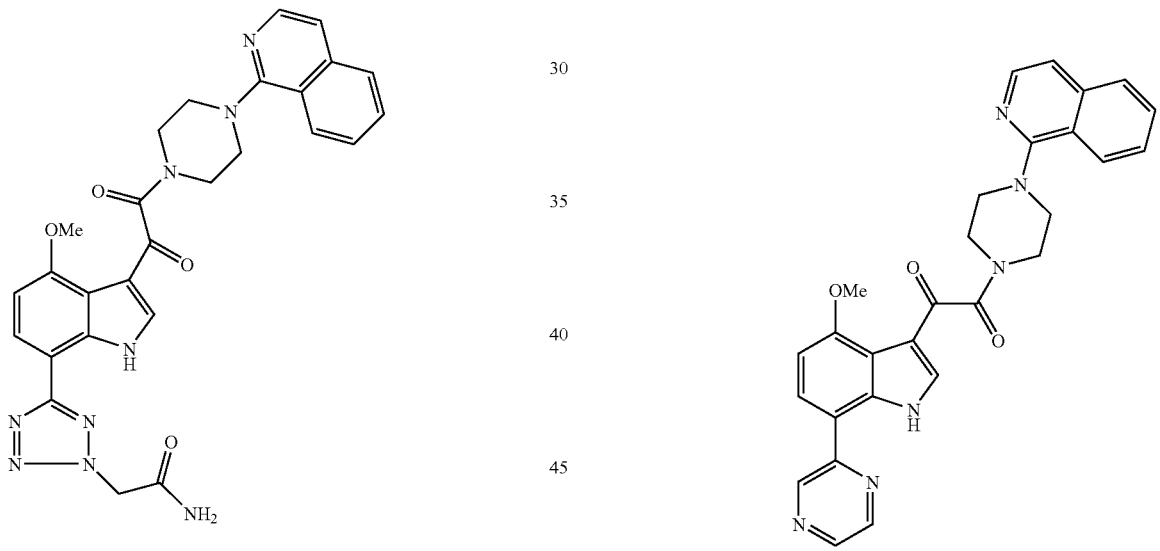

Example 4

Example 30

To a mixture of Example 27 (20 mg, 0.037 mol) in DMF (1.5 mL) was added NH$_4$Cl (16 mg, 0.30 mol), HOBT (35 mg, 0.26 mmol), EDC (42 mg, 0.22 mmol), and NMM (50 μL, 0.45 mmol). The reaction mixture was stirred at ambient temperature for twenty-four hours, diluted with MeOH and then purified by preparative reverse phase HPLC using the separation method: Start % B=0, Final % B=100, Gradient time=18 min, Flow Rate=30 mL/min, Column: Xterra Prep MS C18 5 um 19×50 mm, Fraction Collection: 7.11-7.51 min. $^1$H NMR: (CD$_3$OD) δ 8.38 (d, J=8.5, 1H), 8.24 (s, 1H), 8.10 (d, J=8.5, 1H), 8.03 (d, J=8.0, 1H), 7.97 (t, J=7.5, 1H), 7.87 (d, J=6.5, 1H), 7.82 (t, J=7.8, 1H), 7.59 (d, J=6.5, 1H), 6.97 (d, J=8.0, 1H), 5.57 (s, 2H), 4.13-4.11 (m, 2H), 4.04 (s, To a mixture of Example 4 (31.5 mg, 63.8 mmol) and 2-tributylstannyl pyridazine (30 mg, 81.3 mmol) in 1,4-dioxane (4 ml) in a re-usable sealed tube at r.t. was added Pd(PPh$_3$)$_4$ (20 mg, 17.3 mmol). The tube was tightly closed, and the mixture stirred at 135° C. for 3 h. After cooled to r.t., the mixture was diluted with MeOH (4 ml), filtered through a cake of celite and the filtrate evaporated. The resulting residue was titurated with hexane (3×2 ml), and the hexane removed by pipet. The residue was dried under vacuum, dissolved in MeOH and purified by preparative reverse phase HPLC using the separation method: Start % B=0, Final % B=100, Gradient time=6 min, Flow Rate=30 mL/min, Column: Xterra Prep MS C18 5 um 19×50 mm, Fraction Collection: 3.72-4.24 min. $^1$H NMR: (CD$_3$OD) δ 9.30 (s, 1H), 8.73 (app t, 1H), 8.48 (d, J=3.0, 1H), 8.42 (d, J=9.0, 1H), 8.25 (s, 1H), 8.08-8.06 (m, 1H), 8.07 (d, J=8.5, 1H), 8.03-8.00 (m, 1H), 7.84 (d, J=6.5, 2H), 7.64 (d, J=6.5, 1H), 6.99 (d, J=8.5, 1H), 4.17-4.14 (m, 2H), 4.06 (s, 3H), 4.00-3.98 (m, 2H), 3.90 (b s, 4H); LC/MS: (ES+) m/z (M+H)$^+$=493, HPLC R$_t$=1.063

EXAMPLE 31

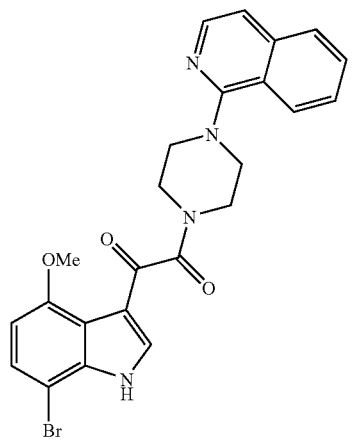

Example 4

→

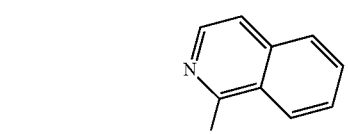

Example 31

Example 31 was prepared in a similar manner as described before and purified by preparative reverse-phase HPLC using the separation method: Start % B=20, Final % B=80, Gradient time=6 min, Flow Rate=30 mL/min, Column: Xterra Prep MS C18 5 μm 19×50 mm, Fraction Collection: 2.35-2.96 min. $^1$H NMR: (CD$_3$OD) δ 9.08 (s, 1H), 8.42 (d, J=8.0, 1H), 8.30 (s, 1H), 8.20 (s, 1H), 8.08-8.01 (m, 2H), 7.87-7.83 (m, 2H), 7.65-7.64 (m, 1H), 7.60 (d, J=8.5, 1H), 6.91 (d, J=8.5, 1H), 4.15-4.13 (m, 2H), 4.03 (s, 3H), 4.03-4.00 (m, overlapped with s, 3H), 3.91 (b s, 2H), 3.91-3.88 (m, overlapped with s, 1H); LC/MS: (ES+) m/z (M+H)$^+$=482, HPLC R$_t$=0.893.

EXAMPLE 32

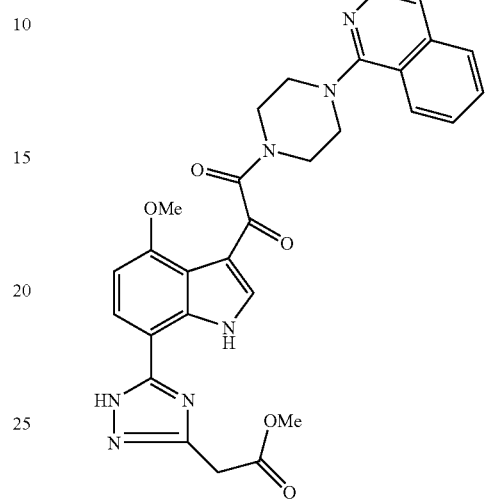

To a solution of Example 24 (45 mg, 0.086 mmol) in MeOH (1.0 mL) in a re-usable sealed tube was bubbled with anhydrous hydrogen chloride gas for 15 min. The tube was closed, and the mixture stirred at ambient temperature for 3 hour. The volatiles were evaporated in vacuo to give Example 32. $^1$H NMR: (CD$_3$OD) δ 8.44 (d, J=8.5, 1H), 8.26 (s, 1H), 8.10-8.03 (m, 2H), 7.93 (d, J=8.5, 1H), 7.89 (t, J=7.5, 1H), 7.83 (d, J=6.5, 1H), 7.67 (d, J=7.0, 1H), 6.99 (d, J=8.0, 1H), 4.15 (b s, 3H), 4.05 (b s, 4H), 3.94 (b m, 4H), 3.81 (s, 3H), 3.34 (s, 2H); LC/MS: (ES+) m/z (M+H)$^+$=554, HPLC R$_t$=0.997.

EXAMPLE 33

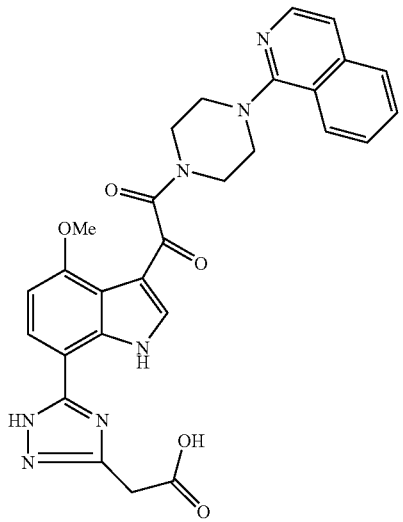

To a mixture of Example 32 (13 mg, 0.024 mmol) in MeOH (0.5 mL) was added 1N NaOH (0.1 mL), and stirred for 2 hours at room temperature. The reaction was then quenched with 1N HCl (0.1 mL), and the volatiles evaporated to give a clear film. ¹H NMR: (CD₃OD) δ 8.44 (d, J=6.5, 1H), 8.26 (s, 1H), 8.11-7.99 (m, 2H), 7.90-7.83 (m, 3H), 7.65 (d, J=6.0, 1H), 7.01 (d, J=8.0, 1H), 4.27 (b s, 1H), 4.16 (b s, 2H), 4.07 (b s, 4H), 3.97 (b d, 4H), 3.34 (s, 2H); LC/MS: (ES+) m/z (M+H)⁺=540, HPLC R$_t$=0.917.

EXAMPLE 34

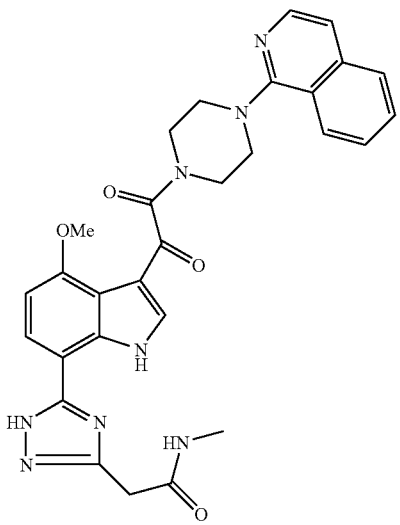

To a mixture of Example 33 (23 mg, 0.043 mmol) in DMF (1.5 mL) were added methylamine hydrochloride (10 mg, 0.32 mmol), HOBT (31 mg, 0.23 mmol), EDC (43 mg, 0.22 mmol), and NMM (50 μL, 0.45 mmol). The mixture was stirred overnight at room temperature, and then kept in the freezer over 48 hours. The desired product was isolated by preparative reverse-phase HPLC using the separation method: Start % B=0, Final % B=100, Gradient time=18 min, Flow Rate=30 mL/min, Column: Xterra Prep MS C18 5 μm 19×50 mm, Fraction Collection: 6.73-7.34 min. ¹H NMR: (CD₃OD) δ 8.40 (d, J=8.5, 1H), 8.23 (s, 1H), 8.06-8.00 (m, 2H), 7.91 (d, J=8.5, 1H), 7.86-7.81 (m, 2H), 7.63 (d, J=7.0, 1H), 6.92 (d, J=8.5, 1H), 4.13 (b s, 2H), 4.02 (s, 3H), 4.00-3.98 (m, 2H), 3.88 (b s, 4H), 3.84 (s, 2H), 2.80 (s, 3H); LC/MS: (ES+) m/z (M+H)⁺=553, HPLC R$_t$=0.900.

EXAMPLE 35

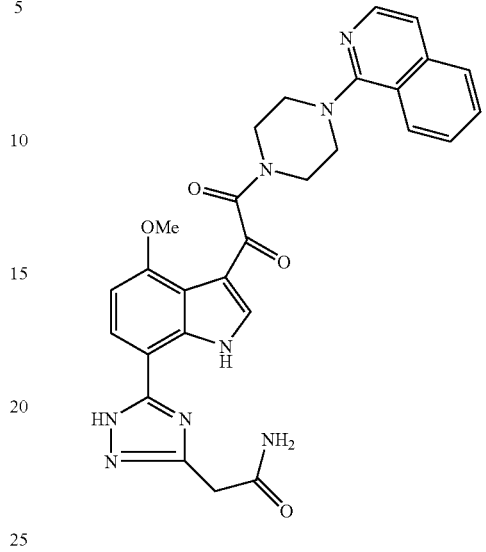

To a mixture of Example 33 (23 mg, 0.043 mmol) in DMF (1.5 mL) was added ammonium chloride (15 mg, 0.28 mmol), HOBT (35 mg, 0.28 mmol), EDC (43 mg, 0.22 mmol), and NMM (50 μL, 0.45 mmol). The mixture was stirred overnight at room temperature, and then kept in the freezer over 48 hours. The desired product was isolated by preparative reverse-phase HPLC using the separation method: Start % B=0, Final % B=100, Gradient time=18 min, Flow Rate=30 mL/min, Column: Xterra Prep MS C18 5 μm 19×50 mm, Fraction Collection: 6.18-6.78 min. ¹H NMR: (CD₃OD) δ 8.42 (d, J=8.5, 1H), 8.25 (s, 1H), 8.07 (d, J=8.0, 1H), 8.04 (t, J=7.3, 1H), 7.93 (d, J=8.5, 1H), 7.87-7.82 (m, 2H), 7.64 (d, J=6.5, 1H), 6.93 (d, J=8.0, 1H), 4.14 (b s, 2H), 4.03 (s, 3H), 4.00 (b s, 2H), 3.89 (s, 4H), 3.88 (s, 2H); LC/MS: (ES+) m/z (M+H)⁺=539, HPLC R$_t$=0.850.

EXAMPLE 36

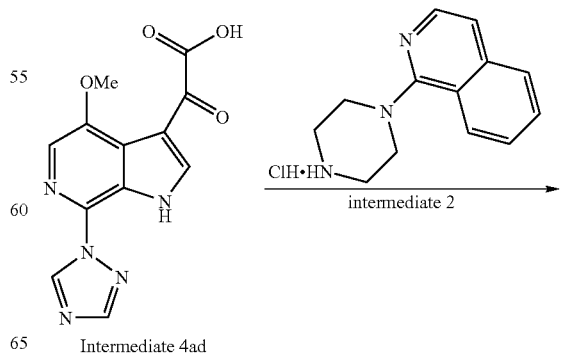

Intermediate 4ad

-continued

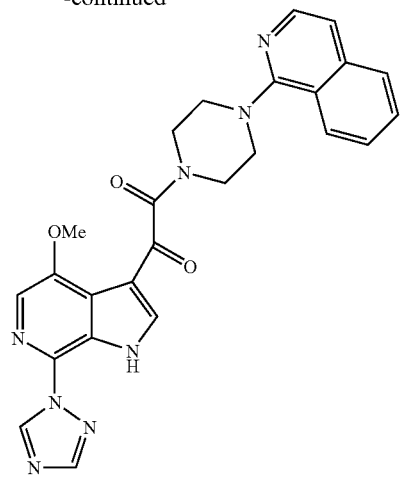

Example 36

To a mixture of Intermediate 4ad (22 mg, 0.077 mmol) in DMF (1 mL) was added piperazine hydrochloride Intermediate 2 (85 mg, 0.40 mmol), DEPBT (72 mg, 0.24 mmol), and N,N-diisopropylethylamine (0.1 mL, 0.57 mmol). The reaction mixture was stirred for 18 hours at room temperature, and the desired product was isolated by preparative reverse phase HPLC using the following method: Start % B=0, Final % B=60, Gradient time=18 min, Flow Rate=30 mL/min, Column: Xterra Prep MS C18 5 µm 19×50 mm, Fraction Collection: 9.53-10.14 min. $^1$H NMR: (CD$_3$OD) δ 9.38 (s, 1H), 8.44 (d, J=8.5, 1H), 8.38 (s, 1H), 8.34 (s, 1H), 8.09 (d, J=8.0, 1H), 8.05 (t, J=7.5, 1H), 7.94 (s, 1H), 7.88-7.84 (m, 2H), 7.67 (d, J=7.0, 1H), 4.16 (b s, 2H), 4.12 (s, 3H), 4.03 (b s, 2H), 3.92 (s, 4H); LC/MS: (ES+) m/z (M+H)$^+$=483, HPLC R$_t$=0.930.

Precursor 2a

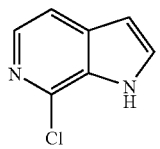

Typical procedure for preparing azaindole from nitropyridine: Preparation of 7-chloro-6-azaindole, Precursor 2a, is an example of Step A of Scheme 1. 2-chloro-3-nitropyridine (5.0 g, 31.5 mmol) was dissolved in dry THF (200 mL). After the solution was cooled to −78° C., vinyl magnesium bromide (1.0M in THF, 100 mL) was added dropwise. The reaction temperature was maintained at −78° C. for 1 h, and then at −20° C. for another 12 h before it was quenched by addition of 20% NH$_4$Cl aqueous solution (150 mL). The aqueous phase was extracted with EtOAc (3×150 mL). The combined organic layer was dried over MgSO$_4$, filtered and the filtrate was concentrated in vacuo to give a residue which was purified by silica gel column chromatography (EtOAc/Hexane, 1/10) to afford 1.5 g (31%) of 7-chloro-6-azaindole, Precursor 2a. $^1$H NMR (500 MHz, CD$_3$OD) δ 7.84 (d, 1H, J=10.7 Hz), 7.55 (dd, 1H, J=10.9, 5.45 Hz), 6.62 (d, 1H, J=5.54 Hz), 4.89 (s, 1H). MS m/z: (M+H)$^+$ calcd for C$_7$H$_6$ClN$_2$: 153.02; found 152.93. HPLC retention time: 0.43 minutes (column A).

Precursor 3a

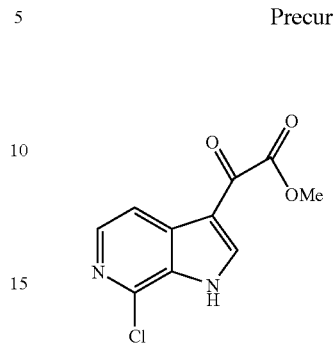

Typical procedure for acylation of azaindole: Preparation of Methyl (7-chloro-6-azaindol-3-yl)-oxoacetate, Precursor 3a is an example of Step B of Scheme 1. 7-Chloro-6-azaindole, Precursor 2a (0.5 g, 3.3 mmol) was added to a suspension of AlCl$_3$ (2.2 g, 16.3 mmol) in CH$_2$Cl$_2$ (100 mL). Stirring was continued at rt for 10 minutes before methyl chlorooxoacetate (2.0 g, 16.3 mmol) was added dropwise. The reaction was stirred for 8 h. The reaction was quenched with iced aqueous NH$_4$OAc solution (10%, 200 mL). The aqueous phase was extracted with CH$_2$Cl$_2$ (3×100 mL). The combined organic layer was dried over MgSO$_4$, filtered and the filtrate was concentrated in vacuo to give a residue which was carried to the next step without further purification. Precursor 2, Methyl (7-chloro-6-azaindol-3-yl)-oxoacetate: MS m/z: (M+H)$^+$ calcd for C$_{10}$H$_8$ClN$_2$O$_3$: 239.02; found 238.97. HPLC retention time: 1.07 minutes (column A).

Precursor 4a

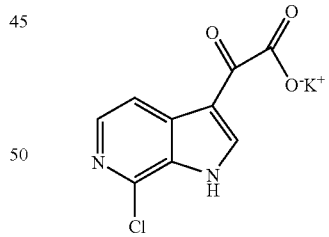

Typical procedure of hydrolysis of ester: Preparation of Potassium (7-chloro-6-azaindol-3-yl)-oxoacetate, Precursor 4a, is an example of Step C of Scheme 1. Crude methyl (7-chloro-6-azaindol-3-yl)-oxoacetate, Precursor 3a, and an excess of K$_2$CO$_3$ (2 g) were dissolved in MeOH (20 mL) and H$_2$O (20 mL). After 8 h, the solution was concentrated and the residue was purified by silica gel column chromatography to provide 200 mg of Potassium (7-chloro-6-azaindol-3-yl)-oxoacetate. MS m/z: (M+H)$^+$ of the corresponding acid was observed. Calc'd for $C_9H_6ClN_2O_3$: 225.01; found 225.05. HPLC retention time: 0.83 minutes (column A).

Precursor 2g

Precursor 2g, 7-chloro-4-azaindole was prepared by the same method as Precursor 2a, starting from 4-Chloro-3-nitropyridine (HCl salt, available from Austin Chemical Company, Inc.). MS m/z: $(M+H)^+$ calcd for $C_7H_6ClN_2$: 153.02. found 152.90. HPLC retention time: 0.45 minutes (column A).

Precursor 3f

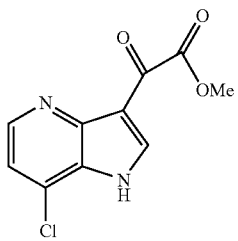

Precursor 3f, Methyl (7-chloro-4-azaindol-3-yl)-oxoacetate was prepared by the same method as Precursor 3a, starting from Precursor 2g, 7-chloro-4-azaindole. MS m/z: $(M+H)^+$ calcd for $C_{10}H_8ClN_2O_3$: 239.02; found 238.97. HPLC retention time: 0.60 minutes (column A).

Precursor 4e

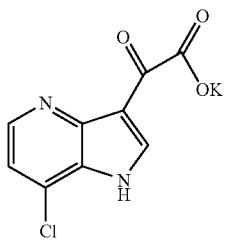

Precursor 4e, Potassium (7-chloro-4-azaindol-3-yl)-oxoacetate was prepared by the same method as Precursor 4a, starting from Methyl (7-chloro-4-azaindol-3-yl)-oxoacetate, Precursor 3f. MS m/z: $(M+H)^+$ of the corresponding acid of compound 4e $(M-K^+ H)^+$ calcd for $C_9H_6ClN_2O_3$: 225.01; found 225.27. HPLC retention time: 0.33 minutes (column A).

EXAMPLE 37

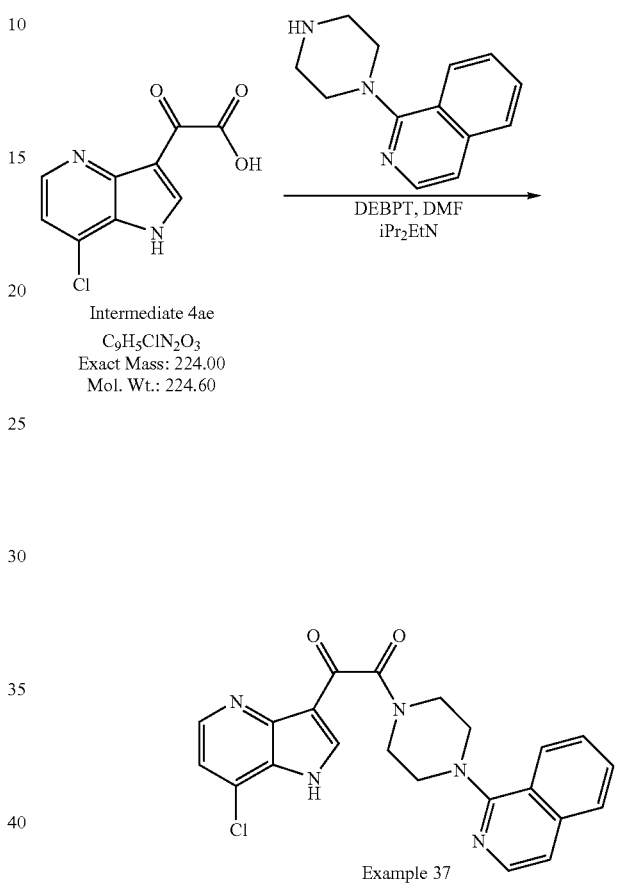

The standard coupling procedures described earlier were used to couple intermediates 4ae and intermediate 1 with procedures to provide Example 37 ret. time=0.65 min (column G, solvent A) Exact Mass: 419.11

EXAMPLE 38

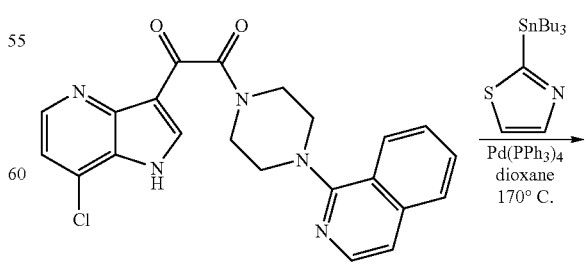

$C_{22}H_{18}ClN_5O_2$
Exact Mass: 419.11
Mol. Wt.: 419.86

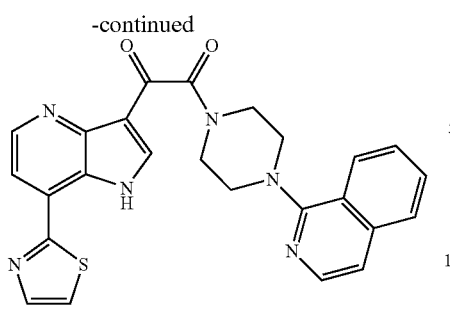

Standard Stille coupling conditions as described earlier were used to provide Example 38 after coupling with 2-tributyl stannyl thiazole. ret. time=0.78 min (column G, solvent a)

Exact Mass: 468.14

LCMS Conditions:

Solvent A: 10% MeOH—90% H2O—0.1% TFA

Solvent B: 90% MeOH—10% H2O—0.1% TFA

Column: XTERRA C18 S7 3.0×50 mm

Start % B=0

Final % B=100

Gradient Time=2 min

Flow Rate=5 ml/min

Wavelength=220

EXAMPLE 39

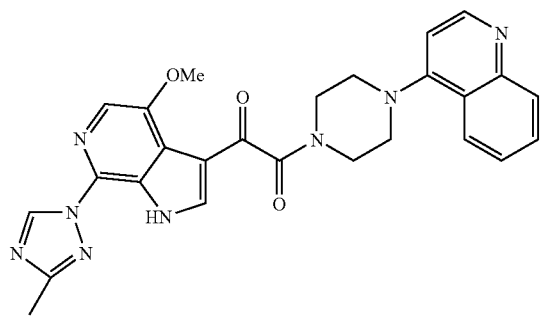

Using the procedures described herein the title compound was prepared:

$^1$H NMR: (CD$_3$OD) δ 9.23 (s, 1H), 8.59 (d, J=7.0, 1H), 8.37 (s, 1H), 8.32 (d, J=8.5, 1H), 8.01-7.96 (dd overlapped with d, 2H), 7.90 (s, 1H), 7.76 (app t, 1H), 7.28 (d, J=7.0, 1H), 4.09 (s overlapped with m, 7H), 3.98 (m, 2H), 3.88 (m, 2H), 2.56 (s, 3H); LC/MS: (ES+) m/z (M+H)$^+$=497; HPLC R$_f$=0.937.

EXAMPLE 40

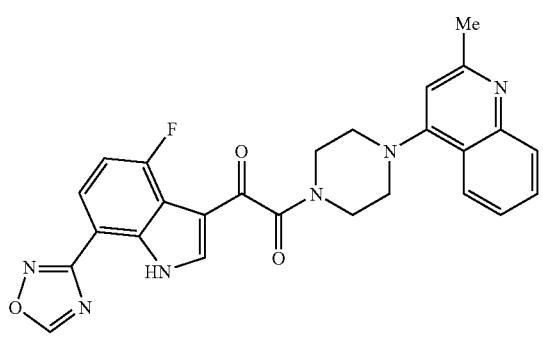

General Procedure 25 mgs (0.085147 mmol) of (4-Methoxy-7-[1,2,4]oxadiazol-3-yl-1H-pyrrolo[2,3-c]pyridin-3-yl)-oxo-acetyl chloride and 19.4 mgs (0.085 mmol) of 2-Methyl-4-piperazin-1-yl-quinoline were suspended in 2 mL of dichloromethane in a vial and cooled to −10° C. Diisopropylethylamine (22.2 μL, 1.5 equivalents) was then added and the reaction was shaken for 10 min. The reaction was allowed to stand. A pale yellow precipitate formed after 10 min. After standing for two hours total, the suspension was dissolved with 20 mL of dichloromethane and 15 mL water. Extraction and then reextraction with 10 mL of dichloromethane provided combined organic extracts which were dried over anhydrous Magnesium Sulfate, filtered and concentrated in vacuo to provide ~20 mgs of the desired product [M+H]+=485 and LC purity=87% at 215 nM and a ten minute elution.

EXAMPLES 41-42

41

42

(i) RNH$_2$ (1 eq)
DIPEA, (1.1 eq)DCM, r.t., o/n
(ii) O—NH$_2$ (PAMPS), DCM, r.t. o/n (0.2 eq.)
(iii) Aq. 10% citiric acid wash
(iv) silica plus elutions (element = 9 EtOAc = 1 MeOH)

(1.1 eq.)

A well of a standard 96 well plate was loaded with 1 mL of dichloromethane then 1.1 eq of the corresponding piperazine and then acid chloride (1.1 eq, 0.0470 to 0.0532 mmol) were then added. Next 5 eqs of Hunig's base (diisopropylethylamine) were added and the plate shaken overnight at ambient temperature. Two equivalents of PAMPS (n-propylaminomethylolystyrene, 1/mmol per gram) were added for each equivalent of acid chloride and the reaction mixture shaken overnight. The wells were agitated by adding, pipetting, and re-adding 0.5 mL citric acid about ten times. The contents of the well was passed through anhydrous MgSO4, and the products either used as formed or purified by passage over SiO2 using 9:1 ethylacetate: methanol.
Data for Examples 40-42
10 minute HPLC method for example 40
1. Apparatus and Reagents
1.1 Common Apparatus 0.1% Trifluoroacetic acid (aq)—Mobile phase "A"
0.1% Trifluoroacetic acid (acetonitrile)—Mobile phase "B"
Phenomenex Luna C8 (2) 100×2.0 mm, 3 μm column
Waters Millennium$^{32}$™ Chromatography Data System (V3.2 or better)
1.2 Instrumentation
Waters 2790 LC system ("LC19"), comprising:
Waters 2790 Separations Module
Waters 2487 Dual Wavelength Absorbance Detector—wavelength set at 215 nm.
2. Instrument Parameters
LC Conditions The dashed line represents re-equilibration. Overall run time is ~13.5 minutes, the mass spectrometer and Millennium$^{32}$ captures the first 10 minutes of the run.

| | Flow rate = 0.3 ml/min | |
| | Run time = 13.5 minutes | |
| Gradient: | Time (mins) | % Organic |
| | 0.00 | 5 |
| | 6.30 | 95 |
| | 9.50 | 95 |
| | 9.70 | 5 |
| | 13.5 | 5 |

3. Integration and Reporting
Data is integrated using Millennium and reported via the Millennium software.
2.5 Minute HPLC method for Examples 41 and 42
4. Apparatus and Reagents
4.1 Common Apparatus
0.1% Trifluoroacetic acid (aq)—Mobile phase "A"
0.1% Trifluoroacetic acid (acetonitrile)—Mobile phase "B"
Hypersil BDS C18 column 5 um, 2.1×50 mm
Micromass MassLynx™ Operating Software with OpenLynx™ Browser Option (V3.5 or better)
Waters Millennium$^{32}$™ Chromatography Data System (V3.2 or better)
4.2 Instrumentation
4.2.1 Micromass Single Quadrupole LCMS Systems ("MS1", "MS4", "MS6" or "MS7"), Comprising:
Agilent HP1100 LC system comprising the following modules:
G1315A Diode Array Detector or G1314A Single Wavelength UV Detector
G1312A Binary Pump with Pulse Dampener and Mixer fitted
G1316A Vacuum Degasser (optional)
G1316A Column Oven (optional)

Polymer LabsPL1000 Evaporative Light Scattering Detector (ELSD) with either
   CTC Analytics HTC PAL Autosampler
   or
   Gilson 215 Single Probe Autosampler
with either
   Micromass Platform LC
   or
   Micromass ZMD single quadrupole mass spectrometer
4.2.2 Micromass LCT Systems ("MS5", "MS8" or "MS9"), Comprising:
   MS5
      Agilent HP1100 LC system comprising the following modules:
      G1314A Single Wavelength UV Detector
      G1312A Binary Pump with Pulse Dampener and Mixer fitted
      CTC Analytics HTC PAL Autosampler
      Micromass LCT with Z-spray Interface
   MS8
      Waters 600 Binary Pump
      8× Waters 2487 Dual Wavelength Detector
      Gilson 215 Multiprobe 8-way Autosampler
      Micromass LCT with MUX™ 8-way interface
   MS9
      Waters 1525 Binary Pump
      1×2488 Dual Wavelength 8-way detector
      CTC Analytics HTS PAL Autosampler with 4-fold injection valve
      Micromass LCT with MUX™ 5-way interface
5. LC Conditions
5.1.1 LC Conditions—for MS8.
   Flow rate=8.0 ml/min–split 8 ways to deliver 1 ml/min through all 8 lines

| Time (mins) | % B |
|---|---|
| 0 | 0 |
| 1.80 | 95 |
| 2.10 | 95 |
| 2.30 | 0 |
| 2.90 | 0 |

5.1.2 LC Conditions—for MS9.
   Flow rate=4.0 ml/min–split 4 ways to deliver 1 ml/min through all 4 lines

| Time (mins) | % B |
|---|---|
| 0 | 0 |
| 1.80 | 95 |
| 2.10 | 95 |
| 2.30 | 0 |
| 2.39 | 0 |

5.2 Mass Spectrometer Conditions
   Data is typically collected over the range m/z 150 to 850 at a sampling rate of 2 scans per second (1 scan per 1.2 seconds per line on MS8).
6. Integration and Reporting
   Data is integrated using OpenLynx and reported via the OpenLynx Browser software.

| Example # | MW | HPLC Method | HPLC Ret. Time | Mass spec (purity) |
|---|---|---|---|---|
| Example 40 | 484.49 | 10 Min. | 4.23 min. | 485.25 (100%) |
| Example 41 | 434.43 | 2.5 Min. | 1.03 min. | 435.25 (100%) |
| Example 42 | 453.86 | 2.5 Min. | 1.56 min. | 454.22 (100%) |

Intermediate 9 (HCl Salt)

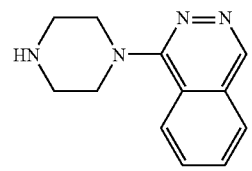

Hydrochloride salt of intermediate 9 was prepared from the corresponding 1-hydroxyphthalazine by conversion to the 1-chloro derivative (neat POCl$_3$, 130° C.), followed by condensation with tert-butyl 1-piperazinecarboxylate (Et$_3$N, nBuOH, 130° C.) and then deprotection (4N HCl in 1,4-dioxane, r.t.); HCl salt $^1$H NMR: (CD$_3$OD) δ 9.83 (s, 1H), 8.54-8.49 (m, 2H), 8.38 (app t, 1H), 8.28 (app t, 1H), 4.01 (b s, 4H), 3.58 (b s, 4H); Analytical HPLC method: Start % B=0, Final % B=100, Gradient time=2 min, Flow Rate=5 mL/min, Column: Xterra C18 S7 3.0×50 mm, LC/MS: (ES+) m/z (M+H)$^+$=215.12, HPLC R$_t$=0.083.

Intermediate 10 (HCl Salt)

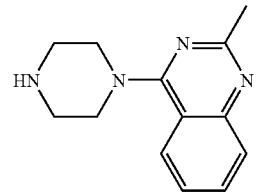

Hydrochloride salt of Intermediate 10 was prepared in a similar manner as Intermediate 9, except that the following chlorination conditions were used: POCl$_3$, N,N-diethylaniline, benzene, reflux (Connolly, D. J.; Guiry, P. J. *Synlett* 2001, 1707.); HCl salt $^1$H NMR: (CD$_3$OD) δ 8.26 (d, J=10, 1H), 8.05 (app t, 1H), 7.83 (d, J=5, 1H), 7.76 (app t, 1H), 4.53 (b s, 4H), 3.56 (b s, 4H), 2.75 (s, 3H); Analytical HPLC method: Start % B=0, Final % B=100, Gradient time=2 min, Flow Rate=5 mL/min, Column: Xterra C18 S7 3.0×50 mm, LC/MS: (ES+) m/z (M+H)⁺=229.40, HPLC $R_t$=0.077.

Intermediate 11 (HCl Salt)

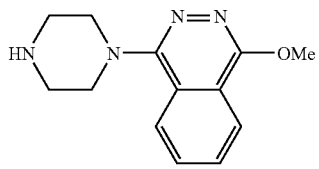

Hydrochloride salt of Intermediate 11 was isolated as a side product during the preparation of the corresponding 1-chloro analog; Analytical HPLC method: Start % B=0, Final % B=100, Gradient time=2 min, Flow Rate=5 mL/min, Column: Xterra C18 S7 3.0×50 mm, LC/MS: (ES+) m/z (M+H)⁺= 245.13, HPLC $R_t$=0.523.

EXAMPLE 44

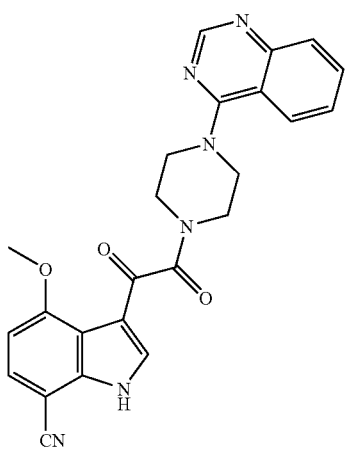

Example 44 was prepared in a similar manner as Example 43 using EDC/DMAP as the coupling reagents, and purification by preparative reverse phase HPLC. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 2.88-3.49 min; ¹H NMR: (CD₃OD) δ 8.74 (s, 1H), 8.29 (d, J=10, 1H), 8.21 (s, 1H), 8.05 (d, J=10, 1H), 7.83-7.76 (m, 2H), 7.67 (d, J=10, 1H), 6.91 (d, J=10, 1H), 4.49 (b s, 2H), 4.37 (b s, 2H), 4.00 (b s, 5H), 3.80 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)⁺=441.27, HPLC $R_t$=1.123.

EXAMPLE 45

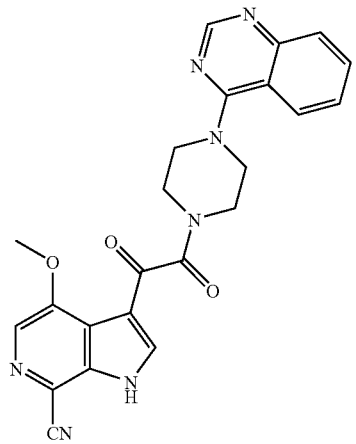

Example 45 was prepared in a similar manner as Example 9 using HATU/DMAP as the coupling reagents. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 2.72-3.30 min; ¹H NMR: (CD₃OD) δ 8.74 (s, 1H), 8.44 (s, 1H), 8.30 (d, J=10, 1H), 8.19 (s, 1H), 8.06 (t, J=10, 1H), 7.83-7.77 (m, 2H), 4.49 (b s, 2H), 4.38 (b s, 2H), 4.12 (b s, 3H), 4.01 (b s, 2H), 3.82 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)⁺=442.24, HPLC $R_t$=1.053.

EXAMPLE 46

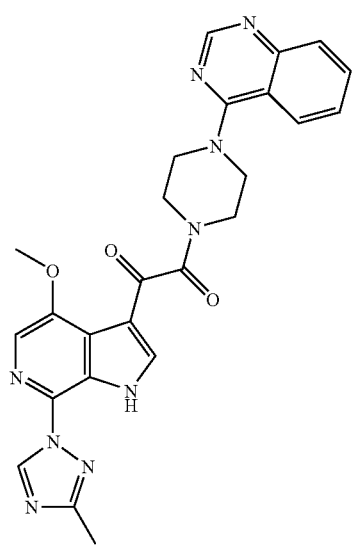

Example 46 was prepared in a similar manner as Example 36 using HATU/DMAP as the coupling reagents. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 3.14-3.74 min; $^1$H NMR: (CD$_3$OD) δ 9.23 (s, 1H), 8.74 (s, 1H), 8.35 (s, 1H), 8.31 (d, J=5, 1H), 8.06 (app t, 1H), 7.86 (s, 1H), 7.83 (d, J=5, 1H), 7.78 (app t, 1H), 4.52 (b s, 2H), 4.41 (b s, 2H), 4.06 (s, 3H), 4.04 (b s, 2H), 3.84 (b s, 2H), 2.55 (s, 3H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=498.19, HPLC R$_f$=0.910.

EXAMPLE 47

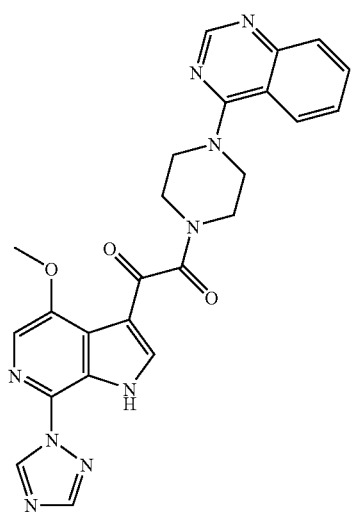

Example 47 was prepared in a similar manner as Example 46. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 3.08-3.40 min; $^1$H NMR: (CD$_3$OD) δ 9.37 (s, 1H), 8.74 (s, 1H), 8.36 (s, 1H), 8.33 (s, 1H), 8.30 (d, J=10, 1H), 8.05 (app t, 1H), 7.90 (s, 1H), 7.83 (d, J=10, 1H), 7.77 (app t, 1H), 4.50 (b s, 2H), 4.39 (b s, 2H), 4.07 (s, 3H), 4.04 (b s, 2H), 3.84 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=484.18, HPLC R$_f$=0.843.

EXAMPLE 48

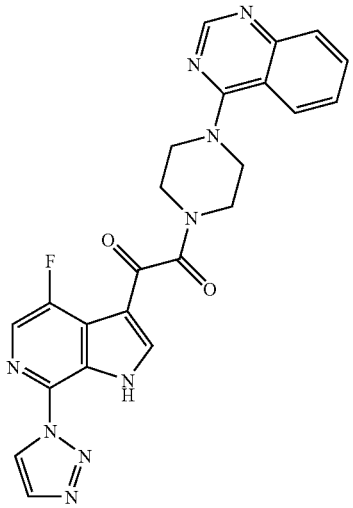

Example 48 was prepared in a similar manner as Example 46. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 3.18-3.79 min; $^1$H NMR: (CD$_3$OD) δ 8.91 (s, 1H), 8.74 (s, 1H), 8.47 (s, 1H), 8.29 (d, J=10, 1H), 8.20 (d, J=5, 1H), 8.05 (app t, 1H), 8.00 (s, 1H), 7.83 (d, J=5, 1H), 7.77 (app t, 1H), 4.50 (b s, 2H), 4.40 (b s, 2H), 4.04 (b s, 2H), 3.89 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=472.14, HPLC R$_f$=1.007.

EXAMPLE 49

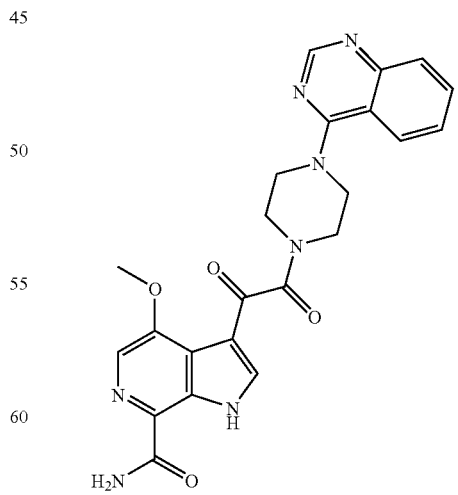

Example 49 was prepared from Example 45. Preparative reverse phase HPLC separation method: Start % B=0, Final % B=100, Gradient time=5 min, Flow Rate=25 mL/min, Column: Xterra Prep 19×50 mm S5, Fraction Collection: 2.29-2.98 min; $^1$H NMR: (CD$_3$OD) δ 8.75 (s, 1H), 8.54 (s, 1H), 8.32 (d, J=5, 1H), 8.14 (s, 1H), 8.06 (d, J=5, 1H), 7.84 (d, J=10, 1H), 7.78 (b s, 1H), 4.52 (b s, 2H), 4.41 (b s, 2H), 4.15 (b s, 3H), 4.04 (b s, 2H), 3.86 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=460.28, HPLC R$_t$=0.763.

EXAMPLE 50

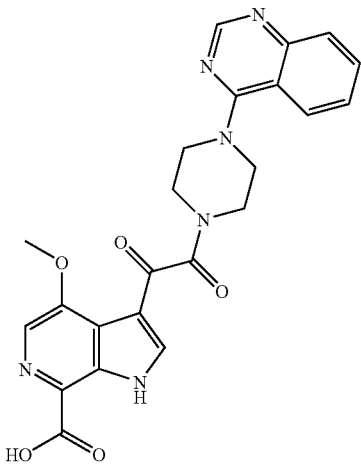

Example 50 was prepared from Example 49. $^1$H NMR: (CD$_3$OD) δ 8.64 (s, 1H), 8.32 (s, 1H), 8.10 (s, 2H), 7.85 (d, J=5, 2H), 7.60-7.57 (m, 1H), 4.11 (s, 3H), 4.01 (b s, 2H), 3.99 (b s, 2H), 3.90 (b s, 2H), 3.73 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=461.17, HPLC R$_t$=0.743.

EXAMPLE 51

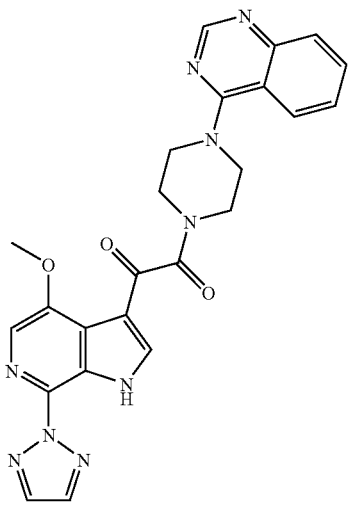

Example 51 was prepared in a similar manner as Example 46. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 1.62-2.06 min; $^1$H NMR: (CD$_3$OD) δ 8.74 (s, 1H), 8.39 (s, 1H), 8.31 (d, J=10, 1H), 8.14 (s, 2H), 8.06 (app t, 1H), 7.92 (b s, 1H), 7.83 (d, J=5, 1H), 7.78 (app t, 1H), 4.52 (b s, 2H), 4.40 (b s, 2H), 4.09 (s, 3H), 4.04 (b s, 2H), 3.85 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=484.18, HPLC R$_t$=0.893.

EXAMPLE 52

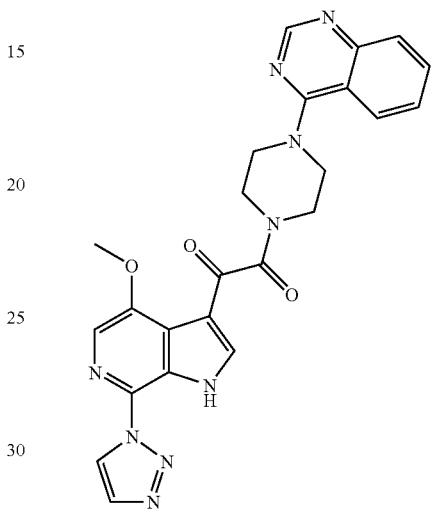

Example 52 was prepared in a similar manner as Example 46. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 3.13-3.69 min; $^1$H NMR: (CD$_3$OD) δ 8.86 (s, 1H), 8.74 (s, 1H), 8.39 (s, 1H), 8.31 (d, J=10, 1H), 8.06 (app t, 1H), 7.98 (s, 1H), 7.97 (s, 1H), 7.83 (d, J=5, 1H), 7.78 (app t, 1H), 4.51 (b s, 2H), 4.41 (b s, 2H), 4.09 (s, 3H), 4.04 (b s, 2H), 3.85 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=484.10, HPLC R$_t$=0.990.

EXAMPLE 53

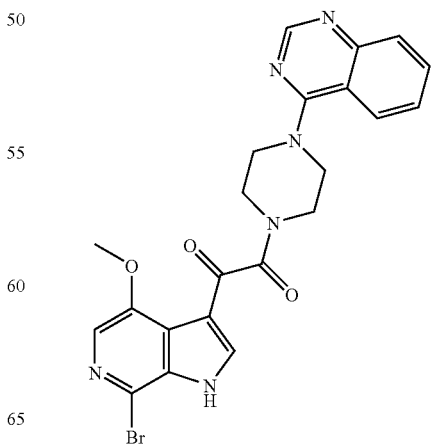

Example 53 was prepared in a similar manner as Example 9 using HATU/DMAP as the coupling reagents. $^1$H NMR: (CD$_3$OD) δ 8.72 (s, 1H), 8.35 (s, 1H), 8.26 (d, J=10, 1H), 8.02 (app t, 1H), 7.84 (d, J=5, 1H), 7.80 (s, 1H), 7.74 (app t, 1H), 4.41 (b s, 2H), 4.29 (b s, 2H), 4.01 (b s, 5H), 3.80 (b s, 2H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=496.97, HPLC R$_t$=0.773.

EXAMPLE 54

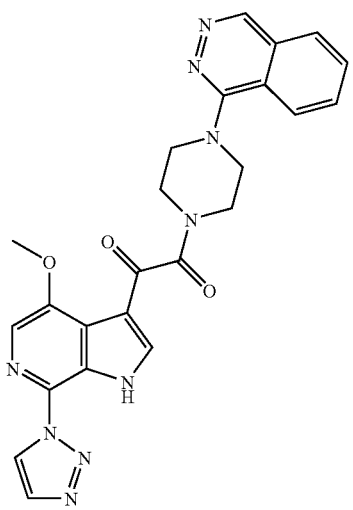

Example 54 was prepared in a similar manner as Example 46. Preparative reverse phase HPLC separation method: Start % B=0, Final % B=100, Gradient time=6 min, Flow Rate=30 mL/min, Column: Xerra Prep MS C18 5 uM 19×50 mm, Fraction Collection: 3.70-4.16 min; $^1$H NMR: (CD$_3$OD) δ 9.51 (s, 1H), 8.86 (b s, 2H), 8.48 (d, J=10, 1H), 8.39 (s, 1H), 8.25 (t, J=10, 1H), 8.21 (d, J=10, 1H), 7.98 (b s, 2H), 4.13 (s, 3H), 4.09 (b s, 2H), 4.07 (s, 2H), 3.95 (b s, 2H), 3.86 (b s, 2H); Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)$^+$= 484.11, HPLC R$_t$=1.213.

EXAMPLE 55

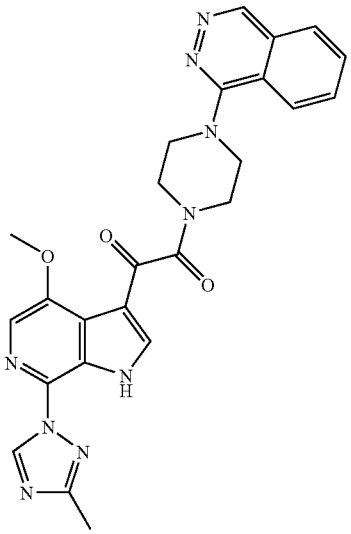

Example 55 was prepared in a similar manner as Example 46. Preparative reverse phase HPLC separation method: Start % B=0, Final % B=100, Gradient time=6 min, Flow Rate=25 mL/min, Column: Xterra 5 uM 19×50 mm, Fraction Collection: 3.17-3.87 min; $^1$H NMR: (CD$_3$OD) δ 9.56 (s, 1H), 9.24 (s, 1H), 8.51 (d, J=10, 1H), 8.43 (d, J=5, 1H), 8.34 (s, 1H), 8.29 (app t, 1H), 8.24 (app t, 1H), 7.87 (s, 1H), 4.09 (b s, 5H), 3.99 (b s, 2H), 3.89 (b s, 2H), 3.87 (b s, 2H), 2.55 (s, 3H); Analytical HPLC method: Start % B=0, Final % B=100, Gradient time=2 min, Flow Rate=5 mL/min, Column: Xterra C18 S7 3.0×50 mm; LC/MS: (ES+) m/z (M+H)$^+$=498.12, HPLC R$_t$=0.907.

EXAMPLE 56

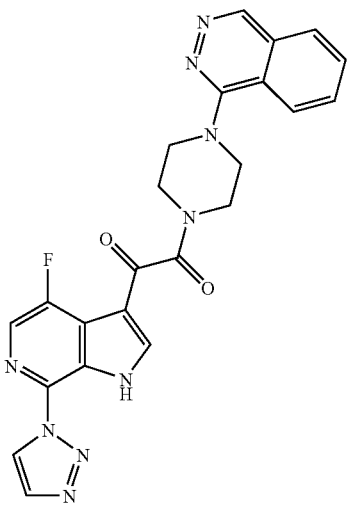

Example 56 was prepared in a similar manner as Example 46. Preparative reverse phase HPLC separation method: Start % B=0, Final % B=100, Gradient time=6 min, Flow Rate=30 mL/min, Column: Xterra 5 uM 19×50 mm, Fraction Collection: 3.86-4.47 min; $^1$H NMR: (CD$_3$OD) δ 9.52 (s, 1H), 8.92 (s, 1H), 8.47 (s, 1H), 8.39 (d, J=5, 1H), 8.26 (t, J=10, 1H), 8.22 (b s, 2H), 8.00 (s, 2H), 4.10 (b s, 2H), 3.96 (b s, 2H), 3.89 (b s, 2H), 3.87 (b s, 2H); Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)$^+$=472.08, HPLC R$_t$=1.313.

EXAMPLE 57

EXAMPLE 58

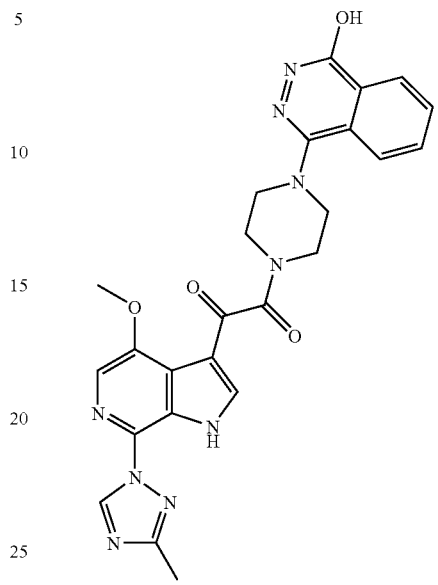

Example 58 was isolated as a side product of Example 57. Preparative reverse phase HPLC separation method: Start % B=0, Final % B=100, Gradient time=6 min, Flow Rate=30 mL/min, Column: Xterra 5 uM 19×50 mm, Fraction Collection: 4.51-4.89 min; $^1$H NMR: (CD$_3$OD) δ 9.25 (s, 1H), 8.35 (s, 1H), 8.33 (s, 1H), 8.10 (d, J=10, 1H), 7.94 (t, J=5, 1H), 7.89 (s, 1H), 7.86 (s, 1H), 4.11 (s, 3H), 4.01 (b s, 2H), 3.94 (b s, 2H), 3.82 (b s, 2H), 3.75 (b s, 2H), 2.56 (s, 3H); Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)$^+$=514.27, HPLC R$_t$=1.643.

EXAMPLE 59

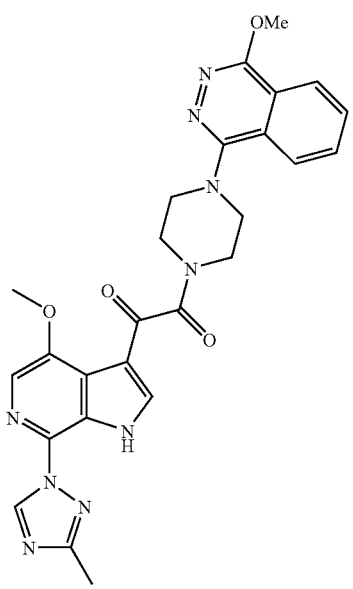

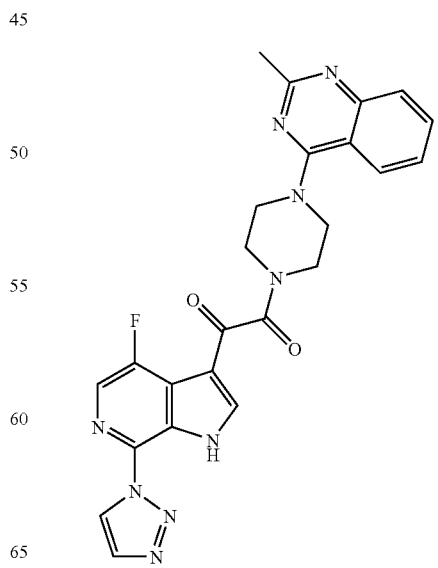

Example 57 was prepared in a similar manner as Example 46. Preparative reverse phase HPLC separation method: Start % B=0, Final % B=100, Gradient time=6 min, Flow Rate=30 mL/min, Column: Xterra 5 uM 19×50 mm, Fraction Collection: 3.88-4.47 min; $^1$H NMR: (CD$_3$OD) δ 9.23 (s, 1H), 8.47 (d, J=10, 1H), 8.35 (s, 1H), 8.31 (s, 1H), 8.19 (t, J=5, 1H), 7.88 (s, 1H), 7.82 (s, 1H), 4.22 (s, 3H), 4.13 (b s, 2H), 4.10 (s, 3H), 4.00 (b s, 2H), 3.89 (b s, 2H), 3.85 (b s, 2H), 2.55 (s, 3H); Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)$^+$= 528.29, HPLC R$_t$=1.543.

Example 59 was prepared in a similar manner as Example 46. Preparative reverse phase HPLC separation method: Start % B=0, Final % B=100, Gradient time=6 min, Flow Rate=30 mL/min, Column: Xterra 5 uM 19×50 mm, Fraction Collection: 3.20-4.27 min; $^1$H NMR: (CD$_3$OD) δ 8.91 (s, 1H), 8.47 (s, 1H), 8.25 (d, J=10, 1H), 8.19 (s, 1H), 8.02-7.99 (m, 2H), 7.75-7.70 (m, 2H), 4.48 (b s, 2H), 4.37 (b s, 2H), 4.03 (b s, 2H), 3.89 (b s, 2H), 2.70 (s, 3H); Analytical HPLC method: Start % B=0, Final % B=100, Gradient time=2 min, Flow Rate=5 mL/min, Column: Xterra 3.0×50 mm; LC/MS: (ES+) m/z (M+H)$^+$=486.09, HPLC R$_t$=1.160.

EXAMPLE 60

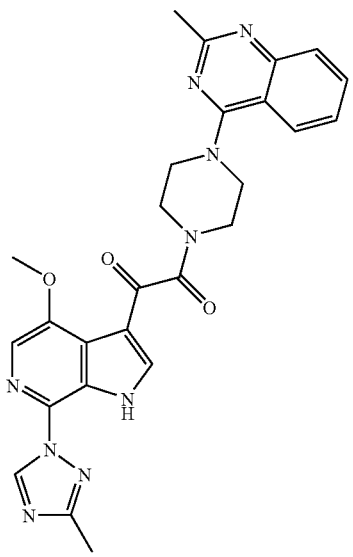

Example 60 was prepared in a similar manner as Example 46. Preparative reverse phase HPLC separation method: Start % B=0, Final % B=100, Gradient time=6 min, Flow Rate=30 mL/min, Column: Xterra 5 uM 19×50 mm, Fraction Collection: 3.04-3.65 min; $^1$H NMR: (CD$_3$OD) δ 9.21 (s, 1H), 8.33 (s, 1H), 8.26 (d, J=5, 1H), 8.00 (t, J=5, 1H), 7.84 (s, 1H), 7.75-7.69 (m, 2H), 4.49 (b s, 2H), 4.37 (b s, 2H), 4.05 (s, 3H), 4.02 (b s, 2H), 3.83 (b s, 2H), 2.69 (s, 3H), 2.55 (s, 3H); Analytical HPLC method: Start % B=0, Final % B=100, Gradient time=2 min, Flow Rate=5 mL/min, Column: Xterra 3.0×50 mm; LC/MS: (ES+) m/z (M+H)$^+$=512.13, HPLC R$_t$=1.090.

EXAMPLE 61

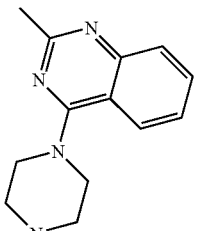

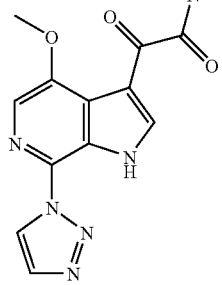

Example 61 was prepared in a similar manner as Example 46. Preparative reverse phase HPLC separation method: Start % B=0, Final % B=100, Gradient time=6 min, Flow Rate=30 mL/min, Column: Xterra 5 uM 19×50 mm, Fraction Collection: 2.90-3.97 min; $^1$H NMR: (CD$_3$OD) δ 8.85 (s, 1H), 8.38 (s, 1H), 8.27 (d, J=5, 1H), 8.01 (t, J=5, 1H), 7.98 (s, 1H), 7.95 (s, 1H), 7.75-7.70 (m, 2H), 4.49 (b s, 2H), 4.38 (b s, 2H), 4.09 (s, 3H), 4.03 (b s, 2H), 3.84 (b s, 2H), 2.70 (s, 3H); Analytical HPLC method: Start % B=0, Final % B=100, Gradient time=2 min, Flow Rate=5 mL/min, Column: Xterra 3.0×50 mm; LC/MS: (ES+) m/z (M+H)$^+$=498.15, HPLC R$_t$=0.983.

EXAMPLE 62

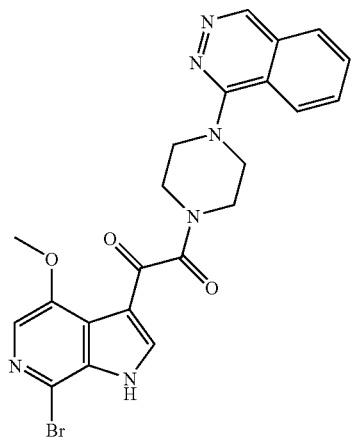

Example 62 was prepared in a similar manner as Example 53 using EDC/HOBT as the coupling reagents. Preparative reverse phase HPLC separation method: Start % B=0, Final % B=100, Gradient time=6 min, Flow Rate=30 mL/min, Column: Xterra 5 uM 19×50 mm, Fraction Collection: 2.25-2.65 min; ¹H NMR: (CD₃OD) δ 9.55 (s, 1H), 8.70 (d, J=5, 1H), 8.50 (d, J=5, 1H), 8.40 (d, J=10, 1H), 8.27 (app t, 1H), 8.22 (appt, 1H), 8.08 (s, 1H), 4.11 (s, 3H), 4.09 (b s, 2H), 3.96 (b s, 4H), 3.91 (b s, 2H); Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)⁺=497.11, HPLC R$_t$=0.910.

EXAMPLE 63

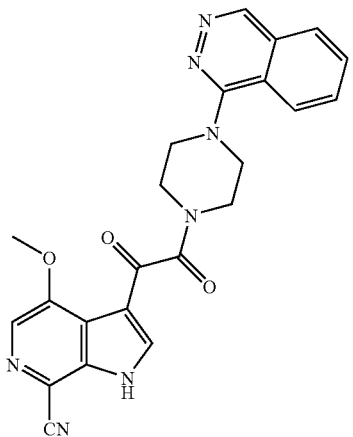

Example 63 was prepared from Example 62 and used as crude for the preparation of Example 64; Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)⁺=442.24, HPLC R$_t$=1.133.

EXAMPLE 64

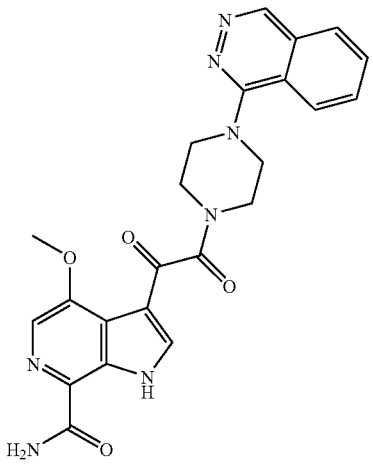

Example 64 was prepared from Example 63. Preparative reverse phase HPLC separation method: Start % B=0, Final % B=100, Gradient time=6 min, Flow Rate=30 mL/min, Column: Xterra 5 uM 19×50 mm, Fraction Collection: 2.76-3.14 min; ¹H NMR: (CD₃OD) δ 9.46 (s, 1H), 8.44 (d, J=5, 1H), 8.33 (s, 1H), 8.21 (t, J=5, 1H), 8.13 (s, 1H), 7.89 (d, J=5, 1H), 7.72-7.70 (m, 1H), 4.21 (b s, 2H), 4.14 (s, 3H), 4.08 (b s, 2H), 3.90 (b s, 2H), 3.83 (b s, 2H); Analytical HPLC method: Start % B=0, Final % B=100, Gradient time=2 min, Flow Rate=5 mL/min, Column: Waters Atlantis 4.6×50 mm C18 5 um; LC/MS: (ES+) m/z (M+H)⁺=460.21, HPLC R$_t$=1.077.

Intermediate 12 (HCl Salt)

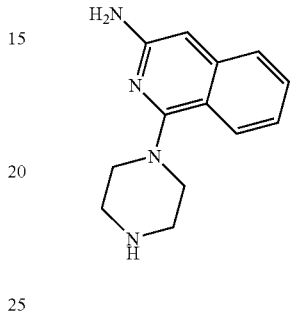

Hydrochloride salt of Intermediate 12 was prepared from 3-amino 1-bromoisoquinoline in a similar manner as Intermediate 9. Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=229.12, HPLC R$_t$=0.343.

Intermediate 13 (HCl Salt)

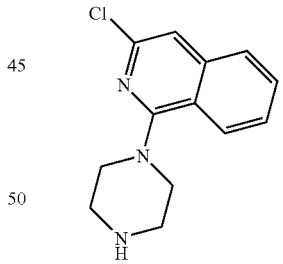

Hydrochloride salt of Intermediate 13 was prepared from 1,3-dichloroisoquinoline in a similar manner as Intermediate 2. ¹H NMR: (CD₃OD, 300 MHz) δ 8.15 (d, J=8.4, 1H), 7.84 (d, J=8.1, 1H), 7.74 (app t, 1H), 7.63 (app t, 1H), 7.51 (s, 1H), 3.71-3.68 (m, 4H), 3.54-3.50 (m, 4H); Analytical HPLC method: Start % B=0, Final % B=100, Gradient time=2 min, Flow Rate=5 mL/min, Column: Xterra C18 4.6×50 mm C18 5 um; LC/MS: (ES+) m/z (M+H)⁺=248.02, 250.02, HPLC R$_t$=1.253.

EXAMPLE 65

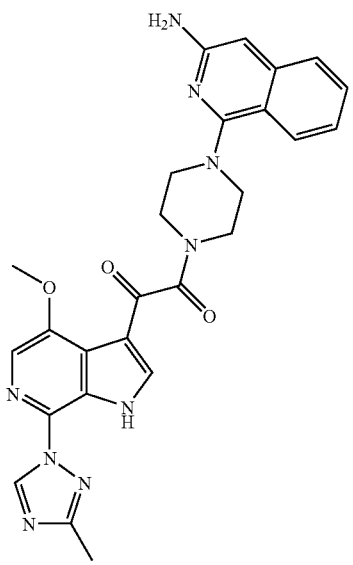

Example 65 was prepared in a similar manner as Example 46. Preparative reverse phase HPLC separation method: Start % B=0, Final % B=100, Gradient time=6 min, Flow Rate=45 mL/min, Column: phenomenex-Luna 30×50 mm S5, Fraction Collection: 4.51-4.92 min; $^1$H NMR: (CD$_3$OD) δ 9.22 (s, 1H), 8.77 (s, 1H), 8.31 (s, 1H), 8.13 (d, J=8, 1H), 7.88 (d, J=8, 1H), 7.84 (s, 1H), 7.70 (t, J=8, 1H), 7.56 (t, J=7.5, 1H), 3.98 (s, 3H), 3.73 (m, 4H), 3.54 (m, 4H), 2.58 (s, 3H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)$^+$=512.20, HPLC R$_t$=1.277.

EXAMPLE 66

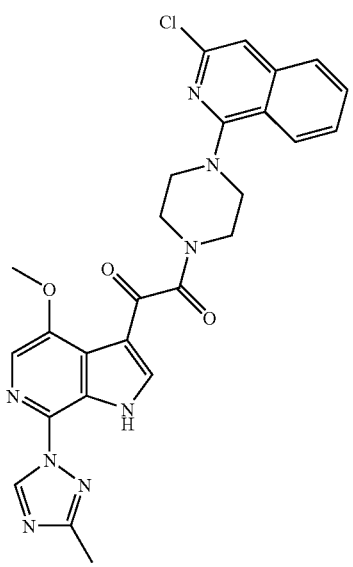

Example 66 was prepared in a similar manner as Example 65. Preparative reverse phase HPLC separation method: Start % B=0, Final % B=100, Gradient time=6 min, Flow Rate=30 mL/min, Column: Xterra 19×50 mm S5, Fraction Collection: 5.76-6.32 min; $^1$H NMR: (CD$_3$OD) δ 9.24 (s, 1H), 8.34 (s, 1H), 8.16 (d, J=8.5, 1H), 7.89 (s, 1H), 7.79 (d, J=8, 1H), 7.69 (app t, 1H), 7.58 (app t, 1H), 7.41 (s, 1H), 4.10 (s, 3H), 4.03 (m, 2H), 3.77 (m, 2H), 3.61 (m, 2H), 3.50 (m, 2H), 2.56 (s, 3H); Analytical HPLC method: Start % B=0, Final % B=100, Gradient time=2 min, Flow Rate=5 mL/min, Column: Xterra 4.6×50 mm C18 5 um; LC/MS: (ES+) m/z (M+H)$^+$=530.99, 532.98, HPLC R$_t$=1.840.

EXAMPLE 67

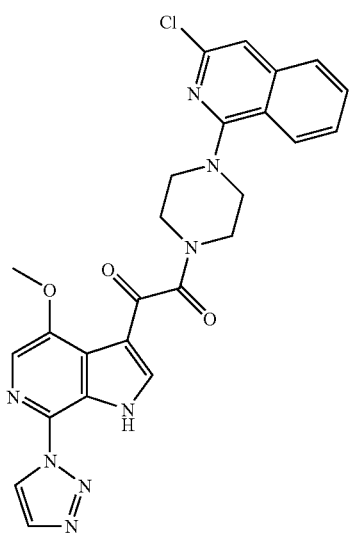

Example 67 was prepared in a similar manner as Example 65. Preparative reverse phase HPLC separation method: Start % B=0, Final % B=100, Gradient time=6 min, Flow Rate=30 mL/min, Column: Xterra 19×50 mm S5, Fraction Collection: 5.59-6.20 min; $^1$H NMR: (CD$_3$OD) δ 8.86 (s, 1H), 8.38 (s, 1H), 8.18 (d, 1H), 7.98 (overlapping s, 2H), 7.79 (d, J=8.5, 1H), 7.69 (app t, 1H), 7.59 (app t, 1H), 7.41 (s, 1H), 4.13 (s, 3H), 4.05 (m, 2H), 3.80 (m, 2H), 3.62 (m, 2H), 3.50 (m, 2H); Analytical HPLC method: Start % B=0, Final % B=100, Gradient time=2 min, Flow Rate=5 mL/min, Column: Xterra 4.6×50 mm C18 5 um; LC/MS: (ES+) m/z (M+H)$^+$=517.00, 518.90, HPLC R$_t$=1.903.

EXAMPLE 68

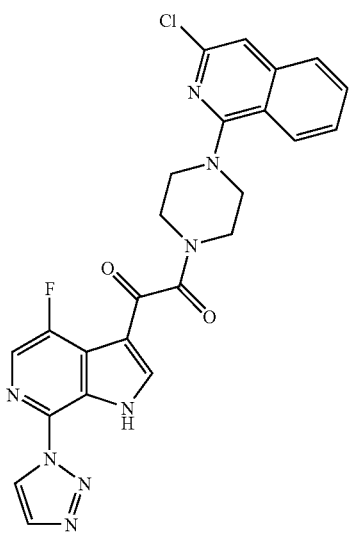

Example 68 was prepared in a similar manner as Example 65. Preparative reverse phase HPLC separation method: Start % B=0, Final % B=100, Gradient time=6 min, Flow Rate=30 mL/min, Column: Xterra 19×50 mm S5, Fraction Collection: 5.79-6.39 min; $^1$H NMR: (CD$_3$OD) δ 8.92 (s, 1H), 8.44 (s, 1H), 8.12 (m, 1H), 8.06 (s, 1H), 7.99 (d, H), 7.78 (app t, 1H), 7.69 (m, 1H), 7.58 (m, 1H), 7.40 (d, 1H), 4.10-3.55 (m, 8H); Analytical HPLC method: Start % B=0, Final % B=100, Gradient time=2 min, Flow Rate=5 mL/min, Column: Xterra 4.6×50 mm C18 5 um; LC/MS: (ES+) m/z (M+H)$^+$=504.95, 506.95, HPLC R$_t$=1.907.

EXAMPLE 69

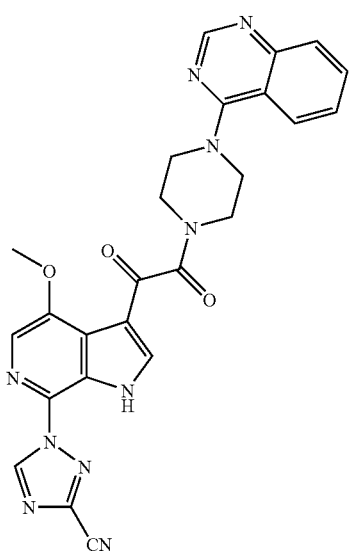

Example 69 was prepared from condensation of the Example 53 with 3-cyano-1,2,4-triazole at 150° C. Preparative reverse phase HPLC separation method: Start % B=0, Final % B=100, Gradient time=6 min, Flow Rate=30 mL/min, Column: Xterra 19×50 mm S5, Fraction Collection: 3.46-3.96 min; $^1$H NMR: (CD$_3$OD) δ 9.52 (s, 1H), 8.75 (s, 1H), 8.37 (s, 1H), 8.31 (d, J=8.5, 1H), 8.06 (app t, 1H), 7.94 (s, 1H), 7.83 (d, 1H), 7.78 (app t, 1H), 4.51 (m, 2H), 4.40 (m, 2H), 4.09 (s, 3H), 4.03 (m, 2H), 3.85 (m, 2H); Analytical HPLC method: Start % B=0, Final % B=100, Gradient time=2 min, Flow Rate=5 mL/min, Column: Xterra 4.6×50 mm C18 5 um; LC/MS: (ES+) m/z (M+H)$^+$=509.01, HPLC R$_t$=1.140.

EXAMPLE 70

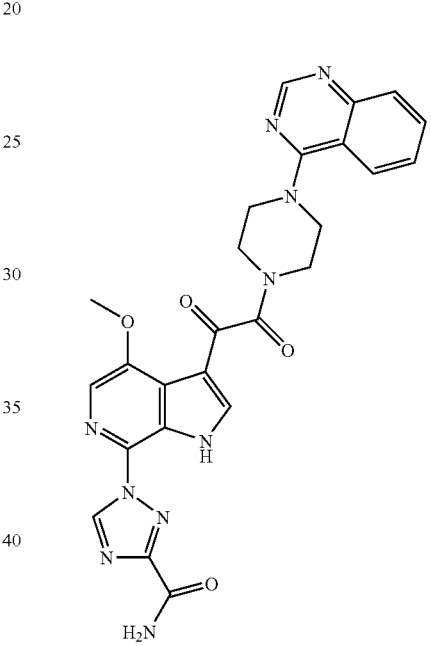

Example 70 was prepared from Example 69 using concentrated methanolic hydrogen chloride. Preparative reverse phase HPLC separation method: Start % B=0, Final % B=100, Gradient time=6 min, Flow Rate=30 mL/min, Column: Xterra 19×50 mm S5, Fraction Collection: 3.64-3.84 min; $^1$H NMR: (CD$_3$OD) δ 9.40 (s, 1H), 8.77 (s, 1H), 8.42 (s, 1H), 8.33 (d, J=8.6, 1H), 8.07 (d, J=8.2, 1H), 7.91 (s, 1H), 7.85 (d, J=8.6, 1H), 7.80 (app t, 1H), 4.55-4.53 (m, 2H), 4.44-4.42 (m, 2H), 4.10 (s, 3H), 4.07-4.05 (m, 2H), 3.89-3.87 (m, 2H); Analytical HPLC method: Start % B=0, Final % B=100, Gradient time=2 min, Flow Rate=5 mL/min, Column: Xterra 4.6×50 mm C18 5 um; LC/MS: (ES+) m/z (M+H)$^+$=527.05, HPLC R$_t$=1.050.

EXAMPLE 71

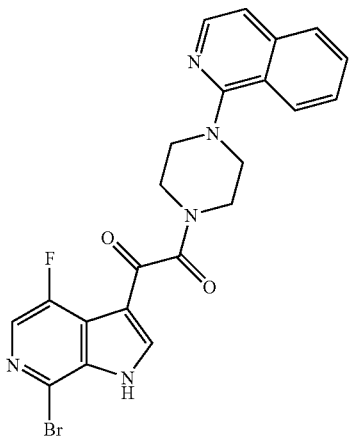

Example 71 was prepared in a similar manner as Example 53. Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=482, 484, HPLC R$_t$=0.980.

EXAMPLE 72

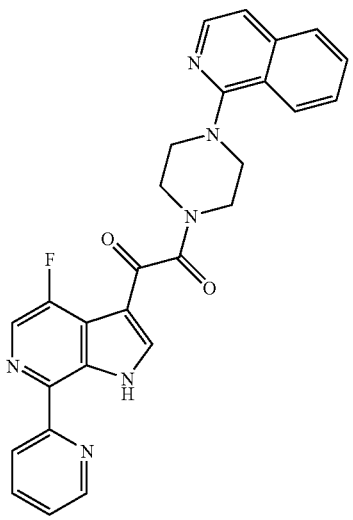

Example 72 was prepared from Example 71 in a similar manner as Example 30. Preparative reverse phase HPLC separation method: Start % B=0, Final % B=100, Gradient time=6 min, Flow Rate=45 mL/min, Column: phenomenex-Luna 30×50 mm S5, Fraction Collection: 4.51-4.92 min; ¹H NMR: (CD$_3$OD) δ 8.83 (d, J=4.5, 1H), 8.56 (d, J=8, 1H), 8.48 (s, 1H), 8.43 (d, J=8.5, 1H), 8.38 (d, J=2, 1H), 8.10-8.00 (overlapping m, 3H), 7.90-7.86 (d overlapping with m, 2H), 7.67 (d, J=7, 1H), 7.50 (app t, 1H), 4.18 (m, 2H), 4.03 (m, 2H), 3.96 (m, 4H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=481.23, HPLC R$_t$=1.147.

EXAMPLE 73

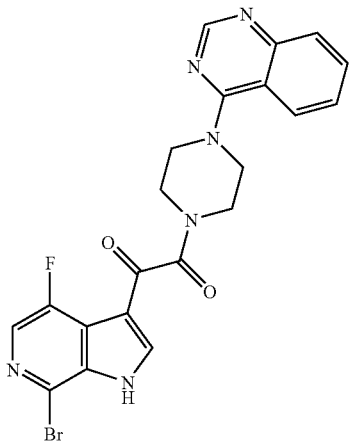

Example 73 was prepared in a similar manner as Example 53. ¹H NMR: (CD$_3$OD) δ 8.76 (s, 1H), 8.47 (s, 1H), 8.30 (d, J=8.5, 1H), 8.07 (app t overlapping with s, 2H), 7.85 (d, J=8, 1H), 7.79 (app t, 1H), 4.50 (m, 2H), 4.39 (m, 2H), 4.04 (m, 2H), 3.88 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES–) m/z (M+H)⁺=481, 483, HPLC R$_t$=1.11.

EXAMPLE 74

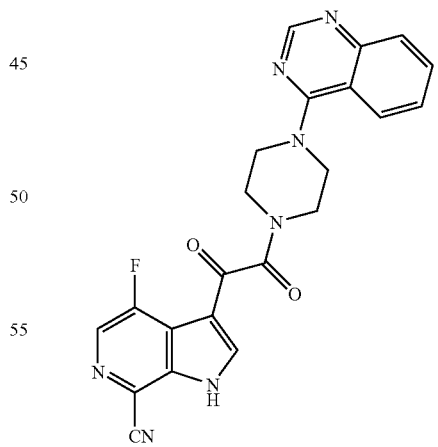

Example 74 was prepared from Example 73 with nBu$_3$SnCN (Pd(PPh$_3$)$_4$, 1,4-dioxane 135° C.). Preparative reverse phase HPLC separation method: Start % B=0, Final % B=100, Gradient time=6 min, Flow Rate=30 mL/min, Column: Xterra 19×50 mm S5, Fraction Collection: 3.26-3.65 min; Analytical HPLC method: Start % B=0, Final %

B=100, Gradient time=2 min, Flow Rate=5 mL/min, Column: Xterra 4.6×50 mm C18 5u; LC/MS: (ES+) m/z (M+H)+= 429.99, HPLC R$_t$=1.020.

EXAMPLE 75

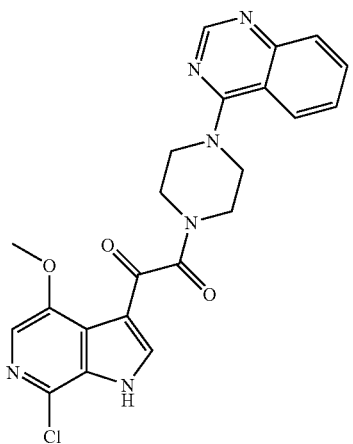

Example 75 was prepared in as similar as Example 53. Preparative reverse phase HPLC separation method: Start % B=0, Final % B=100, Gradient time=6 min, Flow Rate=30 mL/min, Column: Xterra 19×50 mm S5, Fraction Collection: 3.43-4.03 min; $^1$H NMR: (CD$_3$OD) δ 8.76 (s, 1H), 8.37 (s, 1H), 8.31 (d, J=8, 1H), 8.08 (app t, 1H), 7.85 (d, J=8, 1H), 7.79 (app t overlapping with s, 2H), 4.53 (m, 2H), 4.41 (m, 2H), 4.05-4.03 (m, 2H), 4.03 (s, 3H), 3.84 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES-) m/z (M+H)+=449.16, 451.21, HPLC R$_t$=1.033.

EXAMPLE 76

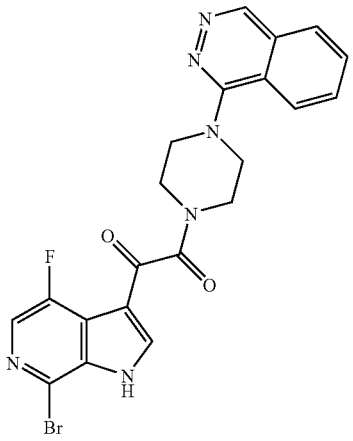

Example 76 was prepared in a similar manner as Example 73. Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES-) m/z (M+H)+=481, 483, HPLC R$_t$=1.108.

EXAMPLE 77

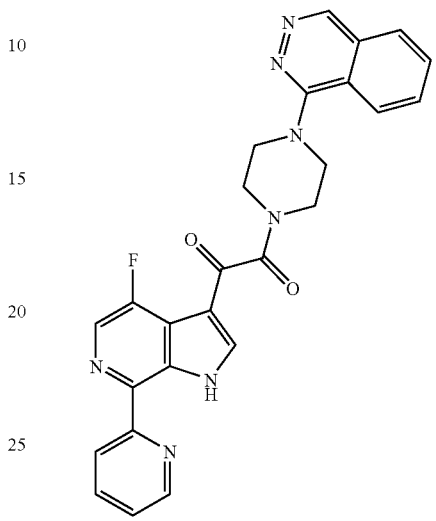

Example 77 was prepared from Example 76 in a similar manner as Example 72. Preparative reverse phase HPLC separation method: Start % B=0, Final % B=100, Gradient time=10 min, Flow Rate=30 mL/min, Column: Xterra 19×50 mm S5, Fraction Collection: 5.47-5.72 min; $^1$H NMR: (CD$_3$OD) δ 9.39 (s, 1H), 8.82 (b s, 1H), 8.71-8.70 (m, 1H), 8.59-8.56 (m, 1H), 8.45 (d, J=9.2, 1H), 8.36 (dd, 1H), 8.27-8.25 (m, 1H), 8.15-8.09 (m, 1H), 8.03-7.99 (m, 1H), 7.53 (s, 1H), 7.50-7.47 (m, 1H), 4.12 (m, 2H), 3.90 (m, 2H), 3.85 (m, 2H), 3.74 (m, 2H); Analytical HPLC method: Start % B=0, Final % B=100, Gradient time=2 min, Flow Rate=5 mL/min, Column: phenomenex C18 3.0×50 mm 10u, HPLC R$_t$=1.417.

EXAMPLE 78

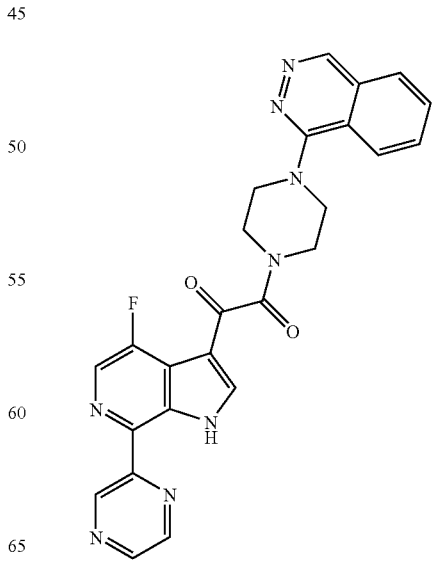

Example 78 was prepared from Example 76 in a similar manner as Example 77. Preparative reverse phase HPLC separation method: Start % B=0, Final % B=100, Gradient time=6 min, Flow Rate=30 mL/min, Column: Xterra 19×50 mm S5, Fraction Collection: 3.06-3.48 min; $^1$H NMR: (CD$_3$OD) δ 9.82 (s, 1H), 9.52 (s, 1H), 8.83 (b s, 1H), 8.70 (m, 1H), 8.64 (s, 1H), 8.48 (m, 1H), 8.42 (m, 1H), 8.39 (d, J=8.6, 1H), 8.11 (d, 1H), 7.79 (m, 1H), 4.13 (m, 2H), 3.92-3.96 (m, 2H), 3.86 (m, 2H), 3.61 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES+) m/z (M+H)$^+$=483.08, HPLC R$_t$=1.142.

EXAMPLE 79

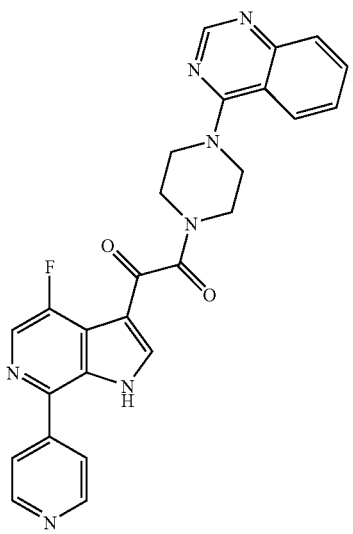

Example 79 was prepared from Example 73 in a similar manner as Example 77. Preparative reverse phase HPLC separation method: Start % B=0, Final % B=100, Gradient time=14 min, Flow Rate=30 mL/min, Column: Xterra 19×50 mm S5, Fraction Collection: 4.00-4.37 min; $^1$H NMR: (CD$_3$OD) δ 8.87-8.84 (b m, 2H), 8.77 (s, 1H), 8.50 (s, 1H), 8.43 (d, J=2.5, 1H), 8.32 (d, J=10, 1H), 8.09 (overlapping m, 3H), 7.85 (d, J=10, 1H), 7.81 (app t, 1H), 4.54-4.51 (m, 2H), 4.43-4.40 (m, 2H), 4.08-4.05 (m, 2H), 3.93-3.90 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES−) m/z (M+H)$^+$=480.16, HPLC R$_t$=1.05.

EXAMPLE 80

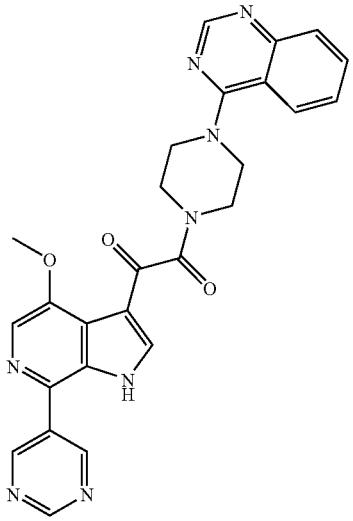

Example 80 was prepared from Example 53 and pyrimidine-5-boronic acid (Pd(PPh$_3$)$_4$, K$_2$CO$_3$, 2:1 DMF/H$_2$O, 135° C., re-usable sealed tube). Preparative reverse phase HPLC separation method: Start % B=0, Final % B=100, Gradient time=14 min, Flow Rate=30 mL/min, Column: Xterra 19×50 mm S5, Fraction Collection: 3.33-3.39 min; $^1$H NMR: (300 MHz, CD$_3$OD) δ 9.34 (s, 1H), 9.25, (s, 2H), 8.77 (s, 1H), 8.49 (s, 1H), 8.34 (d, J=8.4, 1H), 8.24 (s, 1H), 8.09 (app t, 1H), 7.85 (d, J=9, 1H), 7.81 (app t, 1H), 4.57-4.53 (m, 2H), 4.46-4.42 (m, 2H), 4.14 (s, 3H), 4.09-4.05 (m, 2H), 3.91-3.87 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES−) m/z (M+H)$^+$=493.21, HPLC R$_t$=0.957.

EXAMPLE 81

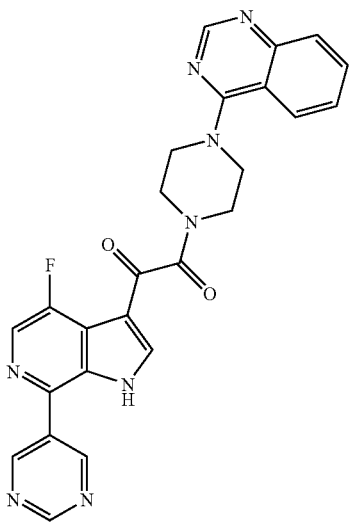

Example 81 was prepared from Example 73 in a similar manner as Example 80. Preparative reverse phase HPLC separation method: Start % B=0, Final % B=100, Gradient time=13 min, Flow Rate=30 mL/min, Column: Xterra 19×50 mm S5, Fraction Collection: 4.28-4.89 min; $^1$H NMR: (CD$_3$OD) δ 9.34 (s, 1H), 9.27, (s, 2H), 8.77 (s, 1H), 8.51 (s, 1H), 8.43 (d, J=2.5, 1H), 8.32 (d, J=8.5, 1H), 8.08 (app t, 1H), 7.86 (d, J=8.5, 1H), 7.81 (app t, 1H), 4.55-4.53 (m, 2H), 4.44-4.42 (m, 2H), 4.07-4.05 (m, 2H), 3.92-3.90 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES+) m/z (M+H)$^+$=483.16, HPLC R$_t$=0.997.

EXAMPLE 82

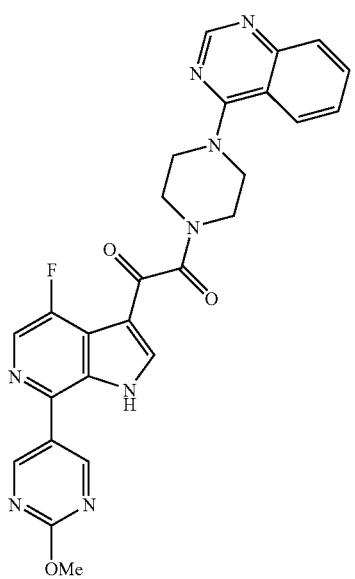

Example 82 was prepared from Example 73 in a similar manner as Example 81. Preparative reverse phase HPLC separation method: Start % B=0, Final % B=100, Gradient time=12 min, Flow Rate=30 mL/min, Column: Xterra 19×50 mm S5, Fraction Collection: 4.69-5.30 min; $^1$H NMR: (CD$_3$OD) δ 9.03 (s, 2H), 8.77 (s, 1H), 8.53 (s, 1H), 8.40 (d, J=3, 1H), 8.32 (d, J=8.5, 1H), 8.08 (app t, 1H), 7.86 (d, J=8, 1H), 7.80 (app t, 1H), 4.55-4.53 (m, 2H), 4.44-4.42 (m, 2H), 4.15 (s, 3H), 4.07-4.05 (m, 2H), 3.92-3.90 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES-) m/z (M+H)$^+$=511.27, HPLC R$_t$=1.070.

EXAMPLE 83

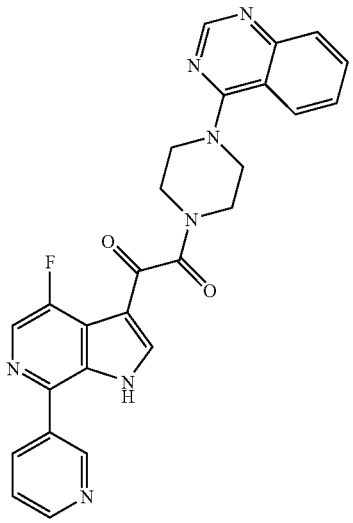

Example 83 was prepared from Example 73 in a similar manner as Example 81. Preparative reverse phase HPLC separation method: Start % B=0, Final % B=100, Gradient time=13 min, Flow Rate=30 mL/min, Column: Xterra 19×50 mm S5, Fraction Collection: 3.24-3.85 min; $^1$H NMR: (CD$_3$OD) δ 9.31 (s, 1H), 8.96 (d, J=5, 1H), 8.92 (d, J=5, 1H), 8.77 (s, 1H), 8.56 (s, 1H), 8.46 (d, J=2.5, 1H), 8.32 (d, J=8, 1H), 8.15 (dd, J=8, 5.5, 1H), 8.09 (app t, 1H), 7.87 (d, J=5, 1H), 7.81 (app t, 1H), 4.55-4.53 (m, 2H), 4.45-4.43 (m, 2H), 4.08-4.05 (m, 2H), 3.93-3.91 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES-) m/z (M+H)$^+$=480.26, HPLC R$_t$=1.033.

EXAMPLE 84

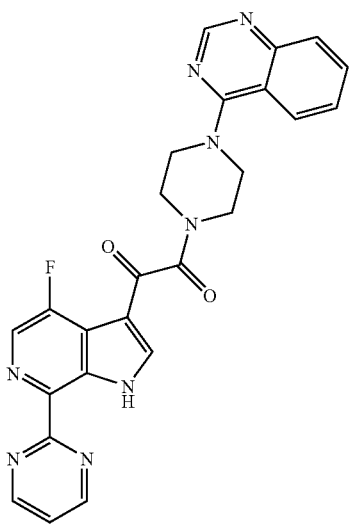

Example 84 was prepared from Example 73 in a similar manner as Example 72. Preparative reverse phase HPLC separation method: Start % B=0, Final % B=100, Gradient time=10 min, Flow Rate=30 mL/min, Column: Xterra 19×50 mm S5, Fraction Collection: 5.40-5.55 min; Analytical HPLC method: Solvent A 5% MeCN—95% H₂O—10 mM NH₄OAc; Solvent B 95% MeCN—5% H₂O—10 mM NH₄OAc; Start % B=0, Final % B=100, Gradient time=2 min, Flow Rate=5 mL/min, Column: phenomenex 5u 4.6×50 mm C18; LC/MS: (ES+) m/z (M+H)⁺=483.48, HPLC R$_t$=1.048.

EXAMPLE 85

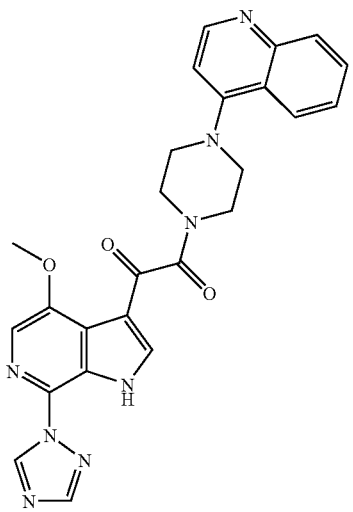

As for the preparation of Example 39, Example 85 was prepared in a similar manner as Example 36 using 4-piperazinylquinoline, which was prepared from the coupling of 4-chloroquinoline with tert-butyl 1-piperazinecarboxylate (CuBr, Cs₂CO₃, DMF, sealed tube, 150° C.) followed by deprotection (HCl, 1,4-dioxane, r.t.). Preparative reverse phase HPLC separation method: Start % B=0, Final % B=100, Gradient time=6 min, Flow Rate=45 mL/min, Column: Xterra MS C18 5 um 30×50 mm, Fraction Collection: 3.49-3.89 min; ¹H NMR: (CD₃OD) δ 9.37 (s, 1H), 8.62 (d, J=6, 1H), 8.36 (s, 1H), 8.34 (app d, 1H), 8.27 (d, J=8.5, 1H), 7.98 (d, J=8.5, 1H), 7.92 (s, 1H), 7.93-7.92 (b m, 1H), 7.71 (app t, 1H), 7.23 (d, J=6.5, 1H), 4.10 (s overlapping with m, 5H), 3.89-3.86 (m, 6H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=483.18, HPLC R$_t$=0.893.

EXAMPLE 86

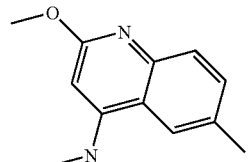
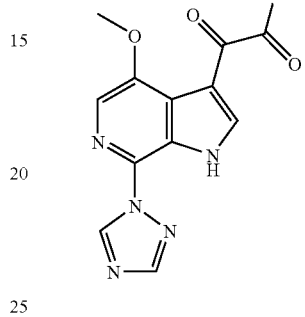

Example 86 and the corresponding 2-methoxy-6-methyl-4-piperazinylquinoline were prepared in a similar manner as those described for Example 85. The crude material was purified by preparative TLC (10% MeOH/CH₂Cl₂) to give a white solid. Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=527.31, HPLC R$_t$=1.100.

EXAMPLE 87

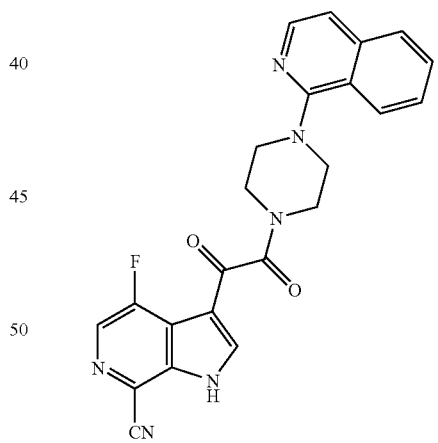

Example 87 was prepared from Example 71 in a similar manner as Example 74. Preparative reverse phase HPLC separation method: Start % B=0, Final % B=100, Gradient time=6 min, Flow Rate=45 mL/min, Column: phenomenex-Luna 30×50 mm S5, Fraction Collection: 3.73-4.06 min; ¹H NMR: (CD₃OD) 8.60 (s, 1H), 8.45-8.39 (overlapping m, 2H), 8.09 (app d, 1H), 8.04 (app t, 1H), 7.88 (d, J=6.5, 1H), 7.87 (m, overlapping with d, 1H), 7.66 (d, J=6.5, 1H), 4.18-4.14 (m, 2H), 4.03-3.99 (m, 2H), 3.96-3.91 (m, 4H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=429.13, HPLC R$_t$=0.933.

EXAMPLE 88

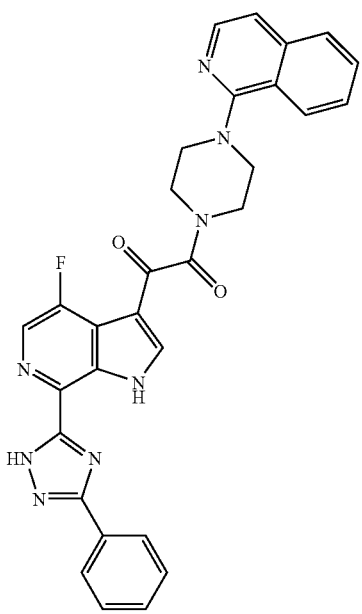

Example 88 was prepared from Example 87 and benzoic hydrazide by stirring in "BuOH in the presence of $K_2CO_3$ in an sealed tube at 150° C. for 2 h. After evaporation of the volatile, the crude mixture was diluted with methanol and purified by preparative reverse phase HPLC; Separation method: Start % B=0, Final % B=100, Gradient time=6 min, Flow Rate=45 mL/min, Column: phenomenex-Luna 30×50 mm S5, Fraction Collection: 4.64-4.95 min; $^1$H NMR: (CD$_3$OD) 8.56 (s, 1H), 8.42 (d, J=8, 1H), 8.28 (d, J=7.5, 1H), 8.08 (app d, 1H), 8.02 (app t, 1H), 7.89 (d, J=6.5, 1H), 7.86 (m overlapping with d, 2H), 7.65 (d, J=6.5, 1H), 7.59-7.54 (m, 4H), 4.19-4.17 (m, 2H), 4.01-3.97 (m, 4H), 3.93-3.89 (m, 2H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: Phenomenex Luna C18 5 um 3.0×50 mm; LC/MS: (ES−) m/z (M+H)$^+$=545.16, HPLC R$_t$=1.343.

EXAMPLE 89

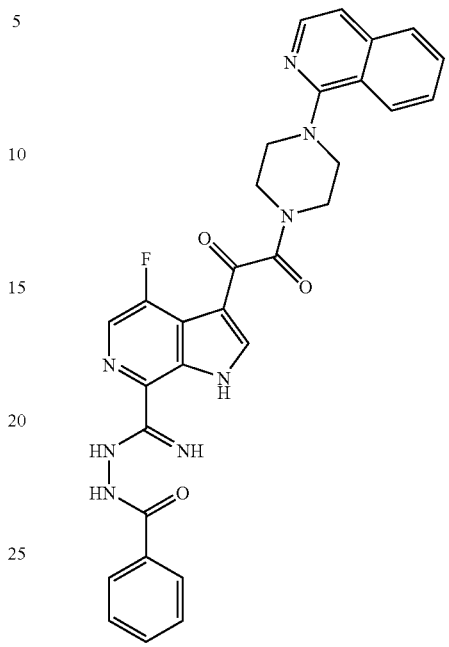

Example 89 was isolated from the crude mixture of the reaction to prepare Example 88. Preparative reverse phase HPLC separation method: Start % B=0, Final % B=100, Gradient time=6 min, Flow Rate=45 mL/min, Column: phenomenex-Luna 30×50 mm S5, Fraction Collection: 4.36-4.63 min; $^1$H NMR: (CD$_3$OD) 8.52 (s, 1H), 8.43 (d, J=8.5, 1H), 8.36 (d, J=2.5, 1H), 8.09 (app d, 1H), 8.04 (app t, 1H), 8.01 (d, J=7.5, 2H), 7.88 (m overlapping with d, 1H), 7.87 (d, J=6.5, 1H), 7.66 (d, J=6.5, 1H), 7.64 (app t, 1H), 7.58 (d, J=7.5, 1H), 7.57 (app t, 1H), 4.19-4.17 (m, 2H), 4.03-4.01 (m, 2H), 3.98-3.90 (m, 4H); Analytical HPLC method: Start % B=0, Final % B=100, Gradient time=2 min, Flow Rate=5 mL/min, Column: Xterra MS C18 5 um 3.0×50 mm; LC/MS: (ES+) m/z (M+H)$^+$=565.17, HPLC R$_t$=1.137.

EXAMPLE 90

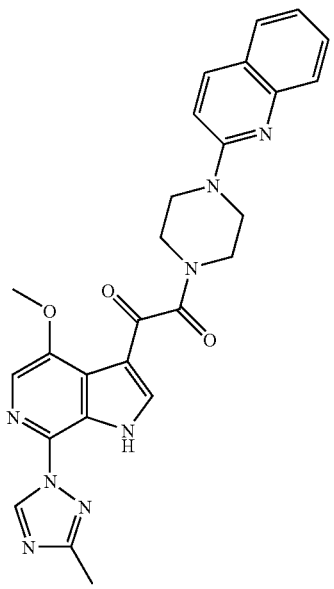

Example 90 was prepared in a similar manner as Example 46 using quipazine maleate salt. Preparative reverse phase HPLC separation method: Start % B=0, Final % B=100, Gradient time=6 min, Flow Rate=30 mL/min, Column: Xterra 19×50 mm S5, Fraction Collection: 3.25-3.85 min; $^1$H NMR: (CD$_3$OD) δ 9.25 (s, 1H), 8.50 (d, J=9.5, 1H), 8.39 (s, 1H), 7.98 (d, J=8, 1H), 7.95 (d, J=8.5, 1H), 7.91 (s, 1H), 7.88 (app t, 1H), 7.61 (t, J=7, 1H), 7.57 (d, J=10, 1H), 4.20-4.18 (m, 2H), 4.09 (s, 3H), 4.09-4.06 (m, 4H), 3.90-3.88 (m, 2H), 2.58 (2, 3H); Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES) m/z (M+H)$^+$=495.32, HPLC R$_t$=1.307.

EXAMPLE 91

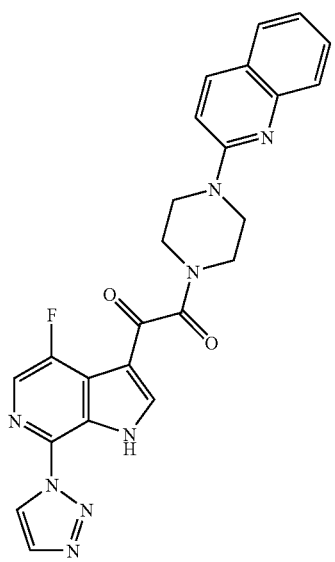

Example 91 was prepared in a similar manner as Example 90. Preparative reverse phase HPLC separation method: Start % B=0, Final % B=100, Gradient time=6 min, Flow Rate=30 mL/min, Column: Xterra 19×50 mm S5, Fraction Collection: 3.35-3.96 min; Analytical HPLC method: Solvent A 5% MeCN—95% H$_2$O—10 mM NH$_4$OAc; Solvent B 95% MeCN—5% H$_2$O—10 mM NH$_4$OAc; Start % B=0, Final % B=100, Gradient time=2 min, Flow Rate=5 mL/min, Column: phenomenex 5u 4.6×50 mm C18; LC/MS: (ES) m/z (M+H)$^+$=469.30, HPLC R$_t$=1.407.

EXAMPLE 92

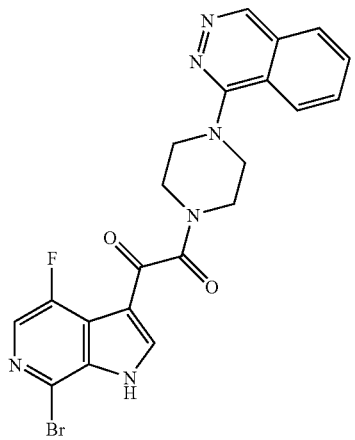

Example 92 was prepared in a similar manner as Example 73. Preparative reverse phase HPLC separation method: Start % B=0, Final % B=100, Gradient time=6 min, Flow Rate=45 mL/min, Column: Xterra C18 30×50 mm 5u, Fraction Collection: 3.36-3.76 min; $^1$H NMR: (CD$_3$OD) δ 9.57 (s, 1H), 8.51 (d, J=8.5, 1H), 8.47 (s, 1H), 8.44 (d, J=8, 1H), 8.31 (app t, 1H), 8.26 (app t, 1H), 8.09 (d, J=2.5, 1H), 4.12-4.19 (m, 2H), 4.01-3.99 (m, 2H), 3.90 (s, 4H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)$^+$=483, 485, HPLC R$_t$=0.890.

EXAMPLE 93

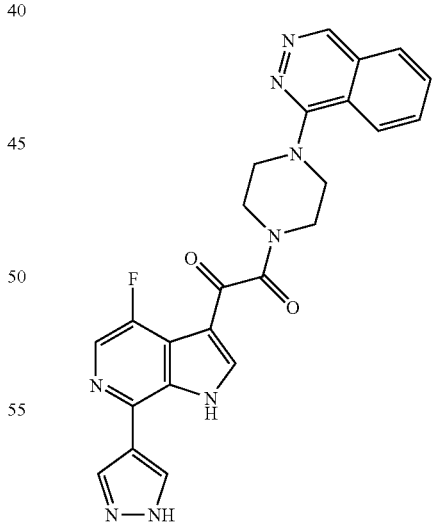

Example 93 was prepared from Example 92 and 4,4,5,5-tetramethyl-2-(1H-pyrazol-4-yl)-1,3,2-dioxaborolane in a similar manner as Example 80. Preparative reverse phase HPLC separation method: Start % B=0, Final % B=100, Gradient time=6 min, Flow Rate=45 mL/min, Column: Xterra C18 30×50 mm 5u, Fraction Collection: 2.71-3.11 min; ¹H NMR: (CD₃OD) δ 9.59 (s, 1H), 8.67 (s, 1H), 8.51 (d, J=8.5, 1H), 8.44 (d, J=8, 1H), 8.41 (d, J=3.5, 1H), 8.37 (s, 2H), 8.32 (app t, 1H), 8.26 (app t, 1H), 4.14-4.12 (m, 2H), 4.01-3.99 (m, 2H), 3.94-3.92 (m, 4H); Analytical HPLC method: Solvent A 5% MeCN—95% H₂O—10 mM NH₄OAc; Solvent B 95% MeCN—5% H₂O—10 mM NH₄OAc; Start % B=0, Final % B=100, Gradient time=2 min, Flow Rate=5 mL/min, Column:Phenomenex Lina C18 5 um 3.0×50 mm; LC/MS: (ES+) m/z (M+H)⁺=471.10, HPLC R$_t$=0.880.

EXAMPLE 94

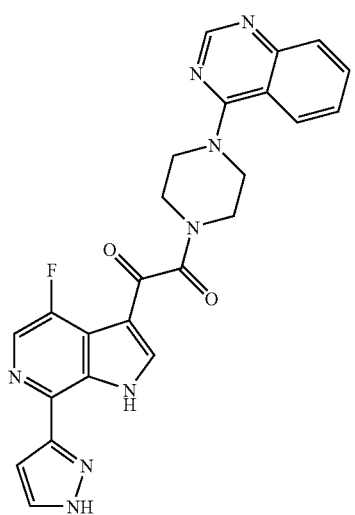

Example 94 was prepared from Example 73 in a similar manner as Example 30. Preparative reverse phase HPLC separation method: Start % B=0, Final % B=100, Gradient time=6 min, Flow Rate=45 mL/min, Column: Xterra C18 30×50 mm 5u, Fraction Collection: 3.21-3.60 min; ¹H NMR: (CD₃OD) δ 8.77 (s, 1H), 8.52 (d, J=5.5, 1H), 8.32 (d, J=8.5, 1H), 8.29 (dd, J=10, 3, 1H), 8.09 (app t, 1H), 7.91 (app dd, 1H), 7.85 (d, J=8.5, 1H), 7.80 (app t, 1H), 7.12 (dd, J=16, 2.5, 1H), 4.55-4.53 (m, 2H), 4.44-4.42 (m, 2H), 4.08-4.06 (m, 2H), 3.92-3.90 (m, 2H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=471.09, HPLC R$_t$=0.833.

EXAMPLE 95

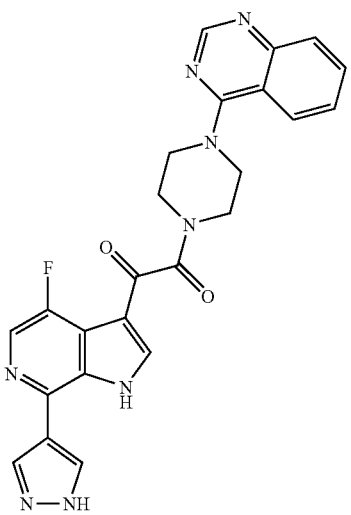

Example 95 was prepared from Example 73 in a similar manner as Example 93. Preparative reverse phase HPLC separation method: Start % B=0, Final % B=100, Gradient time=6 min, Flow Rate=45 mL/min, Column: Xterra C18 30×50 mm 5u, Fraction Collection: 2.65-3.05 min; ¹H NMR: (CD₃OD) δ 8.78 (s, 1H), 8.73 (s, 1H), 8.43 (d, J=3.5, 1H), 8.38 (s, 2H), 8.33 (d, J=8.5, 1H), 8.09 (app t, 1H), 7.86 (d, J=8.5, 1H), 7.81 (app t, 1H), 4.55-4.53 (m, 2H), 4.46-4.44 (m, 2H), 4.08-4.06 (m, 2H), 3.95-3.93 (m, 2H); Analytical HPLC method: Start % B=0, Final % B=100, Gradient time=2 min, Flow Rate=5 mL/min, Column: Xterra MS C18 S7 3.0×50 mm; LC/MS: (ES+) m/z (M+H)⁺=471.05, HPLC R$_t$=0.740.

EXAMPLE 96

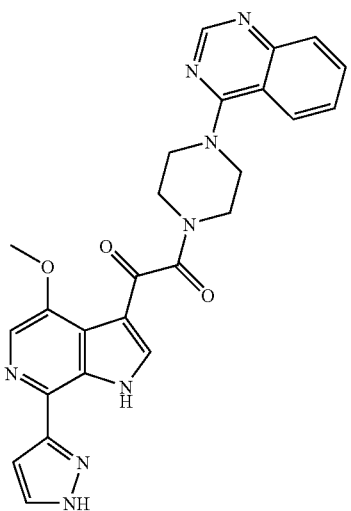

Example 96 was prepared from Example 75 in a similar manner as Example 30. Preparative reverse phase HPLC separation method: Start % B=0, Final % B=100, Gradient time=6 min, Flow Rate=45 mL/min, Column: Xterra C18 30×50 mm 5u, Fraction Collection: 2.74-2.90 min; ¹H NMR: (CD₃OD) δ 8.79 (s, 1H), 8.70 (d, J=2.5, 1H), 8.35 (d, J=8, 1H), 8.11-8.02 (overlapping m, 3H), 7.86 (d, J=9.5, 1H), 7.82

(t, J=7.5, 1H), 7.25 (dd, J=16.5, 2.5, 1H), 4.56-4.54 (m, 2H), 4.47-4.45 (m, 2H), 4.18 (d, J=4, 3H), 4.09-4.07 (m, 2H), 3.94-3.92 (m, 2H); Analytical HPLC method: Solvent A 5% MeCN—95% $H_2O$—10 mM $NH_4OAc$; Solvent B 95% MeCN—5% $H_2O$—10 mM $NH_4OAc$; Start % B=0, Final % B=100, Gradient time=2 min, Flow Rate=5 mL/min, Column:Phenomenex Lina C18 5 um 3.0×50 mm; LC/MS: (ES+) m/z $(M+H)^+$=483.12, HPLC $R_t$=0.920.

Biology

"µM" means micromolar;
"mL" means milliliter;
"µl" means microliter;
"mg" means milligram;

The materials and experimental procedures used to obtain the results reported in Tables 1-2 are described below.

Cells:
Virus production—Human embryonic Kidney cell line, 293, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref 41). Transfections were performed using lipofectAMINE PLUS reagent as described by the manufacturer (Invitrogen, Carlsbad, Calif.).

Experiment

1. HeLa CD4 cells were plated in 96 well plates at a cell density of $1 \times 10^4$ cells per well in 100 µl Dulbecco's Modified Eagle Medium containing 10% fetal Bovine serum and incubated overnight.
2. Compound was added in a 2 µl dimethylsulfoxide solution, so that the final assay concentration would be ≦10 µM.
3. 100 µl of single-round infectious reporter virus in Dulbecco's Modified Eagle Medium was then added to the plated cells and compound at an approximate multiplicity of infection (MOI) of 0.01, resulting in a final volume of 200 µl per well.
4. Virally-infected cells were incubated at 37 degrees Celsius, in a $CO_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac microbeta scintillation counter.
6. The percent inhibition for each compound was calculated by quantifying the level of luciferase expression in cells infected in the presence of each compound as a percentage of that observed for cells infected in the absence of compound and subtracting such a determined value from 100.
7. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data for the compounds is shown in Table 2. Table 1 is the key for the data in Table 2.

Results

TABLE 1

| Biological Data Key for $EC_{50}$s | | |
|---|---|---|
| Compounds* with $EC_{50}$s >5 µM | Compounds with $EC_{50}$s >1 µM but <5 µM | Compounds with $EC_{50}$ <1 µM |
| Group C | Group B | Group A |

*Some of these compounds may have been tested at a concentration lower than their $EC_{50}$ but showed some ability to cause inhibition and thus should be evaluated at a higher concentration to determine the exact $EC_{50}$.

In Table 2, $X_w$, $X_z$ and $X_a$ indicates the point of attachment.

TABLE 2

| Table Entry (Example Number.) | Z | W | A | $EC_{50}$ Group from Table 1 |
|---|---|---|---|---|
| 1 (Example 1) | Examples (structure with F, indole, oxadiazole, Xw) | Xz—N piperazine N—Xa | Xw—isoquinoline | A |

TABLE 2-continued $$\underset{Z}{\overset{A}{\underset{W}{\diagup}}}$$

Examples

| Table Entry (Example Number.) | Z | W | A | EC$_{50}$ Group from Table 1 |
|---|---|---|---|---|
| 2 (Example 2) | 4-fluoro-7-(1,3,4-oxadiazol-3-yl)-1H-indol-3-yl with glyoxylyl (Xw) | Xz—N⁀N—Xa (piperazine) | furo[3,2-b]pyridin-7-yl (Xw) | A |
| 3 (Example 3) | 4-fluoro-7-(1,3,4-oxadiazol-3-yl)-1H-indol-3-yl with glyoxylyl (Xw) | Xz—N⁀N—Xa (piperazine) | quinazolin-4-yl (Xw) | A |
| 4 (Example 4) | 4-methoxy-7-bromo-1H-indol-3-yl with glyoxylyl (Xw) | Xz—N⁀N—Xa (piperazine) | isoquinolin-1-yl (Xw) | A |
| 5 (Example 5) | 4-methoxy-7-(1H-imidazol-1-yl)-1H-indol-3-yl with glyoxylyl (Xw) | Xz—N⁀N—Xa (piperazine) | isoquinolin-1-yl (Xw) | A |
| 6 (Example 6) | 4-methoxy-7-(1H-pyrrol-1-yl)-1H-indol-3-yl with glyoxylyl (Xw) | Xz—N⁀N—Xa (piperazine) | isoquinolin-1-yl (Xw) | A |

TABLE 2-continued
| Table Entry (Example Number.) | Z | W | A | EC$_{50}$ Group from Table 1 |
|---|---|---|---|---|
| 7 (Example 7) | 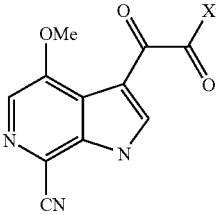 | 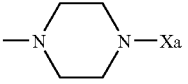 | 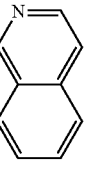 | A |
| 8 (Example 8) | 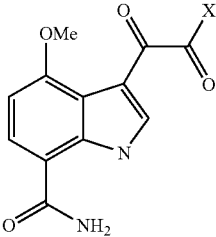 | 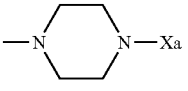 | 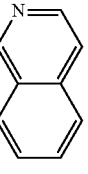 | A |
| 9 (Example 9) | 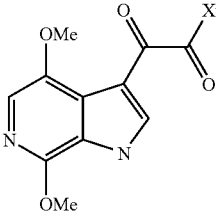 | 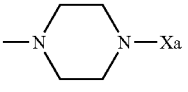 | 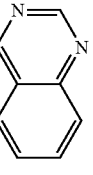 | A |
| 10 (Example 10) | 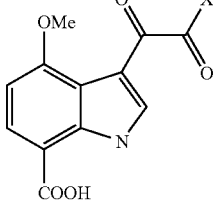 | 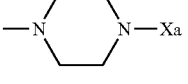 |  | A |
| 11 (Example 11) | 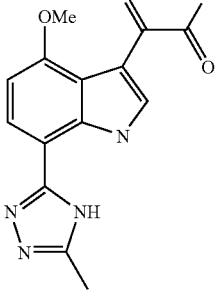 | 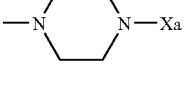 |  | A |

TABLE 2-continued

Examples

| Table Entry (Example Number.) | Z | W | A | EC$_{50}$ Group from Table 1 |
|---|---|---|---|---|
| 12 (Example 12) | 4-OMe, 7-C(O)NH$_2$ indol-3-yl with -C(O)C(O)-Xw | Xz-N(piperazine)N-Xa | 1-isoquinolinyl-Xw | A |
| 13 (Example 13) | 4-OMe, 7-C(O)OEt indol-3-yl with -C(O)C(O)-Xw | Xz-N(piperazine)N-Xa | 1-isoquinolinyl-Xw | A |
| 14 (Example 14) | 4-OMe, 7-C(=NOH)NH$_2$ indol-3-yl with -C(O)C(O)-Xw | Xz-N(piperazine)N-Xa | 1-isoquinolinyl-Xw | A |
| 15 (Example 15) | 4-OMe, 7-(1H-tetrazol-5-yl) indol-3-yl with -C(O)C(O)-Xw | Xz-N(piperazine)N-Xa | 1-isoquinolinyl-Xw | A |
| 16 (Example 16) | 4-OMe, 7-(2-methyl-2H-tetrazol-5-yl) indol-3-yl with -C(O)C(O)-Xw | Xz-N(piperazine)N-Xa | 1-isoquinolinyl-Xw | A |

TABLE 2-continued

|  | Examples | | | |
|---|---|---|---|---|
| Table Entry (Example Number.) | Z | W | A | EC$_{50}$ Group from Table 1 |
| 17 (Example 17) | 4-OMe-7-(1,2,4-oxadiazol-3-yl)indol-3-yl -C(O)C(O)-Xw | Xz-N(piperazine)N-Xa | Xw-isoquinolin-1-yl | A |
| 18 (Example 18) | 4-OMe-7-(N-cyclopropylcarbamimidoyl)-1H-indol-3-yl -C(O)C(O)-Xw | Xz-N(piperazine)N-Xa | Xw-isoquinolin-1-yl | A |
| 19 (Example 19) | 4-OMe-7-(1H-benzimidazol-2-yl)indol-3-yl -C(O)C(O)-Xw | Xz-N(piperazine)N-Xa | Xw-isoquinolin-1-yl | A |
| 20 (Example 20) | 4-OMe-7-(5-methyl-1,2,4-oxadiazol-3-yl)indol-3-yl -C(O)C(O)-Xw | Xz-N(piperazine)N-Xa | Xw-isoquinolin-1-yl | A |

TABLE 2-continued
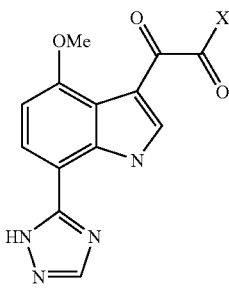
Examples
| Table Entry (Example Number.) | Z | W | A | EC$_{50}$ Group from Table 1 |
|---|---|---|---|---|
| 21 (Example 21) | 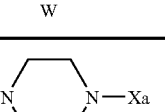 |  Xz—N͡‌‌‌‌‌‌‌‌N—Xa | 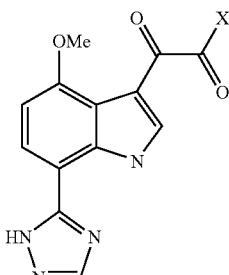 | A |
| 22 (Example 22) | 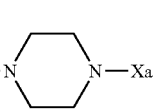 | Xz—N͡‌‌‌‌‌‌‌‌N—Xa |  | A |
| 23 (Example 23) | 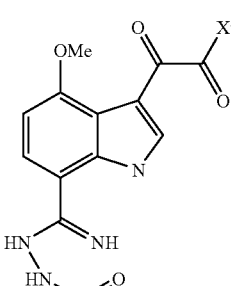 | Xz—N͡‌‌‌‌‌‌‌‌N—Xa | 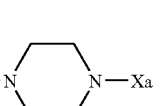 | A |

TABLE 2-continued

Examples

| Table Entry (Example Number.) | Z | W | A | EC$_{50}$ Group from Table 1 |
|---|---|---|---|---|
| 24 (Example 24) | 4-OMe-7-(5-(cyanomethyl)-1H-1,2,4-triazol-3-yl)indol-3-yl glyoxylyl-Xw | Xz—N(piperazine)N—Xa | Xw-(isoquinolin-1-yl) | A |
| 25 (Example 25) | 4-OMe-7-(N'-(cyanoacetyl)carbamimidoyl)indol-3-yl glyoxylyl-Xw | Xz—N(piperazine)N—Xa | Xw-(isoquinolin-1-yl) | A |
| 26 (Example 26) | 4-OMe-7-(2-(methoxycarbonylmethyl)-2H-tetrazol-5-yl)indol-3-yl glyoxylyl-Xw | Xz—N(piperazine)N—Xa | Xw-(isoquinolin-1-yl) | A |
| 27 (Example 27) | 4-OMe-7-(2-(carboxymethyl)-2H-tetrazol-5-yl)indol-3-yl glyoxylyl-Xw | Xz—N(piperazine)N—Xa | Xw-(isoquinolin-1-yl) | A |

TABLE 2-continued $$\underset{Z}{\diagdown}W\underset{}{\diagup}A$$

Examples

| Table Entry (Example Number.) | Z | W | A | EC$_{50}$ Group from Table 1 |
|---|---|---|---|---|
| 28 (Example 28) | OMe-indole-7-(2-CONHMe-tetrazol-5-yl), 3-C(O)C(O)-Xw | Xz—N(piperazine)N—Xa | Xw-isoquinolin-1-yl | A |
| 29 (Example 29) | OMe-indole-7-(2-CONH$_2$-tetrazol-5-yl), 3-C(O)C(O)-Xw | Xz—N(piperazine)N—Xa | Xw-isoquinolin-1-yl | A |
| 30 (Example 30) | OMe-indole-7-(pyrazin-2-yl), 3-C(O)C(O)-Xw | Xz—N(piperazine)N—Xa | Xw-isoquinolin-1-yl | A |
| 31 (Example 31) | OMe-indole-7-(1,2,4-triazol-1-yl), 3-C(O)C(O)-Xw | Xz—N(piperazine)N—Xa | Xw-isoquinolin-1-yl | A |

TABLE 2-continued
$$Z-W-A$$
Examples
| Table Entry (Example Number.) | Z | W | A | EC$_{50}$ Group from Table 1 |
|---|---|---|---|---|
| 32 (Example 32) | 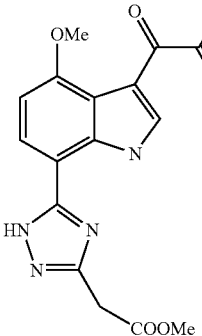 | 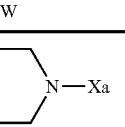 | 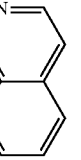 | A |
| 33 (Example 33) | 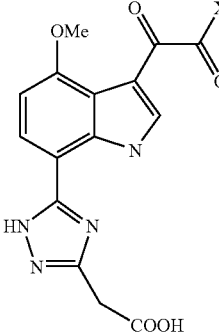 | 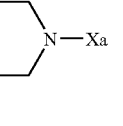 | 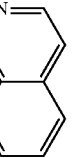 | A |
| 34 (Example 34) | 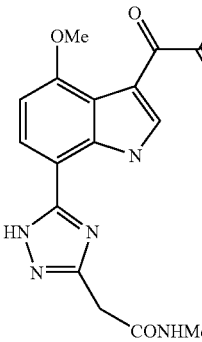 | 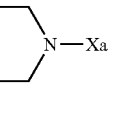 | 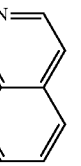 | A |
| 35 (Example 35) | 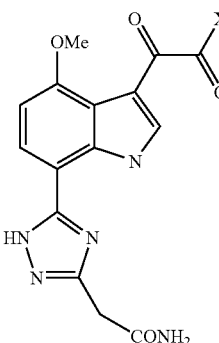 | 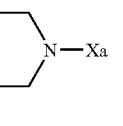 | 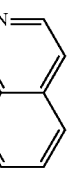 | A |

TABLE 2-continued

Examples

| Table Entry (Example Number.) | Z | W | A | EC$_{50}$ Group from Table 1 |
|---|---|---|---|---|
| 36 (Example 36) | 4-methoxy-7-(1H-1,2,4-triazol-1-yl)-1H-pyrrolo[3,2-c]pyridin-3-yl glyoxylyl (Xw) | Xz—N(piperazine)N—Xa | Xw—isoquinolin-1-yl | A |
| 37 (Example 37) | 7-chloro-1H-pyrrolo[3,2-b]pyridin-3-yl glyoxylyl (Xw) | Xz—N(piperazine)N—Xa | Xw—isoquinolin-1-yl | A |
| 38 (Example 38) | 7-(thiazol-2-yl)-1H-pyrrolo[3,2-b]pyridin-3-yl glyoxylyl (Xw) | Xz—N(piperazine)N—Xa | Xw—isoquinolin-1-yl | A |
| 39 (Example 39) | 4-methoxy-7-(3-methyl-1H-1,2,4-triazol-1-yl)-1H-pyrrolo[2,3-c]pyridin-3-yl glyoxylyl (Xw) | Xz—N(piperazine)N—Xa | Xw—isoquinolin-1-yl | A |

TABLE 2-continued

Examples

| Table Entry (Example Number.) | Z | W | A | EC$_{50}$ Group from Table 1 |
|---|---|---|---|---|
| 40 (Example 40) | 4-fluoro-7-(1,2,4-oxadiazol-3-yl)-1H-indol-3-yl glyoxyl, Xw | Xz—N(piperazine)N—Xa | 2-methylquinolin-4-yl, Xw | A |
| 41 (Example 41) | 4-fluoro-7-(1,2,4-oxadiazol-3-yl)-1H-indol-3-yl glyoxyl, Xw | Xz—N(piperazine)N—Xa | pyridin-2-yl, Xw | B |
| 42 (Example 42) | 4-fluoro-7-(1,2,4-oxadiazol-3-yl)-1H-indol-3-yl glyoxyl, Xw | Xz—N(piperazine)N—Xa | 6-methylpyridin-2-yl, Xw | A |
| 43 (Example 43) | 4-methoxy-7-cyano-1H-indol-3-yl glyoxyl, Xw | Xz—N(piperazine)N—Xa | isoquinolin-1-yl, Xw | A |
| 44 (Example 44) | 4-methoxy-7-cyano-1H-indol-3-yl glyoxyl, Xw | Xz—N(piperazine)N—Xa | quinazolin-4-yl, Xw | A |

TABLE 2-continued

Examples

| Table Entry (Example Number.) | Z | W | A | EC$_{50}$ Group from Table 1 |
|---|---|---|---|---|
| 45 (Example 45) | 4-methoxy-7-cyano-6-azaindole | Xz—N(piperazine)N—Xa | Xw—quinazolin-4-yl | A |
| 46 (Example 46) | 4-methoxy-7-(3-methyl-1,2,4-triazol-1-yl)-6-azaindole | Xz—N(piperazine)N—Xa | Xw—quinazolin-4-yl | A |
| 47 (Example 47) | 4-methoxy-7-(1,2,4-triazol-1-yl)-6-azaindole | Xz—N(piperazine)N—Xa | Xw—quinazolin-4-yl | A |
| 48 (Example 48) | 4-fluoro-7-(1,2,3-triazol-1-yl)-6-azaindole | Xz—N(piperazine)N—Xa | Xw—quinazolin-4-yl | A |

TABLE 2-continued

Examples

| Table Entry (Example Number.) | Z | W | A | EC$_{50}$ Group from Table 1 |
|---|---|---|---|---|
| 49 (Example 49) | | Xz—N⟨piperazine⟩N—Xa | Xw—quinazoline | A |
| 50 (Example 50) | | Xz—N⟨piperazine⟩N—Xa | Xw—quinazoline | A |
| 51 (Example 51) | | Xz—N⟨piperazine⟩N—Xa | Xw—quinazoline | A |
| 52 (Example 52) | | Xz—N⟨piperazine⟩N—Xa | Xw—quinazoline | A |
| 53 (Example 53) | | Xz—N⟨piperazine⟩N—Xa | Xw—quinazoline | A |

TABLE 2-continued
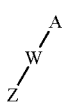
Examples
| Table Entry (Example Number.) | Z | W | A | EC$_{50}$ Group from Table 1 |
|---|---|---|---|---|
| 54 (Example 54) | | Xz—N⌒N—Xa | | A |
| 55 (Example 55) | | Xz—N⌒N—Xa | | A |
| 56 (Example 56) | | Xz—N⌒N—Xa | | A |
| 57 (Example 57) | | Xz—N⌒N—Xa | | A |

TABLE 2-continued
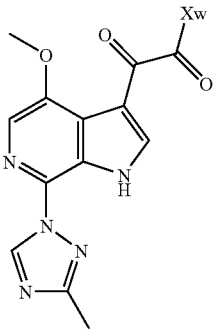
Examples
| Table Entry (Example Number.) | Z | W | A | EC$_{50}$ Group from Table 1 |
|---|---|---|---|---|
| 58 (Example 58) | 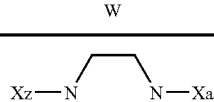 | 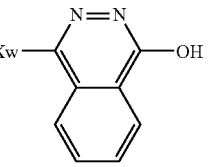 | 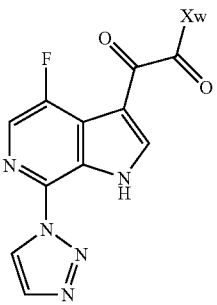 | A |
| 59 (Example 59) | 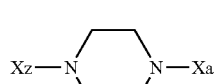 | 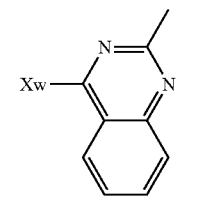 | 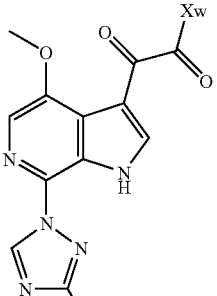 | A |
| 60 (Example 60) | 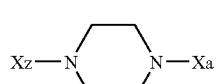 | 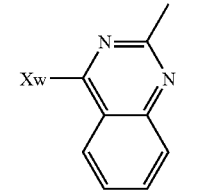 | 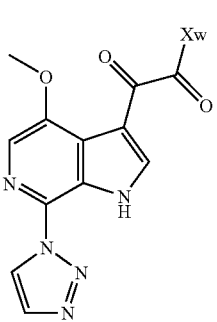 | A |
| 61 (Example 61) | 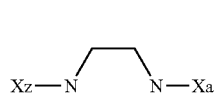 | 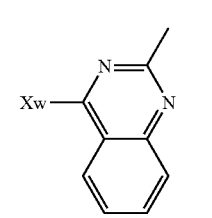 | | A |

TABLE 2-continued

Examples

| Table Entry (Example Number.) | Z | W | A | EC$_{50}$ Group from Table 1 |
|---|---|---|---|---|
| 62 (Example 62) | 4-methoxy-7-bromo-6-azaindole with C(O)C(O)Xw at 3 | Xz—N(piperazine)N—Xa | 1-Xw-phthalazine | A |
| 63 (Example 64) | 4-methoxy-7-carboxamide-6-azaindole with C(O)C(O)Xw at 3 | Xz—N(piperazine)N—Xa | 1-Xw-phthalazine | A |
| 64 (Example 65) | 4-methoxy-7-(3-methyl-1,2,4-triazol-1-yl)-6-azaindole with C(O)C(O)Xw at 3 | Xz—N(piperazine)N—Xa | 1-Xw-3-amino-isoquinoline | A |
| 65 (Example 66) | 4-methoxy-7-(3-methyl-1,2,4-triazol-1-yl)-6-azaindole with C(O)C(O)Xw at 3 | Xz—N(piperazine)N—Xa | 1-Xw-3-chloro-isoquinoline | A |

TABLE 2-continued

Examples

| Table Entry (Example Number.) | Z | W | A | EC$_{50}$ Group from Table 1 |
|---|---|---|---|---|
| 66 (Example 67) | 4-methoxy-7-(1H-1,2,3-triazol-1-yl)-1H-pyrrolo[2,3-c]pyridin-3-yl glyoxylyl-Xw | Xz—N(piperazine)N—Xa | 3-chloroisoquinolin-1-yl-Xw | A |
| 67 (Example 68) | 4-fluoro-7-(1H-1,2,3-triazol-1-yl)-1H-pyrrolo[2,3-c]pyridin-3-yl glyoxylyl-Xw | Xz—N(piperazine)N—Xa | 3-chloroisoquinolin-1-yl-Xw | A |
| 68 (Example 69) | 4-methoxy-7-(3-cyano-1H-1,2,4-triazol-1-yl)-1H-pyrrolo[2,3-c]pyridin-3-yl glyoxylyl-Xw | Xz—N(piperazine)N—Xa | quinazolin-4-yl-Xw | A |
| 69 (Example 70) | 4-methoxy-7-(3-carboxamido-1H-1,2,4-triazol-1-yl)-1H-pyrrolo[2,3-c]pyridin-3-yl glyoxylyl-Xw | Xz—N(piperazine)N—Xa | quinazolin-4-yl-Xw | A |

TABLE 2-continued

Examples

| Table Entry (Example Number.) | Z | W | A | EC₅₀ Group from Table 1 |
|---|---|---|---|---|
| 70 (Example 72) | 4-fluoro-7-(pyridin-2-yl)-6-azaindole with 3-glyoxylyl-Xw | Xz—N(piperazine)N—Xa | Xw-isoquinolin-1-yl | A |
| 71 (Example 73) | 4-fluoro-7-bromo-6-azaindole with 3-glyoxylyl-Xw | Xz—N(piperazine)N—Xa | Xw-quinazolin-4-yl | A |
| 72 (Example 75) | 4-methoxy-7-chloro-6-azaindole with 3-glyoxylyl-Xw | Xz—N(piperazine)N—Xa | Xw-quinazolin-4-yl | A |
| 73 (Example 77) | 4-fluoro-7-(pyridin-2-yl)-6-azaindole with 3-glyoxylyl-Xw | Xz—N(piperazine)N—Xa | Xw-phthalazin-1-yl | A |

TABLE 2-continued

Examples

| Table Entry (Example Number.) | Z | W | A | EC$_{50}$ Group from Table 1 |
|---|---|---|---|---|
| 74 (Example 78) | | Xz—N⌒N—Xa | | A |
| 75 (Example 79) | | Xz—N⌒N—Xa | | B |
| 76 (Example 80) | | Xz—N⌒N—Xa | | A |
| 77 (Example 81) | | Xz—N⌒N—Xa | | A |

TABLE 2-continued
| Table Entry (Example Number.) | Z | W | A | EC50 Group from Table 1 |
|---|---|---|---|---|
| 78 (Example 82) | 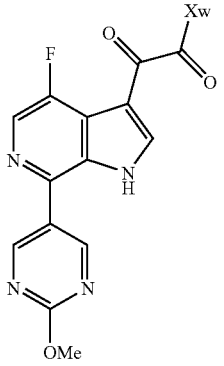 | 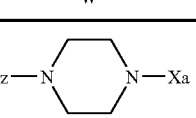 | 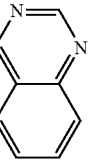 | A |
| 79 (Example 83) | 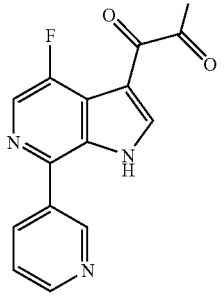 | 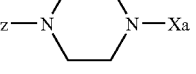 | 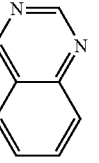 | A |
| 80 (Example 84) | 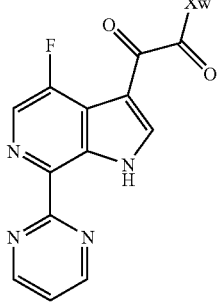 | 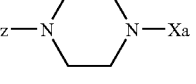 | 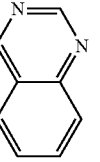 | A |
| 81 (Example 85) | 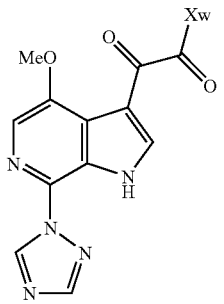 | 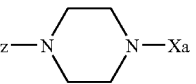 | 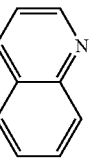 | A |

TABLE 2-continued

| Table Entry (Example Number.) | Z | W | A | EC$_{50}$ Group from Table 1 |
|---|---|---|---|---|
| 82 (Example 86) | 4-methoxy-7-(1,2,4-triazol-1-yl)-6-azaindol-3-yl (with Xw on carbonyl) | Xz—N(piperazine)N—Xa | 2-methoxy-6-methylquinolin-4-yl (Xw) | A |
| 83 (Example 87) | 4-fluoro-7-cyano-6-azaindol-3-yl | Xz—N(piperazine)N—Xa | isoquinolin-1-yl (Xw) | A |
| 84 (Example 88) | 4-fluoro-7-(5-phenyl-1H-1,2,4-triazol-3-yl)-6-azaindol-3-yl | Xz—N(piperazine)N—Xa | isoquinolin-1-yl (Xw) | A |
| 85 (Example 89) | 4-fluoro-7-(N-benzoylcarbamimidohydrazide)-6-azaindol-3-yl | Xz—N(piperazine)N—Xa | isoquinolin-1-yl (Xw) | A |

TABLE 2-continued

Examples

| Table Entry (Example Number.) | Z | W | A | EC$_{50}$ Group from Table 1 |
|---|---|---|---|---|
| 86 (Example 90) | 4-methoxy-7-(3-methyl-1,2,4-triazol-1-yl)-1H-pyrrolo[2,3-c]pyridine-3-yl glyoxyl, Xw | Xz—N(piperazine)N—Xa | Xw-2-quinolinyl | A |
| 87 (Example 91) | 4-fluoro-7-(1,2,3-triazol-1-yl)-1H-pyrrolo[2,3-c]pyridine-3-yl glyoxyl, Xw | Xz—N(piperazine)N—Xa | Xw-2-quinolinyl | A |
| 88 (Example 92) | 4-fluoro-7-bromo-1H-pyrrolo[2,3-c]pyridine-3-yl glyoxyl, Xw | Xz—N(piperazine)N—Xa | Xw-phthalazinyl | A |
| 89 (Example 93) | 4-fluoro-7-(1H-pyrazol-4-yl)-1H-pyrrolo[2,3-c]pyridine-3-yl glyoxyl, Xw | Xz—N(piperazine)N—Xa | Xw-phthalazinyl | A |

TABLE 2-continued

| Table Entry (Example Number.) | Z | W | A | EC$_{50}$ Group from Table 1 |
|---|---|---|---|---|
| 90 (Example 94) | 4-fluoro-7-(1H-pyrazol-3-yl)-1H-pyrrolo[2,3-c]pyridin-3-yl glyoxylyl (Xw) | Xz—N(piperazine)N—Xa | Xw-4-quinazolinyl | A |
| 91 (Example 95) | 4-fluoro-7-(1H-pyrazol-4-yl)-1H-pyrrolo[2,3-c]pyridin-3-yl glyoxylyl (Xw) | Xz—N(piperazine)N—Xa | Xw-4-quinazolinyl | A |
| 92 (Example 96) | 4-methoxy-7-(1H-pyrazol-3-yl)-1H-pyrrolo[2,3-c]pyridin-3-yl glyoxylyl (Xw) | Xz—N(piperazine)N—Xa | Xw-4-quinazolinyl | A |

Guide to reading the structures shown in Table 2 above. The structure of example 1 in the table above is:

Example 1, Table 2

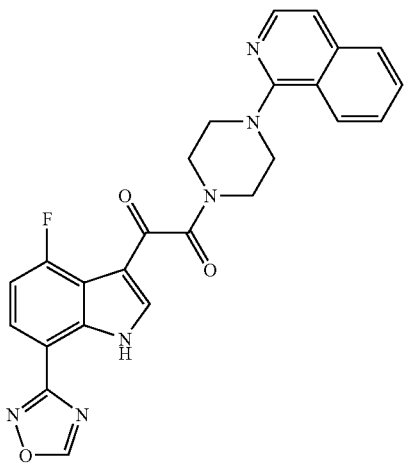

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present invention.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound of Formula I, including pharmaceutically acceptable salts thereof,

(I)

wherein:
z is

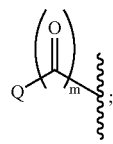

Q is selected from the group consisting of

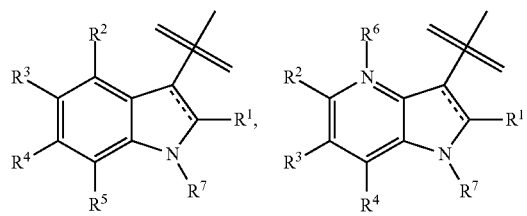

and

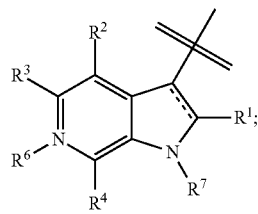

$R^1$ is hydrogen;
provided when Q is

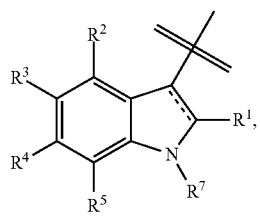

then
$R^2$ is hydrogen, methoxy or halogen; $R^3$ and $R^4$ are hydrogen; and $R^5$ is selected from the group consisting of hydrogen, halogen, cyano, $COOR^8$, $XR^9$ and B;

or provided when Q is

[chemical structure with R¹, R², R³, R⁴, R⁶, R⁷]

then

R² is hydrogen, methoxy or halogen; R³ is hydrogen; and R⁴ is selected from the group consisting of hydrogen, halogen, cyano, COOR⁸, XR⁹ and B;

or provided when Q is

[chemical structure with R¹, R², R³, R⁴, R⁶, R⁷]

then

R² and R³ are each hydrogen; and R⁴ is selected from the group consisting of hydrogen, halogen, cyano, COOR⁸, XR⁹ and B;

m is 2;

R⁶ does not exist;

R⁷ is hydrogen;

R¹⁰ is selected from the group consisting of $(C_{1-6})$alkyl, —CH₂CN, —CH₂COOH, —CH₂C(O)N R¹¹R¹², phenyl and pyridinyl;

R¹¹ and R¹² are each independently H or $(C_{1-3})$alkyl;

——— represents a carbon-carbon bond;

A is selected from the group consisting of

[chemical structures: isoquinoline, furopyridine, quinazoline, quinoline, phthalazine]

where Xw is the point of attachment and each member is independently optionally substituted with one group selected from the group consisting of methyl, methoxy, hydroxy, amino and halogen;

—W— is

[chemical structure of piperazine with R¹⁵–R²²]

$R^{15}$, $R^{16}$, $R^{17}$, $R^{18}$, $R^{19}$, $R^{20}$, $R^{21}$, $R^{22}$ are each;

B is selected from the group consisting of C(O)NR¹¹R¹², C(=NH)NHNHC(O)—R¹⁰, C(=NH)cyclopropyl, C(=NOH)NH₂, and heteroaryl; wherein said heteroaryl is independently optionally substituted with a substituent selected from F;

heteroaryl is selected from the group consisting of pyridinyl, pyrazinyl, pyrimidinyl, thiazolyl, pyrrolyl, imidazolyl, benzoimidazolyl, oxadiazolyl, pyrazolyl, tetrazolyl and triazolyl;

F is selected from the group consisting of $(C_{1-6})$alkyl, $(C_{1-6})$alkoxy, cyano, COOR⁸ —CONR¹¹R¹²; —CH₂CN, —CH₂COOH, —CH₂C(O)N R¹¹R¹², phenyl and pyridinyl;

R⁸ and R⁹ are independently selected from the group consisting of hydrogen and $(C_{1-6})$alkyl; and X is O.

2. A compound of claim 1 wherein:

B is selected from the group consisting of C(O)NR¹¹R¹² and heteroaryl; wherein said heteroaryl is independently optionally substituted with a substituent selected from F;

heteroaryl is selected from the group consisting of pyridinyl, pyrazinyl, pyrimidinyl, thiazolyl, pyrrolyl, imidazolyl, benzoimidazolyl, oxadiazolyl, tetrazolyl and triazolyl.

3. A compound of claim 2 wherein:

B is heteroaryl wherein said heteroaryl is independently optionally substituted with a substituent selected from F.

4. A compound of claim 2 wherein:

A is selected from the group consisting of

[chemical structures: isoquinoline, quinazoline, quinoline, phthalazine]

where Xw is the point of attachment.

5. A compound of claim 4 wherein:

B is heteroaryl; wherein said heteroaryl is independently optionally substituted with a substituent selected from F; and heteroaryl is selected from the group consisting of triazolyl, pyridinyl, pyrazinyl and pyrimidinyl.

6. A compound of claim 5 wherein:

B is heteroaryl; wherein said heteroaryl is independently optionally substituted with a substituent selected from F; and heteroaryl is selected from the group consisting of triazolyl.

7. A compound of claim 6 where F is methyl.

8. A pharmaceutical composition which comprises an antiviral effective amount of a compound of Formula I, including pharmaceutically acceptable salts thereof, as claimed in claim 1, and one or more pharmaceutically acceptable carriers, excipients or diluents.

9. The pharmaceutical composition of claim 8, useful for treating infection by HIV, which additionally comprises an antiviral effective amount of an AIDS treatment agent selected from the group consisting of:

(a) an AIDS antiviral agent;
(b) an anti-infective agent;
(c) an immunomodulator; and
(d) HIV entry inhibitors.

10. A method for treating a mammal infected with the HIV virus comprising administering to said mammal an antiviral effective amount of a compound of Formula I, including pharmaceutically accceptable salts thereof, as claimed in claim 1, and one or more pharmaceutically acceptable carriers, excipients or diluents.

11. The method of claim 10, comprising administering to said mammal an antiviral effective amount of a compound of Formula I, including pharmaceutically accceptable salts thereof, in combination with an antiviral effective amount of an AIDS treatment agent selected from the group consisting of an AIDS antiviral agent; an anti-infective agent; an immunomodulator; and an HIV entry inhibitor.

* * * * *

UNITED STATES PATENT AND TRADEMARK OFFICE
CERTIFICATE OF CORRECTION

| | |
|---|---|
| PATENT NO. | : 8,039,486 B2 |
| APPLICATION NO. | : 12/028189 |
| DATED | : October 18, 2011 |
| INVENTOR(S) | : Kap-Sun Yeung et al. |

It is certified that error appears in the above-identified patent and that said Letters Patent is hereby corrected as shown below:

On the Title Page:

Item (56) References Cited, under OTHER PUBLICATIONS,
    Column 2, D.L. Romero, et al., reference, change "Bis(heteroaryl)pipera;ine" to -- Bis(heteroaryl)piperazine --.

The reference should read:

-- D.L. Romero, et al., Bis(heteroaryl)piperazine (BHAP) Reverse Transcriptase Inhibitors: Structure-Activity Relationships of Novel Substituted Indole Analogues and the Identification of 1-[(5-Methanesulfonamido-1$H$-indole-2-yl)-carbonyl]-4-[3-[(1-methylethyl)amino]-pyridinyl]piperazine Monomethanesulfonate (U-90152S), a Second-Generation Clinical Candidate, J. Med. Chem., 36, pp. 1505-1508, 1993. --.

In the Claims:

Claim 1:
    Column 228, line 19, change "z" to -- Z --.
    Column 229, line 42, change "—CH$_2$C(O)N R$^{11}$R$^{12}$" to -- —CH$_2$C(O)NR$^{11}$R$^{12}$ --.
    Column 230, line 13, after "each", insert -- H --.
    Column 230, line 21, change "thiazolyl,pyrrolyl" to -- thiazolyl, pyrrolyl --.
    Column 230, line 26, change "—CH$_2$C(O)N R$^{11}$R$^{12}$" to -- —CH$_2$C(O)NR$^{11}$R$^{12}$ --.

Claim 10:
    Column 232, line 8, change "accceptable" to -- acceptable --.

Claim 11:
    Column 232, line 13, change "accceptable" to -- acceptable --.

Signed and Sealed this
Twenty-fifth Day of September, 2012

David J. Kappos
*Director of the United States Patent and Trademark Office*